United States Patent
Bajji

(10) Patent No.: US 11,603,372 B2
(45) Date of Patent: Mar. 14, 2023

(54) COMPOUNDS AND THERAPEUTIC USES THEREOF

(71) Applicant: VioGen Biosciences, LLC, Salt Lake City, UT (US)

(72) Inventor: Ashok Bajji, Salt Lake City, UT (US)

(73) Assignee: VioGen Biosciences, LLC, Salt Lake City, UT (US)

( * ) Notice: Subject to any disclaimer, the term of this patent is extended or adjusted under 35 U.S.C. 154(b) by 0 days.

(21) Appl. No.: 16/894,485

(22) Filed: Jun. 5, 2020

(65) Prior Publication Data

US 2021/0122752 A1 Apr. 29, 2021

Related U.S. Application Data

(63) Continuation of application No. PCT/US2018/064584, filed on Dec. 7, 2018.

(60) Provisional application No. 62/596,470, filed on Dec. 8, 2017.

(51) Int. Cl.
| | |
|---|---|
| *C07D 473/34* | (2006.01) |
| *C07D 487/04* | (2006.01) |
| *C07D 491/048* | (2006.01) |
| *C07D 495/04* | (2006.01) |
| *C07D 498/04* | (2006.01) |
| *C07D 513/04* | (2006.01) |

(52) U.S. Cl.
CPC ......... *C07D 473/34* (2013.01); *C07D 487/04* (2013.01); *C07D 491/048* (2013.01); *C07D 495/04* (2013.01); *C07D 498/04* (2013.01); *C07D 513/04* (2013.01)

(58) Field of Classification Search
None
See application file for complete search history.

(56) References Cited

U.S. PATENT DOCUMENTS

2008/0076738 A1 3/2008 Cai et al.
2008/0153783 A1 6/2008 Jin et al.

FOREIGN PATENT DOCUMENTS

WO 2016118709 A1 7/2016

OTHER PUBLICATIONS

Zhu, Wu Fu. Synthesis and cytotoxic activity of novel 2,6-disubstituted-4-mor-pholinothieno[3,2-d]pyrimidines as potent anti-tumor agents. Chinese Chemical Letters. 23 (2012) 703-706.*
Database Registry Chemical Abstracts Service, Columbus, Ohio, Accession No. RN 209678-73-9. Entered STN: Aug. 9, 1998.*
Database Registry Chemical Abstracts Service, Columbus, Ohio, Accession No. RN 1262120-90-0, Entered STN: Feb. 4, 2011.*
National Center for Biotechnology Information, "Substance Record for SID 24724290", Pub Chem, https://pubchem.ncbi.nlm.nih.gov/substance/24724290.
Gayle et al., "Identification of apilimod as a first-in-class PIKfyve kinase inhibitor for treatment of B-cell non-Hodgkin lymphoma", Blood, Mar. 30, 2017, pp. 1768-1778 129(13).
Wilson et al., "PI(3,5)P2 controls vacuole potassium transport to support cellular osmoregulation", Molecular Biology of the Cell, Jul. 15, 2018, pp. 1675-1777, 29(14).
International Search Report and Written Opinion for PCT/US2018/064584 dated Mar. 6, 2019, 9 pages.

* cited by examiner

*Primary Examiner* — Samantha L Shterengarts
(74) *Attorney, Agent, or Firm* — EcholsIP LLC

(57) ABSTRACT

The invention relates to compounds, pharmaceutical compositions and methods useful for treating cancer, systemic or chronic inflammation, rheumatoid arthritis, diabetes, obesity, T-cell mediated autoimmune disease, diseases associated with over production of IL12/IL23, lysosomal storage disorders, filovirus infections, ischemia, and other complications associated with these diseases and disorders.

18 Claims, No Drawings

COMPOUNDS AND THERAPEUTIC USES THEREOF

CROSS-REFERENCE TO RELATED APPLICATIONS

This application is a continuation of International Patent Application No. PCT/US2018/064584, filed Dec. 7, 2018 and entitled "COMPOUNDS AND THERAPEUTIC USES THEREOF," which claims priority to U.S. Provisional Patent Application No. 62/596,470, filed Dec. 8, 2017 and entitled "COMPOUNDS AND THERAPEUTIC USES THEREOF," the contents of each of which are incorporated herein in their entirety.

FIELD OF THE INVENTION

The present invention relates generally to the field of medicinal chemistry. Specifically, the present invention provides compounds and therapeutic uses thereof.

BACKGROUND OF THE INVENTION

PIKfyve is an endosomal lipid kinase targeted to the cytoplasmic leaflet of endosomes via protein-lipid interactions between its FYVE domain and phosphatidylinositol-3-phosphate (PI3P) within the endosomal membrane. At endosomes, PIKfyve phosphorylates PI3P to generate PI(3,5) P2, which in turn serves to control endolysosomal membrane traffic.

Lipid kinases regulate a wide variety of cellular functions, including cell growth and proliferation. Thus, lipid kinases are potential cancer therapeutic targets. In fact, there is currently a PIKfyve inhibitor being clinically investigated for the treatment of B-cell non-Hodgkin's lymphoma. There is a need for additional and alternative cancer therapeutics.

Interleukin (IL)12 and IL23 play important roles in the development of experimental autoimmune disease models and numerous afflictions affecting humans. There is a clear relationship between IL12, IL23 and the generation of pathogenic T helper cells capable of orchestrating tissue inflammation. It has been shown that IL12p40e, a common subunit shared by IL12 and IL23, is critical to pathologies associated with psoriasis, inflammatory bowel disease (IBD) and tumor growth. PIKfyve is involved in IL12/23p40 expression. There is a need for therapeutics that modulate production of IL12/IL23.

PIKfyve may impact lysosomal storage disorders. Lysosomes are organelles central to degradation and recycling processes in animal cells. Lysosomal storage disorders (LSDs) are inherited disorders that are thought to be caused by a deficiency of specific enzymes that are normally required for the breakdown of cellular metabolite substrates. If a specific lysosomal enzyme is not present in sufficient quantities, the normal breakdown of the substrate is incomplete or blocked. The cell is then unable to breakdown the material and it accumulates in the lysosomes of the cell. This accumulation disrupts the cell's normal functioning and gives rise to the clinical manifestations of LSDs.

Lysosomal storage disorders include diseases such as cholesteryl ester storage disease, gangliosidosis, Neimann-Pick disease, and MPS disorders. LSDs tend to be progressive, with the rate of progression, the severity of symptoms, and the organ systems affected varying between disorders and even within each disorder type. LSDs affect different body organs or systems including the skeleton and joints, eyes, heart, lungs, kidneys, skin, and frequently the central nervous system. There is a need for lysosomal storage disorder treatments.

Ebola virus (EBOV) is a member of the Filoviridae virus family along with Marburg virus (MARV). They are commonly known as filoviruses. PIKfyve inhibitors may be effective at inhibiting infection by filoviruses.

Consequently, there is a clear need for compounds that inhibit PIKfyve.

BRIEF SUMMARY OF THE INVENTION

The present invention provides chemical compounds that inhibit the activity of PIKfyve. These compounds can be used in the treatment of cancer, systemic or chronic inflammation, rheumatoid arthritis, diabetes, obesity, T-cell mediated autoimmune disease, diseases associated with over production of IL12/IL23, lysosomal storage disorders, filovirus infections, ischemia, and other complications associated with these diseases and disorders.

Specifically, the present invention provides compounds of Formula I

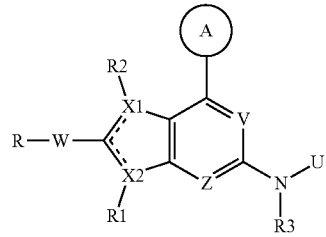

Formula I and pharmaceutically acceptable salts and solvates thereof; wherein R, R1, R2, R3, U, X1, X2, V, Z, W and ring A are as defined herein below.

The present invention further provides compounds of Formula II

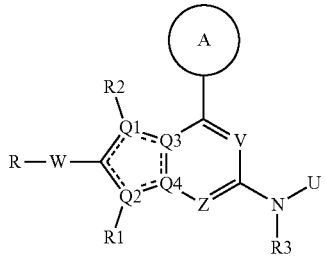

Formula II and pharmaceutically acceptable salts and solvates thereof; wherein R, R1, R2, R3, U, V, Q1, Q2, Q3, Q4, Z, W and ring A are as defined herein below.

The compounds of the present invention include the compounds of the Formula I and Formula II (including Formulae IIa-c), as illustrated herein, as well as their geometric isomers, enantiomers, diastereomers, or racemates thereof. The compounds of the present invention also include pharmaceutically acceptable salts, prodrugs and solvates of all such compounds.

As noted above, the present invention provides chemical compounds that selectively inhibit the activity of PIKfyve, and therefore can be used in the treatment of cancer, systemic or chronic inflammation, rheumatoid arthritis, diabetes, obesity, T-cell mediated autoimmune disease, ischemia, and other complications associated with these diseases and disorders. Thus, in a related aspect, the present invention also provides methods for treating cancer, systemic or chronic inflammation, rheumatoid arthritis, diabetes, obesity, T-cell mediated autoimmune disease, diseases associated with over production of IL12/IL23, lysosomal storage disorders, filovirus infections, ischemia, and other complications associated with these diseases and disorders, by administering to a patient in need of such treatment a therapeutically effective amount of a compound of the present invention.

Also provided is the use of the compound of the present invention for the manufacture of a medicament useful for therapy, particularly for the treatment of cancer, systemic or chronic inflammation, rheumatoid arthritis, diabetes, obesity, T-cell mediated autoimmune disease, diseases associated with over production of IL12/IL23, lysosomal storage disorders, filovirus infections, ischemia, and other complications associated with these diseases and disorders. In addition, the present invention also provides a pharmaceutical composition having a compound of the present invention and one or more pharmaceutically acceptable excipients. Further, methods for the treatment of cancer, systemic or chronic inflammation, rheumatoid arthritis, diabetes, obesity, T-cell mediated autoimmune disease, diseases associated with over production of IL12/IL23, lysosomal storage disorders, filovirus infections, ischemia, and other complications associated with these diseases and disorders, by administering to a patient in need of such treatment, a pharmaceutical composition of the invention, are also encompassed.

In addition, the present invention further provides methods for treating or delaying the onset of the symptoms associated with cancer, systemic or chronic inflammation, rheumatoid arthritis, type 2 diabetes, obesity, T-cell mediated autoimmune disease, diseases associated with over production of IL12/IL23, lysosomal storage disorders, filovirus infections, ischemia, and other complications associated with these diseases and disorders. These methods comprise administering an effective amount of a compound of the present invention, preferably in the form of a pharmaceutical composition or medicament, to an individual having, or at risk of having, cancer, systemic or chronic inflammation, rheumatoid arthritis, diabetes, obesity, T-cell mediated autoimmune disease, diseases associated with over production of IL12/IL23, lysosomal storage disorders, filovirus infections, ischemia, and other complications associated with these diseases and disorders.

The compounds of the present invention can be used in combination therapies. Thus, combination therapy methods are also provided for treating or delaying the onset of the symptoms associated with cancer, systemic or chronic inflammation, rheumatoid arthritis, type 2 diabetes, obesity, T-cell mediated autoimmune disease, diseases associated with over production of IL12/IL23, lysosomal storage disorders, filovirus infections, ischemia, and other complications associated with these diseases and disorders. Such methods comprise administering to a patient in need thereof a compound of the present invention and, together or separately, at least one other agent for the treatment of cancer, systemic or chronic inflammation, rheumatoid arthritis, diabetes, obesity, T-cell mediated autoimmune disease, diseases associated with over production of IL12/IL23, lysosomal storage disorders, filovirus infections, ischemia, and other complications associated with these diseases and disorders.

For the convenience of combination therapy, the compound of the present invention can be administered together in the same formulation with another agent for the treatment of cancer, systemic or chronic inflammation, rheumatoid arthritis, diabetes, obesity, T-cell mediated autoimmune disease, diseases associated with over production of IL12/IL23, lysosomal storage disorders, filovirus infections, ischemia, and other complications associated with these diseases and disorders. Thus, the present invention also provides a pharmaceutical composition or medicament for combination therapy, comprising an effective amount of a first compound according to the present invention, and an effective amount of at least one other agent for the treatment of cancer, systemic or chronic inflammation, rheumatoid arthritis, diabetes, obesity, T-cell mediated autoimmune disease, diseases associated with over production of IL12/IL23, lysosomal storage disorders, filovirus infections, ischemia, and other complications associated with these diseases and disorders, which is different from the first compound.

The foregoing and other advantages and features of the invention, and the manner in which they are accomplished, will become more readily apparent upon consideration of the following detailed description of the invention taken in conjunction with the accompanying examples, which illustrate preferred and exemplary embodiments.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent to one of skill in the art from the following detailed description, and from the claims.

DETAILED DESCRIPTION OF THE INVENTION

1. Definitions

As used herein, the term "alkyl" as employed herein by itself or as part of another group refers to a saturated aliphatic hydrocarbon straight chain or branched chain group having, unless otherwise specified, 1 to 20 carbon atoms (whenever it appears herein, a numerical range such as "1 to 20" refers to each integer in the given range; e.g., "1 to 20 carbon atoms" means that the alkyl group may consist of 1, 2 or 3 carbon atoms, or up to 20 carbon atoms). An alkyl group may be in unsubstituted form or substituted form with one or more substituents (generally one to three substituents except in the case of halogen substituents, e.g., perchloro). For example, a $C_{1-6}$ alkyl group refers to a straight or branched aliphatic group containing 1 to 6 carbon atoms (e.g., include methyl, ethyl, propyl, isopropyl, butyl, sec-butyl, tert-butyl, 3-pentyl, and hexyl), which may be optionally substituted.

The term "alkylene" as used herein means a saturated aliphatic hydrocarbon straight chain or branched chain group having 1 to 20 carbon atoms having two connecting points. For example, "ethylene" represents the group —$CH_2$—$CH_2$—. Alkylene groups may also be in unsubstituted form or substituted form with one or more substituents.

The term "alkenyl" as employed herein by itself or as part of another group means a straight or branched chain radical of 2-10 carbon atoms, unless the chain length is limited thereto, including at least one double bond between two of the carbon atoms in the chain. The alkenyl group may be in unsubstituted form or substituted form with one or more substituents (generally one to three substituents except in the case of halogen substituents, e.g., perchloro or perfluoroalkyls). For example, a $C_{1-6}$ alkenyl group refers to a straight or branched chain radical containing 1 to 6 carbon atoms and having at least one double bond between two of the carbon atoms in the chain (e.g., ethenyl, 1-propenyl, 2-propenyl, 2-methyl-1-propenyl, 1-butenyl and 2-butenyl, which may be optionally substituted).

The term "alkenylene" as used herein means an alkenyl group having two connecting points. For example, "ethenylene" represents the group —CH=CH—. Alkenylene groups may also be in unsubstituted form or substituted form with one or more substituents.

The term "alkynyl" as used herein by itself or as part of another group means a straight or branched chain radical of 2-10 carbon atoms, unless the chain length is limited thereto, wherein there is at least one triple bond between two of the carbon atoms in the chain. The alkynyl group may be in unsubstituted form or substituted form with one or more substituents (generally one to three substituents except in the case of halogen substituents, e.g., perchloro or perfluoroalkyls). For example, a $C_{1-6}$ alkynyl group refers to a straight or branched chain radical containing 1 to 6 carbon atoms and having at least one triple bond between two of the carbon atoms in the chain (e.g., ethynyl, 1-propynyl, 1-methyl-2-propynyl, 2-propynyl, 1-butynyl and 2-butynyl), which may be optionally substituted. The term "alkynylene" as used herein means an alkynyl having two connecting points. For example, "ethynylene" represents the —CH=CH— group. Alkynylene groups may also be in unsubstituted form or substituted form with one or more substituents.

The term "carbocycle" as used herein by itself or as part of another group means cycloalkyl and non-aromatic partially saturated carbocyclic groups such as cycloalkenyl and cycloalkynyl. A carbocycle may be in unsubstituted form or substituted form with one or more substituents so long as the resulting compound is sufficiently stable and suitable for the treatment method of the present invention.

The term "cycloalkyl" as used herein by itself or as part of another group refers to a fully saturated 3- to 8-membered cyclic hydrocarbon ring (i.e., a cyclic form of an unsubstituted alkyl) alone ("monocyclic cycloalkyl") or fused to another cycloalkyl, cycloalkynyl, cycloalkenyl, heterocycle, aryl or heteroaryl ring (i.e., sharing an adjacent pair of carbon atoms with such other rings) ("polycyclic cycloalkyl"). Thus, a cycloalkyl may exist as a monocyclic ring, bicyclic ring, or a spiral ring. When a cycloalkyl is referred to as a $C_x$ cycloalkyl, this means a cycloalkyl in which the fully saturated cyclic hydrocarbon ring (which may or may not be fused to another ring) has x number of carbon atoms. When a cycloalkyl is recited as a substituent on a chemical entity, it is intended that the cycloalkyl moiety is attached to the entity through a carbon atom within the fully saturated cyclic hydrocarbon ring of the cycloalkyl. In contrast, a substituent on a cycloalkyl can be attached to any carbon atom of the cycloalkyl. A cycloalkyl group may be unsubstituted or substituted with one or more substituents so long as the resulting compound is sufficiently stable and suitable for the treatment method of the present invention. Examples of cycloalkyl groups include cyclopropyl, cyclobutyl, cyclopentyl, cyclohexyl and cycloheptyl.

The term "cycloalkenyl" as used herein by itself or as part of another group refers to a non-aromatic partially saturated 3- to 8-membered cyclic hydrocarbon ring having a double bond therein (i.e., a cyclic form of an unsubstituted alkenyl) alone ("monocyclic cycloalkenyl") or fused to another cycloalkyl, cycloalkynyl, cycloalkenyl, heterocycle, aryl or heteroaryl ring (i.e., sharing an adjacent pair of carbon atoms with such other rings) ("polycyclic cycloalkenyl"). Thus, a cycloalkenyl may exist as a monocyclic ring, bicyclic ring, polycyclic or a spiral ring. When a cycloalkenyl is referred to as a $C_x$ cycloalkenyl, this means a cycloalkenyl in which the non-aromatic partially saturated cyclic hydrocarbon ring (which may or may not be fused to another ring) has x number of carbon atoms. When a cycloalkenyl is recited as a substituent on a chemical entity, it is intended that the cycloalkenyl moiety is attached to the entity through a carbon atom within the non-aromatic partially saturated ring (having a double bond therein) of the cycloalkenyl. In contrast, a substituent on a cycloalkenyl can be attached to any carbon atom of the cycloalkenyl. A cycloalkenyl group may be in unsubstituted form or substituted form with one or more substitutents. Examples of cycloalkenyl groups include cyclopentenyl, cycloheptenyl and cyclooctenyl.

The term "heterocycle" (or "heterocyclyl" or "heterocyclic") as used herein by itself or as part of another group means a saturated or partially saturated 3-7 membered non-aromatic cyclic ring formed with carbon atoms and from one to four heteroatoms independently selected from the group consisting of O, N, and S, wherein the nitrogen and sulfur heteroatoms can be optionally oxidized, and the nitrogen can be optionally quaternized ("monocyclic heterocycle"). The term "heterocycle" also encompasses a group having the non-aromatic heteroatom-containing cyclic ring above fused to another monocyclic cycloalkyl, cycloalkynyl, cycloalkenyl, heterocycle, aryl or heteroaryl ring (i.e., sharing an adjacent pair of carbon atoms with such other rings) ("polycyclic heterocylce"). Thus, a heterocycle may exist as a monocyclic ring, bicyclic ring, polycyclic or a spiral ring. When a heterocycle is recited as a substituent on a chemical entity, it is intended that the heterocycle moiety is attached to the entity through an atom within the saturated or partially saturated ring of the heterocycle. In contrast, a substituent on a heterocycle can be attached to any suitable atom of the heterocycle. In a "saturated heterocycle" the non-aromatic heteroatom-containing cyclic ring described above is fully saturated, whereas a "partially saturated heterocyle" contains one or more double or triple bonds within the non-aromatic heteroatom-containing cyclic ring regardless of the other ring it is fused to. A heterocycle may be in unsubstituted form or substituted form with one or more substituents so long as the resulting compound is sufficiently stable and suitable for the treatment method of the present invention.

Some examples of saturated or partially saturated heterocyclic groups include oxetanyl, azitidinyl, tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups.

As used herein, "aryl" by itself or as part of another group means an all-carbon aromatic ring with up to 7 carbon atoms in the ring ("monocylic aryl"). In addition to monocyclic aromatic rings, the term "aryl" also encompasses a group having the all-carbon aromatic ring above fused to another cycloalkyl, cycloalkynyl, cycloalkenyl, heterocycle, aryl or heteroaryl ring (i.e., sharing an adjacent pair of carbon atoms with such other rings) ("polycyclic aryl"). When an aryl is referred to as a $C_x$ aryl, this means an aryl in which the all-carbon aromatic ring (which may or may not be fused to another ring) has x number of carbon atoms. When an aryl is recited as a substituent on a chemical entity, it is intended that the aryl moiety is attached to the entity through an atom within the all-carbon aromatic ring of the aryl. In contrast, a substituent on an aryl can be attached to any suitable atom of the aryl. Examples, without limitation, of aryl groups are phenyl, naphthalenyl and anthracenyl. An aryl may be in unsubstituted form or substituted form with one or more substituents so long as the resulting compound is sufficiently stable and suitable for the treatment method of the present invention.

The term "heteroaryl" as employed herein refers to a stable aromatic ring having up to 7 ring atoms with 1, 2, 3 or 4 hetero ring atoms in the ring which are oxygen, nitrogen or sulfur or a combination thereof ("monocylic heteroaryl"). In addition to monocyclic hetero aromatic rings, the term "heteroaryl" also encompasses a group having the monocyclic hetero aromatic ring above fused to another cycloalkyl, cycloalkynyl, cycloalkenyl, heterocycle, aryl or heteroaryl ring (i.e., sharing an adjacent pair of carbon atoms with such other rings) ("polycyclic heteroaryl"). When a heteroaryl is recited as a substituent on a chemical entity, it is intended that the heteroaryl moiety is attached to the entity through an atom within the hetero aromatic ring of the heteroaryl. In contrast, a substituent on a heteroaryl can be attached to any suitable atom of the heteroaryl. A heteroaryl may be in unsubstituted form or substituted form with one or more substituents so long as the resulting compound is sufficiently stable and suitable for the treatment method of the present invention.

Useful heteroaryl groups include thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, thaizolyl, isothiazolyl, phenothiazinyl, oxazolyl, isoxazolyl, furazanyl, phenoxazinyl, 1,4-dihydroquinoxaline-2,3-dione, 7-aminoisocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl and 2-oxobenzimidazoly, oxadiazolyl, and thiadiazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

As used herein, the term "halo" refers to chloro, fluoro, bromo, or iodo substitutents.

As used herein, the term "hydro" refers to a bound hydrogen atom (—H group).

As used herein, the term "hydroxyl" refers to an —OH group.

As used herein, the term "alkoxy" refers to an —O—($C_{1-12}$ alkyl). Lower alkoxy refers to —O-(lower alkyl) groups.

As used herein, the term "alkynyloxy" refers to an —O—($C_{1-12}$ alkynyl).

As used herein, the term "cycloalkyloxy" refers to an —O-cycloakyl group.

As used herein, the term "heterocycloxy" refers to an —O-heterocycle group.

As used herein, the term "aryloxy" refers to an —O-aryl group.

The term "heteroaryloxy" refers to an —O-heteroaryl group.

The terms "arylalkoxy" and "heteroarylalkoxy" are used herein to mean an alkoxy group substituted with an aryl group and a heteroaryl group, respectively.

As used herein, the term "mercapto" group refers to an —SH group.

The term "alkylthio" group refers to an —S— alkyl group.

The term "arylthio" group refers to an —S-aryl group.

The term "arylalkyl" is used herein to mean an above-defined alkyl group substituted by an aryl group defined above. Examples of arylalkyl groups include benzyl, phenethyl and naphthylmethyl, etc. An arylalkyl group may be unsubstituted or substituted with one or more substituents so long as the resulting compound is sufficiently stable and suitable for the treatment method of the present invention.

The term "heteroarylalkyl" is used herein to mean an alkyl group defined above substituted by any heteroaryl groups. A heteroarylalkyl may be unsubstituted or substituted with one or more substituents so long as the resulting compound is sufficiently stable and suitable for the treatment method of the present invention.

The term "heteroarylalkenyl" is used herein to mean any of the above-defined alkenyl groups substituted by any of the above-defined heteroaryl groups.

The term "arylalkynyl" is used herein to mean any of the above-defined alkynyl groups substituted by any of the above-defined aryl groups.

The term "heteroarylalkenyl" is used herein to mean any of the above-defined alkenyl groups substituted by any of the above-defined heteroaryl groups.

The term "aryloxy" is used herein to mean aryl-O— wherein aryl is as defined above. Useful aryloxy groups include phenoxy and 4-methylphenoxy.

The term "heteroaryloxy" is used herein to mean heteroaryl-O— wherein heteroaryl is as defined above.

The term "arylalkoxy" is used herein to mean an alkoxy group substituted by an aryl group as defined above. Useful arylalkoxy groups include benzyloxy and phenethyloxy.

"Heteroarylalkoxy" is used herein to mean any of the above-defined alkoxy groups substituted by any of the above-defined heteroaryl groups.

"Haloalkyl" means an alkyl group that is substituted with one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

As used herein, the term "carbonyl" group refers to a —C(═O)R" group, where R" is selected from the group consisting of hydro, alkyl, cycloalkyl, aryl, heteroaryl (bonded through a ring carbon) and heterocyclic (bonded through a ring carbon), as defined herein.

As used herein, the term "aldehyde" group refers to a carbonyl group where R" is hydro.

As used herein, the term "cycloketone" refers to a cycloalkyl group in which one of the carbon atoms which form the ring has a "═O" bonded to it; i.e., one of the ring carbon atoms is a —C(═O)-group As used herein, the term "thiocarbonyl" group refers to a —C(═S)R" group, with R" as defined herein.

"Alkanoyl" refers to an alkyl-C(═O)— group.

The term "acetyl" group refers to a —C(═O)$CH_3$ group.

"Alkylthiocarbonyl" refers to an alkyl-C(═S)— group.

The term "cycloketone" refers to a carbocycle or heterocycle group in which one of the carbon atoms which form the ring has an oxygen double-bonded to it—i.e., one of the ring carbon atoms is a —C(=O)— group.

The term "O-carboxy" group refers to an R"C(=O)O— group, where R" is as defined herein.

The term "C-carboxy" group refers to a —C(=O)OR" group where R" is as defined herein.

As used herein, the term "carboxylic acid" refers to a C-carboxy group in which R" is hydro. In other words, the term "carboxylic acid" refers to —COOH.

As used herein, the term "ester" is a C-carboxy group, as defined herein, wherein R" defined above except that it is not hydro (e.g., methyl, ethyl, lower alkyl).

As used herein, the term "C-carboxy salt" refers to a —C(=O)O$^-$ M$^+$ group wherein M$^+$ is selected from the group consisting of lithium, sodium, magnesium, calcium, potassium, barium, iron, zinc and quaternary ammonium.

The term "carboxyalkyl" refers to —C$_{1-6}$ alkylene-C(=O)OR" (that is, a C$_{1-6}$ alkyl group connected to the main structure wherein the alkyl group is substituted with —C(=O)OR" with R" being defined herein). Examples of carboxyalkyl include, but are not limited to, —CH$_2$COOH, —(CH$_2$)$_2$COOH, —(CH$_2$)$_3$COOH, —(CH$_2$)$_4$COOH, and —(CH$_2$)$_5$COOH.

"Carboxyalkenyl" refers to -alkenylene-C(=O)OR" with R" being defined herein.

The term "carboxyalkyl salt" refers to a —(CH$_2$)$_r$C(=O)O$^-$M$^+$ wherein M$^+$ is selected from the group consisting of lithium, sodium, potassium, calcium, magnesium, barium, iron, zinc and quaternary ammonium.

The term "carboxyalkoxy" refers to —O—(CH$_2$)$_r$C(=O)OR" wherein r is 1-6, and R" is as defined herein.

"C$_x$ carboxyalkanoyl" means a carbonyl group (—(O=)C—) attached to an alkyl or cycloalkylalkyl group that is substituted with a carboxylic acid or carboxyalkyl group, wherein the total number of carbon atoms is x (an integer of 2 or greater).

"C$_x$ carboxyalkenoyl" means a carbonyl group (—(O=)C—) attached to an alkenyl or alkyl or cycloalkylalkyl group that is substituted with a carboxylic acid or carboxyalkyl or carboxyalkenyl group, wherein at least one double bond (—CH=CH—) is present and wherein the total number of carbon atoms is x (an integer of 2 or greater).

"Carboxyalkoxyalkanoyl" refers to R"OC(=O)—C$_{1-6}$ alkylene-O—C$_{1-6}$ alkylene-C(=O)—, where R" is as defined herein.

"Amino" refers to an —NR$^x$R$^y$ group, with R$^x$ and R$^y$ as defined herein.

"Alkylamino" means an amino group with a substituent being a C$_{1-6}$ alkyl.

"Aminoalkyl" means an alkyl group connected to the main structure of a molecule where the alkyl group has a substituent being amino.

"Quaternary ammonium" refers to a —$^+$N(R$^x$)(R$^y$)(R$^z$) group wherein R$^x$, R$^y$, and R$^z$ are as defined herein.

The term "nitro" refers to a —NO$_2$ group.

The term "O-carbamyl" refers to a —OC(=O)N(R$^x$)(R$^y$) group with R$^x$ and R$^y$ as defined herein.

The term "N-carbamyl" refers to a R$^y$OC(=O)N(R$^x$)— group, with R$^x$ and R$^y$ as defined herein.

The term "O-thiocarbamyl" refers to a —OC(=S)N(R$^x$)(R$^y$) group with R$^x$ and R$^y$ as defined herein.

The term "N-thiocarbamyl" refers to a R$^x$OC(=S)NR$^y$— group, with R$^x$ and R$^y$ as defined herein.

"C-amido" refers to a —C(=O)N(R$^x$)(R$^y$) group with R$^x$ and R$^y$ as defined herein.

"N-amido" refers to a R$^x$C(=O)N(R$^y$)— group with R$^x$ and R$^y$ as defined herein.

"Aminothiocarbonyl" refers to a —C(=S)N(R$^x$)(R$^y$) group with R$^x$ and R$^y$ as defined herein.

"Hydroxyaminocarbonyl" means a —C(=O)N(R$^x$)(OH) group with R$^x$ as defined herein.

"Alkoxyaminocarbonyl" means a —C(=O)N(R$^x$)(alkoxy) group with R$^x$ as defined herein.

The terms "cyano" and "cyanyl" refer to a —C≡N group.

The term "nitrile" group, as used herein, refers to a —C≡N substituent.

The term "cyanato" refers to a —CNO group.

The term "isocyanato" refers to a —NCO group.

The term "thiocyanato" refers to a —CNS group. The term "isothiocyanato" refers to a —NCS group.

The term "sulfinyl" refers to a —S(=O)R" group, where R" is as defined herein.

The term "sulfonyl" refers to a —S(=O)$_2$R" group, where R" is as defined herein.

The term "sulfonamide" refers to a —(R$^x$)N—S(=O)$_2$R" group, with R" and R$^x$ as defined herein.

"Aminosulfonyl" means (R$^x$)(R$^y$)N—S(=O)$_2$— with R$^x$ and R$^y$ as defined herein.

"Aminosulfonyloxy" means a (R$^x$)(R$^y$)N—S(=O)$_2$—O— group with R$^x$ and R$^y$ as defined herein.

"Sulfonamidecarbonyl" means R"—S(=O)$_2$—N(R$^x$)—C(=O)— with R" and R$^x$ as defined herein.

"Alkanoylaminosulfonyl" refers to an alkyl-C(=O)—N(R$^x$)—S(=O)$_2$— group with R$^x$ as defined herein.

The term "trihalomethylsulfonyl" refers to a X$_3$CS(=O)$_2$— group with X being halo.

The term "trihalomethylsulfonamide" refers to a X$_3$CS(=O)$_2$N(R$^x$)— group with X being halo and R$^x$ as defined herein.

R" is selected from the group consisting of hydro, alkyl, cycloalkyl, aryl, heteroaryl and heterocycle, each being optionally substituted.

R$^x$, R$^y$, and R$^z$ are independently selected from the group consisting of hydro and optionally substituted alkyl.

The term "methylenedioxy" refers to a —OCH$_2$O— group wherein the oxygen atoms are bonded to adjacent ring carbon atoms.

The term "ethylenedioxy" refers to a —OCH$_2$CH$_2$O— group wherein the oxygen atoms are bonded to adjacent ring carbon atoms.

The term "bioisostere," as used herein, generally refers to compounds or moieties that have chemical and physical properties producing broadly similar biological properties. Examples of carboxylic acid bioisosteres include, but are not limited to, carboxyalkyl, carboxylic acid ester, tetrazole, oxadiazole, isoxazole, hydroxythiadiazole, thiazolidinedione, oxazolidinedione, sulfonamide, aminosulfonyl, sulfonamidecarbonyl, C-amido, sulfonylcarboxamide, phosphonic acid, phosphonamide, phosphinic acid, sulfonic acid, alkanoylaminosufonyl, mercaptoazole, trifluoromethylcarbonyl, and cyanamide.

Unless specifically stated otherwise or indicated by a bond symbol (dash, double dash, or triple dash), the connecting point to a recited group will be on the right-most stated group. Thus, for example, a hydroxyalkyl group is connected to the main structure through the alkyl and the hydroxyl is a substituent on the alkyl.

2. Therapeutic Compounds

The present invention provides chemical compounds that selectively inhibit the activity of PIKfyve. These compounds can be used in the treatment of cancer, systemic or chronic inflammation, rheumatoid arthritis, diabetes, obesity, T-cell mediated autoimmune disease, diseases associated with over production of IL12/IL23, lysosomal storage disorders, filovirus infections, ischemia, and other complications associated with these diseases and disorders.

Specifically, the present invention provides compounds represented by Formula I, and pharmaceutically acceptable salts or solvates thereof

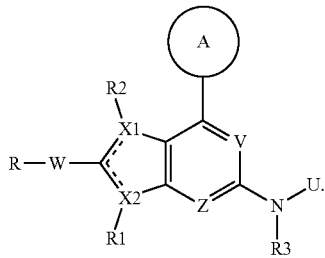

Formula I

In some embodiments, R can be selected from hydrogen, aryl, heteroaryl, alkyl, cycloalkyl, and/or heterocyclyl, and R can be optionally substituted. Each of X1 and X2 can be independently selected from O, S, N, and/or C.

W can be selected from a single bond, O, S, CH$_2$, —(CH2)n-, S(O), S(O2), NRa, C(O), C(O)NRa, NRaC(O), S(O2)NRa, NRaS(O2), CRa=CRb, C=NRa, and/or NRa=CRb. Furthermore, n=0-5 (e.g., 0, 1, 2, 3, 4, or 5) and each of Ra and Rb can be independently selected from hydrogen, C1-C6 alkyl, aryl, heteroaryl, cycloalkyl, and/or cycloheteroalkyl. Each of Ra and Rb can be optionally substituted.

Each of R1 and R2 may be optionally present depending on the valence of the atom to which R1 or R2 is attached. If present, each of R1 and R2 may be independently selected from hydrogen, halo, hydroxyl, aryl, heteroaryl, cycloalkyl, and/or heterocyclyl. Each of R1 and R2 can be optionally substituted.

R3 may be selected from hydrogen, alkyl, alkylsulfonyl, acyl, alkoxycarbonyl, C-amido, aliphatic ring, aryl, heteroaryl, and/or aliphatic ring with one or more heteroatoms. R3 may be optionally substituted. Moreover, U may be selected from hydrogen and/or a group of one of the following general formulae:

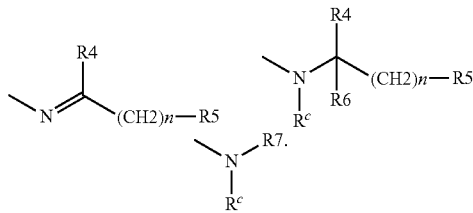

In various embodiments, n=0-3 (e.g., 0, 1, 2, or 3). Each of R4, R5, R6, R7, and R$^c$ can be independently selected from hydrogen, C1-C6 alkyl, aryl, heteroaryl, cycloalkyl, and/or heterocyclyl. Each of R4, R5, R6, R7, and R$^c$ may be optionally substituted. In some embodiments, R3 and U together may form a 4 to 6 membered heterocyclic or heteroaryl ring, optionally substituted by one or more substituents selected from hydrogen, C1-C6 alkyl, aryl, heteroaryl, cycloalkyl, and/or heterocyclyl. The one or more substituents may be optionally substituted.

In certain embodiments, ------- may be selected from a single bond, an aromatic bond, and/or a double bond, such that at least one bond within the five membered ring is a double bond if ------- is not an aromatic bond.

V and Z can be independently selected from N and CH. Ring A may be selected from carbocycle, heterocycle, and/or heteroaryl. Ring A may be optionally substituted. In some embodiments, V is N. In certain embodiments, Z is N. In various embodiments, each of V and Z is N. W may be a single bond. W may be C(O)NRa.

In some embodiments, X1 may be S, wherein X1 is bound to each adjacent C in the five membered ring by an aromatic bond. X2 may be S, wherein X2 is bound to each adjacent C in the five membered ring by an aromatic bond. X1 may be O, wherein X1 is bound to each adjacent C in the five membered ring by an aromatic bond. X2 may be O, wherein X2 is bound to each adjacent C in the five membered ring by an aromatic bond. X1 may be NH, wherein X1 is bound to each adjacent C in the five membered ring by an aromatic bond. X1 may be S, wherein X1 is bound to each adjacent C in the five membered ring by an aromatic bond, and X2 may be N, wherein X2 is bound to each adjacent C in the five membered ring by an aromatic bond. X1 may be O, wherein X1 is bound to each adjacent C in the five membered ring by an aromatic bond, and X2 may be N, wherein X2 is bound to each adjacent C in the five membered ring by an aromatic bond. X1 may be N, wherein X1 is bound to each adjacent C in the five membered ring by an aromatic bond, and X2 may be S, wherein X2 is bound to each adjacent C in the five membered ring by an aromatic bond. X1 may be N, wherein X1 is bound to each adjacent C in the five membered ring by an aromatic bond and X2 may be O, wherein X2 is bound to each adjacent C in the five membered ring by an aromatic bond. Furthermore, X1 may be NH, wherein X1 is bound to each adjacent C in the five membered ring by an aromatic bond, and X2 may be N, wherein X2 is bound to each adjacent C in the five membered ring by an aromatic bond.

In certain embodiments, Ring A may have the following formula:

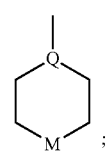

wherein Q may be selected from N and CH. M may be selected from O, S, S(O), S(O2), and/or NRd. Moreover, Rd may be selected from hydrogen, hydroxyl, optionally substituted alkyl, and/or acyl. Ring A may be a 5-6 membered saturated heterocyclic ring or a 5-6 membered partially unsaturated heterocyclic ring, wherein Ring A has one or two heteroatoms independently selected from nitrogen, oxygen, and/or sulfur, and wherein Ring A may be optionally substituted. Ring A may be an unsubstituted morpholinyl. Ring A may be an optionally substituted tetrahydropyranyl.

Ring A may be selected from one of the following:

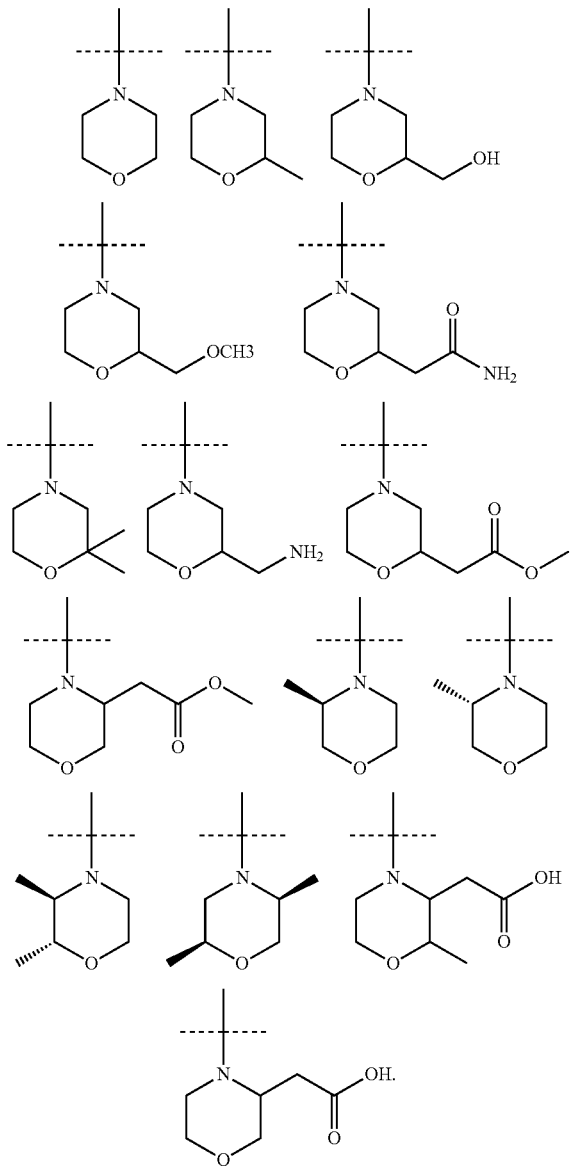

Ring A may be selected from optionally substituted 5-10 membered saturated bridged bicyclic heterocyclic ring and partially unsaturated bridged bicyclic heterocyclic ring having at least one N, at least one O, and optionally 1-2 additional heteroatoms independently selected from N, O, and/or S. Ring A may be a bridged, bicyclic morpholino. Furthermore, Ring A may be selected from:

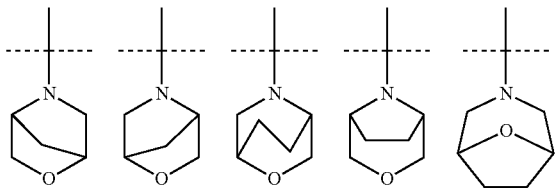

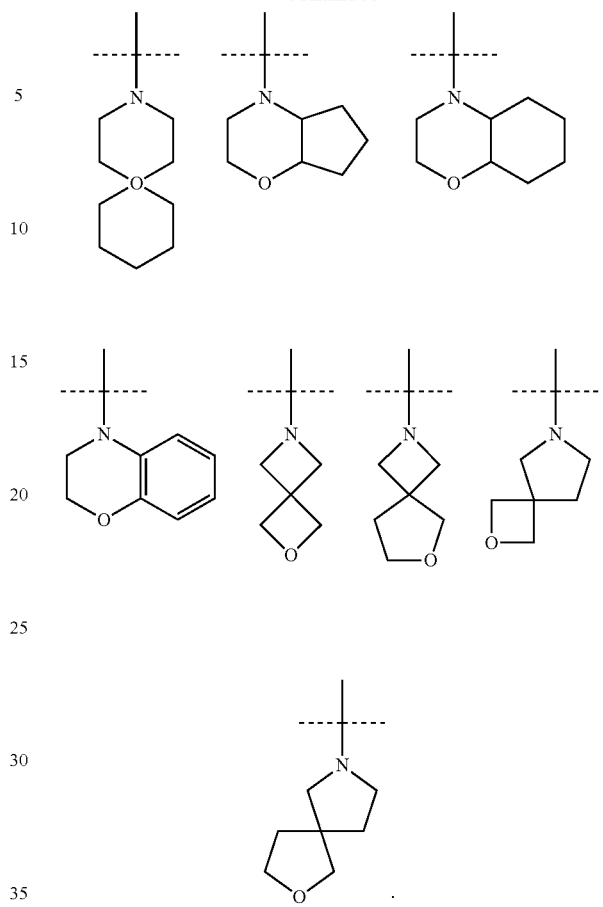

Another aspect of the disclosure is directed to compounds represented by compound represented by Formula II and pharmaceutically acceptable salts or solvates thereof Formula II

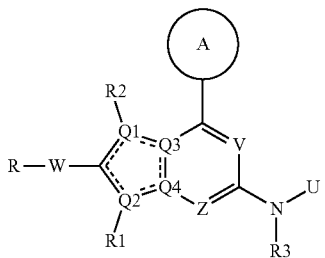

Each of R, R1, R2, R3, U, V, W, Z, and Ring A can be as defined above in reference to Formula I. Each of Q1, Q2, Q3, and Q4 may be independently selected from C and N, such that at least one of Q1, Q2, Q3, and Q4 is N. ⋯⋯ may be selected from a single bond, an aromatic bond, and/or a double bond, such that at least one bond within the five membered ring is a double bond if ⋯⋯ is not an aromatic bond.

Another aspect of the disclosure is directed to compounds represented by compound represented by Formula IIa and pharmaceutically acceptable salts or solvates thereof

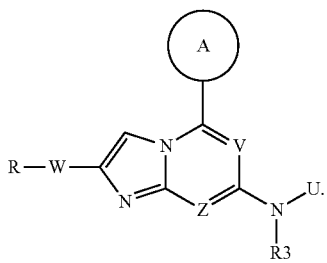

Formula IIa

Each of R, R3, U, V, W, Z, and Ring A may be as defined above in reference to Formula I.

Another aspect of the disclosure is directed to compounds represented by compound represented by Formula IIb and pharmaceutically acceptable salts or solvates thereof

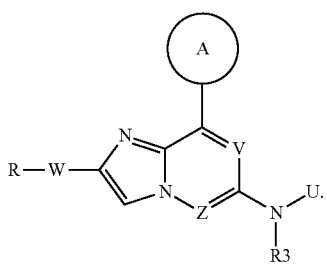

Formula IIb

Each of R, R3, U, V, W, Z, and Ring A may be as defined above in reference to Formula I.

Another aspect of the disclosure is directed to compounds represented by compound represented by Formula IIc and pharmaceutically acceptable salts or solvates thereof

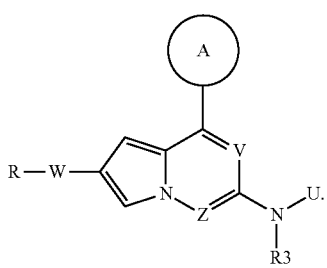

Formula IIc

Each of R, R3, U, V, W, Z, and Ring A may be as defined above in reference to Formula I.

For therapeutic use, salts of the compounds of the present invention are those particular salts wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are within the ambit of the present invention.

The pharmaceutically acceptable addition salts as mentioned herein are meant to comprise the therapeutically active non-toxic acid addition salt forms which the compounds of Formula I and Formula II (including Formulae IIa-c) are able to form. The latter can conveniently be obtained by treating the base form with such appropriate acids as inorganic acids, for example, hydrohalic acids, e.g., hydrochloric, hydrobromic and the like; sulfuric acid; nitric acid; phosphoric acid and the like; or organic acids, for example, acetic, propanoic, hydroxy-acetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of the present invention containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g., the lithium, sodium, potassium, magnesium, calcium salts and the like, salts with organic bases, e.g., primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term "addition salt" also comprises the hydrates and solvent addition forms which the compounds of the present invention are able to form. Examples of such forms are, e.g., hydrates, alcoholates and the like.

The term "quaternary amine" as used hereinbefore defines the quaternary ammonium salts which the compounds of the present invention are able to form by reaction between a basic nitrogen of a compound of the present invention and an appropriate quaternizing agent, such as, for example, an optionally substituted alkylhalide, arylhalide or arylalkylhalide, e.g., methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Pharmaceutically acceptable salts of the compounds of the present invention include all salts that are exemplified by alkaline salts with an inorganic acid and/or a salt with an organic acid that are known in the art. In addition, pharmaceutically acceptable salts include acid salts of inorganic bases, as well as acid salts of organic bases. Their hydrates, solvates, and the like are also encompassed in the present invention. In addition, N-oxide compounds are also encompassed in the present invention.

It will be appreciated that some of the compounds of the present invention and their N-oxides, addition salts, quaternary amines and stereochemically isomeric forms may contain one or more centers of chirality and exist as stereochemically isomeric forms.

The term "stereochemically isomeric forms" as used hereinbefore defines all the possible stereoisomeric forms which the compounds of the present invention, and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of the compounds of the present invention and their N-oxides, salts, solvates or quaternary amines substantially free, i.e., associated with less than 10%, preferably less than 5%, in particular less than 2% and most preferably less than 1% of the other isomers. In particular, stereogenic centers may have the R- or S-configuration; substituents on bivalent cyclic (partially) saturated radicals may have either the cis- or trans-configuration. Compounds encompassing double bonds can have an E- or Z-stereochemistry at said double bond. Stereochemically isomeric forms of the compounds of the present invention are fully intended to be embraced within the scope of this invention.

The N-oxide forms of the present compounds are meant to comprise the compounds of the present invention wherein one or several nitrogen atoms are oxidized to the so-called N-oxide.

Some of the compounds of the present invention may also exist in their tautomeric form. Such forms although not explicitly indicated in the above formula are intended to be included within the scope of the present invention.

Whenever used hereinafter, the term "compounds of the present invention" is meant to also include their N-oxide forms, their salts, their solvates, their clathrates, their hydrates, their polymorphs, their prodrugs, their bioisosteres, their quaternary amines, their stereochemically isomeric forms, and any other of their analogs or derivatives. Further, it should be understood that the methods of the present invention include the use of all such forms, and especially those forms that possesses PIKfyve inhibitory activity, or other advantageous properties. Of special interest are those compounds of the present invention that are stereochemically pure.

In all compounds of the present invention, reference to any bound hydrogen atom can also encompass a deuterium atom bound at the same position. Substitution of hydrogen atoms with deuterium atoms is conventional in the art. See, e.g., U.S. Pat. Nos. 5,149,820 & 7,317,039, which are incorporated by reference herein in their entirety. Such deuteration sometimes results in a compound that is functionally indistinct from its hydrogenated counterpart, but occasionally results in a compound having beneficial changes in the properties relative to the non-deuterated form. For example, in certain instances, replacement of specific bound hydrogen atoms with deuterium atoms dramatically slows the catabolism of the deuterated compound, relative to the non-deuterated compound, such that the deuterated compound exhibits a significantly longer half-life in the bodies of individuals administered such compounds. This is particularly so when the catabolism of the hydrogenated compound is mediated by cytochrome P450 systems. See Kushner et al., *Can. J. Physiol. Pharmacol.* (1999) 77:79-88, which is incorporated by reference herein in its entirety.

3. Pharmaceutical Compositions and Formulations

In another aspect, the present invention further provides a medicament or a pharmaceutical composition having a therapeutically or prophylactically effective amount of a therapeutic compound according to the present invention (i.e., a compound of the present invention) and a pharmaceutically-acceptable excipient.

Typically, therapeutic compounds according to the present invention can be effective at an amount of from about 0.01 µg/kg to about 100 mg/kg per day based on total body weight. The active ingredient may be administered at once, or may be divided into a number of smaller doses to be administered at predetermined intervals of time. The suitable dosage unit for each administration can be, e.g., from about 1 µg to about 2000 mg, preferably from about 5 µg to about 1000 mg. In the case of combination therapy, a therapeutically effective amount of one or more other anti-cancer compounds can be administered in a separate pharmaceutical composition, or alternatively included in the pharmaceutical composition according to the present invention which contains a compound according to the present invention. The pharmacology and toxicology of many of such other anticancer compounds are known in the art. See, e.g., *Physicians Desk Reference*, Medical Economics, Montvale, N.J.; and *The Merck Index*, Merck & Co., Rahway, N.J. The therapeutically effective amounts and suitable unit dosage ranges of such compounds used in the art can be equally applicable in the present invention.

It should be understood that the dosage ranges set forth above are exemplary only and are not intended to limit the scope of this invention. The therapeutically effective amount for each active compound can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can be adjusted as the various factors change over time.

In the pharmaceutical compositions, the active agents (i.e., the compounds of the present invention) can be in any pharmaceutically acceptable salt form, as further described above.

For oral delivery, the active compounds can be incorporated into a formulation that includes pharmaceutically acceptable excipients or carriers such as binders, lubricants, disintegrating agents, and sweetening or flavoring agents, all known in the art. The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of a solution, suspension, syrup, chewing gum, wafer, elixir, and the like. If desired, conventional agents for modifying flavors, tastes, colors, and shapes of the special forms can also be included.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and antioxidants can all be included. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. A special form of topical administration is delivery by a transdermal patch. Methods for preparing transdermal patches are disclosed, e.g., in Brown, et al., *Annual Review of Medicine,* 39:221-229 (1988), which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al., *J. Clin. Psych.* 45:242-247 (1984). Hydrogels can be used as a carrier for the sustained release of the active compounds. Hydrogels are generally known in the art. They are typically made by crosslinking high molecular weight biocompatible polymers into a network, which swells in water to form a gel-like material. Preferably, hydrogels are biodegradable or biosorbable. See, e.g., Phillips et al., *J. Pharmaceut. Sci.,* 73:1718-1720 (1984).

The active compounds can also be conjugated to a water soluble non-immunogenic non-peptidic high molecular weight polymer to form a polymer conjugate. For example, an active compound is covalently linked to polyethylene glycol to form a conjugate. Typically, such a conjugate exhibits improved solubility, stability, and reduced toxicity and immunogenicity. Thus, when administered to a patient, the active compound in the conjugate can have a longer half-life in the body, and exhibit better efficacy. See generally Burnham, *Am. J. Hosp. Pharm.,* 15:210-218 (1994). PEGylated proteins are currently being used in protein replacement therapies and for other therapeutic uses. For example, PEGylated interferon (PEG-INTRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art.

Liposomes can also be used as carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., *Methods in Cell Biology,* Volume XIV, Academic Press, New York, N.Y. (1976).

The active compounds of the present invention can also be administered in combination with another active agent that synergistically treats or prevents the same symptoms or is effective for another disease or symptom in the patient being treated, so long as the other active agent does not interfere with, or adversely affect, the effects of the active compounds of the present invention. Such other active agents include but are not limited to agents for treating cancer, systemic or chronic inflammation, rheumatoid arthritis, diabetes, obesity, T-cell mediated autoimmune disease, ischemia, IL12/IL23 excess production diseases, filoviral, lysosomal disorders, and the like.

4. Therapeutic Methods

The present invention provides therapeutic methods for treating diseases and disorders that will respond to therapy with a PIKfyve inhibitor. Consequently, the present invention provides therapeutic methods for treating cancer, systemic or chronic inflammation, rheumatoid arthritis, diabetes, obesity, T-cell mediated autoimmune disease, ischemia, IL12/IL23 excess production diseases, filoviral, lysosomal disorders and other complications associated with these diseases and disorders. These therapeutic methods involve treating a patient (either a human or another animal) in need of such treatment, with a therapeutically effective amount of a compound of the present invention, or a pharmaceutical composition comprising a therapeutically effective amount of a compound of the present invention.

The present invention also comprises treating isolated cells with a therapeutically effective amount of a compound of the present invention, or a pharmaceutical composition comprising a therapeutically effective amount of a compound of the present invention.

As used herein, the phrase "treating . . . with . . . a compound" means either administering a compound of the present invention, or a pharmaceutical composition comprising a compound of the present invention, directly to isolated cells or to an animal, or administering to cells or an animal another agent to cause the presence or formation of a compound of the present invention inside the cells or the animal. Preferably, the methods of the present invention comprise administering to cells in vitro or to a warm-blooded animal, particularly a mammal, and more particularly a human, a pharmaceutical composition comprising an effective amount of a compound according to the present invention causing the presence or formation of the compound of the present invention inside the cells or the animal.

As would be appreciated by the skilled artisan, a therapeutic compound of the present invention may be administered in one dose at one time, or may be divided into a number of smaller doses to be administered at predetermined intervals of time. The suitable dosage unit for each administration can be determined based on the effective daily amount and the pharmacokinetics of the compounds. In the case of combination therapy, a therapeutically effective amount of one or more other therapeutically effective compounds can be administered in a separate pharmaceutical composition, or alternatively included in the same pharmaceutical composition according to the present invention which contains a compound according to the present invention. The pharmacology and toxicology of many therapeutically effective compounds are known in the art. See, e.g., *Physicians Desk Reference,* Medical Economics, Montvale, N.J.; and *The Merck Index,* Merck & Co., Rahway, N.J. The therapeutically effective amounts and suitable unit dosage ranges of such compounds used in the art can be equally applicable in the present invention.

It should be understood that the dosage range set forth herein is exemplary only and is not intended to limit the scope of this invention. The therapeutically effective amount for each active compound of the invention can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can be adjusted as the various factors change over time.

In one set of aspects, the present invention also provides methods for combination therapy for treating cancer, systemic or chronic inflammation, rheumatoid arthritis, diabetes, obesity, T-cell mediated autoimmune disease, ischemia, diseases associated with over production of IL12/IL23, lysosomal storage disorders, filovirus infections, and other complications associated with these diseases and disorders, by treating a patient in need thereof, with a therapeutically effective amount of a compound of the present invention together with a therapeutically effective amount of one or more other compounds that have been shown to be effective in the treatment of cancer, systemic or chronic inflammation, rheumatoid arthritis, diabetes, obesity, T-cell mediated autoimmune disease, ischemia, and other complications associated with these diseases and disorders.

For the convenience of combination therapy, the compound of the present invention can be administered together in the same formulation with the one or more other compounds that have been shown to be effective in the treatment of cancer, systemic or chronic inflammation, rheumatoid arthritis, diabetes, obesity, T-cell mediated autoimmune disease, diseases associated with over production of IL12/IL23, lysosomal storage disorders, filovirus infections, ischemia, and other complications associated with these diseases and disorders, in the same formulation or dosage form. Thus, the present invention also provides pharmaceutical compositions or medicaments for combination therapy, comprising an effective amount of a compound of the present invention, and an effective amount of at least one other compound that has been shown to be effective in the treatment of cancer, systemic or chronic inflammation, rheumatoid arthritis, diabetes, obesity, T-cell mediated autoimmune disease, diseases associated with over production of IL12/IL23, lysosomal storage disorders, filovirus infections, ischemia, and other complications associated with these diseases and disorders.

The present invention provides methods for the treatment of cancer in a subject in need thereof by administering to the subject a therapeutically effective amount of a composition of the present invention, said composition comprising a compound of the present invention, or a pharmaceutically acceptable salt, solvate, clathrate, hydrate, polymorph, prodrug, analog or derivative thereof. The present invention further provides the use of a composition for the preparation of a medicament useful for the treatment of cancer.

In another aspect, the invention provides a method for treating an individual having an PIKfyve inhibitor-sensitive disease or disorder chosen from inflammatory diseases, viral or bacterial infections, autoimmune disorders, stroke, diseases associated with over production of IL12/IL23, lysosomal storage disorders, filovirus infections, ischemia, cardiac disorders, neurological disorders, proliferative disorders, neoplasms, malignant diseases, and metabolic diseases.

In yet another aspect, the invention provides a method for treating an individual having a PIKfyve inhibitor-sensitive fibrogenetic disorder, such as, for example, scleroderma, polymyositis, systemic lupus, rheumatoid arthritis, liver cirrhosis, keloid formation, interstitial nephritis and pulmonary fibrosis.

As used herein, the term "pharmaceutically acceptable salt," is a salt formed from, for example, an acid and a basic group of a composition of the invention. Illustrative salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, toluenesulfonate, and pamoate.

a. Treating Cancer

It has been observed that loss of PIKfyve activity results in disruption of endosome and lysosome membrane trafficking. It has been observed that PIKfyve inhibition increases the nuclear abundance of TFEB and induces upregulation of numerous lysosome and autophagy-related genes. It has been predicted that increased lysosomal protein expression under conditions where endolysosomal membrane traffic is impaired may stress tumor cells and contribute to their death. See, e.g., Gayle et al., *Blood*, 129(13):1768-78 (2017).

In view of at least the above, it is believed that inhibition of PIKfyve activity would be effective in treating of a wide range of cancers. Consequently, the present invention provides methods of treating a wide range of cancers by administering therapeutically effective amounts of the PIKfyve-inhibiting compounds of the present invention.

As used herein, the term "cancer" has its conventional meaning in the art. Cancer includes any condition of the animal or human body characterized by abnormal cellular proliferation. The cancers to be treated comprise a group of diseases characterized by the uncontrolled growth and spread of abnormal cells. Compounds of the present invention have been shown to be effective in a variety of standard cancer models, and are thus thought to have utility in treating a broad range of cancers. However, preferred methods of the invention involve treating cancers that have been found to respond favorably to treatment with PIKfyve inhibitors. Further, "treating cancer" should be understood as encompassing treating a patient who is at any one of the several stages of cancer, including diagnosed but as yet asymptomatic cancer.

A patient having cancer can be identified by conventional diagnostic techniques known in the art, and the identified patient can be treated with a compound of the present invention, preferably in a pharmaceutical composition having a pharmaceutically acceptable carrier.

The present invention provides therapeutic methods comprising administering to an animal (e.g., a patient, in need of such treatment) a therapeutically effective amount of one or more compounds of Formulae I and II as defined above, and/or a pharmaceutically acceptable salt thereof.

Specific cancers that can be treated by the methods of the invention are those cancers that respond favorably to treatment with a PIKfyve inhibitor. Such diseases include, but are not limited to, brain cancer, glioma, sarcoma, breast cancer, lung cancer, non-small-cell lung cancer, mesothelioma, appendiceal cancer, genitourinary cancers, renal cell carcinoma, prostate cancer, bladder cancer, testicular cancer, penile cancer, cervical cancer, ovarian cancer, von Hippel Lindau disease, head and neck cancer, gastrointestinal cancer, hepatocellular carcinoma, gallbladder cancer, esophageal cancer, gastric cancer, colorectal cancer, pancreatic cancer, neuroendocrine tumor, thyroid tumor, pituitary tumor, adrenal tumor, hematological malignancy, leukemia, Wilms' tumor, choriocarcinoma, mycosis fungoides, acute lymphocytic leukemia, chronic lymphocytic leukemia, multiple myeloma, neuroblastoma, soft-tissue sarcomaacute granulocytic leukemia, hairy cell leukemia, neuroblastoma, rhabdomyosarcoma, Kaposi's sarcoma, genitourinary carcinoma, thyroid carcinoma, malignant hypercalcemia, cervical hyperplasia, renal cell carcinoma, endometrial carcinoma, polycythemia vera, essential thrombocytosis, adrenal cortex carcinoma, and skin cancer.

In one embodiment the cancer is a lymphoma. In one embodiment, the lymphoma is a B-cell lymphoma. In one embodiment, the B-cell lymphoma is selected from the group consisting of a Hodgkin's B-cell lymphoma and a non-Hodgkin's B-cell lymphoma. In one embodiment, the B-cell lymphoma is a non-Hodgkin's B-cell lymphoma selected from the group consisting of DLBCL, follicular lymphoma, marginal zone lymphoma (MZL) or mucosa associated lymphatic tissue lymphoma (MALT), small cell lymphocytic lymphoma (overlaps with chronic lymphocytic leukemia) and mantle cell lymphoma. In one embodiment, the B-cell lymphoma is a non-Hodgkin's B-cell lymphoma selected from the group consisting of Burkitt lymphoma, Primary mediastinal (thymic) large B-cell lymphoma, lymphoplasmacytic lymphoma, which may manifest as Waldenstrom macroglobulinemia, Nodal marginal zone B-cell lymphoma (NMZL), splenic marginal zone lymphoma (SMZL), intravascular large B-cell lymphoma, primary effusion lymphoma, lymphomatoid granulomatosis, T-cell/histiocyte-rich large B-cell lymphoma, primary central nervous system lymphoma, primary cutaneous diffuse large B-cell lymphoma, leg type (primary cutaneous DLBCL, leg type), EBV positive diffuse large B-cell lymphoma of the elderly, diffuse large B-cell lymphoma associated with inflammation, intravascular large B-cell lymphoma, ALK-positive large B-cell lymphoma, and plasmablastic lymphoma.

b. Treating IL12/IL23 Excessive Production

Interleukin (IL)12 and IL23 play important roles in the development of experimental autoimmune disease models and numerous afflictions affecting humans. There is a clear relationship between IL12, IL23 and the generation of pathogenic T helper cells capable of orchestrating tissue inflammation. It has been shown that IL12p40, a common subunit shared by IL12 and IL23, is critical to pathologies associated with psoriasis, inflammatory bowel disease (IBD) and tumor growth. PIKfyve is involved in IL12/23p40 expression.

IL12/IL23 excessive production is involved in various diseases, e.g., multiple sclerosis, systemic sclerosis, sepsis, myasthenia gravis, autoimmune neurological disease, Guillain-Barre syndrome, autoimmune uveitides, autoimmune hemolytic anemia, pernicious anemia, autoimmune thrombocytopenia, temporal arteritis, antiphospholipid syndrome, vasculitis, Wegener's granulomatosis, Behcet's disease, psoriasis, psoriatic arthritis, herpetic dermatitis, pemphigus vulgaris, vitiligo, Crohn's disease, ulcerative colitis, interstitial fibroid lung, myelofibrosis, hepatic fibrosis, myocarditis, autoimmune thyroid disease (Graves' disease, Hashimoto's disease), primary biliary cirrhosis, autoimmune hepatitis, immune-mediated diabetes mellitus, autoimmune oophoritis and orchitis, autoimmune adrenalitis, rheumatoid arthritis, juvenile rheumatoid arthritis, systemic lupus erythematosus, scleroderma, polymyositis, and dermatomyositis.

In view of the above, it is believed that inhibition of PIKfyve activity would be effective in treating diseases associated with over production of IL12/IL23. Consequently, the present invention provides methods of treating systemic or chronic inflammation by administering therapeutically effective amounts of the PIKfyve-inhibiting compounds of the present invention.

c. Lysosomal Storage Disorders

Lysosomes are organelles central to degradation and recycling processes in animal cells. Lysosomal storage disorders (LSDs) are inherited disorders that are thought to be caused by a deficiency of specific enzymes that are normally required for the breakdown of cellular metabolite substrates. If a specific lysosomal enzyme is not present in sufficient quantities, the normal breakdown of the substrate is incomplete or blocked. The cell is then unable to break down the material and it accumulates in the lysosomes of the cell. This accumulation disrupts the cell's normal functioning and gives rise to the clinical manifestations of LSDs.

Lysosomal storage disorders include diseases such as cholesteryl ester storage disease, gangliosidosis, Neimann-Pick disease, and MPS disorders. LSDs tend to be progressive, with the rate of progression, the severity of symptoms, and the organ systems affected varying between disorders and even within each disorder type. LSDs affect different body organs or systems including the skeleton and joints, eyes, heart, lungs, kidneys, skin, and frequently the central nervous system.

In some embodiments, the lysosomal storage disease may be selected from the group consisting of activator deficiency; aspartylglucosaminuria; GM2-gangliosidosis; GM2-gangliosidosis, AB variant; alpha-mannosidosis; beta-mannosidosis; bilateral temporooccipital polymicrogyria (BTOP); lysosomal acid lipase deficiency; lysosomal acid lipase deficiency; cystinosis; Chanarin-Dorfman syndrome; Danon disease; Dent-1; Dent disease 2; Fabry disease; Farber disease; Farber lipogranulomatosis; fucosidosis; galactosialidosis (combined neuraminidase and beta-galactosidase deficiency); Gaucher disease; GM1-gangliosidosis; globoid cell leukodystrophy; infantile free sialic acid storage disease (ISSD); Kanzaki disease; Krabbe disease; metachromatic leukodystrophy; a mucopolysaccharidoses disorder; Morquio syndrome, type A/MPS IVA; Morquio syndrome, type B/MPS IVB; MPS IX hyaluronidase deficiency; MPS VI Maroteaux-Lamy syndrome; MPS VII Sly syndrome; mucolipidosis I, sialidosis; I-cell disease; Leroy disease; mucolipidosis II; pseudo-Hurler polydystrophy/mucolipidosis type III; mucolipidosis IIIC/ML III GAMMA; mucolipidosis type IV; multiple sulfatase deficiency; Niemann-Pick disease; a neuronal ceroid lipofuscinoses, Pompe disease (glycogen storage disease type II), pycnodysostosis, Sandhoff disease/GM2 gangliosidosis; Sanfilippo syndrome Type A/MPS IIIA; Sanfilippo syndrome Type B/MPS IIIB; Sanfilippo syndrome Type C/MPS IIIC; Sanfilippo syndrome Type D/MPS IIID; Schindler disease; Salla disease; spinal muscular atrophy with progressive myoclonic epilepsy (SMAPME); myoclonic epilepsy (SMAPME); Tay-Sachs disease/GM2 gangliosidosis; Christianson syndrome; Lowe oculocerebrorenal syndrome; Charcot-Marie-Tooth type 4J; CMT4J; Yunis-Varon syndrome; and/or X-linked hypercalciuric nephrolithiasis.

The mucopolysaccharidoses disorder may be selected from the group consisting of MPS I, Hurler syndrome; MPS I, Hurler-Scheie syndrome; MPS I, Scheie syndrome; and/or MPS II, Hunter syndrome. The neuronal ceroid lipofuscinosis may be selected from the group consisting of CLN6 disease—Atypical Late Infantile, Late-Onset variant, Early Juvenile, Batten-Spielmeyer-Vogt/Juvenile NCL/CLN3 disease, Finnish Variant Late Infantile CLN5, Jansky-Bielschowsky disease/Late infantile CLN2/TPP1 Disease, Kufs/ Adult-onset NCL/CLN4 disease, Northern Epilepsy/variant late infantile CLN8, and/or Santavuori-Haltia/Infantile CLN1/PPT disease.

In view of the above, it is believed that inhibition of PIKfyve activity would be effective in treating lysosomal storage disorders. Consequently, the present invention provides methods of treating lysosomal storage disorders by administering therapeutically effective amounts of the PIKfyve-inhibiting compounds of the present invention.

d. Treating Filovirus Infections

Cell entry by EBOV is a complex process (Moller-Tank et al., PLoS Pathog. 2015; 11: e100473; White et al., Traffic. John Wiley & Sons A/S; 2016) entailing virus binding to cell surface attachment factors, internalization by macropinocytosis, processing by endosomal proteases, and transport to endolysosomes containing Niemann-Pick C1 (NPC1) (Cote et al. Nature. 2011; 477: 344-348; Carette et al., Nature. 2011; 477: 340-343), the intracellular receptor for EBOV (Miller et al., EMBO J. 2012; 31: 1947-1960). Finally, EBOV fuses with the limiting membrane of NPC1+ endolysosomes (Simmons et al., J Virol. American Society for Microbiology; 2015; 90: 605-610; Spence et al., MBio. American Society for Microbiology; 2016; 7: e01857-15; Mingo et al., J Virol. 2015; 89: 2931-2943) liberating its genome and associated proteins into the cytoplasm to begin replication. The essential role of NPC1 in EBOV entry and infection was powerfully illuminated in a haploid genetic screen (Carette et al., Nature. 2011; 477: 340-343). The same screen revealed other gene products critical for EBOV entry (Chandran et al., Science. 2005; 308: 1643-1645; Schornberg et al., J Virol. 2006; 80: 4174-4178) including many involved in endosome and lysosome biogenesis and maturation. One of the latter proteins was phosphatidylinositol-3-phosphate 5-kinase (PIKfyve) (Carette et al., Nature. 2011; 477: 340-343), a lipid kinase that phosphorylates phosphatidylinositol-3-phosphate (PI3P) to generate phosphatidylinositol-3,5-bisphosphate (PI(3,5)P2). PIKfyve and PI(3,5)P2 are known to be critical for endosome maturation (Elizabeth et al., PLoSNegl Trop Dis 11(4): e0005540).

PIKfyve inhibitor reportedly inhibits infection by both EBOV and MARV, being reported as notably effective in primary human macrophages, which are initial targets of filoviral infection (Dahlmann et al., Journal of Infectious Diseases. 2015; Martinez et al., J Virol. 2013; 87: 3801-3814). Mechanistic studies suggested that PIKfyve inhibitor blocks EBOV entry into the cell cytoplasm by working through PIKfyve and that its effect is to block viral particle trafficking to NPC1+ endolysosomes, the site of EBOV fusion (Simmons et al., J Virol. American Society for Microbiology; 2015; 90: 605-610; Spence et al., MBio. American Society for Microbiology; 2016; 7: e01857-15; Mingo et al., J Virol. 2015; 89: 2931-2943).

In view of the above, it is believed that inhibition of PIKfyve activity would be effective in treating filoviral entry and infection, and other complications associated with this condition. Consequently, the present invention provides methods of treating filoviruses, such as EBOV and MARV, and other complications associated with this condition, by administering therapeutically effective amounts of the PIKfyve-inhibiting compounds of the present invention alone or in a cocktail of small molecules to combat EVD.

5. Methods of Making the Compounds of the Present Invention

Methods of making the compounds of the present invention, and intermediates used in their synthesis, are provided in the General Synthetic Schemes and Specific Syntheses Procedures below.

All reactions were performed in flame-dried or oven-dried glassware under a positive pressure of dry nitrogen or dry argon and were stirred magnetically unless otherwise indicated. All solvents and chemicals were purchased from standard commercial vendors and used as received unless otherwise noted. Any necessary preparations not referenced or described herein were facile and known to one of ordinary skill in the art. Yields are not optimized. The chemical names were generated using the BIOVIA DRAW™ 2017 R2 chemical drawing program, available from MDL INFORMATION SYSTEMS™, a division of SYMYX® TECHNOLOGIES, INC. (Santa Clara, Calif.).

Reactions were monitored by thin layer chromatography (TLC) using 0.25 mm silica gel 60 F254 plates purchased from EMD MILLIPORE™. Purification was performed with TELEDYNE ISCO™ COMBIFLASH® TLC retention factor (Rf). 1H nuclear magnetic resonance spectroscopy (NMR) spectra were recorded on a VARIAN MERCURY™ 400 MHz instrument. Proton chemical shifts are expressed in parts per million (ppm) relative to TMS and calibrated using residual undeuterated solvent as an internal reference. Mass spectra were recorded on AGILENT™ Q-TOF paired with an AGILENT™ 1290 INFINITY high performance liquid chromatography (HPLC) system. Compound purity was determined by an AGILENT™ HP1050 instrument with 4.6 mm×150 mm XTERRA® MS C18 3.5 μm column and UPCHURCH® 5 μm precolumn 24×12 mm. The flow rate was 1.2 mL/minute, and the injection volume was 5 μL. HPLC conditions were as follows: mobile phase A, HPLC grade water (0.1% trifluoroacetic acid (TFA)); mobile phase B, HPLC grade acetonitrile (0.1% TFA); UV detector, 250 nm; 95% A/5% B to 0% A/100% B in 10 minutes, 100% B in 10-11 minutes, 100% B to 95% A/5% B in 11-13 minutes, 95% A/5% B in 13-15 minutes.

Abbreviations and Acronyms

When the following abbreviations are used herein, they have the following meaning:
Ac2O acetic anhydride
anhy Anhydrous
n-BuOH n-butanol
t-BuOH t-butanol
CD3OD methanol-d4
Celite® diatomaceous earth filter agent, ®Celite Corp.
$CH_2Cl_2$ methylene chloride
DCM dichloromethane
CI-MS chemical ionization mass spectroscopy
conc concentrated
dec decomposition
bs broad singlet
br broad
DME dimethoxyethane
DMF N,N-dimethylformamide
DMSO dimethylsulfoxide
DMSO-d6 dimethylsulfoxide-d6
ELSD evaporative light scattering device
EtOAc ethyl acetate
EtOH ethanol (100%)
$Et_2O$ diethyl ether Et₃N triethylamine
HPLC ESI-MS high performance liquid chromatography-electrospray mass spectroscopy
MPLC medium pressure liquid chromatography
NMR nuclear magnetic resonance spectroscopy
TOF-MS time-of-flight-mass spectroscopy
NMM 4-methylmorpholine
Ph₃P triphenylphosphine
Pd(dppf)Cl₂ [1,1'-bis(diphenylphosphino)ferrocene]dichloropalladium(II)
Pd(PPh₃)₄ tetrakis(triphenylphosphine)palladium(0)
Pd(OAc)₂ palladium(II) acetate
P(O)Cl₃ phosphorous oxychloride
Rf TLC retention factor
Rt retention time (HPLC)
rt room temperature
THF tetrahydrofuran
TFA trifluoroacetic acid
TLC thin layer chromatography
LC-MS (ESI) liquid chromatography-mass spectroscopy (electrospray ionization)
DIEA diisopropylethylamine
MSCl methanesulfonylchloride
AcOH acetic acid
HCl hydrochloric acid
H₂SO₄ sulfuric acid
HNO₃ nitric acid
HBr hydrobromic acid
CDCl₃ chloroform-d3
CHCl₃ chloroform
H₂O water
NaOAc sodium acetate
KOH potassium hydroxide
NaOH sodium hydroxide
NaCl sodium chloride
NaHCO₃ sodium bicarbonate
Na₂CO₃ sodium carbonate
K₂CO₃ potassium carbonate
Na₂SO₄ sodium sulfate
MgSO₄ magnesium sulfate
MeOH methanol
SiO₂ silica gel
K₃PO₄ potassium phosphate
NH₄Cl ammonium chloride
AIBN 2,2'-axo bisisobutyronitrile
DMAP N,N-Dimethyl aminopyridine
LG leaving group
TsCl p-toluenesulfonyl chloride
PG protecting group Synthetic Schemes

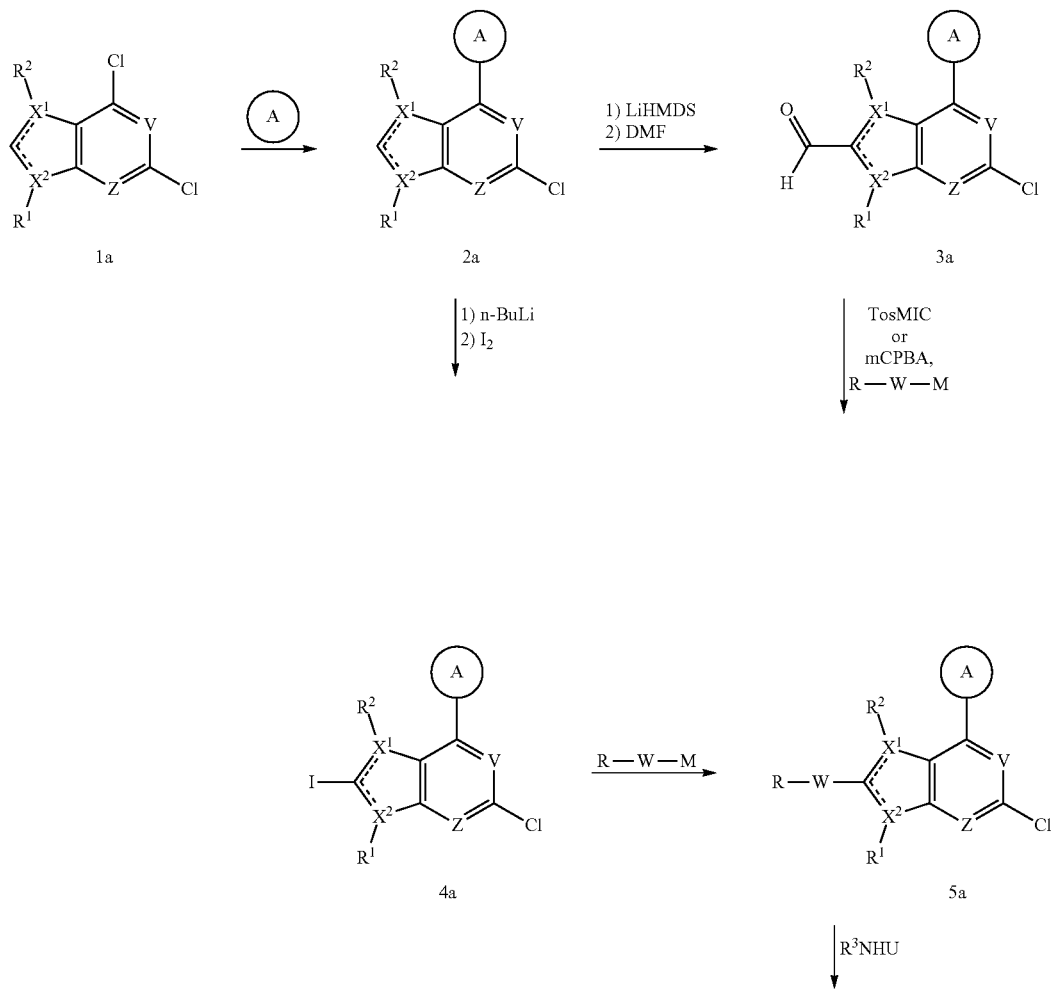

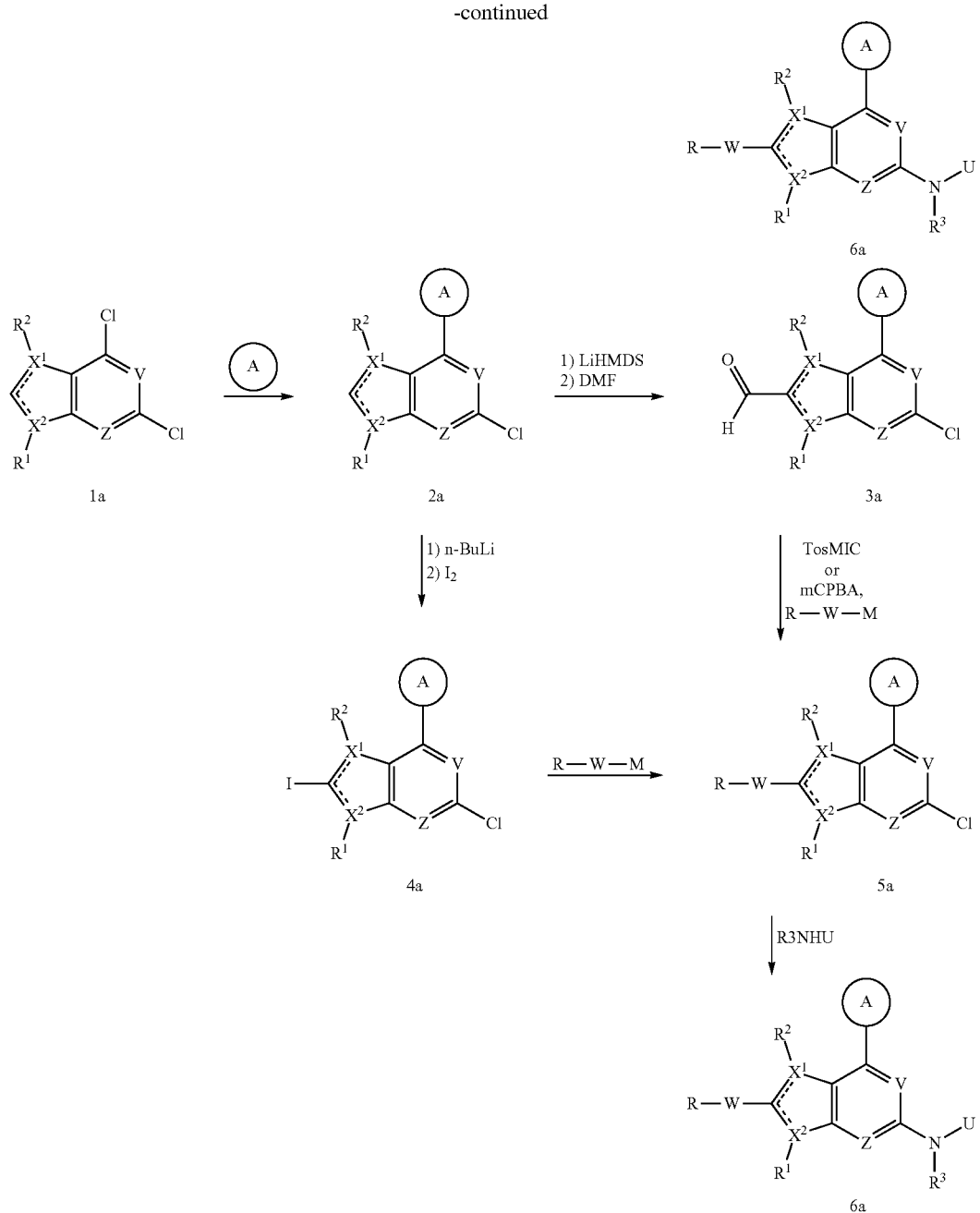

4-Chloro from compounds 1a can be replaced by a cyclic amine in organic solvent to provide 2a. Formyl group can be introduced by lithiating 1a followed by quenching with DMF at low temperature. The formyl group is oxidized to corresponding acids by treating 3a with mCPBA in organic solvent, followed by coupling with various amines using standard coupling chemistry to provide corresponding amides 5a. Various five membered heterocyclic compounds can be synthesized using aldehydes 3a and TosMIC reagent in organic solvent to provide compounds of formula 5a. The compounds of formula 4a can be synthesized by lithiating 3a followed by quenching with iodine in organic solvents at low temperature. Using standard coupling chemistry various groups can be introduced using 4a to provide 5a. The compounds 5a can be further derivitized to 6a using $R^3NHU$ in organic solvents.

Scheme B

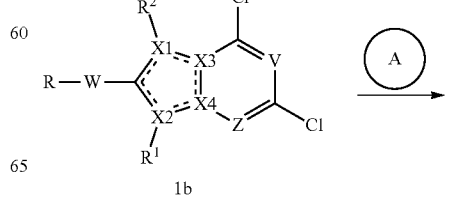

31
-continued
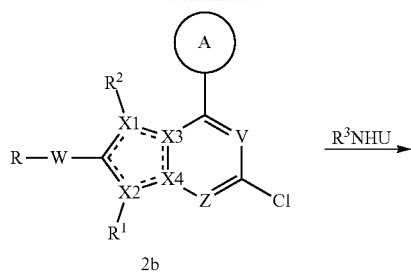
2b
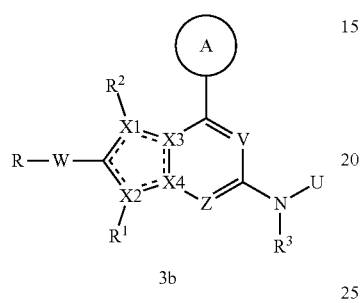
3b
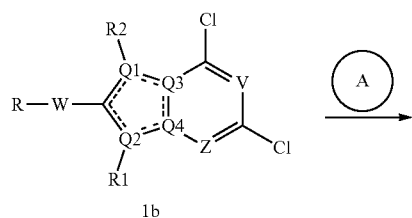
1b
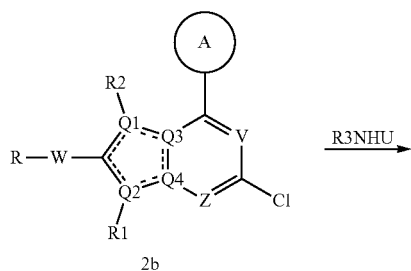
2b
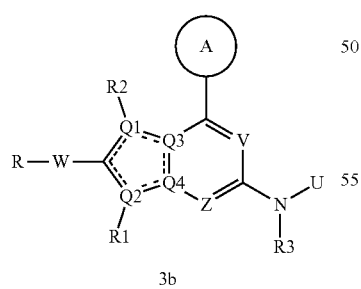
3b
The compounds of the general formula 1b can be synthesized by known methods. The compounds of general formula 2b can be synthesized by selectively replacing 4-chloro from compounds 1b with cyclic amines in organic solvent. The compounds 3b can be synthesized using 2b and R³NHU in organic solvent.
32
General Synthetic Scheme 1
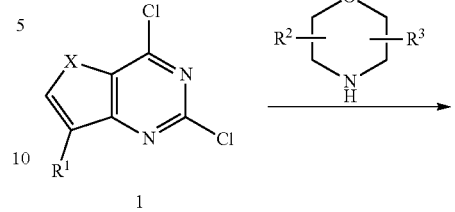
1
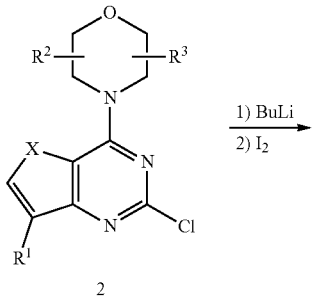
2
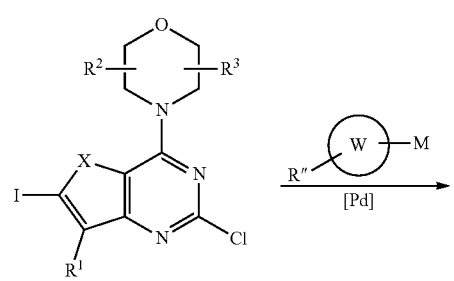
3
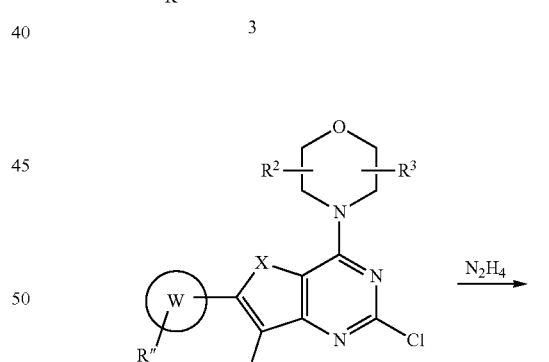
4
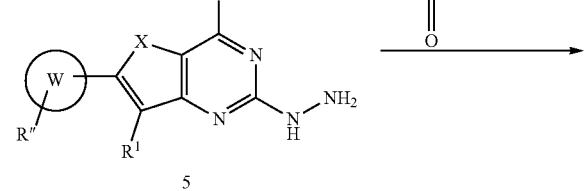
5

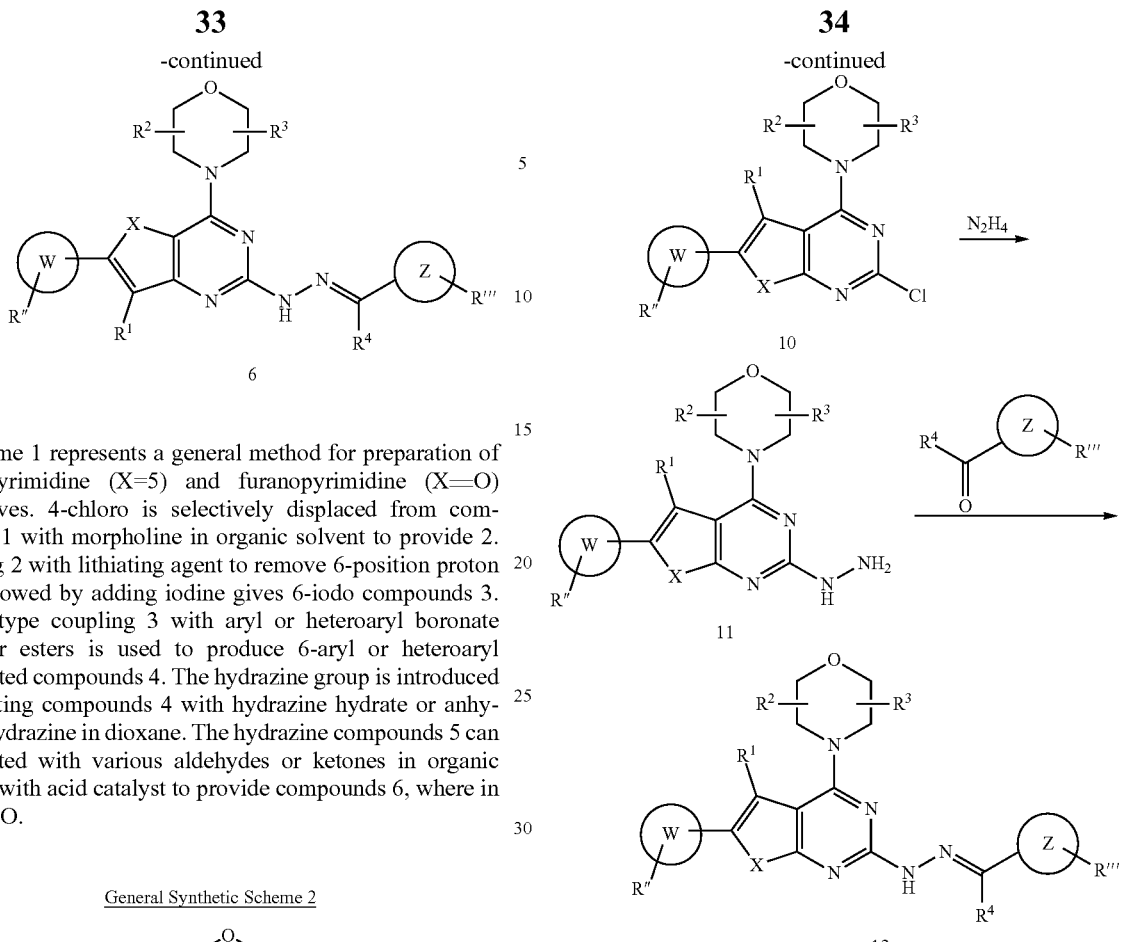

Scheme 1 represents a general method for preparation of thionopyrimidine (X=S) and furanopyrimidine (X=O) derivatives. 4-chloro is selectively displaced from compounds 1 with morpholine in organic solvent to provide 2. Treating 2 with lithiating agent to remove 6-position proton and followed by adding iodine gives 6-iodo compounds 3. Suzuki-type coupling 3 with aryl or heteroaryl boronate acids or esters is used to produce 6-aryl or heteroaryl substituted compounds 4. The hydrazine group is introduced by reacting compounds 4 with hydrazine hydrate or anhydrous hydrazine in dioxane. The hydrazine compounds 5 can be reacted with various aldehydes or ketones in organic solvent with acid catalyst to provide compounds 6, where in X is S, O.

Scheme 2 represents a general method for preparation of thionopyrimidine (X=S) and furanopyrimidine (X=O) derivatives. 4-chloro is selectively displaced from compound 7 with morpholine in organic solvent to provide 8. Treating 8 with an lithiating agent to remove the 6-position proton and followed by adding iodine gives 6-iodo compounds 9. Suzuki-type coupling 9 with aryl or hetoaryl boronate acids or esters is used to produce 6-aryl or heteroaryl substituted compounds 10. The hydrazine group is introduced by reacting compounds 10 with hydrazine hydrate or anhydrous hydrazine in dioxane. The hydrazine compounds 11 can be reacted with various aldehydes or ketones in organic solvent with acid catalyst to provide compounds 12, where in X is S, O.

General Synthetic Scheme 3

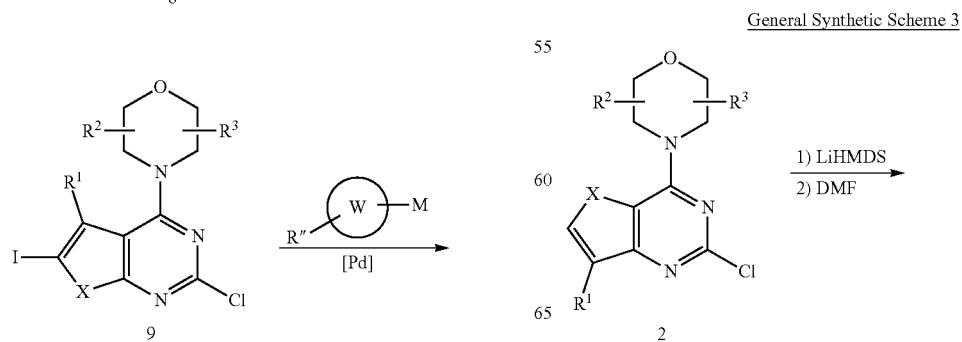

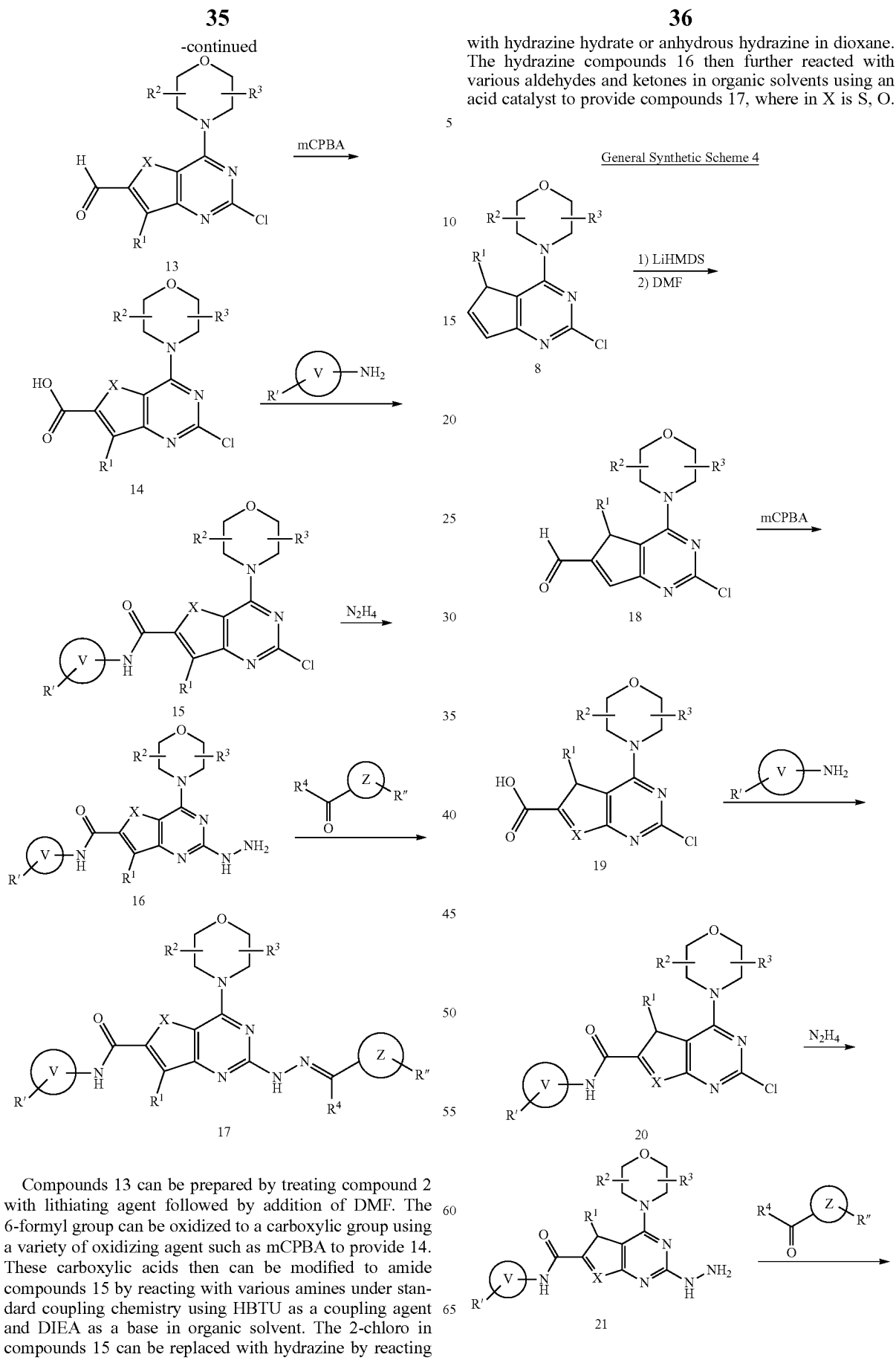

with hydrazine hydrate or anhydrous hydrazine in dioxane. The hydrazine compounds 16 then further reacted with various aldehydes and ketones in organic solvents using an acid catalyst to provide compounds 17, where in X is S, O.

General Synthetic Scheme 4

Compounds 13 can be prepared by treating compound 2 with lithiating agent followed by addition of DMF. The 6-formyl group can be oxidized to a carboxylic group using a variety of oxidizing agent such as mCPBA to provide 14. These carboxylic acids then can be modified to amide compounds 15 by reacting with various amines under standard coupling chemistry using HBTU as a coupling agent and DIEA as a base in organic solvent. The 2-chloro in compounds 15 can be replaced with hydrazine by reacting

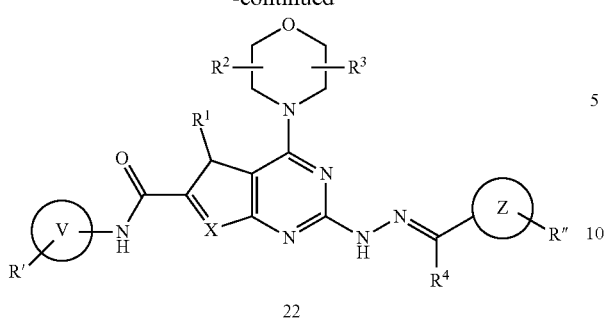

Compounds 18 can be prepared by treating compounds 8 with lithiating agent followed by addition of DMF. The 6-formyl group can be oxidized to a carboxylic group using a variety of oxidizing agents such as mCPBA to provide 18. These carboxylic acids then can be modified to amide compounds 20 by reacting with various amines under standard coupling chemistry using HBTU as a coupling agent and DIEA as a base in organic solvent. The 2-chloro in compounds 20 can be replaced with hydrazine by reacting with hydrazine hydrate or anhydrous hydrazine in dioxane. The hydrazine compounds 21 then further reacted with various aldehydes and ketones in organic solvents using acid catalyst to provide compounds 22.

General Synthetic Scheme 5

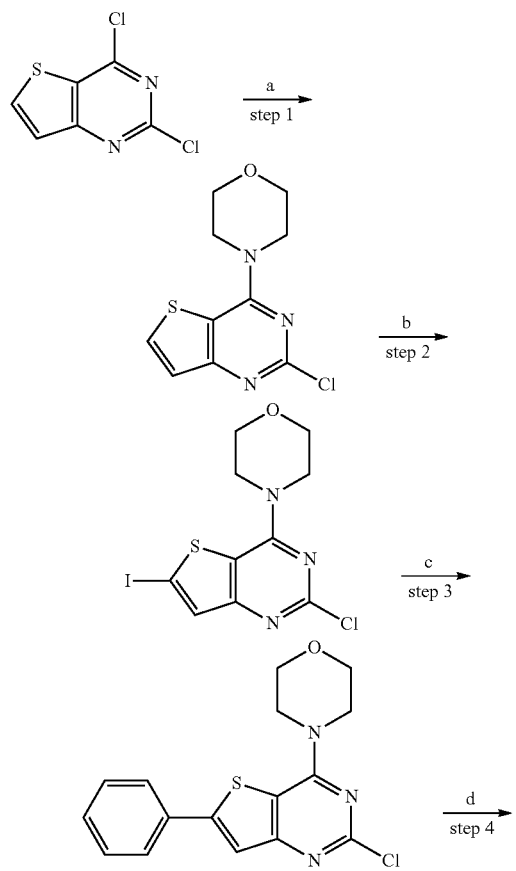

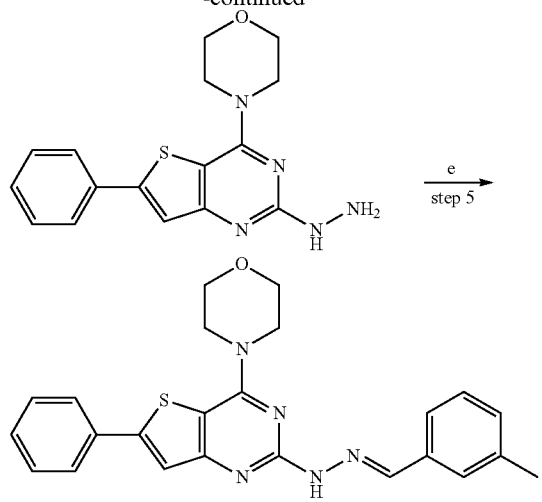

Reagents and conditions: a) MeOH, morpholine, rt 3 h; b) n-BuLi, THF, -78° C., I$_2$, 4 h; c) phenyl boronic acid, Pd(PPh$_3$)$_2$Cl$_2$, 1N Na$_2$CO$_3$, CH$_3$CN, 90° C., 4 h; d) dioxane, anhydrous N$_2$H$_4$, 110° C., 16 h; e) MeOH, m-tolualdehyde, AcOH, 70° C., 6 h.

Specific Syntheses

Example 1

Synthesis of substituted 4-morpholino-N-[(E)-m-tolylmethyleneamino]-6-phenyl-thieno[3,2-d]pyrimidin-2-amine Step 1—synthesis of 4-(2-chlorothieno[3,2-d]pyrimidin-4-yl)morpholine: To a suspension of 2,4-dichlorothieno[3,2-d]pyrimidine (2.0 g, 9.75 mmol) in methanol (25 mL) was added morpholine (1.87 ml, 21.45 mmol) drop wise and stirring continued for 2 h at rt. Then the solid separated was filtered and washed with water followed by methanol (15 mL) and dried to afford title product in quantitative yield. $^1$HNMR (CDCl$_3$): δ 3.84 (t, J=5.0, 4H), 4.01 (t, J=5.0 Hz, 4H), 7.36 (d, J=5.47, 1H), 7.76 (d, J=4.56 Hz, 1H).

Step 2—synthesis of 4-(2-chloro-6-iodo-thieno[3,2-d]pyrimidin-4-yl)morpholine: A suspension of 4-(2-chlorothieno[3,2-d]pyrimidin-4-yl)morpholine (1.50 g, 5.87 mmol) in THF (30 mL) was cooled to −78° C. To the above mixture n-BuLi (2.5 M in THF/Hexane) (4.70 mL, 11.24 mmol) was added dropwise and stirring continued for 1 h. To the reaction mixture 12 (3.00 g, 11.74 mmol) in THF (10 mL) was added drop wise at −78° C., after complete addition the reaction mixture was warmed to rt and stirring continued further for 16 h. At the end of this period reaction mixture was quenched with saturated NH$_4$Cl solution and extracted with EtOAc (2×50 mL). The combined EtOAc layer was washed with water (30 mL) followed by brine (30 mL), dried (Na$_2$SO$_4$), filtered and the solvent evaporated to dryness. The crude was chromatographed over SiO$_2$ using 0-50% gradient of EtOAc in DCM to afford title compound (1.42 g, 64%). $^1$H NMR (CDCl$_3$): δ 3.82 (t, J=5.0 Hz, 4H), 3.93 (t, J=5.1 Hz, 4H), 7.55 (s, 1H). Step 3—synthesis of 4-(2-chloro-6-phenyl-thieno[3,2-d]pyrimidin-4-yl)morpholine: To a mixture of 4-(2-chloro-6-iodothieno[3,2-d]pyrimidin-4-yl)morpholine (0.300 g, 0.786 mmol) and phenylboronic acid (0.105 g, 0.864 mmol) in CH$_3$CN (2.36 mL) and 1N Na$_2$CO$_3$ (2.36 mL) was added Pd(PPh$_3$)$_2$Cl$_2$ (0.055 g, 0.0986 mmol). The mixture was degassed and heated at 90° C. in sealed tube for 2 h. At the end of this period reaction mixture was cooled to rt and the solvent was evaporated to dryness and the crude was chromatographed over SiO$_2$ using gradient of EtOAc in hexanes to afford title product (0.180 g, 69%). $^1$HNMR (CDCl$_3$): δ 3.86 (t, J=5.69 Hz, 4H), 4.02 (t, J=5.1 Hz, 4H), 7.43-7.48 (m, 3H), 7.52 (s, 1H), 7.68-7.71 (m, 2H).

Step 4—synthesis of (4-morpholino-6-phenyl-thieno[3,2-d]pyrimidin-2-yl)hydrazine: To a suspension of 4-(2-chloro-6-phenyl-thieno[3,2-d]pyrimidin-4-yl)morpholine (0.180 g, 0.54 mmol) in dioxane (10 mL) was added anhydrous hydrazine (1 mL) at rt and the mixture was refluxed for 16 h. The it was cooled to rt and solvent and excess hydrazine was evaporated, the residue was co-evaporated with toluene (2×10 mL) to afford title compound in quantitative yield. Product was used for the next step without further characterization.

Step 5—synthesis of 4-morpholino-N-[(E)-m-tolylmethyleneamino]-6-phenyl-thieno[3,2-d]pyrimidin-2-amine: To suspension of (4-morpholino-6-phenyl-thieno[3,2-d]pyrimidin-2-yl)hydrazine (0.170 g, 0.52 mmol) was added 3-methylbenzaldehyde (0.075 g, 0.62 mmol) and AcOH (3 drops). The reaction mixture was refluxed for 6 h and cooled to rt. The solid separated was filtered and the solid cake was washed with cold methanol (3 mL) and dried under vacuum at 60° C. to afford title product (0.07 g, 32%). $^1$H NMR (DMSO-d$_6$): δ 2.33 (s, 3H), 3.76 (t, J=4.79 Hz, 4H), 3.90 (t, J=4.79 Hz, 4H), 7.13 (d, J=8.33 Hz, 1H), 7.28 (t, J=7.62 Hz, 1H), 7.44-7.50 (m, 5H), 7.70 (s, 1H), 7.83 (d, J=7.13 Hz, 2H), 8.05 (s, 1H), 10.76 (s, 1H). LC-MS: m/z 430 [M+H]$^+$ Example 2

Synthesis of 4-morpholino-N-[(E)-m-tolylmethyleneamino]-6-(4-pyridyl)thieno[3,2-d]pyrimidin-2-amine

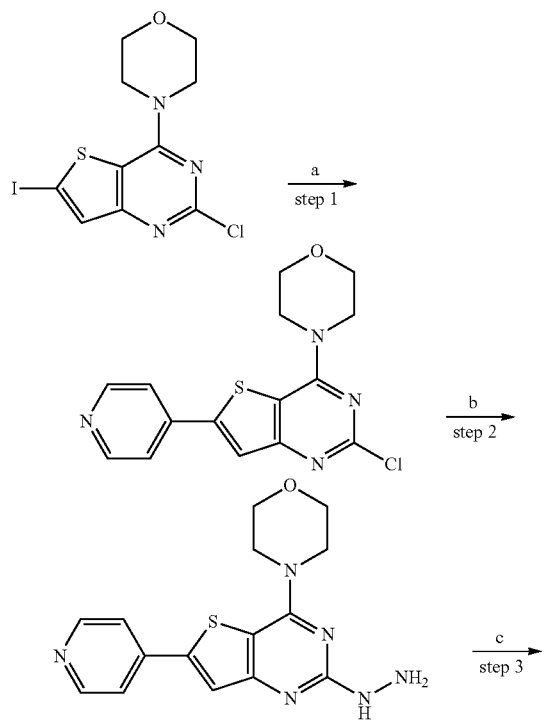

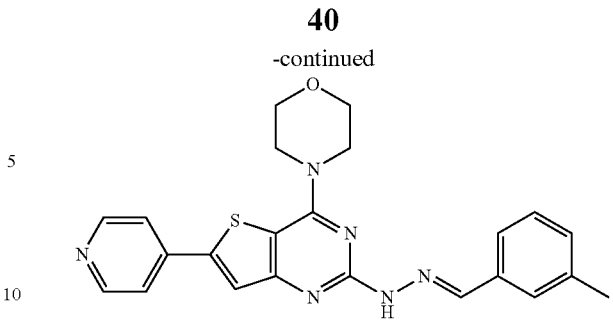

Reagents and conditions: a) 4-pyridyl boronic acid or substituted boronate ester, Pd(PPh$_3$)$_2$Cl$_2$, 1N Na$_2$CO$_3$, CH$_3$CN, 90° C., 4 h; b) dioxane, N$_2$H$_4$ (98%), 110° C., 16 h; c) MeOH, m-tolualdehyde, AcOH, 70° C., 6 h.

Step 1—synthesis of 4-[2-chloro-6-(4-pyridyl)thieno[3,2-d]pyrimidin-4-yl]morpholine: Title compound (0.230 g, 44%) was prepared by a similar procedure described for step 3 of example 1 using 4-(2-chloro-6-iodothieno[3,2-d]pyrimidin-4-yl)morpholine (0.600 g, 1.57 mmol), 4-pyridylboronic acid (0.212 g, 1.72 mmol) and Pd(PPh$_3$)$_2$Cl$_2$ (0.110 g, 0.157 mmol). NMR (DMSO-d$_6$): δ 3.76 3.76 (t, J=4.59, 4H), 3.92 (t, J=4.78 Hz, 4H), 7.83 (d, J=6.15 Hz, 2H), 8.12 (s, 1H), 8.69 (d, J=5.86, 2H).

Step 2—synthesis of [4-morpholino-6-(4-pyridyl)thieno[3,2-d]pyrimidin-2-yl]hydrazine: Title compound (0.170 g, 75%) was prepared by a similar procedure described for step 4 of example 1 using 4-[2-chloro-6-(4-pyridyl)thieno[3,2-d]pyrimidin-4-yl]morpholine (0.230 g, 0.69 mmol) and anhydrous hydrazine (1.0 mL). The solvent and excess hydrazine was evaporated and the residue was co-evaporated with toluene. The crude product was triturated with MeOH. $^1$H NMR (DMSO-d6): δ 3.72 (t, J=4.39 Hz, 4H), 3.84 (t, J=4.40 Hz, 4H), 4.08 (bs, 2H), 7.63 (s, 1H), 7.70 7.78 (m, 2H), 7.85 (s, 1H), 8.63-8.65 (m, 2H).

Step 3—synthesis of 4-morpholino-N-[(E)-m-tolylmethyleneamino]-6-(4-pyridyl)thieno[3,2-d]pyrimidin-2-amine: Title product (0.129 g, 66%) was prepared by a similar procedure described for step 5 of example 1. $^1$H NMR (DMSO-d$_6$): δ 2.33 (s, 3H), 3.76 (bs, 4H), 3.92 (bs, 4H), 7.14 (d, J=7.42, 1H), 7.28 (t, J=7.81, 1H), 7.42-7.46 (m, 2H), 7.80 (d, J=6.25 Hz, 2H), 7.99 (s, 1H), 8.05 (s, 1H), 8.66 (d, J=5.85 Hz, 2H), 10.83 (s, 1H), 11.96 (bs, 1H).

Example 3

Synthesis of 4-morpholino-N-[(E)-m-tolylmethyleneamino]thieno[3,2-d]pyrimidin-2-amine

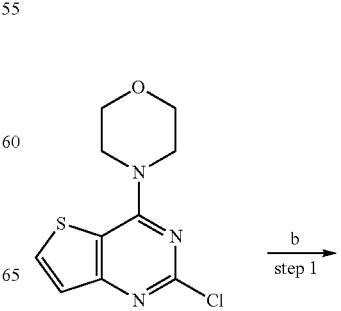

-continued

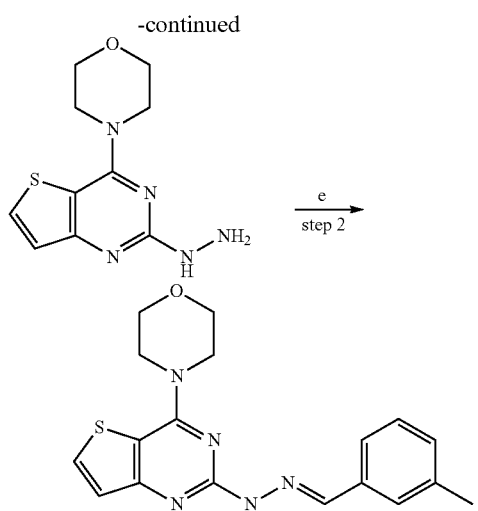

Reagents and conditions: a) dioxane, N₂H₄, 80-90° C., 16 h; b) MeOH, m-tolualdehyde, AcOH, 70° C., 6 h.

Step 1—synthesis of (4-morpholinothieno[3,2-d]pyrimidin-2-yl)hydrazine: The title product (0.124 g, 52%) was prepared by similar procedure described for step 4 example 1. This product was used for the next step without further purifications.

Step 2—synthesis of 4-morpholino-N-[(E)-m-tolylmethyleneamino]thieno[3,2-d]pyrimidin-2-amine: The title product (0.08 g, 78%) prepared by similar procedure described for step 5 of example 1, using (4-morpholinothieno[3,2-d]pyrimidin-2-yl)hydrazine (0.100 g, 0.207 mmol), m-tolualdehyde (0.053 g, 0.248 mmol) and AcOH in MeOH. $^1$H NMR (DMSO-$d_6$): δ 2.32 (s, 3H), 3.74 (t, J=4.2 Hz, 4H), 3.88 (t, J=4.8 Hz, 4H), 7.12 (d, 1H), 7.23-7.29 (m, 2H), 7.421-7.44 (m, 2H), 8.03 (s, 1H), 8.05 (d, J=5.4 Hz, 1H), 10.73 (s, 1H). LC-MS: m/z 354.6[M+H]$^+$

Example 4

Synthesis of 4-morpholino-2-[(2E)-2-(m-tolylmethylene)hydrazino]-N-(3-pyridyl)thieno[3,2-d]pyrimidine-6-carboxamide

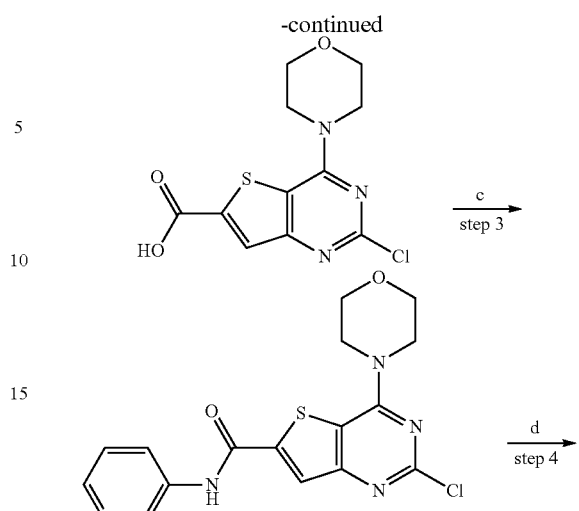

Reagents and conditions: a) LiHDMS, THF, DMF, -78° C.-rt, 14 h; b) mCPBA, DCM, 45° C., 24 h; c) 3-aminopyridine, HBTU, DIEA, DCM, 2 h, rt; d) dioxane, N₂H₄, 80-90° C., 16 h; e) MeOH, m-tolualdehyde, AcOH, 70° C., 8 h.

Step 1—synthesis of 2-chloro-4-morpholino-thieno[3,2-d]pyrimidine-6-carbaldehyde: The title compound was prepared by a known method (US 2011/0230476) using 4-(2-chlorothieno[3,2-d]pyrimidin-4-yl)morpholine. $^1$H NMR (CDCl₃): δ 3.85 (t, J=5.05 Hz, 4H), 4.05 (t, J=5.0 Hz, 4H), 7.96 (s, 1H), 10.16 (s, 1H).

Step 2—synthesis of 2-chloro-4-morpholino-thieno[3,2-d]pyrimidine-6-carboxylic acid: The title compound was prepared by adaption of known method (U.S. Pat. No. 9,725,461).

Step 3: synthesis of 2-chloro-4-morpholino-N-(3-pyridyl)thieno[3,2-d]pyrimidine-6-carboxamide. To a suspension of 2-chloro-4-morpholino-thieno[3,2-d]pyrimidine-6-carboxylic acid (0.200 g, 0.66 mmol), 3-aminopyridine (0.07 g, 0.734 mmol), in DCM (20 mL) was added HBTU (0.321 g, 1.00 mmol) followed by DIEA (0.460 mL, 2.66 mmol) at rt. The mixture was stirred further for 2 h at rt. At the end of this period reaction mixture was diluted with DCM (50 mL) and washed with water (2×20 mL) and dried (Na₂SO₄), filtered and the solvent evaporated to dryness. The crude was triturated with methanol and filtered to provide title product (0.160 g, 64%). $^1$HNMR (DMSO-$d_6$): δ 3.76 (t, J=4.50 Hz, 4H), 3.93 (t, J=4.8 Hz, 4H), 7.41-7.45 (m, 1H), 8.14 (d, J=7.8 Hz, 1H), 8.25 (s, 1H), 8.35 (d, J=3.6 Hz, 1H), 8.96 (s, 1H), 10.87 (s, 1H).

Step 4—synthesis of 2-hydrazino-4-morpholino-N-(3-pyridyl)thieno[3,2-d]pyrimidine-6-carboxamide. To a suspension of 2-chloro-4-morpholino-N-(3-pyridyl)thieno[3,2-d]pyrimidine-6-carboxamide (0.150 g, 0.400 mmol) in dioxane (10 mL) was added anhydrous $N_2H_4$ (98%) at rt and the reaction mixture was refluxed for 16 h. At the end of this period solvent was evaporated to dryness. The crude was triturated with MeOH and the solid was filtered and washed with cold methanol and dried to provide title product (0.090 g, 61%). $^1$H NMR (DMSO-$d_6$): δ 3.71-3.85 (m, 8H), 4.1 (bs, 1H), 4.58 (bs, 1H), 7.33-7.43 (m, 1H), 8.04 (s, 1H), 8.14 (d, 9.0 Hz, 1H), 8.33 (d, J=3.41 Hz, 1H), 8.89 (d, J=2.25 Hz, 1H), 10.10 (bs, 1H), 10.68 (bs, 1H).

Step 5—synthesis of 4-morpholino-2-[(2E)-2-(m-tolylmethylene)hydrazino]-N-(3-pyridyl)thieno[3,2-d]pyrimidine-6-carboxamide. To suspension of 2-hydrazino-4-morpholino-N-(3-pyridyl)thieno[3,2-d]pyrimidine-6-carboxamide (0.090 g, 0.24 mmol) in MeOH was added m-tolualdehyde (0.035 g, 0.290 mmol) and 3 drops of AcOH at rt. The reaction mixture was refluxed for 8 h, at the end of this period mixture was cooled to rt, solvent evaporated and the crude was chromatographed over SiO$_2$ using 0-50% gradient of MeOH in DCM to provide title product (0.042 g, 37%). $^1$H NMR (DMSO-$d_6$): δ 2.33 (s, 3H), 3.77 (bs, 4H), 3.39 (bs, 4H), 7.14 (d, J=7.7 Hz, 1H), 7.27 (t, J=7.5 Hz, 1H), 7.41-7.46 (m, 3H), 8.06 (s, 1H), 8.16 (bs, 2H), 8.34 (d, J=3.8 Hz, 1H), 8.91 (s, 1H), 10.769 s, 1H), 10.88 (s, 1H).

Example 5

4-morpholino-2-[(2E)-2-(m-tolylmethylene)hydrazino]-N-(4-pyridyl)thieno[3,2-d]pyrimidine-6-carboxamide

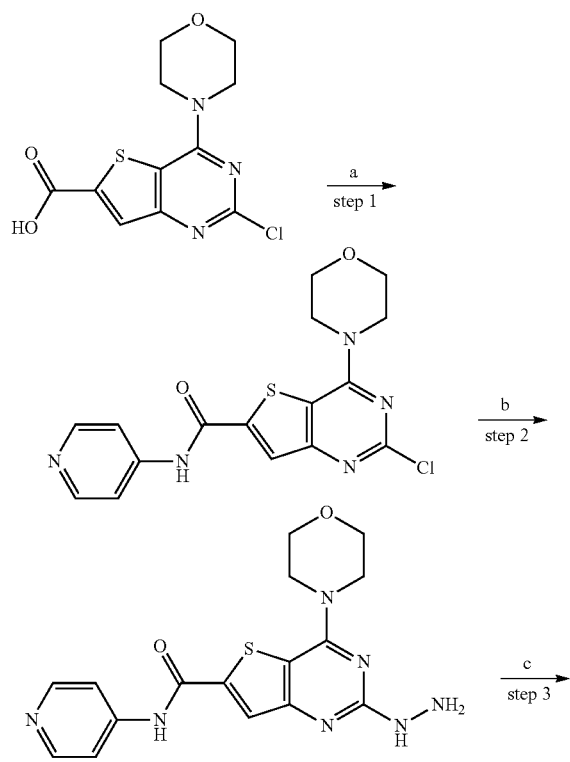

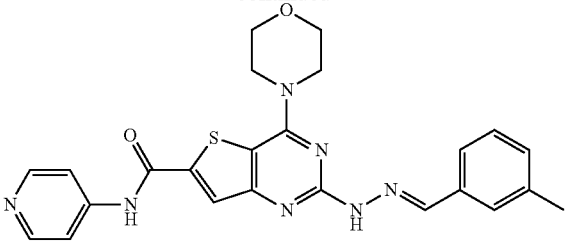

Reagents and Condtions: a) 4-aminopyridine hydrochloride, HBTU, DIEA, DCM, 2 h, rt; b) dioxane, N$_2$H$_4$, 80-90° C., 16 h; c) MeOH, m-tolualdehyde, AcOH, 70° C., 8 h.

Step 1—synthesis of 2-chloro-4-morpholino-N-(4-pyridyl)thieno[3,2-d]pyrimidine-6-carboxamide: To a suspension of 2-chloro-4-morpholino-thieno[3,2-d]pyrimidine-6-carboxylic acid (0.150 g, 0.500 mmol), 4-aminopyridine hydrochloride (0.027 g, 0.550 mmol), in DCM (20 mL) was added HBTU (0.241 g, 0.750 mmol) followed by DIEA (0.35 mL, 2.00 mmol) at rt. The mixture was stirred further for 2 h at rt. At the end of this period reaction mixture was diluted with DCM (50 mL) and washed with water (2×20 mL) and dried (Na$_2$SO$_4$), filtered and the solvent evaporated to dryness. The crude was triturated with methanol and filtered to provide title product (0.160 g, 85%). $^1$H NMR (DMSO-$d_6$): δ 3.76 (t, 5.18 Hz, 4H), 3.93 (t, J=5.0 Hz, 4H), 7.74 (d, J=4.78 Hz, 2H), 8.28 (s, 1H), 8.51 (d, J=4.78 Hz, 2H), 10.94 (s, 1H).

Step 2—synthesis of 2-hydrazino-4-morpholino-N-(4-pyridyl)thieno[3,2-d]pyrimidine-6-carboxamide. To a suspension of 2-chloro-4-morpholino-N-(4-pyridyl)thieno[3,2-d]pyrimidine-6-carboxamide (0.160 g, 0.425 mmol) in dioxane (10 mL) was added N$_2$H$_4$ (98%) (0.200 mL, 6.37 mmol) at rt and the reaction mixture was refluxed for 16 h. At the end of this period solvent was evaporated to dryness. The crude was triturated with MeOH and the solid was filtered and washed with cold methanol and dried to provide title product (0.140 g, 87%). %). $^1$H NMR (DMSO-$d_6$): δ 3.34 (bs, 3H), 3.37 (t, J=5.1 Hz, 4H), 3.74-3.87 (m, 4H), 7.78 (d, J=4.2 Hz, 2H), 8.20 (s, 1H), 8.48 (d, J=4.7 Hz, 2H), 10.95 (bs, 1H).

Step 3—4-morpholino-2-[(2E)-2-(m-tolylmethylene)hydrazino]-N-(4-pyridyl)thieno[3,2-d]pyrimidine-6-carboxamide: To suspension of 2-hydrazino-4-morpholino-N-(4-pyridyl)thieno[3,2-d]pyrimidine-6-carboxamide (0.07 g, 0.188 mmol) in MeOH (4 mL) was added m-tolualdehyde (0.033 mL), 0.276) and AcOH (3 drops) at rt. The reaction mixture was refluxed for 8 h, at the end of this period mixture was cooled to rt, solvent evaporated and the crude was chromatographed over SiO$_2$ using 0-50 gradient of MeOH in DCM to provide title product (0.036 g, 40%). $^1$H NMR (DMSO-$d_6$): δ 2.35 9 s, 3H), 3.90 (t, J=4.7 Hz, 4H), 4.01 (t, J=4.7 Hz, 4H), 7.22 (d, J=7.3 Hz, 1H), 7.34 (t, J=7.7 Hz, 1H), 7.58 (d, J=7.5 Hz, 1H), 7.64 (s, 1H), 8.07 (d, J=6.5 Hz, 2H), 8.17 (s, 1H), 8.49 (s, 1H), 8.63 (d, J=6.7 Hz, 2H), 11.71 (bs, 1H).

Example 6

2-[(2E)-2-[(3,5-dimethylphenyl)methylene]hydrazino]-4-morpholino-N-(4-pyridyl)thieno[3,2-d]pyrimidine-6-carboxamide

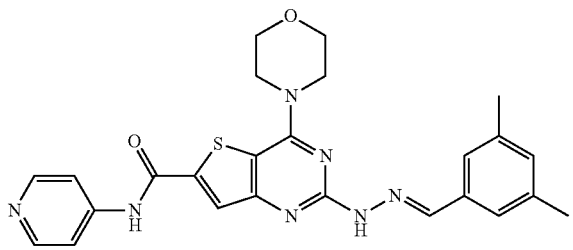

Title compound (0.028 g, 65%) was prepared by a similar procedure described for step 3 of example 5 using 2-hydrazino-4-morpholino-N-(4-pyridyl)thieno[3,2-d]pyrimidine-6-carboxamide (0.07 g, 0.188 mmol), m-tolualdehyde (0.037 g, 0.276 mmol), AcOH (2 drops) and methanol (4 mL). LC-MS: m/z 488.0 [M+H]$^+$

Example 7

4-morpholino-2-[(2E)-2-(m-tolylmethylene)hydrazino]-N-(oxetan-3-yl)thieno[3,2-d]pyrimidine-6-carboxamide

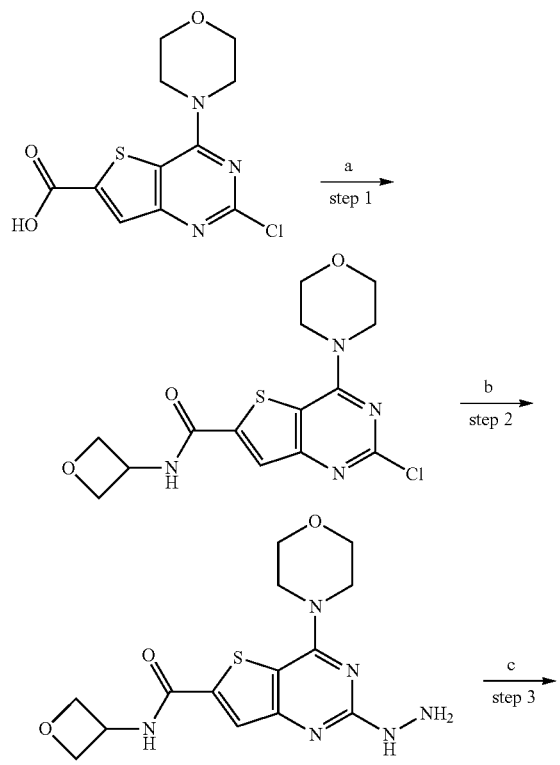

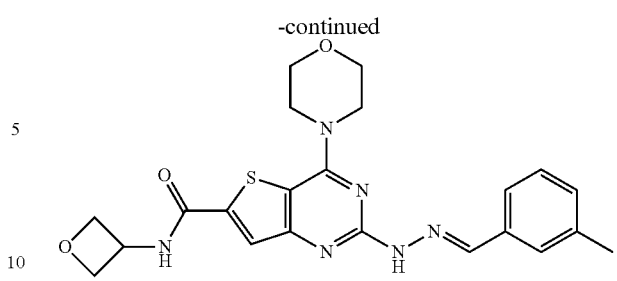

Reagents and Conditions: a) oxetan-3-amine, HBTU, DIEA, DCM, 2 h, rt; b) dioxane, N$_2$H$_4$, 80-90° C., 16 h; c) MeOH, m-tolualdehyde, AcOH, 70° C., 8 h.

Step 1—synthesis of 2-chloro-4-morpholino-N-(oxetan-3-yl)thieno[3,2-d]pyrimidine-6-carboxamide: To a suspension of 2-chloro-4-morpholino-thieno[3,2-d]pyrimidine-6-carboxylic acid (0.200 g, 0.667 mmol), oxetan-3-amine (0.054 g, 0.734 mmol), in DCM (20 mL) was added HBTU (0.321 g, 1.00 mmol) followed by DIEA (0.46 mL, 2.66 mmol) at rt. The mixture was stirred further for 2 h at rt. At the end of this period reaction mixture was diluted with DCM (50 mL) and washed with water (2×20 mL) and dried (Na$_2$SO$_4$), filtered and the solvent evaporated to dryness. The crude was triturated with methanol and filtered to provide title product in quantitative yield. $^1$H NMR (DMSO-d$_6$): δ 3.74 (t, J=4.98 Hz, 4H), 3.90 (t, J=5.0 Hz, 4H), 4.59 (t, J=6.5 Hz, 2H), 4.79 (t, J=6.7 Hz, 2H), 4.98-5.03 (m, 1H), 8.05 (s, 1H), 9.61 (d, J=6.6 Hz, 1H).

Step 2—synthesis of 2-hydrazino-4-morpholino-N-(oxetan-3-yl)thieno[3,2-d]pyrimidine-6-carboxamide: To a suspension of: 2-chloro-4-morpholino-N-(oxetan-3-yl)thieno[3,2-d]pyrimidine-6-carboxamide (0.230 g, 0.65 mmol) in dioxane (10 mL) was added anhydrous N$_2$H$_4$ (0.500 mL) at rt and the reaction mixture was refluxed for 16 h. At the end of this period solvent was evaporated to dryness. The crude was triturated with MeOH and the solid was filtered and washed with cold methanol and dried to provide title product (0.148 g, 65%). $^1$H NMR (DMSO-d$_6$): δ 3.70 (t, J=4.88 Hz, 4H), 3.81 (bs, 4H), 4.08 (bs, 2H), 4.60 (t, J=6.54 Hz, 2H), 4.77 (t, J=6.6 Hz, 2H), 4.96-5.01 (m, 1H), 7.83 (s, 1H), 9.39 (d, J=6.6 Hz, 1H).

Step 3—synthesis of 4-morpholino-2-[(2E)-2-(m-tolylmethylene)hydrazino]-N-(oxetan-3-yl)thieno[3,2-d]pyrimidine-6-carboxamide: To suspension of 2-hydrazino-4-morpholino-N-(oxetan-3-yl)thieno[3,2-d]pyrimidine-6-carboxamide (0.05 g, 0.143 mmol) in MeOH (3 mL) was added m-tolualdehyde (0.020 g, 0.1711 mmol)) and 3 drops of AcOH at rt. The reaction mixture was refluxed for 8 h, at the end of this period mixture was cooled to rt, solvent evaporated and the crude was chromatographed over SiO$_2$ using 0-50 gradient of MeOH in DCM to provide title product (0.035 g, 54%). $^1$H NMR (DMSO-d$_6$): δ 2.36 (s, 3H), 3.80 (t, J=4.4 Hz, 4H), 4.00 (t, J=4.8 Hz, 4H), 4.64 (t, J=6.5 Hz, 2H), 4.76 (t, J=6.6 Hz, 2H), 4.98-5.03 (m, 1H), 7.29 (d, J=7.4 Hz, 1H), 7.38 (t, J=7.6 Hz, 1H), 7.69 (d, J=7.8 Hz, 1H), (7.81 (s, 1H), 8.25 (s, 1H), 8.26 (s, 1H), 10.01 (d, J=6.4 Hz, 1H), 12.61 (bs 1H).

Example 8

2-[(2E)-2-[(3,5-dimethylphenyl)methylene]hydrazino]-4-morpholino-N-(oxetan-3-yl)thieno[3,2-d]pyrimidine-6-carboxamide

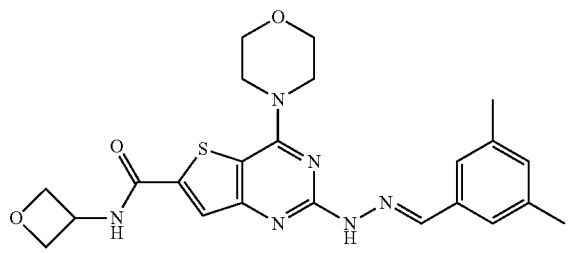

Title compound (0.032 g, 48%) was prepared by a similar procedure described for step 3 of example 7 using 2-hydrazino-4-morpholino-N-(oxetan-3-yl)thieno[3,2-d]pyrimidine-6-carboxamide (0.050 g, 0.142 mmol), m-tolualdehyde (0.023 g, 0.171 mmol), AcOH (2 drops) and methanol (4 mL). LC-MS: m/z 467 [M+H]$^+$

Example 9

4-Morpholino-N-[(E)-m-tolylmethyleneamino]-6-oxazol-5-yl-thieno[3,2-d]pyrimidin-2-amine

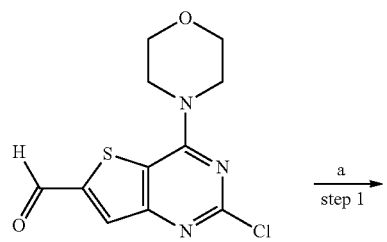

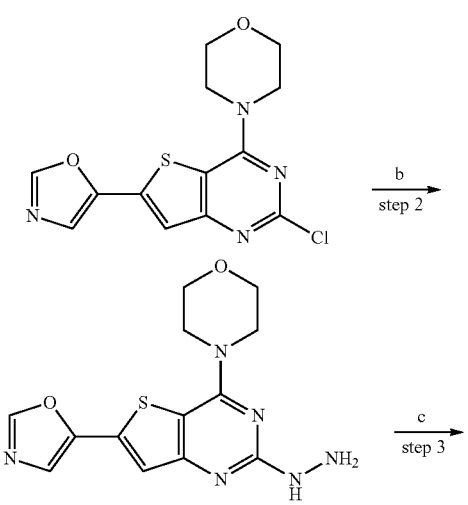

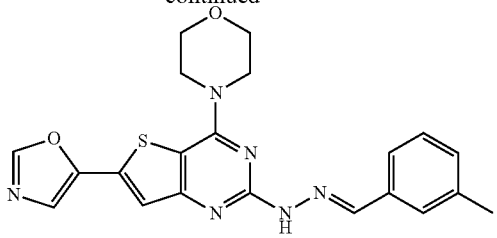

Reagents and Condtions: a) TosMIC, K$_2$CO$_3$, MeOH, 70° C.; b) N$_2$H$_4$·H$_2$O, dioxane, 90° C., 16 h,; c) m-tolualdehyde, AcOH, MeOH, 70° C., 6 h.

Step 1—Synthesis of 4-(2-chloro-6-oxazol-5-yl-thieno[3,2-d]pyrimidin-4-yl)morpholine: A mixture of 2-chloro-4-morpholino-thieno[3,2-d]pyrimidine-6-carbaldehyde (0.500 g, 1.66 mmol), TosMIC (0.325 g, 1.66 mmol) and K$_2$CO$_3$ in MeOH (15 mL) was heated at 70° C. for 2 h. At the end of this period reaction mixture was cooled to rt and the solvent evaporated to dryness and water (25 mL) was added. The solid separated was filtered and washed with water (20 mL). The crude material was chromatographed over SiO$_2$, using 0-15% EtOAc in DCM to provide title product (0.430 g, 80%). $^1$H NMR (DMSO-d$_6$): δ 3.75 (t, J=4.7 Hz, 4H), 3.90 (t, J=5.1 Hz, 4H), 7.76 (s, 1H), 7.93 (s, 1H), 8.61 (s, 1H).

Step 2—synthesis of (4-morpholino-6-oxazol-5-yl-thieno[3,2-d]pyrimidin-2-yl)hydrazine: Title compounds (0.310 g, 73%) was prepared by similar procedure described for step 2 of example 5, using 4-(2-chloro-6-oxazol-5-yl-thieno[3,2-d]pyrimidin-4-yl)morpholine (0.430 g, 1.33 mmol) and N$_2$H$_4$.H$_2$O (0.390 mL, 7.99 mmol). $^1$H NMR (DMSO-d$_6$): δ 3.72-3.82 (m, 8H), 4.08 (bs, 2H), 7.46 (s, 1H), 7.63 (s, 1H), 7.79 (s, 1H), 8.54 (s, 1H).

Step 3—Synthesis of 4-morpholino-N-[(E)-m-tolylmethyleneamino]-6-oxazol-5-yl-thieno[3,2-d]pyrimidin-2-amine: Title compound (0.103 g, 78%) was prepared by a procedure similar to described for step 3 of example 5. $^1$H NMR (DMSO-d$_6$): δ 2.33 (s, 3H), 3.76 (t, J=4.4 Hz, 4H), 3.89 (t, J=5.0 Hz, 4H), 7.14 (d, 7.3 Hz, 1H), 7.28 (t, J=7.5 Hz, 1H), 7.42-7.45 (m, 2H), 7.60 (s, 1H), 7.83 (s, 1H), 8.05 (s, 1H), 8.57 (s, 1H), 10.83 (s, 1H).

Example 10

4-morpholino-N-[(E)-m-tolylmethyleneamino]thieno[2,3-d]pyrimidin-2-amine

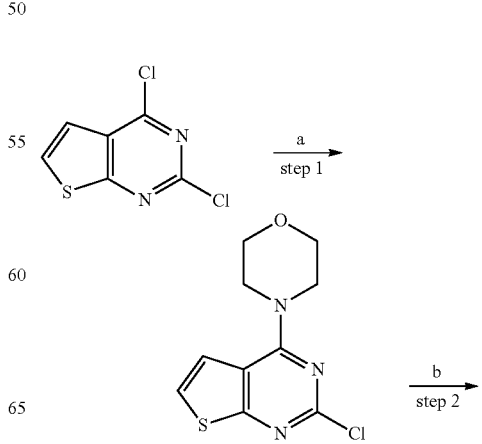

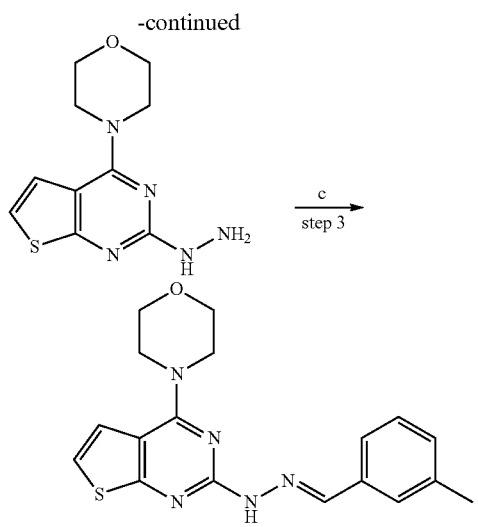

Reagents and conditions: a) MeOH, morpholine, rt 3 h; b) dioxane, anhydrous N₂H₄, 110° C., 6 h; c) MeOH, m-tolualdehyde, AcOH, 70° C., 6 h.

Step 1—synthesis of 4-(2-chlorothieno[2,3-d]pyrimidin-4-yl)morpholine: The title compound (3.82 g, 76%) was prepared by a known methods using 2,4-dichlorothieno[2,3-d]pyrimidine (4.00 g, 19.50 mmol) and morpholine (3.75 mL, 42.91 mmol). ¹H NMR (DMSO-d₆): δ 3.72 (t, J=4.6 Hz, 4H), 3.88 (t, J=5.0 Hz, 4H), 7.60-7.70 (m, 2H).

Step 2—synthesis of (4-morpholinothieno[2,3-d]pyrimidin-2-yl)hydrazine: Title compound (0.200 g, 82%) was prepared by a procedure similar to described for step 2 of example 5 using 2,4-dichlorothieno[2,3-d]pyrimidine (0.250 g, 0.977 mmol) and hydrazine hydrate (0.300 mL, 6.5 mmol). ¹H NMR (DMSO-d₆): δ 3.68-4.76 (m, 8H), 4.15 (bs, 2H), 7.05 (d, 6.1 Hz, 1H), 7.36 (d, J=6.1 Hz, 1H), 7.70 (s, 1H).

Step 3—synthesis of 4-morpholino-N-[(E)-m-tolylmethyleneamino]thieno[2,3-d]pyrimidin-2-amine: Title product (0.086 g, 88%) was prepared by a procedure described for step 3 of example 5 using (4-morpholinothieno[2,3-d]pyrimidin-2-yl)hydrazine (0.07 g, 0.271 mmol), m-tolualdehyde (0.040 mL, 0.334 mmol) and drops of AcOH. ¹H NMR (DMSO-d₆): δ 2.33 (s, 3H), 3.73 (t, J=4.1 Hz, 4H), 3.83 (t, J=4.8 Hz, 4H), 7.14 (d, J=7.0 Hz, 1H), 7.20 (d, J=6.15 Hz, 1H) 1H), 7.28 (t, J=7.7 Hz, 1H), 7.41-7.46 (m, 3H), 8.05 (s, 1H), 10.87 (s, 1H).

Example 11

4-morpholino-N-[(E)-m-tolylmethyleneamino]-6-(4-pyridyl)thieno[2,3-d]pyrimidin-2-amine

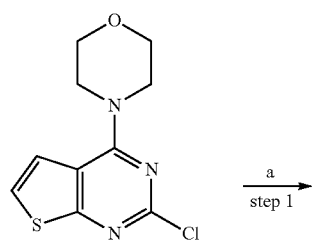

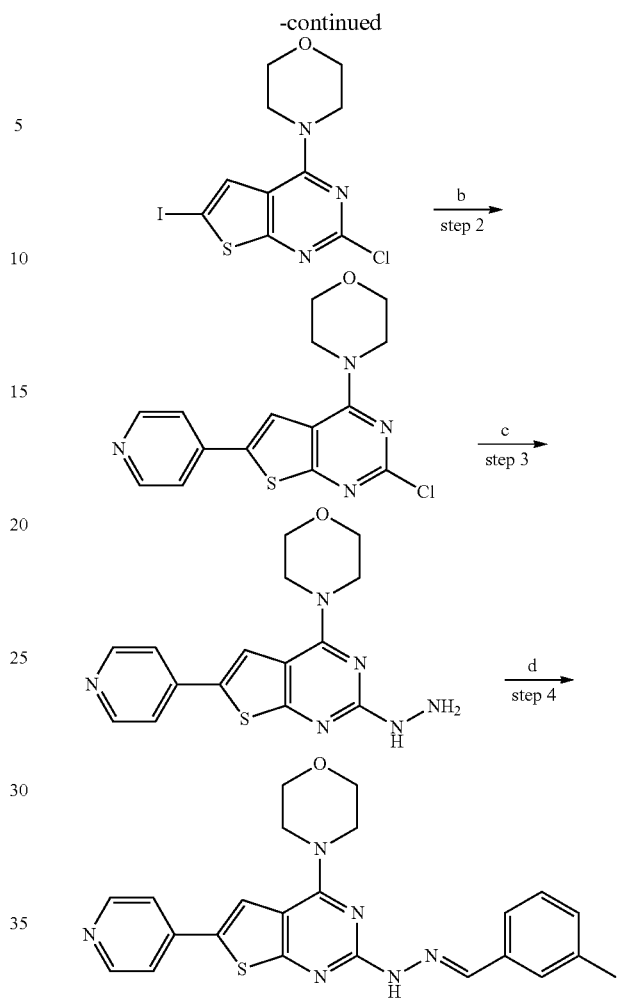

Reagents and conditions: a) n-BuLi, THF, -78° C., I₂, 4 h; b) 4-pyridylboronic acid, Pd(PPh₃)₂Cl₂, 1N Na₂CO₃, CH₃CN, 90° C., 4 h; c) dioxane, N₂H₄·H₂O, 110° C., 16 h; d) MeOH, m-tolualdehyde, AcOH, 70° C., 6 h.

Step 1—synthesis of 4-(2-chloro-6-iodo-thieno[2,3-d]pyrimidin-4-yl)morpholine: Title compound (1.49 g, 67%) was prepared by similar procedure described for step 2 of example 1 using 4-(2-chlorothieno[2,3-d]pyrimidin-4-yl)morpholine (1.50 g, 5.87 mmol), n-BuLi (2.5 M in THF/Hexane) (4.70 mL, 11.24 mmol) and 12 (3.00 g, 11.74 mmol). ¹H NMR (DMSO-d₆): δ 3.70 (t, J=5.0 Hz, 4H), 3.84 (t, J=4.5 Hz, 4H), 7.97 (s, 1H).

Step 2—4-[2-chloro-6-(4-pyridyl)thieno[2,3-d]pyrimidin-4-yl]morpholine. Title compound (0.280 g, 53%) was prepared by a procedure similar to described for step 3 of example 1 using 4-(2-chloro-6-iodo-thieno[2,3-d]pyrimidin-4-yl)morpholine (0.600 g, 1.57 mmol), 4-pyridylboronic acid (0.212 g, 1.72 mmol) and Pd(PPh₃)₂Cl₂ (0.110 g, 0.157 mmol). ¹H NMR (DMSO-d₆): δ 3.76 (t, J=4.7 Hz, 4H), 3.95 (t, J=5.0 Hz, 4H), 7.82 (d, J=5.5 Hz, 2H), 8.28 (s, 1H), 8.64 (d, J=4.5 Hz, 2H).

Step 3—synthesis of [4-morpholino-6-(4-pyridyl)thieno[2,3-d]pyrimidin-2-yl]hydrazine: Title compound (0.180 g, 65%) was prepared by a similar procedure described for step 4 of example 1 using 4-[2-chloro-6-(4-pyridyl)thieno[2,3-d]pyrimidin-4-yl]morpholine (0.280 g, 0.84 mmol) and N₂H₄·H₂O (0.245 mL, 5.04 mmol). ¹H NMR (DMSO-d₆): δ

3.78 (t, J=5.3 Hz, 4H), 3.82 (t, J=4.6 Hz, 4H), 7.07 (bs, 2H), 7.66 (d, J=6.1 Hz, 2H), 8.00 (bs, 1H), 8.06 (s, 1H), 8.53 (d, J=6.1 Hz, 2H).

Step 4—4-morpholino-N-[(E)-m-tolylmethyleneamino]-6-(4-pyridyl)thieno[2,3-d]pyrimidin-2-amine Title product (0.086 g, 88%) was prepared by a procedure described for step 5 of example 1 using [4-morpholino-6-(4-pyridyl)thieno[2,3-d]pyrimidin-2-yl]hydrazine (0.170 g, 0.517 mmol), m-toluadehyde (0.067 mL, 0.569 mmol) and AcOH (2 drops). ¹H NMR (DMSO-d₆): δ 2.34 (s, 3H), 3.77 (t, J=4.3 Hz, 4H), 3.92 (t, J=4.8 Hz, 4H), 7.16 (d, J=7.5 Hz, 1H), 7.29 (t, J=7.5 Hz, 1H), 7.44-7.47 (m, 2H), 7.72 (d, J=6.1 Hz, 2H), 8.08 (s, 1H), 8.14 (s, 1H), 8.57 (d, J=6.0 Hz, 2H), 11.04 (s, 1H).

Example 12

4-morpholino-N-[(E)-m-tolylmethyleneamino]-6-oxazol-5-yl-thieno[2,3-d]pyrimidin-2-amine

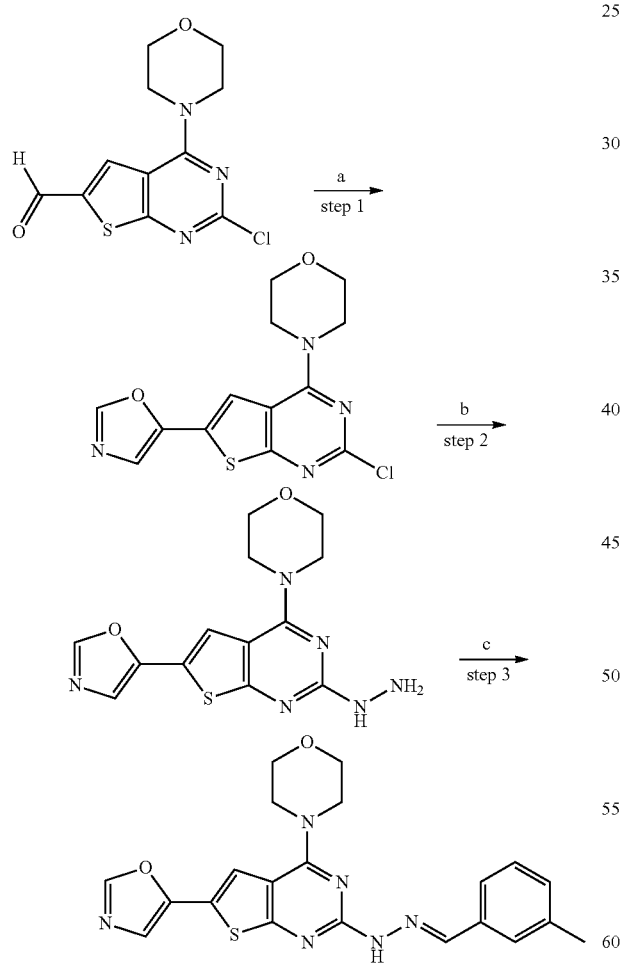

Step 1—4-(2-chloro-6-oxazol-5-yl-thieno[2,3-d]pyrimidin-4-yl)morpholine: Title product (0.290 g, 78%) was prepared by similar procedure described for step 1 of example 9 using 2-chloro-4-morpholino-thieno[2,3-d]pyrimidine-6-carbaldehyde (0.350 g, 1.16 mmol), TosMIC (0.228 g, 1.66 mmol) and K₂CO₃ (0.160 g, 1.16 mmol) in MeOH (20 mL). ¹HNMR (DMSO-d₆): δ 3.76 (t, J=5.1 Hz, 4H), 3.91 (t, J=4.5 Hz, 4H), 7.74 (s, 1H), 7.96 (s, 1H), 8.52 (s, 1H).

Step 2—(4-morpholino-6-oxazol-5-yl-thieno[2,3-d]pyrimidin-2-yl)hydrazine: Title product (0.255 g, 92%) was prepared by a similar procedure described for step 2 of example 9 using 4-(2-chloro-6-oxazol-5-yl-thieno[2,3-d]pyrimidin-4-yl)morpholine (0.28 g, 0.87 mmol) and hydrazine hydrate (0.252 mL, 5.26 mmol) in dioxane (15 mL). ¹HNMR (DMSO-d₆): δ 3.71 (t, J=4.4 Hz, 4H), 3.79 (t, J=4.1 Hz, 4H), 4.75 (bs, 2H), 7.51 (s, 1H), 7.69 (s, 1H), 7.95 bs, 1H), 8.40 (s, 1H).

Step 3—4-morpholino-N-[(E)-m-tolylmethyleneamino]-6-oxazol-5-yl-thieno[2,3-d]pyrimidin-2-amine: Title product (0.110 g, 83%) was prepared by a similar procedure described for step 3 of example 9 using (4-morpholino-6-oxazol-5-yl-thieno[2,3-d]pyrimidin-2-yl)hydrazine (0.100 g, 0.314 mmol), m-toluadehyde (0.037 mL, 0.317 mmol), AcOH (2 drops) and methanol (4 mL). ¹HNMR (DMSO-d₆): δ 2.33 (s, 3H), 3.75 (t, J=4.7 Hz, 4H), 3.87 (t, J=5.0 Hz, 4H), 7.15 (d, J=7.2 Hz, 1H), 7.29 (t, J=7.7 Hz, 1H), 7.43-7.46 (m, 2H), 7.58 (s, 1H), 7.79 (s, 1H), 8.07 (s, 1H), 8.44 (s, 1H), 11.02 (s, 1H).

Example 13

N-[(E)-(3,5-dimethylphenyl)methyleneamino]-4-morpholino-6-oxazol-5-yl-thieno[2,3-d]pyrimidin-2-amine

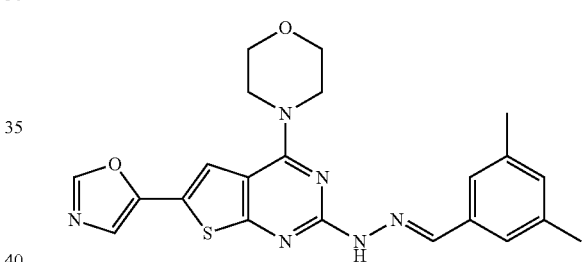

Title product (0.038 g, 68%) was prepared by a similar procedure described for step 3 of example 9 using—(4-morpholino-6-oxazol-5-yl-thieno[2,3-d]pyrimidin-2-yl)hydrazine (0.0.05 g, 0.157 mmol), 3,5-dimethylbenzaldehyde (0.025 g, 0.188 mmol), AcOH (2 drops) and methanol (4 mL). LC-MS: m/z 435.0 [M+H]⁺

Example 14

N-[(E)-(3-chlorophenyl)methyleneamino]-4-morpholino-6-oxazol-5-yl-thieno[2,3-d]pyrimidin-2-amine

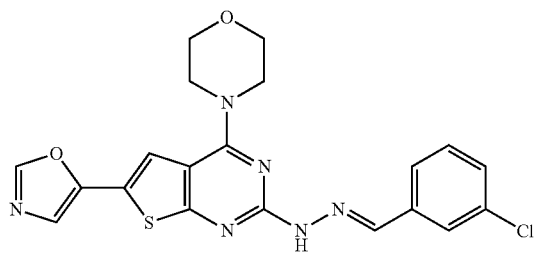

Title product (0.0.42 g, 61%) was prepared by a similar procedure described for step 3 of example 9 using (4-morpholino-6-oxazol-5-yl-thieno[2,3-d]pyrimidin-2-yl)hydrazine (0.05 g, 0.157 mmol), 3-chlorobenzaldehyde (0.026 g, 0.188 mmol), AcOH (2 drops) and methanol (4 mL).

$^1$HNMR (DMSO-$d_6$): δ 3.77 (t, J=4.4 Hz, 4H), 3.89 (t, J=5.0 Hz, 4H), 7.37-7.45 (m, 2H), 7.59-7.61 (m, 2H), 7.68 (s, 1H), 7.80 (s, 1H), 8.07 (s, 1H), 8.44 (s, 1H), 11.19 (s, 1H).

Tables 1 list additional compounds of the present invention.

TABLE 1

| Ex. No. | Structure | Name |
|---|---|---|
| 15 | 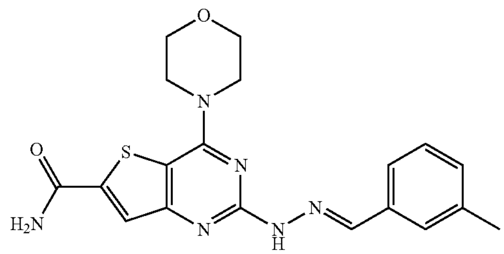 [SMILES: Cc1cccc(/C=N/Nc2nc(N3CCOCC3)c3sc(C(N)=O)cc3n2)c1] | 4-morpholino-2-[(2E)-2-(m-tolylmethylene)hydrazino]thieno[3,2-d]pyrimidine-6-carboxamide |
| 16 | 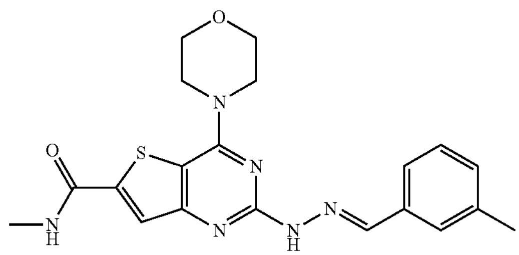 | N-methyl-4-morpholino-2-[(2E)-2-(m-tolylmethylene)hydrazino]thieno[3,2-d]pyrimidine-6-carboxamide |
| 17 | 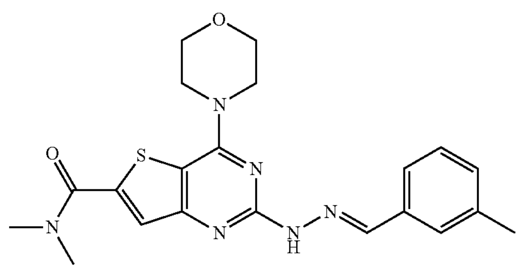 | N,N-dimethyl-4-morpholino-2-[(2E)-2-(m-tolylmethylene)hydrazino]thieno[3,2-d]pyrimidine-6-carboxamide |
| 18 | 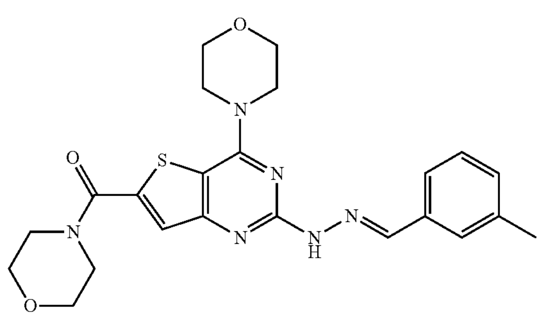 [SMILES: Cc1cccc(/C=N/Nc2nc(N3CCOCC3)c3sc(C(=O)N4CCOCC4)cc3n2)c1] | morpholino-[4-morpholino-2-[(2E)-2-(m-tolylmethylene)hydrazino]thieno[3,2-d]pyrimidin-6-yl]methanone |
| 19 | 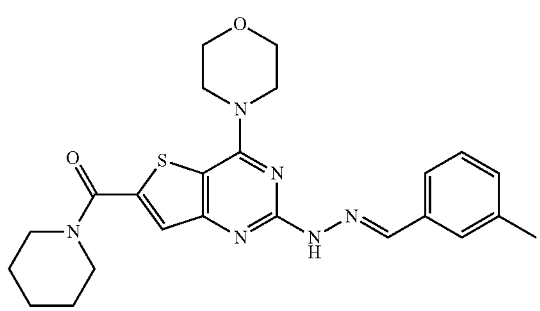 | [4-morpholino-2-[(2E)-2-(m-tolylmethylene)hydrazino]thieno[3,2-d]pyrimidin-6-yl]-(1-piperidyl)methanone |

TABLE 1-continued

| Ex. No. | Structure | Name |
|---|---|---|
| 20 | 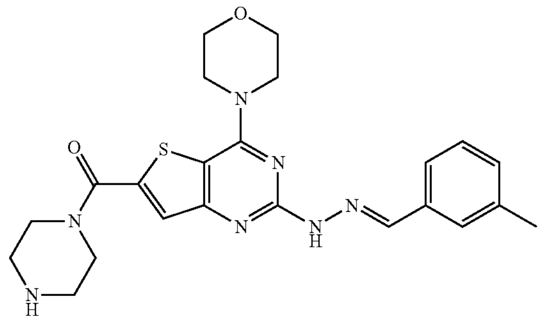 [SMILES: Cc1cccc(/C=N/Nc2nc(N3CCOCC3)c3sc(C(=O)N4CCNCC4)cc3n2)c1] | [4-morpholino-2-[(2E)-2-(m-tolylmethylene)hydrazino]thieno[3,2-d]pyrimidin-6-yl]-piperazin-1-yl-methanone |
| 21 | 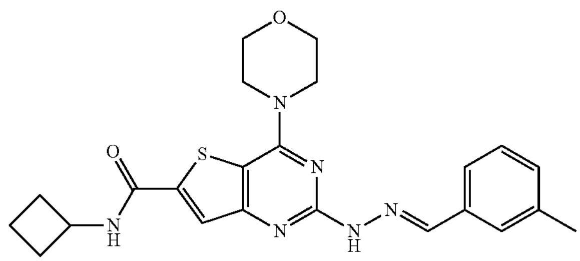 [SMILES: Cc1cccc(/C=N/Nc2nc(N3CCOCC3)c3sc(C(=O)NC4CCC4)cc3n2)c1] | N-cyclobutyl-4-morpholino-2-[(2E)-2-(m-tolylmethylene)hydrazino]thieno[3,2-d]pyrimidine-6-carboxamide |
| 22 | 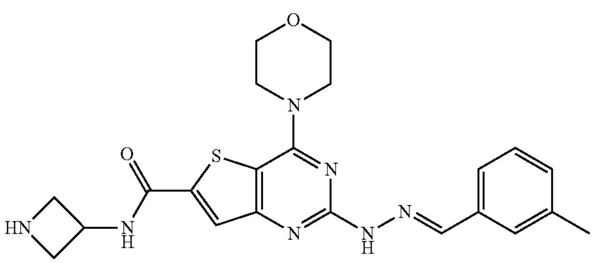 | N-(azetidin-3-yl)-4-morpholino-2-[(2E)-2-(m-tolylmethylene)hydrazino]thieno[3,2-d]pyrimidine-6-carboxamide. LC-MS: m/z 452[M + H]+ |
| 23 | 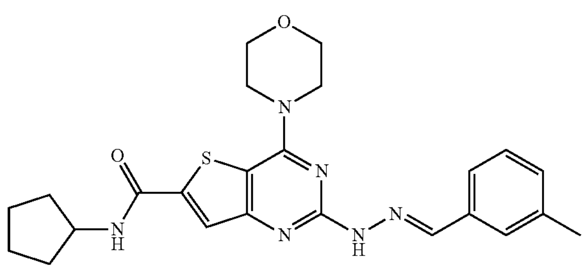 [SMILES: Cc1cccc(/C=N/Nc2nc(N3CCOCC3)c3sc(C(=O)NC4CCCC4)cc3n2)c1] | N-cyclopentyl-4-morpholino-2-[(2E)-2-(m-tolylmethylene)hydrazino]thieno[3,2-d]pyrimidine-6-carboxamide |
| 24 | 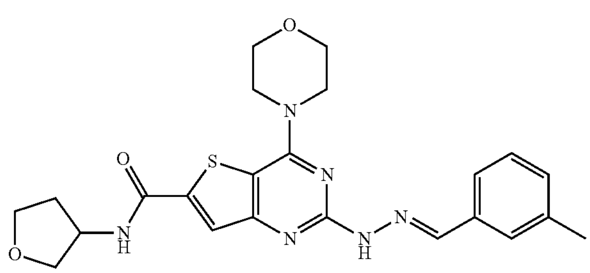 | 4-morpholino-2-[(2E)-2-(m-tolylmethylene)hydrazino]-N-tetrahydrofuran-3-yl-thieno[3,2-d]pyrimidine-6-carboxamide |

TABLE 1-continued

| Ex. No. | Structure | Name |
|---|---|---|
| 25 | 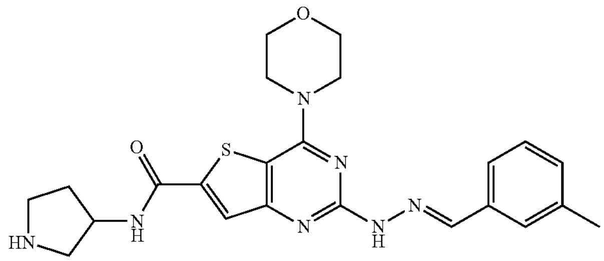 [SMILES: Cc1cccc(/C=N/Nc2nc(N3CCOCC3)c3sc(C(=O)NC4CCNC4)cc3n2)c1] | 4-morpholino-2-[(2E)-2-(m-tolylmethylene)hydrazino]-N-pyrrolidin-3-yl-thieno[3,2-d]pyrimidine-6-carboxamide |
| 26 | 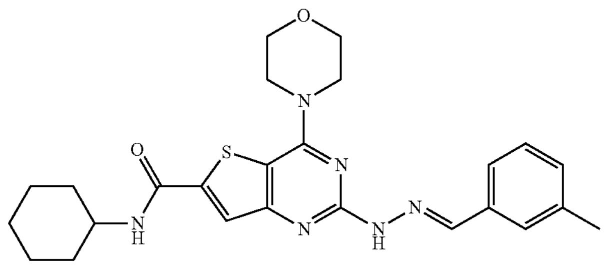 [SMILES: Cc1cccc(/C=N/Nc2nc(N3CCOCC3)c3sc(C(=O)NC4CCCCC4)cc3n2)c1] | N-cyclohexyl-4-morpholino-2-[(2E)-2-(m-tolylmethylene)hydrazino]thieno[3,2-d]pyrimidine-6-carboxamide |
| 27 | 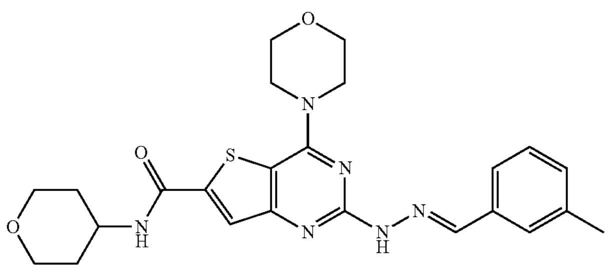 [SMILES: Cc1cccc(/C=N/Nc2nc(N3CCOCC3)c3sc(C(=O)NC4CCOCC4)cc3n2)c1] | 4-morpholino-2-[(2E)-2-(m-tolylmethylene)hydrazino]-N-tetrahydropyran-4-yl-thieno[3,2-d]pyrimidine-6-carboxamide |
| 28 | 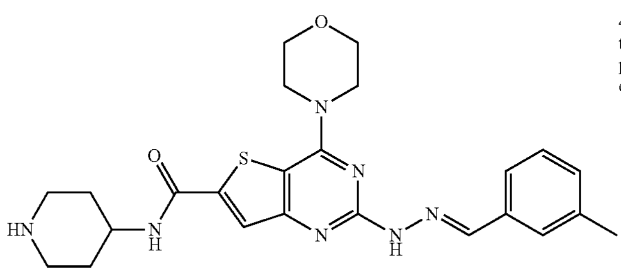 [SMILES: Cc1cccc(/C=N/Nc2nc(N3CCOCC3)c3sc(C(=O)NC4CCNCC4)cc3n2)c1] | 4-morpholino-2-[(2E)-2-(m-tolylmethylene)hydrazino]-N-(4-piperidyl)thieno[3,2-d]pyrimidine-6-carboxamide |
| 29 | 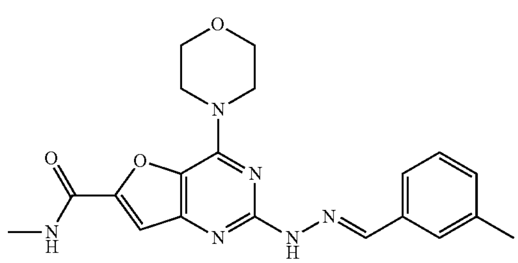 | N-methyl-4-morpholino-2-[(2E)-2-(m-tolylmethylene)hydrazino]furo[3,2-d]pyrimidine-6-carboxamide |
| 30 | 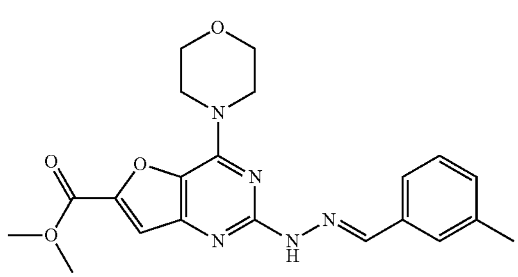 | N,N-dimethyl-4-morpholino-2-[(2E)-2-(-m-tolylmethylene)hydrazino]furo[3,2-d]pyrimidine-6-carboxamide |

TABLE 1-continued

| Ex. No. | Structure | Name |
|---|---|---|
| 31 | 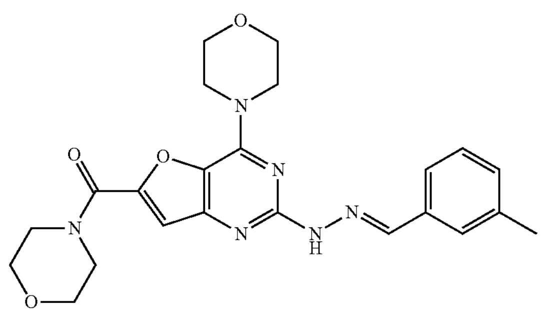 [SMILES: Cc1cccc(/C=N/Nc2nc(N3CCOCC3)c3oc(C(=O)N4CCOCC4)cc3n2)c1] | morpholino-[4-morpholino-2-[(2E)-2-(m-tolylmethylene)hydrazino]furo[3,2-d]pyrimidin-6-yl]methanone |
| 32 | 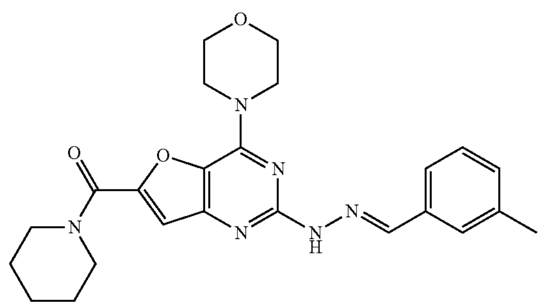 [SMILES: Cc1cccc(/C=N/Nc2nc(N3CCOCC3)c3oc(C(=O)N4CCCCC4)cc3n2)c1] | [4-morpholino-2-[(2E)-2-(m-tolylmethylene)hydrazino]furo[3,2-d]pyrimidin-6-yl]-(1-piperidyl)methanone |
| 33 | 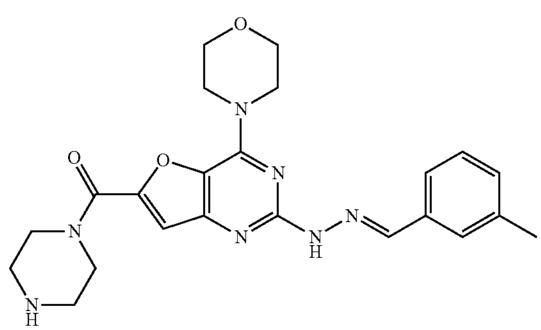 | [4-morpholino-2-[(2E)-2-(m-tolylmethylene)hydrazino]furo[3,2-d]pyrimidin-6-yl]-piperazin-1-yl-methanone |
| 34 | 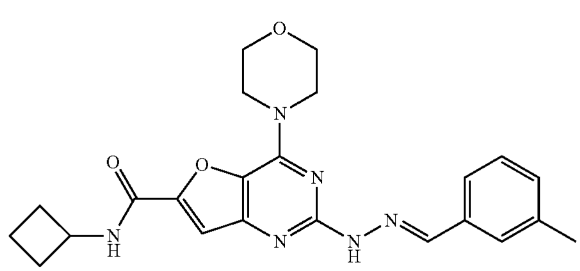 | N-cyclobutyl-4-morpholino-2-[(2E)-2-(m-tolylmethylene)hydrazino]furo[3,2-d]pyrimidine-6-carboxamide |
| 35 | 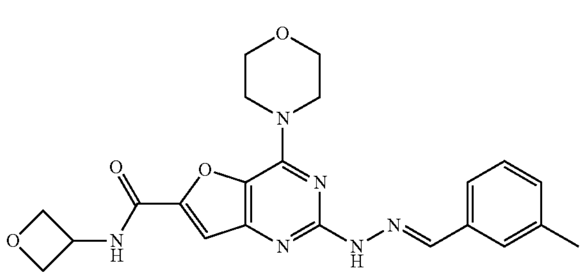 [SMILES: Cc1cccc(/C=N/Nc2nc(N3CCOCC3)c3oc(C(=O)NC4COC4)cc3n2)c1] | 4-morpholino-2-[(2E)-2-(m-tolylmethylene)hydrazino]-N-(oxetan-3-yl)furo[3,2-d]pyrimidine-6-carboxamide |

TABLE 1-continued

| Ex. No. | Structure | Name |
|---|---|---|
| 36 | 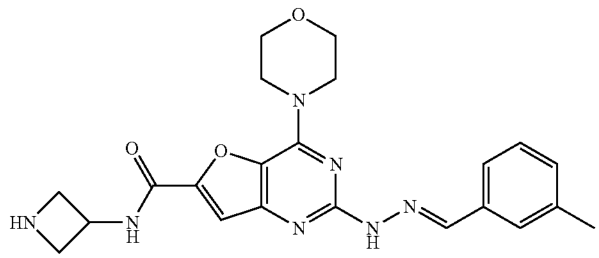 [SMILES: Cc1cccc(/C=N/Nc2nc(N3CCOCC3)c3oc(C(=O)NC4CNC4)cc3n2)c1] | N-(azetidin-3-yl)-4-morpholino-2-[(2E)-2-(m-tolylmethylene)hydrazino]furo[3,4-d]pyrimidine-6-carboxamide |
| 37 | 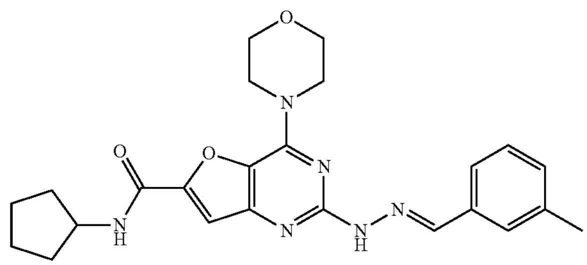 | N-cyclopentyl-4-morpholino-2-[(2E)-2-(m-tolylmethylene)hydrazino]furo[3,2-d]pyrimidine-6-carboxamide |
| 38 | 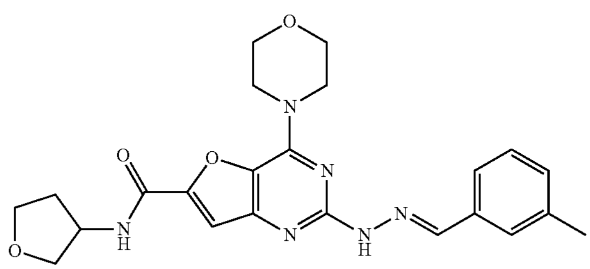 [SMILES: Cc1cccc(/C=N/Nc2nc(N3CCOCC3)c3oc(C(=O)NC4CCOC4)cc3n2)c1] | 4-morpholino-2-[(2E)-2-(m-tolylmethylene)hydrazino]-N-tetrahydrofuran-3-yl-furo[3,2-d]pyrimidine-6-carboxamide |
| 39 | 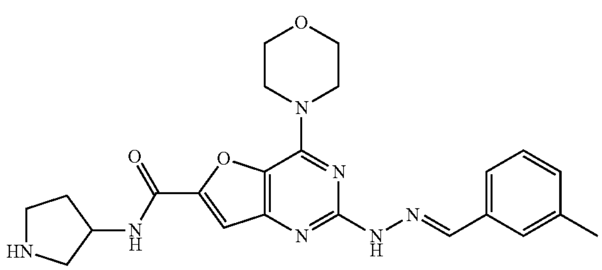 [SMILES: Cc1cccc(/C=N/Nc2nc(N3CCOCC3)c3oc(C(=O)NC4CCNC4)cc3n2)c1] | 4-morpholino-2-[(2E)-2-(m-tolylmethylene)hydrazino]-N-pyrrolidin-3-yl-furo[3,2-d]pyrimidine-6-carboxamide |
| 40 | 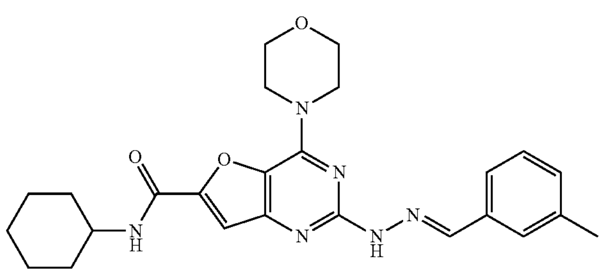 | N-cyclohexyl-4-morpholino-2-[(2E)-2-(m-tolylmethylene)hydrazino]furo[3,2-d]pyrimidine-6-carboxamide |

TABLE 1-continued

| Ex. No. | Structure | Name |
|---|---|---|
| 41 | 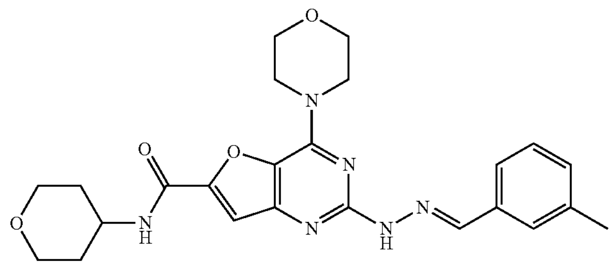 | 4-morpholino-2-[(2E)-2-(m-tolylmethylene)hydrazino]-N-tetrahydropyran-4-yl-furo[3,2-d]pyrimidine-6-carboxamide |
| 42 | 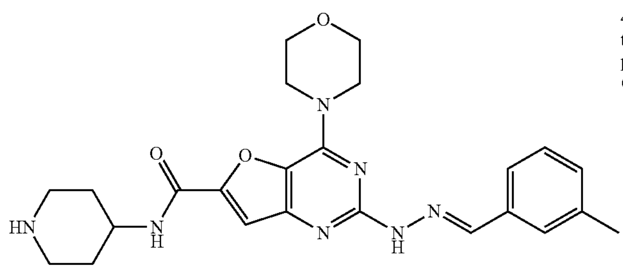 | 4-morpholino-2-[(2E)-2-(m-tolylmethylene)hydrazino]-N-(4-piperidyl)furo[3,2-d]pyrimidine-6-carboxamide |
| 43 | 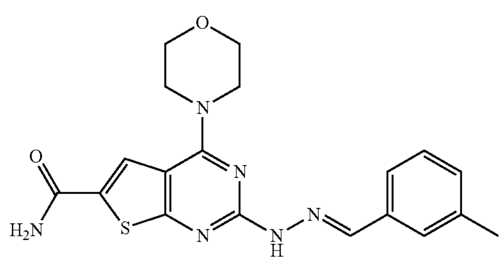 [SMILES: Cc1cccc(/C=N/Nc2nc(N3CCOCC3)c3cc(C(N)=O)sc3n2)c1] | 4-morpholino-2-[(2E)-2-(m-tolylmethylene)hydrazino]thieno[2,3-d]pyrimidine-6-carboxamide |
| 44 | 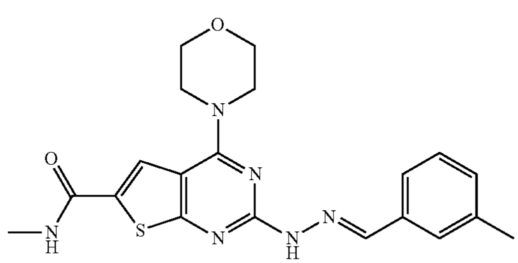 | N-methyl-4-morpholino-2-[(2E)-2-(m-tolylmethylene)hydrazino]thieno[2,3-d]pyrimidine-6-carboxamide |
| 45 | 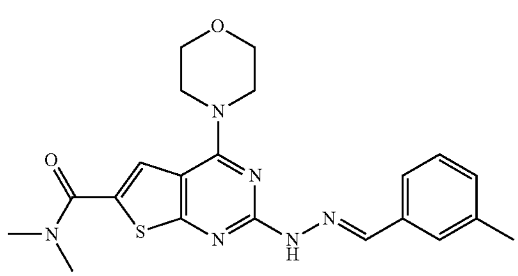 | N,N-dimethyl-4-morpholino-2-[(2E)-2-(m-tolylmethylene)hydrazino]thieno[2,3-d]pyrimidine-6-carboxamide |

TABLE 1-continued

| Ex. No. | Structure | Name |
|---|---|---|
| 46 | 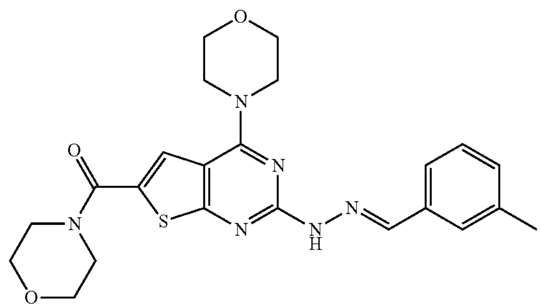 | morpholino-[4-morpholino-2-[(2E)-2-(m-tolylmethylene)hydrazino]thieno[2,3-d]pyrimidin-6-yl]methanone |
| 47 | 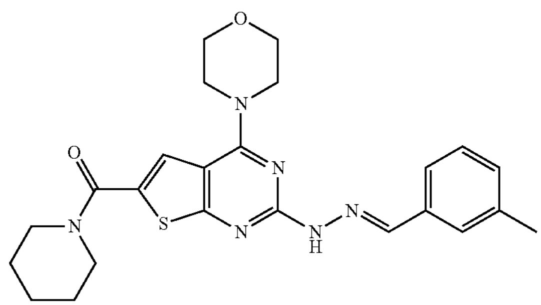 [SMILES: Cc1cccc(/C=N/Nc2nc(N3CCOCC3)c3cc(C(=O)N4CCCCC4)sc3n2)c1] | [4-morpholino-2-[(2E)-2-(m-tolylmethylene)hydrazino]thieno[2,3-d]pyrimidin-6-yl]-(1-piperidyl)methanone |
| 48 | 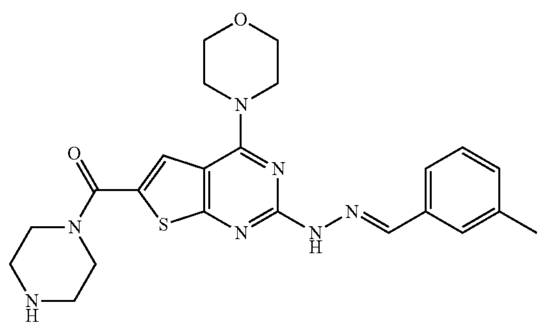 [SMILES: Cc1cccc(/C=N/Nc2nc(N3CCOCC3)c3cc(C(=O)N4CCNCC4)sc3n2)c1] | [4-morpholino-2-[(2E)-2-(m-tolylmethylene)hydrazino]thieno[2,3-d]pyrimidin-6-yl]-piperazin-1-yl-methanone |
| 49 | 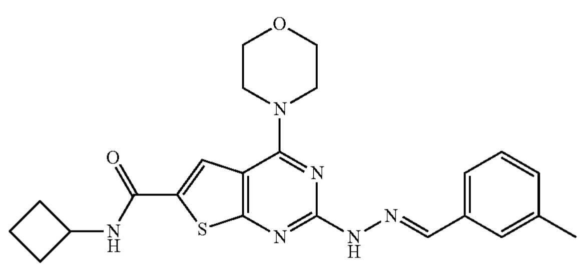 [SMILES: Cc1cccc(/C=N/Nc2nc(N3CCOCC3)c3cc(C(=O)NC4CCC4)sc3n2)c1] | N-cyclobutyl-4-morpholino-2-[(2E)-2-(m-tolylmethylene)hydrazino]thieno[2,3-d]pyrimidine-6-carboxamide |
| 50 | 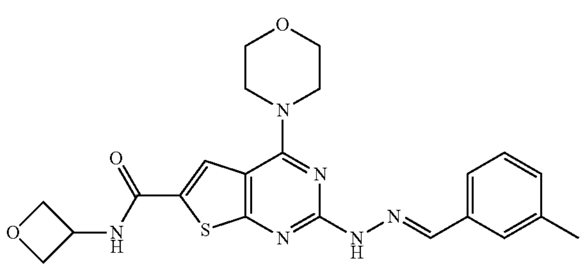 [SMILES: Cc1cccc(/C=N/Nc2nc(N3CCOCC3)c3cc(C(=O)NC4COC4)sc3n2)c1] | 4-morpholino-2-[(2E)-2-(m-tolylmethylene)hydrazino]-N-(oxetan-3-yl)thieno[2,3-d]pyrimidine-6-carboxamide |

TABLE 1-continued

| Ex. No. | Structure | Name |
|---|---|---|
| 51 | 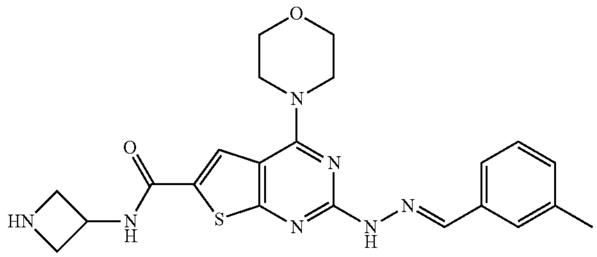 [SMILES: Cc1cccc(/C=N/Nc2nc(N3CCOCC3)c3cc(C(=O)NC4CNC4)sc3n2)c1] | N-(azetidin-3-yl)-4-morpholino-2-[(2E)-2-(m-tolylmethylene)hydrazino]thieno[2,3-d]pyrimidine-6-carboxamide |
| 52 | 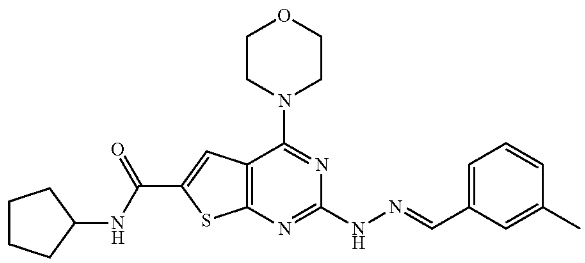 [SMILES: Cc1cccc(/C=N/Nc2nc(N3CCOCC3)c3cc(C(=O)NC4CCCC4)sc3n2)c1] | N-cyclopentyl-4-morpholino-2-[(2E)-2-(m-tolylmethylene)hydrazino]thieno[2,3-d]pyrimidine-6-carboxamide |
| 53 | 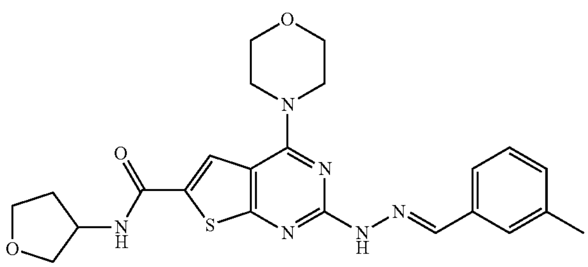 [SMILES: Cc1cccc(/C=N/Nc2nc(N3CCOCC3)c3cc(C(=O)NC4CCOC4)sc3n2)c1] | 4-morpholino-2-[(2E)-2-(m-tolylmethylene)hydrazino]-N-tetrahydrofuran-3-yl-thieno[2,3-d]pyrimidine-6-carboxamide |
| 54 | 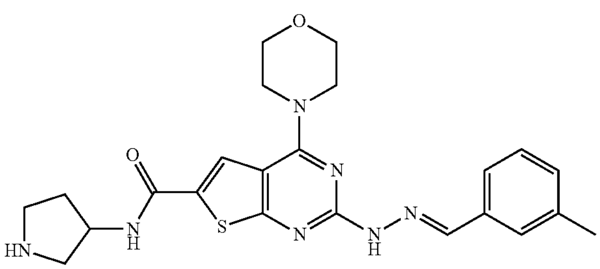 | 4-morpholino-2-[(2E)-2-(m-tolylmethylene)hydrazino]-N-pyrrolidin-3-yl-thieno[2,3-d]pyrimidine-6-carboxamide |
| 55 | 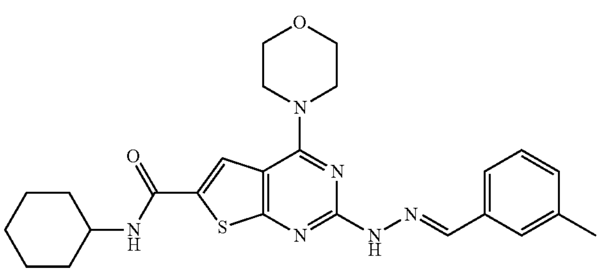 | N-cyclohexyl-4-morpholino-2-[(2E)-2-(m-tolylmethylene)hydrazino]thieno[2,3-d]pyrimidine-6-carboxamide |
| 56 | 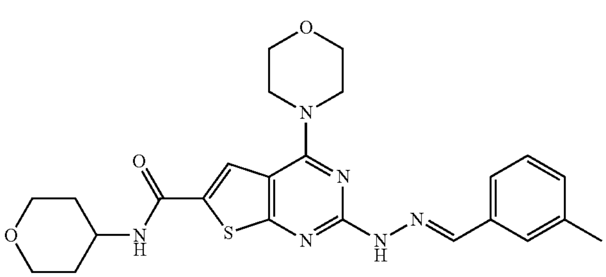 | 4-morpholino-2-[(2E)-2-(m-tolylmethylene)hydrazino]-N-tetrahydropyran-4-yl-thieno[2,3-d]pyrimidine-6-carboxamide |

TABLE 1-continued

| Ex. No. | Structure | Name |
|---|---|---|
| 57 | 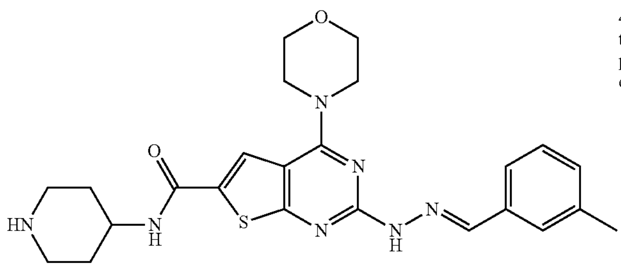 | 4-morpholino-2-[(2E)-2-(m-tolylmethylene)hydrazino]-N-(4-piperidyl)thieno[2,3-d]pyrimidine-6-carboxamide |
| 58 | 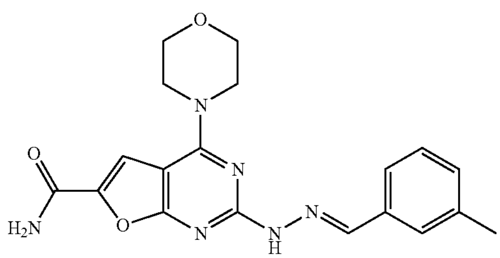 [SMILES: Cc1cccc(/C=N/Nc2nc(N3CCOCC3)c3cc(C(N)=O)oc3n2)c1] | 4-morpholino-2-[(2E)-2-(m-tolylmethylene)hydrazino]furo[2,3-d]pyrimidine-6-carboxamide |
| 59 | 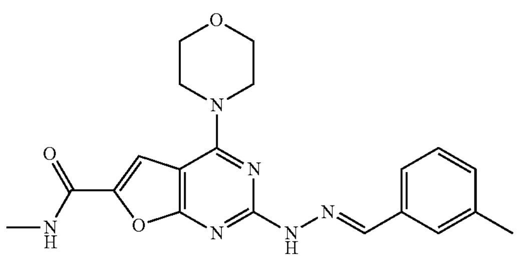 | N-methyl-4-morpholino-2-[(2E)-2-(m-tolylmethylene)hydrazino]furo[2,3-d]pyrimidine-6-carboxamide |
| 60 | 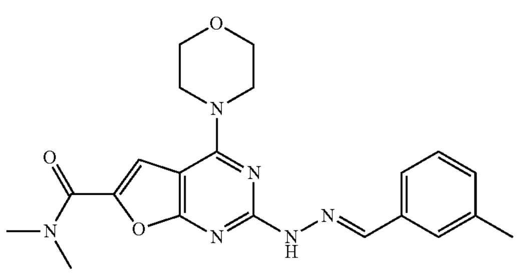 | N,N-dimethyl-4-morpholino-2-[(2E)-2-(m-tolylmethylene)hydrazino]furo[2,3-d]pyrimidine-6-carboxamide |
| 61 | 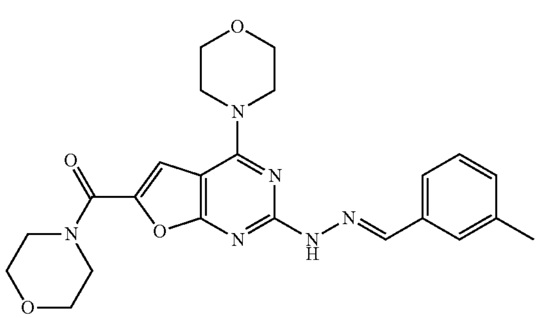 [SMILES: Cc1cccc(/C=N/Nc2nc(N3CCOCC3)c3cc(C(=O)N4CCOCC4)oc3n2)c1] | morpholino-[4-morpholino-2-[(2E)-2-(m-tolylmethylene)hydrazino]furo[2,3-d]pyrimidine-6-yl]methanone |

TABLE 1-continued

| Ex. No. | Structure | Name |
|---|---|---|
| 62 | 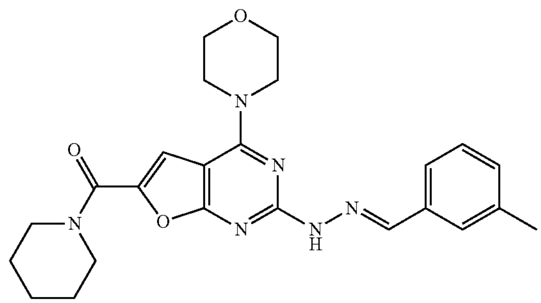 [SMILES: Cc1cccc(/C=N/Nc2nc(N3CCOCC3)c3cc(C(=O)N4CCCCC4)oc3n2)c1] | [4-morpholino-2-[(2E)-2-(m-tolylmethylene)hydrazino]furo[2,3-d]pyrimidin-6-yl]-(1-piperidyl)methanone |
| 63 | 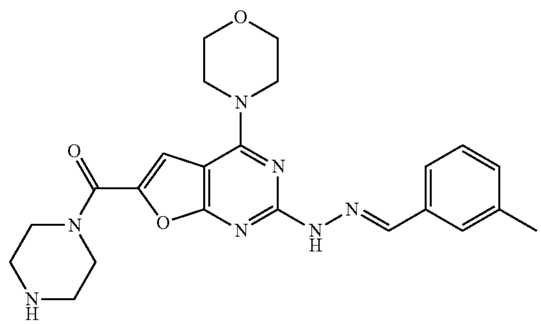 | [4-morpholino-2-[(2E)-2-(m-tolylmethylene)hydrazino]furo[2,3-d]pyrimidin-6-yl]-piperazin-1-yl-methanone |
| 64 | 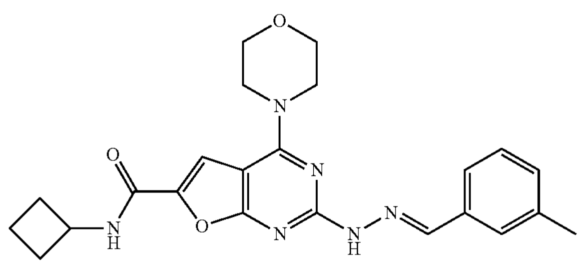 | N-cyclobutyl-4-morpholino-2-[(2E)-2-(m-tolylmethylene)hydrazino]furo[2,3-d]pyrimidine-6-carboxamide |
| 65 | 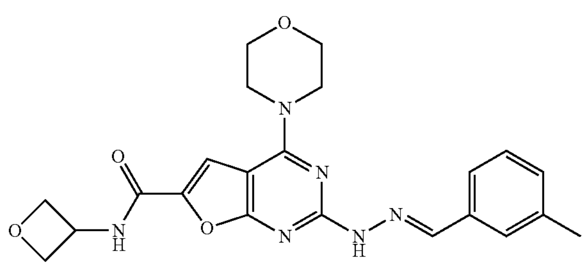 | 4-morpholino-2-[(2E)-2-(m-tolylmethylene)hydrazino]-N-(oxetan-3-yl)furo[2,3-d]pyrimidine-6-carboxamide |
| 66 | 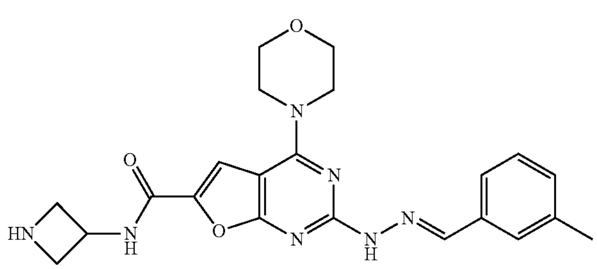 | N-(azetidin-3-yl)-4-morpholino-2-[(2E)-2-(m-tolylmethylene)hydrazino]furo[2,3-d]pyrimidine-6-carboxamide |

TABLE 1-continued

| Ex. No. | Structure | Name |
|---|---|---|
| 67 | 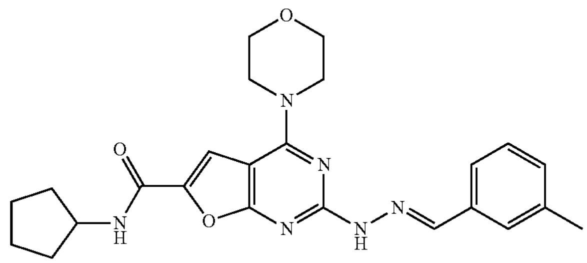 | N-cyclopentyl-4-morpholino-2-[(2E)-2-(m-tolylmethylene)hydrazino]furo[2,3-d]pyrimidine-6-carboxamide |
| 68 | 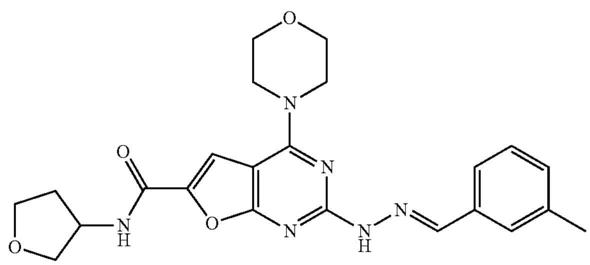 | 4-morpholino-2-[(2E)-2-(m-tolylmethylene)hydrazino]-N-tetrahydrofurna-3-yl-furo[2,3-d]pyrimidine-6-carboxamide |
| 69 | 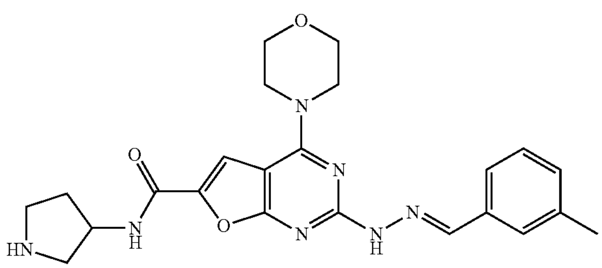 | 4-morpholino-2-[(2E)-2-(m-tolylmethylene)hydrazino]-N-pyrrolidin-3-yl-furo[2,3-d]pyrimidine-6-carboxamide |
| 70 | 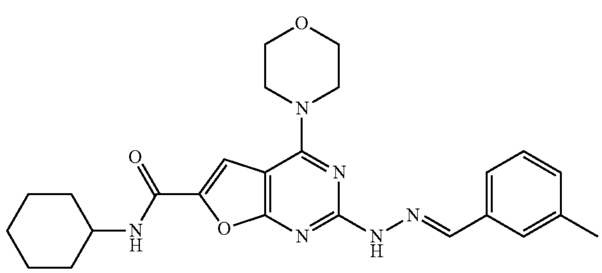 [SMILES: Cc1cccc(/C=N/Nc2nc(N3CCOCC3)c3cc(C(=O)NC4CCCCC4)oc3n2)c1] | N-cyclohexyl-4-morpholino-2-[(2E)-2-(m-tolylmethylene)hydrazino]furo[2,3-d]pyrimidine-6-carboxamide |
| 71 | 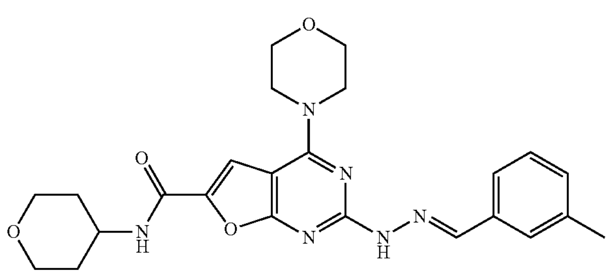 | 4-morpholino-2-[(2E)-2-(m-tolylmethylene)hydrazino]-N-tetrahydropyran-4-yl-furo[2,3-d]pyrimidine-6-carboxamide |

TABLE 1-continued

| Ex. No. | Structure | Name |
|---|---|---|
| 72 | 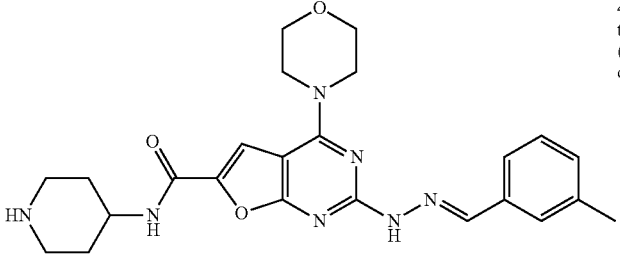 | 4-morpholino-2-[(2E)-2-(m-tolylmethylene)hydrazino]-N-(4-piperidyl)furo[2,3-d]pyrimidine-6-carboxamide |
| 73 | 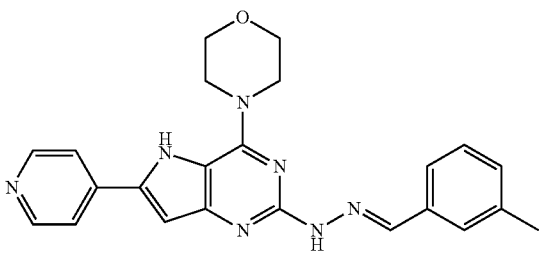 | 4-morpholino-N-[(E)-m-tolylmethyleneamino]-6-(4-pyridyl)-5H-pyrrolo[2,3-d]pyrimidin-2-amine |
| 74 | 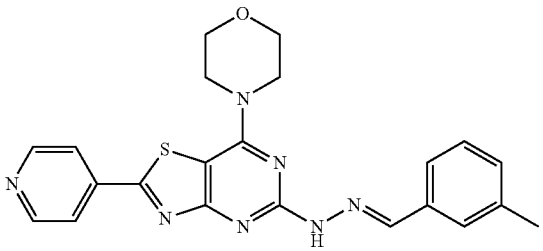 [SMILES: Cc1cccc(/C=N/Nc2nc(N3CCOCC3)c3sc(-c4ccncc4)nc3n2)c1] | 7-morpholino-N-[(E)-m-tolylmethyleneamino]-2-(4-pyridyl)thiazolo[4,5-d]pyrimidin-5-amine |
| 75 | 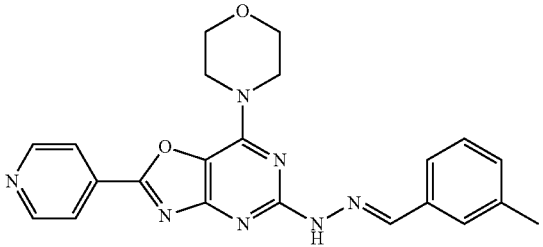 [SMILES: Cc1cccc(/C=N/Nc2nc(N3CCOCC3)c3oc(-c4ccncc4)nc3n2)c1] | 7-morpholino-N-[(E)-m-tolylmethyleneamino]-2-(4-pyridyl)oxazolo[4,5-d]pyrimidin-5-amine |
| 76 | 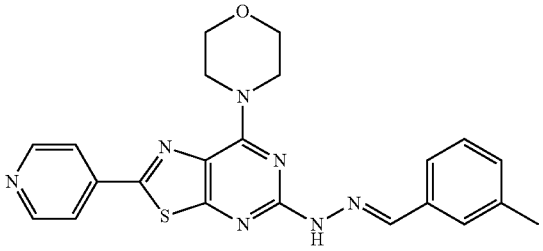 [SMILES: Cc1cccc(/C=N/Nc2nc(N3CCOCC3)c3nc(-c4ccncc4)sc3n2)c1] | 7-morpholino-N-[(E)-m-tolylmethyleneamino]-2-(4-pyridyl)thiazolo[5,4-d]pyrimidin-5-amine |
| 77 | 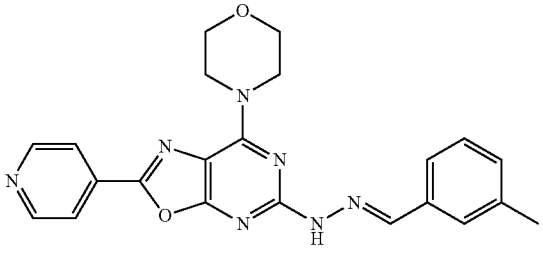 [SMILES: Cc1cccc(/C=N/Nc2nc(N3CCOCC3)c3nc(-c4ccncc4)oc3n2)c1] | 7-morpholino-N-[(E)-m-tolylmethyleneamino]-2-(4-pyridyl)oxazolo[5,4-d]pyrimidin-5-amine |

TABLE 1-continued

| Ex. No. | Structure | Name |
|---|---|---|
| 78 | 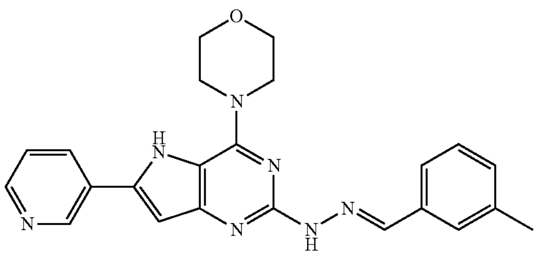 [SMILES: Cc1cccc(/C=N/Nc2nc(N3CCOCC3)c3[nH]c(-c4cccnc4)cc3n2)c1] | 4-morpholino-N-[(E)-m-tolylmethyleneamino]-6-(3-pyridyl)-5H-pyrrolo[3,2-d]pyrimidin-2-amine |
| 79 | 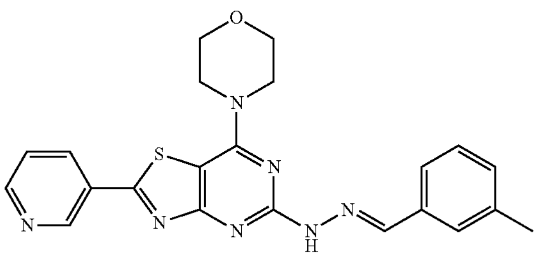 [SMILES: Cc1cccc(/C=N/Nc2nc(N3CCOCC3)c3oc(-c4cccnc4)nc3n2)c1] | 7-morpholino-N-[(E)-m-tolylmethyleneamino]-2-(3-pyridyl)thiazolo[4,5-d]pyrimidin-5-amine |
| 80 | 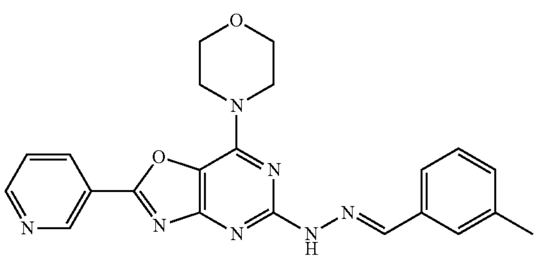 | 7-morpholino-N-[(E)-m-tolylmethyleneamino]-2-(3-pyridyl)oxazolo[4,5-d]pyrimidin-5-amine |
| 81 | 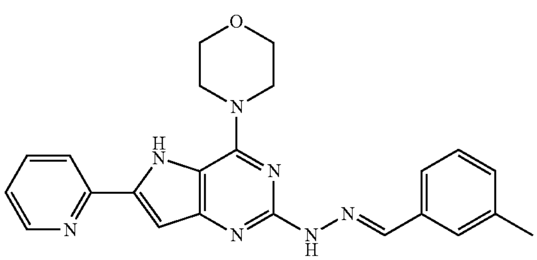 [SMILES: Cc1cccc(/C=N/Nc2nc(N3CCOCC3)c3[nH]c(-c4ccccn4)cc3n2)c1] | 4-morpholino-N-[(E)-m-tolylmethyleneamino]-6-(2-pyridyl)-5H-pyrrolo[3,2-d]pyrimidin-2-amine |
| 82 | 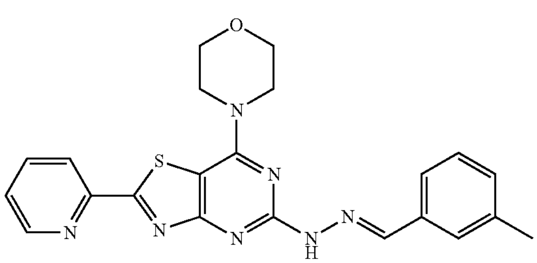 | 7-morpholino-N-[(E)-m-tolylmethyleneamino]-2-(2-pyridyl)thiazolo[4,5-d]pyrimidin-5-amine |
| 83 | 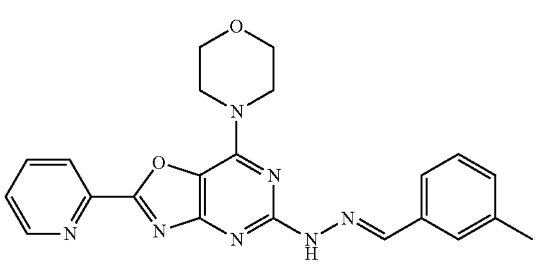 [SMILES: Cc1cccc(/C=N/Nc2nc(N3CCOCC3)c3oc(-c4ccccn4)nc3n2)c1] | 7-morpholino-N-[(E)-m-tolylmethyleneamino]-2-(2-pyridyl)oxazolo[4,5-d]pyrimidin-5-amine |

TABLE 1-continued

| Ex. No. | Structure | Name |
|---|---|---|
| 84 | 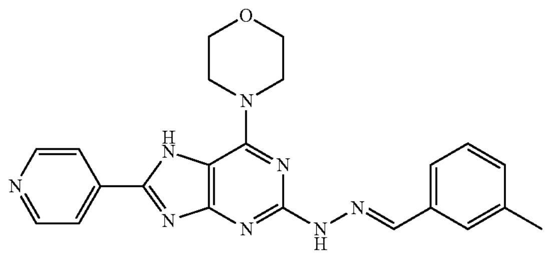 [SMILES: Cc1cccc(/C=N/Nc2nc(N3CCOCC3)c3[nH]c(-c4ccncc4)nc3n2)c1] | 6-morpholino-N-[(E)-m-tolylmethyleneamino]-8-(4-pyridyl)-7H-purin-2-amine |
| 85 | 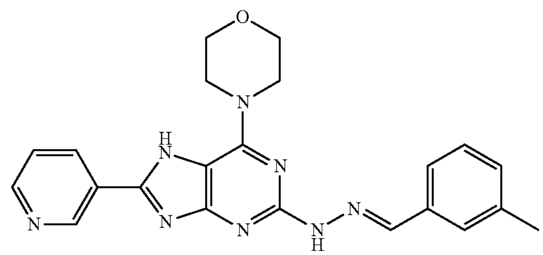 [SMILES: Cc1cccc(/C=N/Nc2nc(N3CCOCC3)c3[nH]c(-c4cccnc4)nc3n2)c1] | 6-morpholino-N-[(E)-m-tolylmethyleneamino]-8-(3-pyridyl)-7H-purin-2-amine |
| 86 | 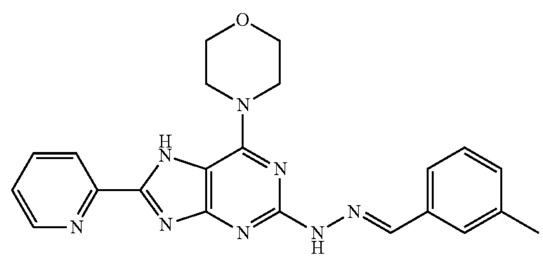 [SMILES: Cc1cccc(/C=N/Nc2nc(N3CCOCC3)c3[nH]c(-c4ccccn4)nc3n2)c1] | 6-morpholino-N-[(E)-m-tolylmethyleneamino]-8-(2-pyridyl)-7H-purin-2-amine |
| 87 | 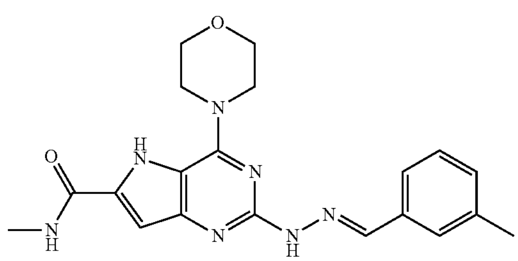 | N-methyl-4-morpholino-2-[(2E)-2-(m-tolylmethylene)hydrazino]-5H-pyrrolo[3,2-d]pyrimidine-6-carboxamide |
| 88 | 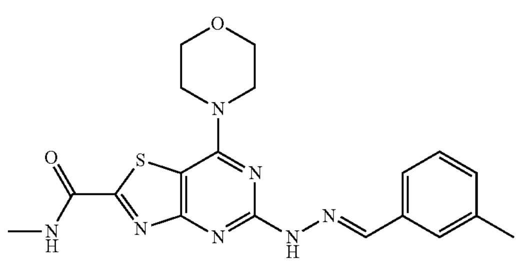 | N-methyl-7-morpholino-5-[(2E)-2-(m-tolylmethylene)hydrazino]thiazolo[4,5-d]pyrimidine-2-carboxamide |
| 89 | 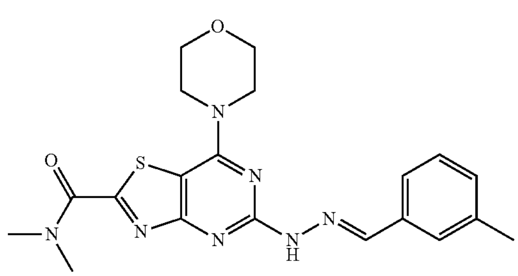 | N,N-dimethyl-7-morpholino-5-[(2E)-2-(m-tolylmethylene)hydrazino]thiazolo[4,5-d]pyrimidine-2-carboxamide |

TABLE 1-continued

| Ex. No. | Structure | Name |
|---|---|---|
| 90 | 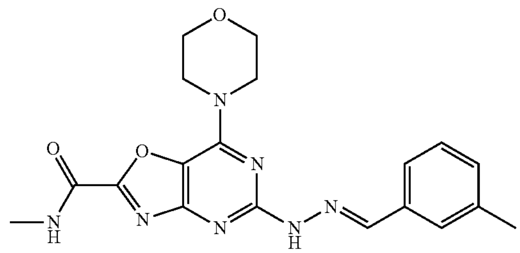 | N-methyl-7-morpholino-5-[(2E)-2-(m-tolylmethylene)hydrazino]oxazolo[4,5-d]pyrimidine-2-carboxamide |
| 91 | 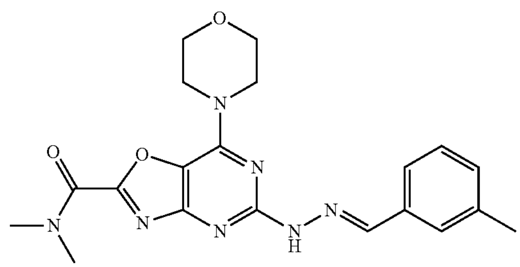 | N,N-dimethyl-7-morpholino-5-[(2E)-2-(m-tolylmethylene)hydrazino]oxazolo[4,5-d]pyrimidine-2-carboxamide |
| 92 | 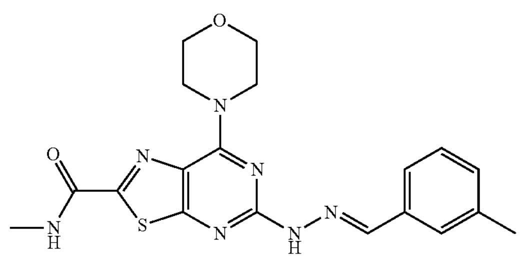 | N-methyl-7-morpholino-5-[(2E)-2-(m-tolylmethylene)hydrazino]thiazolo[5,4-d]pyrimidine-2-carboxamide |
| 93 | 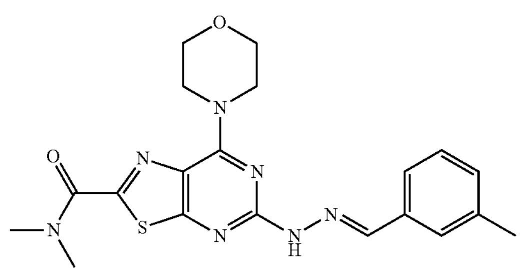 | N,N-dimethyl-7-morpholino-5-[(2E)-2-(m-tolylmethylene)hydrazino]thiazolo[5,4-d]pyrimidine-2-carboxamide |
| 94 | 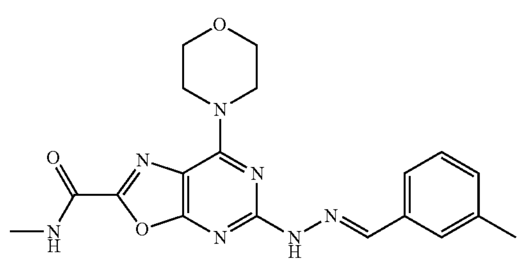 | N-methyl-7-morpholino-5-[(2E)-2-(m-tolylmethylene)hydrazino]oxazolo[5,4-d]pyrimidine-2-carboxamide |
| 95 | 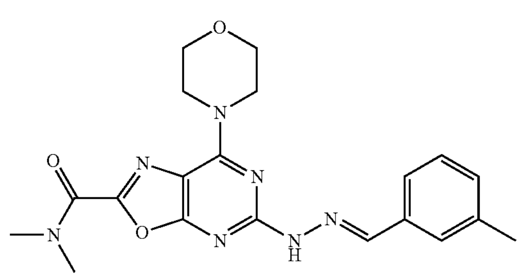 | N,N-dimethyl-7-morpholino-5-[(2E)-2-(m-tolylmethylene)hydrazino]oxazolo[5,4-d]pyrimidine-2-carboxamide |

TABLE 1-continued

| Ex. No. | Structure | Name |
|---|---|---|
| 96 | 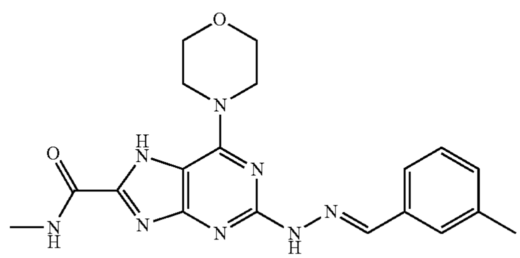 | N-methyl-6-morpholino-2-[(2E)-2-(m-tolylmethylene)hydrazino]-7H-purine-8-carboxamide |
| 97 | 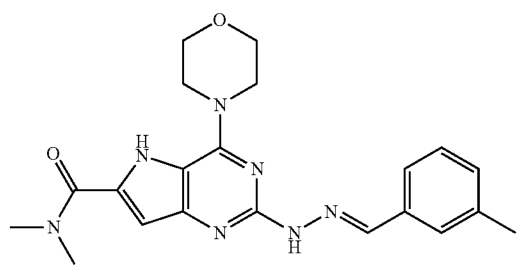 | N,N-dimethyl-4-morpholino-2-[(2E)-2-(m-tolylmethylene)hydrazino]-5H-pyrrolo[3,2-d]pyrimidine-6-carboxamide |
| 98 | 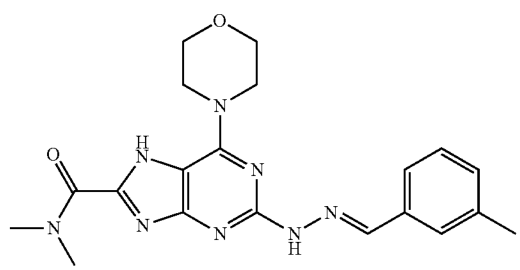 | N,N-dimethyl-6-morpholino-2-[(2E)-2-(m-tolylmethylene)hydrazino]-7H-purine-8-carboxamide |
| 99 | 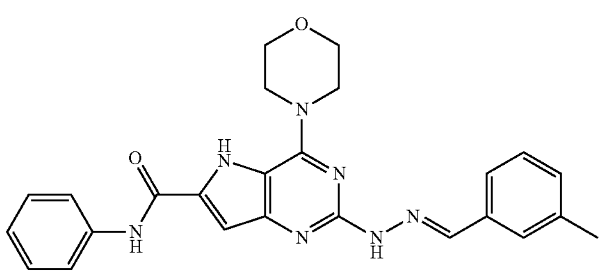 [SMILES: Cc1cccc(/C=N/Nc2nc(N3CCOCC3)c3[nH]c(C(=O)Nc4ccccc4)cc3n2)c1] | 4-morpholino-2-[(2E)-2-(m-tolylmethylene)hydrazino]-N-phenyl-5H-pyrrolo[3,2-d]pyrimidine-6-carboxamide |
| 100 | 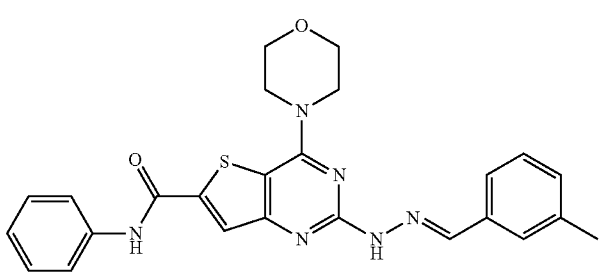 [SMILES: Cc1cccc(/C=N/Nc2nc(N3CCOCC3)c3sc(C(=O)Nc4ccccc4)cc3n2)c1] | 4-morpholino-2-[(2E)-2-(m-tolylmethylene)hydrazino]-N-phenyl-thieno[3,2-d]pyrimidine-6-carboxamide |

TABLE 1-continued

| Ex. No. | Structure | Name |
|---|---|---|
| 101 | 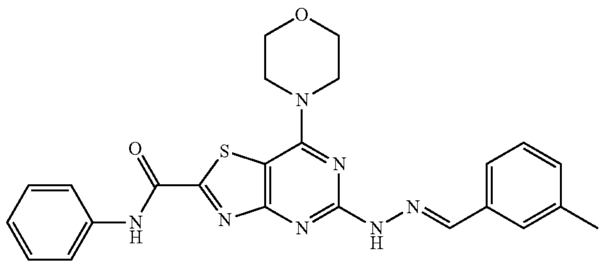 [SMILES: Cc1cccc(/C=N/Nc2nc(N3CCOCC3)c3sc(C(=O)Nc4ccccc4)nc3n2)c1] | 7-morpholino-5-[(2E)-2-(m-tolylmethylene)hydrazino]-N-phenyl-thiazolo[4,5-d]pyrimidine-2-carboxamide |
| 102 | 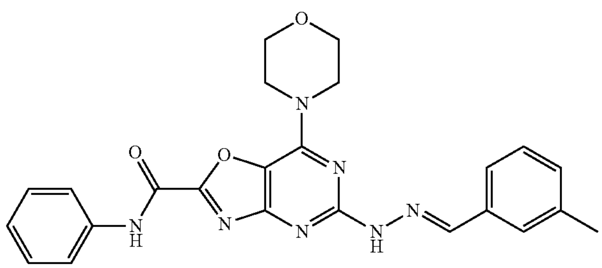 [SMILES: Cc1cccc(/C=N/Nc2nc(N3CCOCC3)c3oc(C(=O)Nc4ccccc4)nc3n2)c1] | 7-morpholino-5-[(2E)-2-(m-tolylmethylene)hydrazino]-N-phenyl-oxazolo[4,5-d]pyrimidine-2-carboxamide |
| 103 | 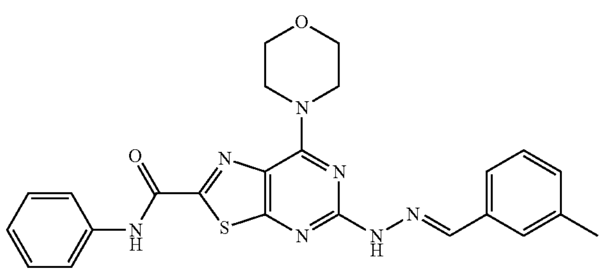 [SMILES: Cc1cccc(/C=N/Nc2nc(N3CCOCC3)c3nc(C(=O)Nc4ccccc4)sc3n2)c1] | 7-morpholino-5-[(2E)-2-(m-tolylmethylene)hydrazino]-N-phenyl-thiazolo[5,4-d]pyrimidine-2-carboxamide |
| 104 | 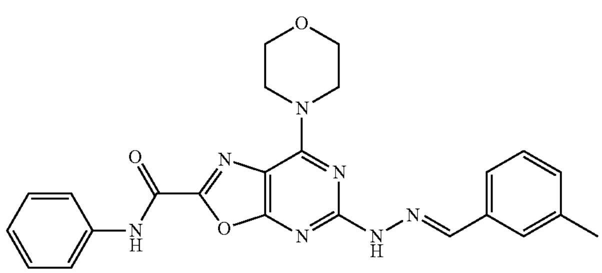 [SMILES: Cc1cccc(/C=N/Nc2nc(N3CCOCC3)c3nc(C(=O)Nc4ccccc4)oc3n2)c1] | 7-morpholino-5-[(2E)-2-(m-tolylmethylene)hydrazino]-N-phenyl-oxazolo[5,4-d]pyrimidine-2-carboxamide |
| 105 | 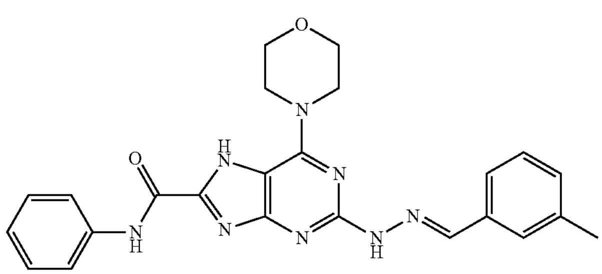 [SMILES: Cc1cccc(/C=N/Nc2nc(N3CCOCC3)c3[nH]c(C(=O)Nc4ccccc4)nc3n2)c1] | 6-morpholino-2-[(2E)-2-(m-tolylmethylene)hydrazino]-N-phenyl-7H-purine-8-carboxamide |

TABLE 1-continued

| Ex. No. | Structure | Name |
|---|---|---|
| 106 | 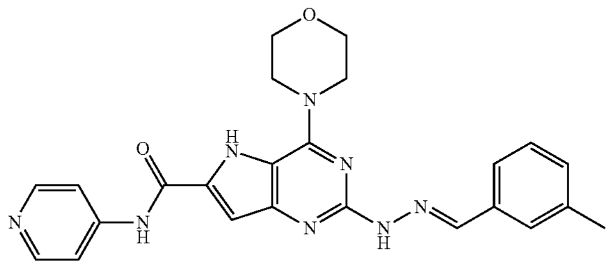 [SMILES: Cc1cccc(/C=N/Nc2nc(N3CCOCC3)c3[nH]c(C(=O)Nc4ccncc4)cc3n2)c1] | 4-morpholino-2-[(2E)-2-(m-tolylmethylene)hydrazino]-N-(4-pyridyl)-5H-pyrrolo[3,2-d]pyrimidine-6-carboxamide |
| 107 | 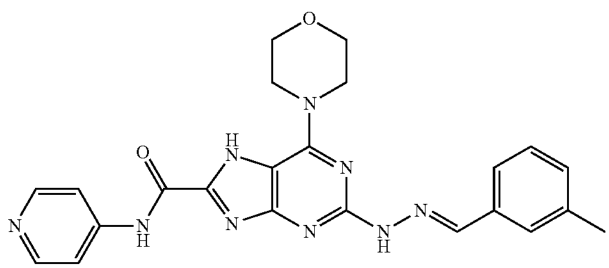 [SMILES: Cc1cccc(/C=N/Nc2nc(N3CCOCC3)c3[nH]c(C(=O)Nc4ccncc4)nc3n2)c1] | 6-morpholino-2-[(2E)-2-(m-tolylmethylene)hydrazino]-N-(4-pyridyl)-7H-purine-8-carboxamide |
| 108 | 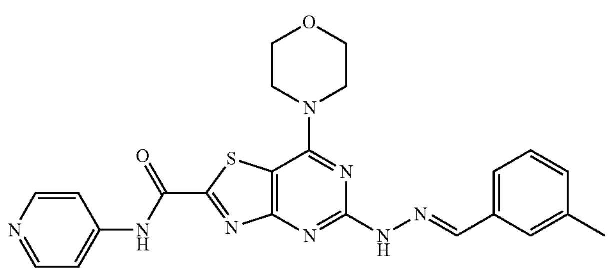 [SMILES: Cc1cccc(/C=N/Nc2nc(N3CCOCC3)c3sc(C(=O)Nc4ccncc4)nc3n2)c1] | 7-morpholino-5-[(2E)-2-(m-tolylmethylene)hydrazino]-N-(4-pyridyl)thiazolo[4,5-d]pyrimidine-2-carboxamide |
| 109 | 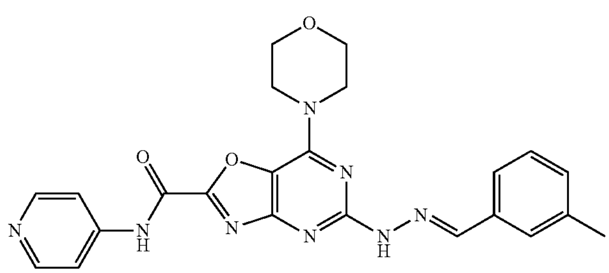 [SMILES: Cc1cccc(/C=N/Nc2nc(N3CCOCC3)c3oc(C(=O)Nc4ccncc4)nc3n2)c1] | 7-morpholino-5-[(2E)-2-(m-tolylmethylene)hydrazino]-N-(4-pyridyl)oxazolo[4,5-d]pyrimidine-2-carboxamide |
| 110 | 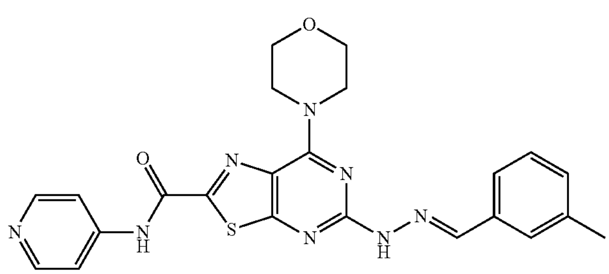 [SMILES: Cc1cccc(/C=N/Nc2nc(N3CCOCC3)c3nc(C(=O)Nc4ccncc4)sc3n2)c1] | 7-morpholino-5-[(2E)-2-(m-tolylmethylene)hydrazino]-N-(4-pyridyl)thiazolo[5,4-d]pyrimidine-2-carboxamide |

TABLE 1-continued

| Ex. No. | Structure | Name |
|---|---|---|
| 111 | 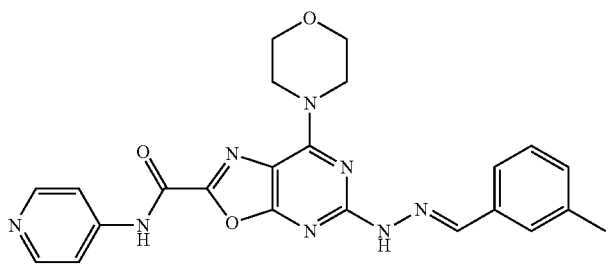 [SMILES: Cc1cccc(/C=N/Nc2nc(N3CCOCC3)c3nc(C(=O)Nc4ccncc4)oc3n2)c1] | 7-morpholino-5-[(2E)-2-(m-tolylmethylene)hydrazino]-N-(4-pyridyl)oxazolo[5,4-d]pyrimidine-2-carboxamide |
| 112 | 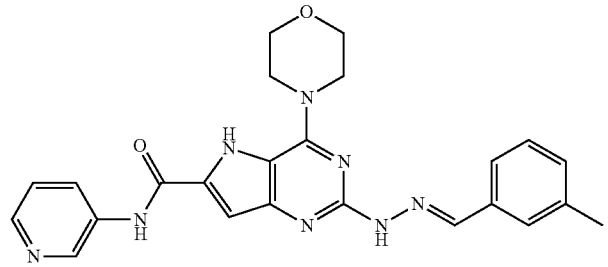 [SMILES: Cc1cccc(/C=N/Nc2nc(N3CCOCC3)c3[nH]c(C(=O)Nc4cccnc4)cc3n2)c1] | 4-morpholino-2-[(2E)-2-(m-tolylmethylene)hydrazino]-N-(3-pyridyl)-5H-pyrrolo[3,2-d]pyrimidine-6-carboxamide |
| 113 | 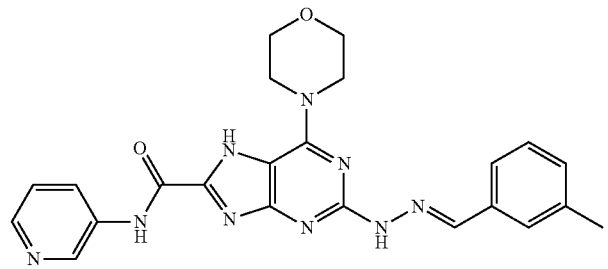 [SMILES: Cc1cccc(/C=N/Nc2nc(N3CCOCC3)c3[nH]c(C(=O)Nc4cccnc4)nc3n2)c1] | 6-morpholino-2-[(2E)-2-(m-tolylmethylene)hydrazino]-N-(3-pyridyl)-7H-purine-8-carboxamide |
| 114 | 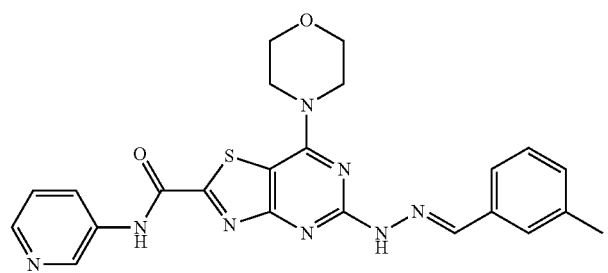 | 7-morpholino-5-[(2E)-2-(m-tolylmethylene)hydrazino]-N-(3-pyridyl)thiazolo[4,5-d]pyrimidine-2-carboxamide |
| 115 | 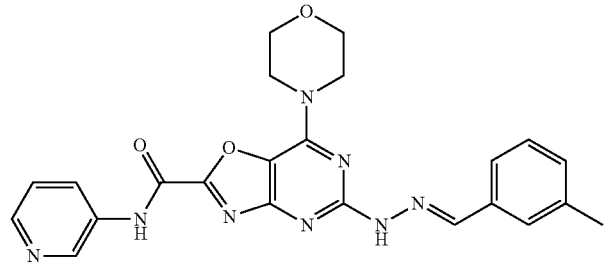 [SMILES: Cc1cccc(/C=N/Nc2nc(N3CCOCC3)c3oc(C(=O)Nc4cccnc4)nc3n2)c1] | 7-morpholino-5-[(2E)-2-(m-tolylmethylene)hydrazino]-N-(3-pyridyl)oxazolo[4,5-d]pyrimidine-2-carboxamide |

TABLE 1-continued

| Ex. No. | Structure | Name |
|---|---|---|
| 116 | 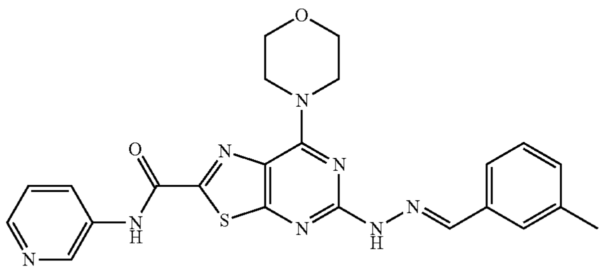 [SMILES: Cc1cccc(/C=N/Nc2nc(N3CCOCC3)c3nc(C(=O)Nc4cccnc4)sc3n2)c1] | 7-morpholino-5-[(2E)-2-(m-tolylmethylene)hydrazino]-N-(3-pyridyl)thiazolo[5,4-d]pyrimidine-2-carboxamide |
| 117 | 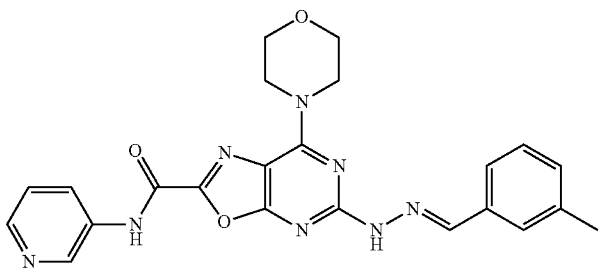 [SMILES: Cc1cccc(/C=N/Nc2nc(N3CCOCC3)c3nc(C(=O)Nc4cccnc4)oc3n2)c1] | 7-morpholino-5-[(2E)-2-(m-tolylmethylene)hydrazino]-N-(3-pyridyl)oxazolo[5,4-d]pyrimidine-2-carboxamide |
| 118 | 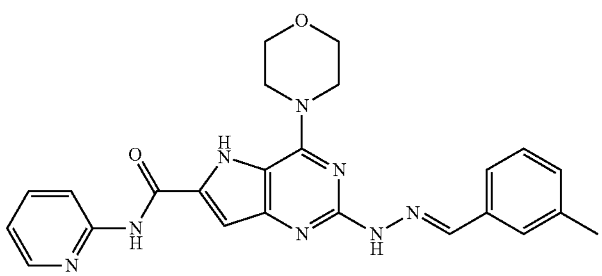 [SMILES: Cc1cccc(/C=N/Nc2nc(N3CCOCC3)c3[nH]c(C(=O)Nc4ccccn4)cc3n2)c1] | 4-morpholino-2-[(2E)-2-(m-tolylmethylene)hydrazino]-N-(2-pyridyl)-5H-pyrrolo[3,2-d]pyrimidine-6-carboxamide |
| 119 | 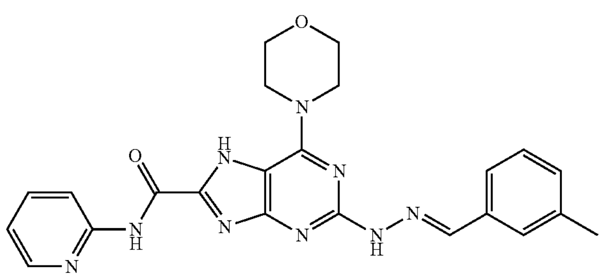 [SMILES: Cc1cccc(/C=N/Nc2nc(N3CCOCC3)c3[nH]c(C(=O)Nc4ccccn4)nc3n2)c1] | 6-morpholino-2-[(2E)-2-(m-tolylmethylene)hydrazino]-N-(2-pyridyl)-7H-purine-8-carboxamide |
| 120 | 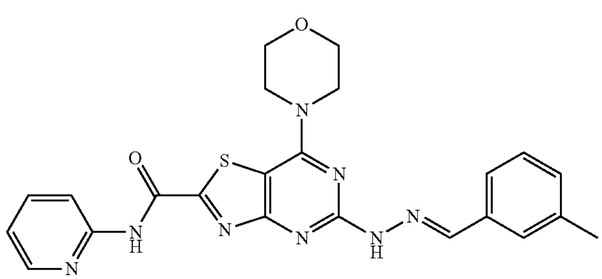 [SMILES: Cc1cccc(/C=N/Nc2nc(N3CCOCC3)c3sc(C(=O)Nc4ccccn4)nc3n2)c1] | 7-morpholino-5-[(2E)-2-(m-tolylmethylene)hydrazino]-N-(2-pyridyl)thiazolo[4,5-d]pyrimidine-2-carboxamide |

TABLE 1-continued

| Ex. No. | Structure | Name |
|---|---|---|
| 121 | 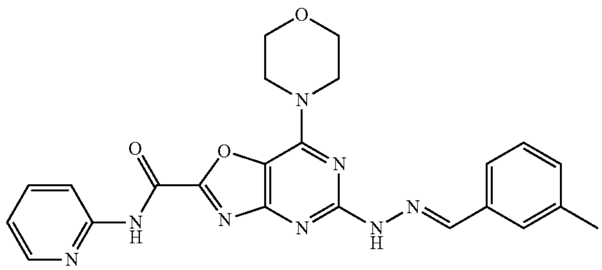 [SMILES: Cc1cccc(/C=N/Nc2nc(N3CCOCC3)c3oc(C(=O)Nc4ccccn4)nc3n2)c1] | 7-morpholino-5-[(2E)-2-(m-tolylmethylene)hydrazino]-N-(2-pyridyl)oxazolo[4,5-d]pyrimidine-2-carboxamide |
| 122 | 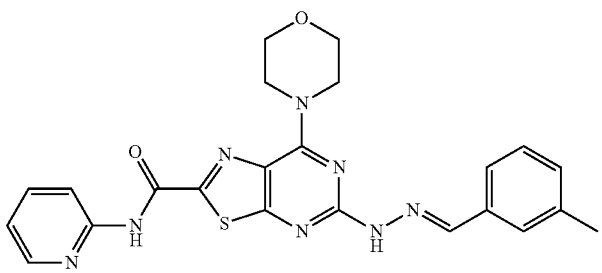 [SMILES: Cc1cccc(/C=N/Nc2nc(N3CCOCC3)c3nc(C(=O)Nc4ccccn4)sc3n2)c1] | 7-morpholino-5-[(2E)-2-(m-tolylmethylene)hydrazino]-N-(2-pyridyl)thiazolo[5,4-d]pyrimidine-2-carboxamide |
| 123 | 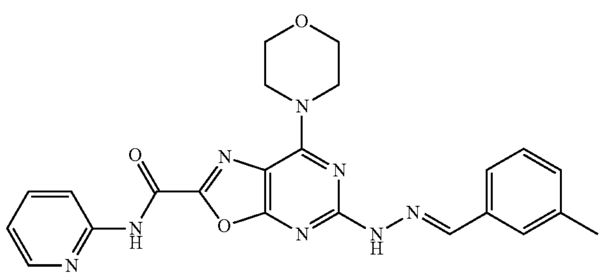 [SMILES: Cc1cccc(/C=N/Nc2nc(N3CCOCC3)c3nc(C(=O)Nc4ccccn4)oc3n2)c1] | 7-morpholino-5-[(2E)-2-(m-tolylmethylene)hydrazino]-N-(2-pyridyl)oxazolo[5,4-d]pyrimidine-2-carboxamide |
| 124 | 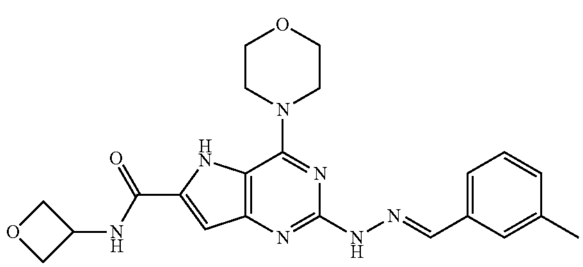 [SMILES: Cc1cccc(/C=N/Nc2nc(N3CCOCC3)c3[nH]c(C(=O)NC4COC4)cc3n2)c1] | 4-morpholino-2-[(2E)-2-(m-tolylmethylene)hydrazino]-N-(oxetan-3-yl)-5H-pyrrolo[3,2-d]pyrimidine-6-carboxamide |
| 125 | 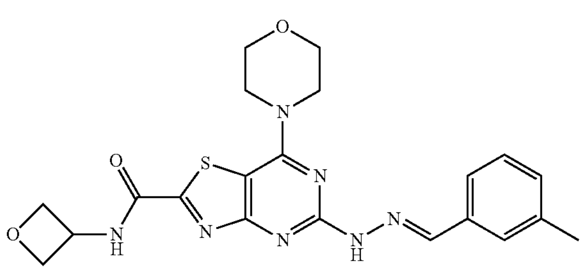 | 7-morpholino-5-[(2E)-2-(m-tolylmethylene)hydrazino]-N-(oxetan-3-yl)thiazolo[4,5-d]pyrimidine-2-carboxamide |

TABLE 1-continued

| Ex. No. | Structure | Name |
|---|---|---|
| 126 | 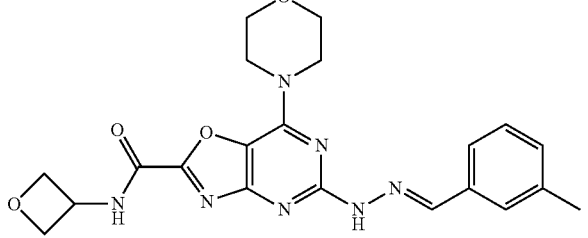 | 7-morpholino-5-[(2E)-2-(m-tolylmethylene)hydrazino]-N-(oxetan-3-yl)oxazolo[4,5-d]pyrimidine-2-carboxamide |
| 127 | 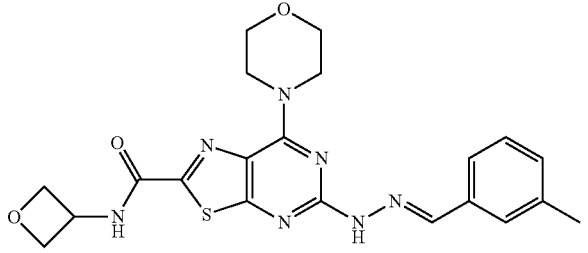 [SMILES: Cc1cccc(/C=N/Nc2nc(N3CCOCC3)c3nc(C(=O)NC4COC4)sc3n2)c1] | 7-morpholino-5-[(2E)-2-(m-tolylmethylene)hydrazino]-N-(oxetan-3-yl)thiazolo[5,4-d]pyrimidine-2-carboxamide |
| 128 | 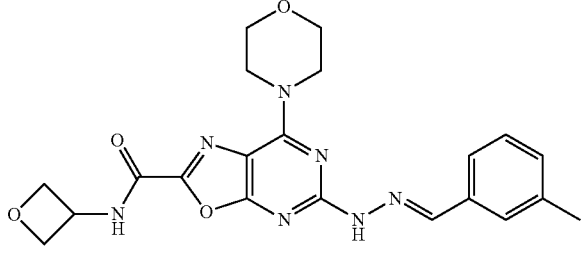 | 7-morpholino-5-[(2E)-2-(m-tolylmethylene)hydrazino]-N-(oxetan-3-yl)oxazolo[5,4-d]pyrimidine-2-carboxamide |
| 129 | 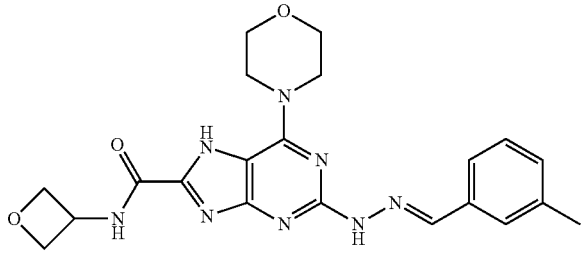 [SMILES: Cc1cccc(/C=N/Nc2nc(N3CCOCC3)c3[nH]c(C(=O)NC4COC4)nc3n2)c1] | 6-morpholino-2-[(2E)-2-(m-tolylmethylene)hydrazino]-N-(oxetan-3-yl)-7H-purine-8-carboxamide |
| 130 | 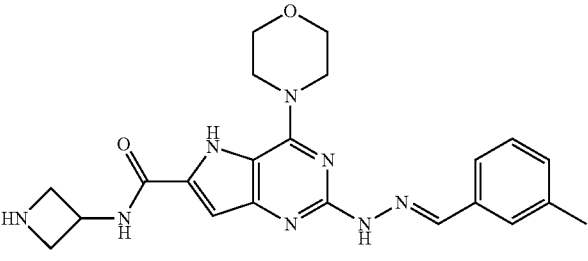 | N-(azetidin-3-yl)-4-morpholino-2-[(2E)-2-(m-tolylmethylene)hydrazino]-5H-pyrrolo[3,2-d]pyrimidine-6-carboxamide |
| 131 | 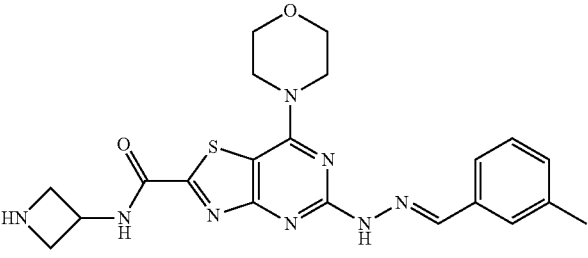 | N-(azetidin-3-yl)-7-morpholino-5-[(2E)-2-(m-tolylmethylene)hydrazino]thiazolo[4,5-d]pyrimidine-2-carboxamide |

TABLE 1-continued

| Ex. No. | Structure | Name |
|---|---|---|
| 132 | 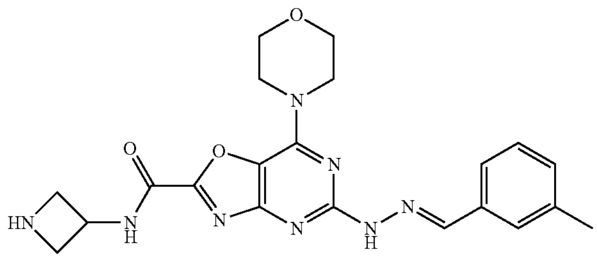 | N-(azetidin-3-yl)-7-morpholino-5-[(2E)-2-(m-tolylmethylene)hydrazino]oxazolo[4,5-d]pyrimidine-2-carboxamide |
| 133 | 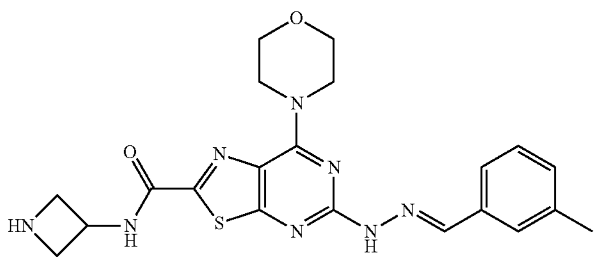 [SMILES: Cc1cccc(/C=N/Nc2nc(N3CCOCC3)c3nc(C(=O)NC4CNC4)sc3n2)c1] | N-(azetidin-3-yl)-7-morpholino-5-[(2E)-2-(m-tolylmethylene)hydrazino]thiazolo[5,4-d]pyrimidine-2-carboxamide |
| 134 | 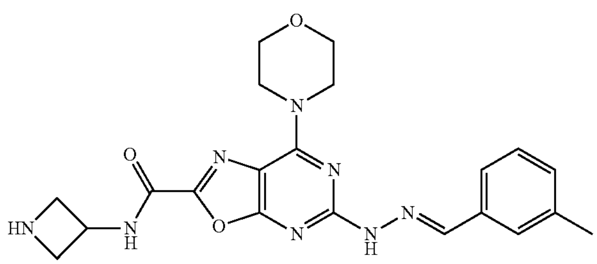 | N-(azetidin-3-yl)-7-morpholino-5-[(2E)-2-(m-tolylmethylene)hydrazino]oxazolo[5,4-d]pyrimidine-2-carboxamide |
| 135 | 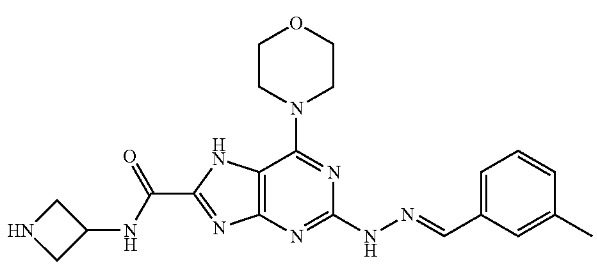 [SMILES: Cc1cccc(/C=N/Nc2nc(N3CCOCC3)c3[nH]c(C(=O)NC4CNC4)nc3n2)c1] | N-(azetidin-3-yl)-6-morpholino-2-[(2E)-2-(m-tolylmethylene)hydrazino]-7H-purine-8-carboxamide |
| 136 | 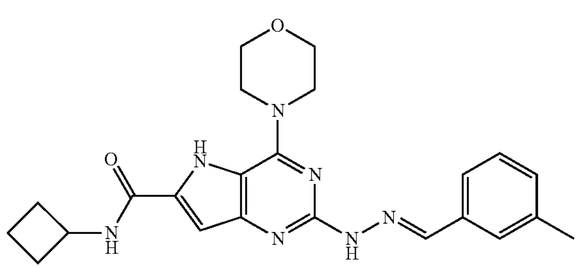 | N-cyclobutyl-4-morpholino-2-[(2E)-2-(m-tolylmethylene)hydrazino]-5H-pyrrolo[3,2-d]pyrimidine-6-carboxamide |
| 137 | 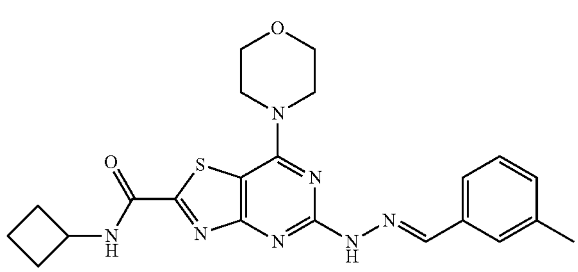 | N-cyclobutyl-7-morpholino-5-[(2E)-2-(m-tolylmethylene)hydrazino]thiazolo[4,5-d]pyrimidine-2-carboxamide |

TABLE 1-continued

| Ex. No. | Structure | Name |
|---|---|---|
| 138 | 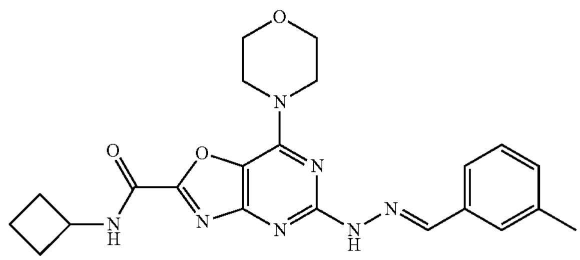 | N-cyclobutyl-7-morpholino-5-[(2E)-2-(m-tolylmethylene)hydrazino]oxazolo[4,5-d]pyrimidine-2-carboxamide |
| 139 | 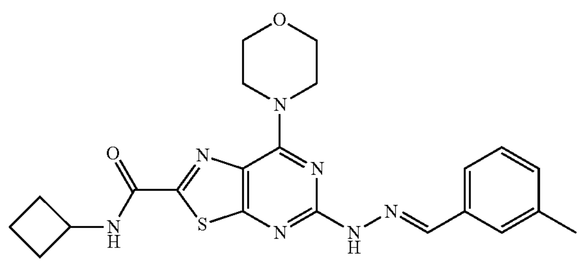 | N-cyclobutyl-7-morpholino-5-[(2E)-2-(m-tolylmethylene)hydrazino]thiazolo[5,4-d]pyrimidine-2-carboxamide |
| 140 | 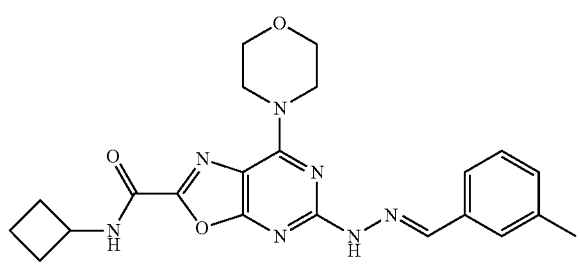 | N-cyclobutyl-7-morpholino-5-[(2E)-2-(m-tolylmethylene)hydrazino]oxazolo[5,4-d]pyrimidine-2-carboxamide |
| 141 | 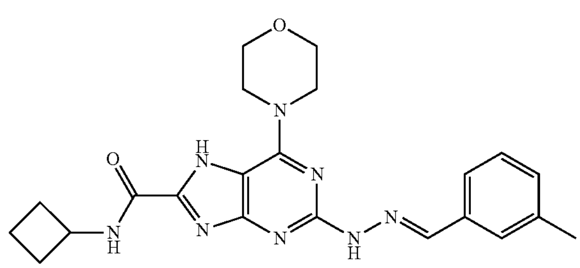 [SMILES: Cc1cccc(/C=N/Nc2nc(N3CCOCC3)c3[nH]c(C(=O)NC4CCC4)nc3n2)c1] | N-cyclobutyl-6-morpholino-2-[(2E)-2-(m-tolylmethylene)hydrazino]-7H-purine-8-carboxamide |
| 142 | 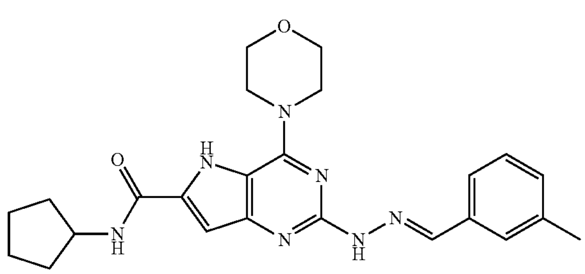 [SMILES: Cc1cccc(/C=N/Nc2nc(N3CCOCC3)c3[nH]c(C(=O)NC4CCCC4)cc3n2)c1] | N-cyclopentyl-4-morpholino-2-[(2E)-2-(m-tolylmethylene)hydrazino]-5H-pyrrolo[3,2-d]pyrimidine-6-carboxamide |

TABLE 1-continued

| Ex. No. | Structure | Name |
|---|---|---|
| 143 | 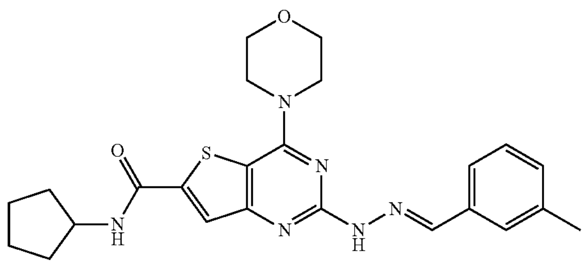 [SMILES: Cc1cccc(/C=N/Nc2nc(N3CCOCC3)c3sc(C(=O)NC4CCCC4)cc3n2)c1] | N-cyclopentyl-4-morpholino-2-[(2E)-2-(m-tolylmethylene)hydrazino]thieno[3,2-d]pyrimidine-6-carboxamide |
| 144 | 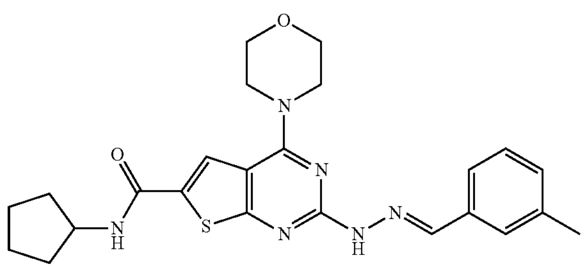 [SMILES: Cc1cccc(/C=N/Nc2nc(N3CCOCC3)c3cc(C(=O)NC4CCCC4)sc3n2)c1] | N-cyclopentyl-4-morpholino-2-[(2E)-2-(m-tolylmethylene)hydrazino]thieno[2,3-d]pyrimidine-6-carboxamide |
| 145 | 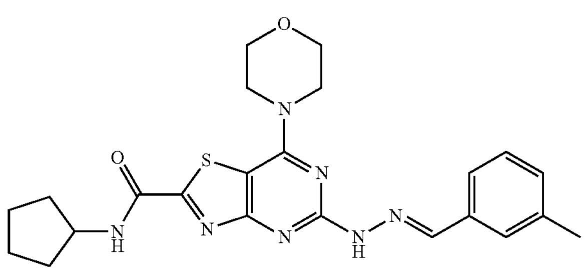 | N-cyclopentyl-7-morpholino-5-[(2E)-2-(m-tolylmethylene)hydrazino]thiazolo[4,5-d]pyrimidine-2-carboxamide |
| 146 | 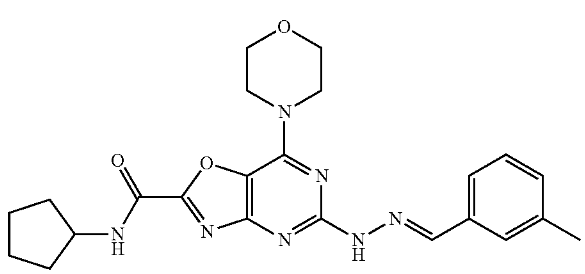 [SMILES: Cc1cccc(/C=N/Nc2nc(N3CCOCC3)c3oc(C(=O)NC4CCCC4)nc3n2)c1] | N-cyclopentyl-7-morpholino-5-[(2E)-2-(m-tolylmethylene)hydrazino]oxazolo[4,5-d]pyrimidine-2-carboxamide |
| 147 | 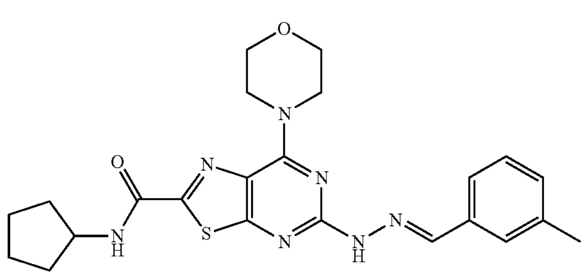 | N-cyclopentyl-7-morpholino-5-[(2E)-2-(m-tolylmethylene)hydrazino]thiazolo[5,4-d]pyrimidine-2-carboxamide |

TABLE 1-continued

| Ex. No. | Structure | Name |
|---|---|---|
| 148 | 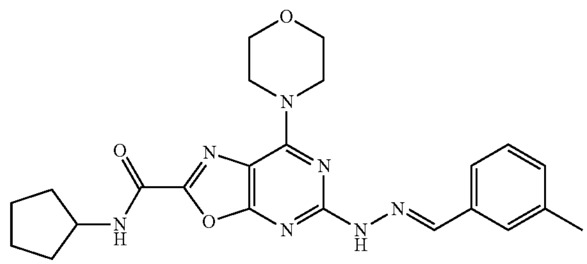 [SMILES: Cc1cccc(/C=N/Nc2nc(N3CCOCC3)c3nc(C(=O)NC4CCCC4)oc3n2)c1] | N-cyclopentyl-7-morpholino-5-[(2E)-2-(m-tolylmethylene)hydrazino]oxazolo[5,4-d]pyrimidine-2-carboxamide |
| 149 | 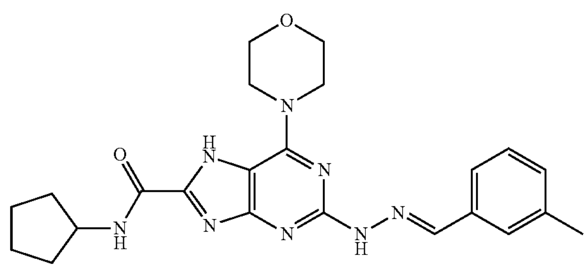 [SMILES: Cc1cccc(/C=N/Nc2nc(N3CCOCC3)c3[nH]c(C(=O)NC4CCCC4)nc3n2)c1] | N-cyclopentyl-6-morpholino-2-[(2E)-2-(m-tolylmethylene)hydrazino]-7H-purine-8-carboxamide |
| 150 | 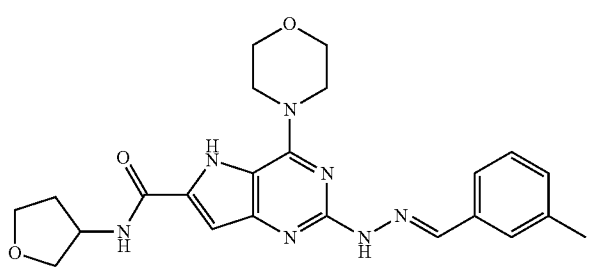 [SMILES: Cc1cccc(/C=N/Nc2nc(N3CCOCC3)c3[nH]c(C(=O)NC4CCOC4)cc3n2)c1] | 4-morpholino-2-[(2E)-2-(m-tolylmethylene)hydrazino]-N-tetrahydrofuran-3-yl-5H-pyrrolo[3,2-d]pyrimidine-6-carboxamide |
| 151 | 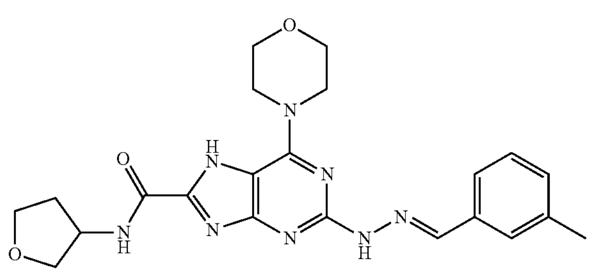 [SMILES: Cc1cccc(/C=N/Nc2nc(N3CCOCC3)c3[nH]c(C(=O)NC4CCOC4)nc3n2)c1] | 6-morpholino-2-[(2E)-2-(m-tolylmethylene)hydrazino]-N-tetrahydrofuran-3-yl-7H-purine-8-carboxamide |
| 152 | 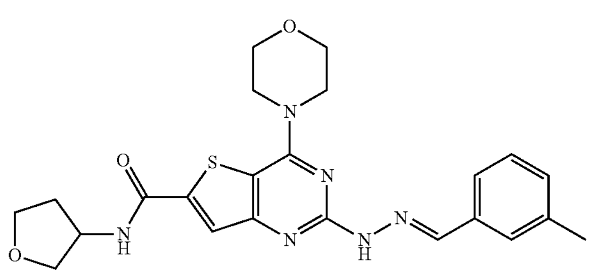 | 4-morpholino-2-[(2E)-2-(m-tolylmethylene)hydrazino]-N-tetrahydrofuran-3-yl-thieno[3,2-d]pyrimidine-6-carboxamide |

TABLE 1-continued

| Ex. No. | Structure | Name |
|---|---|---|
| 153 | 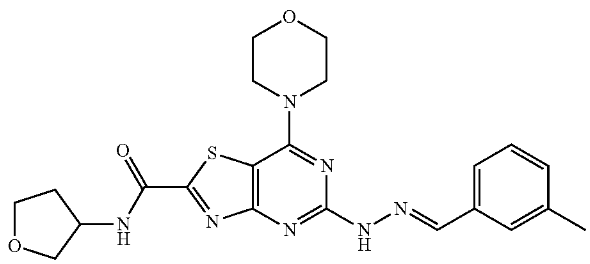 [SMILES: Cc1cccc(/C=N/Nc2nc(N3CCOCC3)c3sc(C(=O)NC4CCOC4)nc3n2)c1] | 7-morpholino-5-[(2E)-2-(m-tolylmethylene)hydrazino]-N-tetrahydrofuran-3-yl-thiazolo[4,5-d]pyrimidine-2-carboxamide |
| 154 | 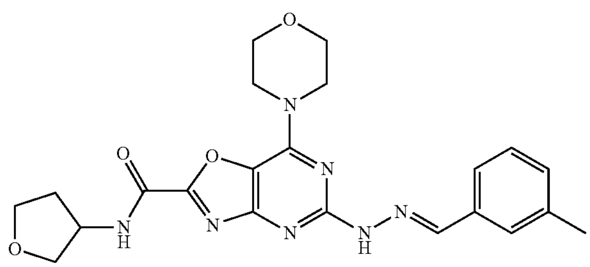 [SMILES: Cc1cccc(/C=N/Nc2nc(N3CCOCC3)c3oc(C(=O)NC4CCOC4)nc3n2)c1] | 7-morpholino-5-[(2E)-2-(m-tolylmethylene)hydrazino]-N-tetrahydrofuran-3-yl-oxazolo[4,5-d]pyrimidine-2-carboxamide |
| 155 | 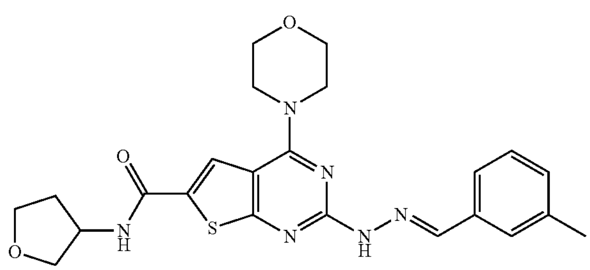 | 4-morpholino-2-[(2E)-2-(m-tolylmethylene)hydrazino]-N-tetrahydrofuran-3-yl-thieno[2,3-d]pyrimidine-6-carboxamide |
| 156 | 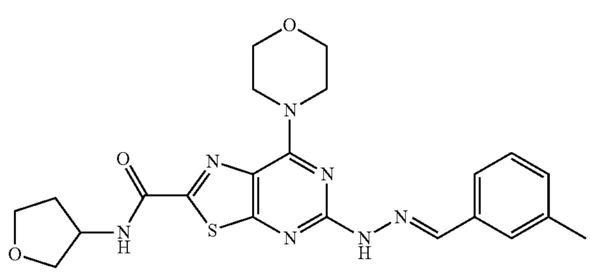 [SMILES: Cc1cccc(/C=N/Nc2nc(N3CCOCC3)c3nc(C(=O)NC4CCOC4)oc3n2)c1] | 7-morpholino-5-[(2E)-2-(m-tolylmethylene)hydrazino]-N-tetrahydrofuran-3-yl-thiazolo[5,4-d]pyrimidine-2-carboxamide |
| 157 | 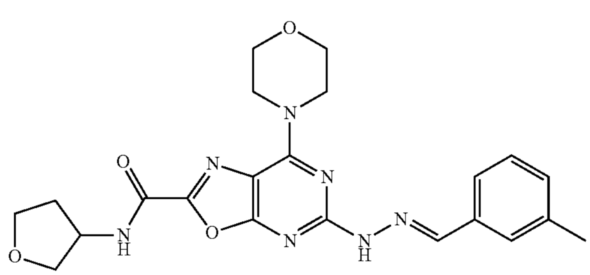 | 7-morpholino-5-[(2E)-2-(m-tolylmethylene)hydrazino]-N-tetrahydrofuran-3-yl-oxazolo[5,4-d]pyrimidine-2-carboxamide |

TABLE 1-continued

| Ex. No. | Structure | Name |
|---|---|---|
| 158 | 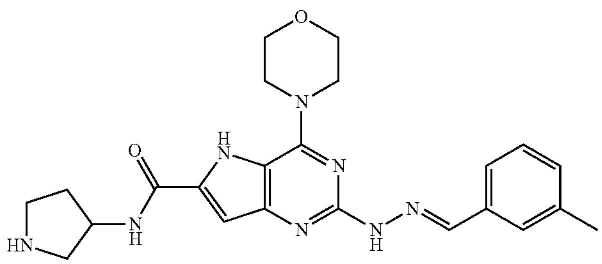 | 4-morpholino-2-[(2E)-2-(m-tolylmethylene)hydrazino]-N-pyrrolidin-3-yl-5H-pyrrolo[3,2-d]pyrimidine-6-carboxamide |
| 159 | 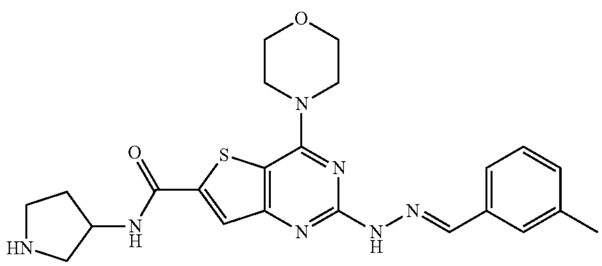 | 4-morpholino-2-[(2E)-2-(m-tolylmethylene)hydrazino]-N-pyrrolidin-3-yl-thieno[3,2-d]pyrimidine-6-carboxamide |
| 160 | 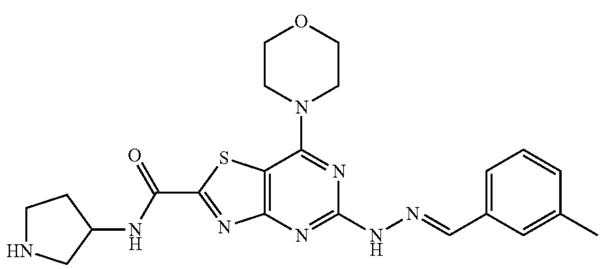 | 7-morpholino-5-[(2E)-2-(m-tolylmethylene)hydrazino]-N-pyrrolidin-3-yl)-thiazolo[4,5-d]pyrimidine-2-carboxamide |
| 161 | 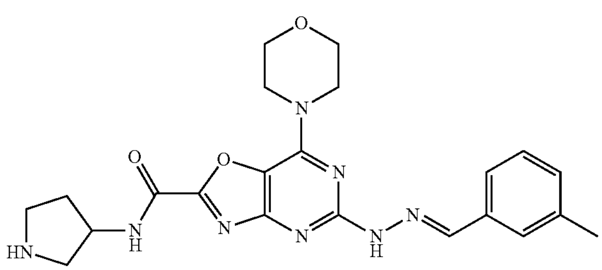 | 7-morpholino-5-[(2E)-2-(m-tolylmethylene)hydrazino]-N-pyrrolidin-3-yl-oxazolo[4,5-d]pyrimidine-2-carboxamide |
| 162 | 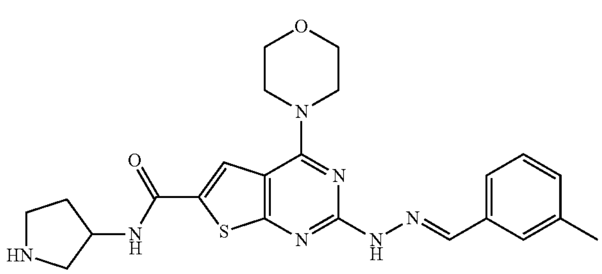 [SMILES: Cc1cccc(/C=N/Nc2nc(N3CCOCC3)c3cc(C(=O)NC4CCNC4)sc3n2)c1] | 4-morpholino-2-[(2E)-2-(m-tolylmethylene)hydrazino]-N-pyrrolidin-3-yl-thieno[2,3-d]pyrimidine-6-carboxamide |

TABLE 1-continued

| Ex. No. | Structure | Name |
|---|---|---|
| 163 | 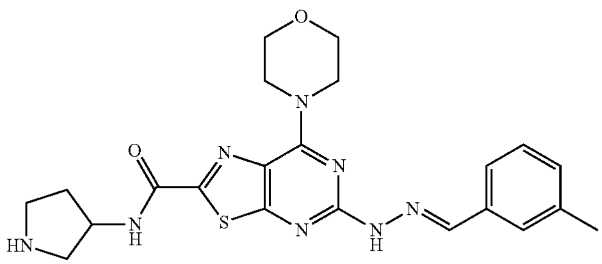 | 7-morpholino-5-[(2E)-2-(m-tolylmethylene)hydrazino]-N-pyrrolidin-3-yl-thiazolo[5,4-d]pyrimidine-2-carboxamide |
| 164 | 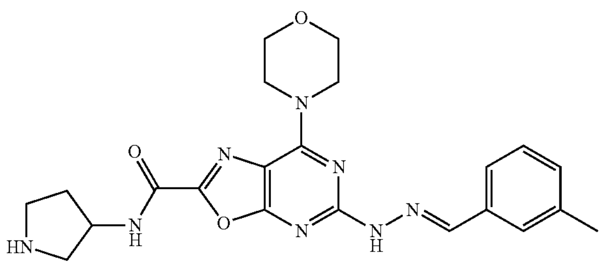 | 7-morpholino-5-[(2E)-2-(m-tolylmethylene)hydrazino]-N-pyrrolidin-3-yl-oxazolo[5,4-d]pyrimidine-2-carboxamide |
| 165 | 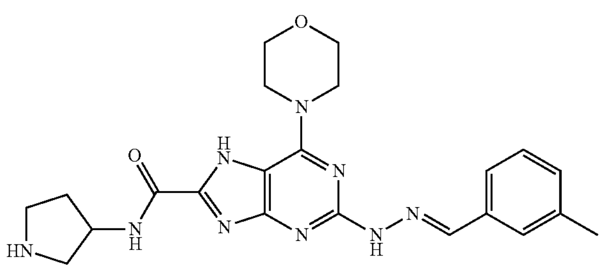 | 6-morpholino-2-[(2E)-2-(m-tolylmethylene)hydrazino]-N-pyrrolidin-3-yl)-7H-purine-8-carboxamide |
| 166 | 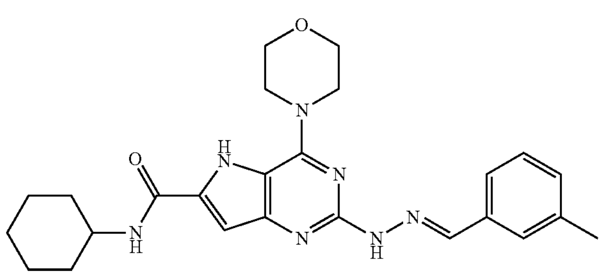 [SMILES: Cc1cccc(/C=N/Nc2nc(N3CCOCC3)c3[nH]c(C(=O)NC4CCCCC4)cc3n2)c1] | N-cyclohexyl-4-morpholino-2-[(2E)-2-(m-tolylmethylene)hydrazino]-5H-pyrrolo[3,2-d]pyrimidine-6-carboxamide |
| 167 | 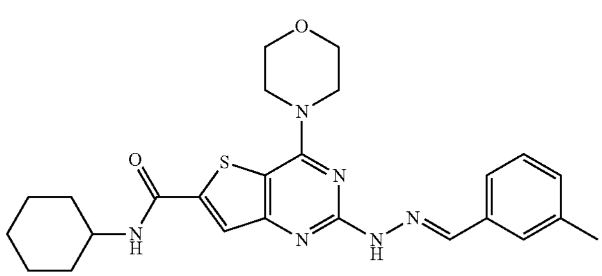 | N-cyclohexyl-4-moprholino-2-[(2E)-2-(m-tolylmethylene)hydrazino]thieno[3,2-d]pyrimidine-6-carboxamide |

TABLE 1-continued

| Ex. No. | Structure | Name |
|---|---|---|
| 168 | 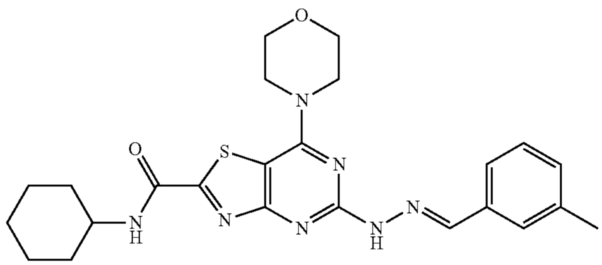 | N-cyclohexyl-7-morpholino-5-[(2E)-2-(m-tolylmethylene)hydrazino]thiazolo[4,5-d]pyrimidine-2-carboxamide |
| 169 | 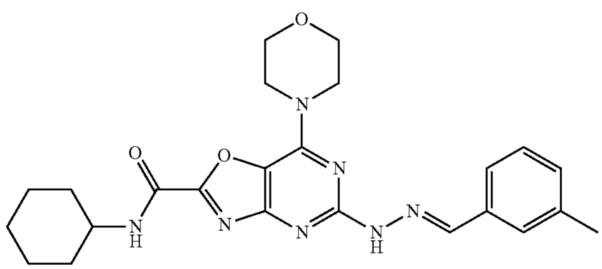 [SMILES: Cc1cccc(/C=N/Nc2nc(N3CCOCC3)c3oc(C(=O)NC4CCCCC4)nc3n2)c1] | N-cyclohexyl-7-morpholino-5-[(2E)-2-(m-tolylmethylene)hydrazino]oxazolo[4,5-d]pyrimidine-2-carboxamide |
| 170 | 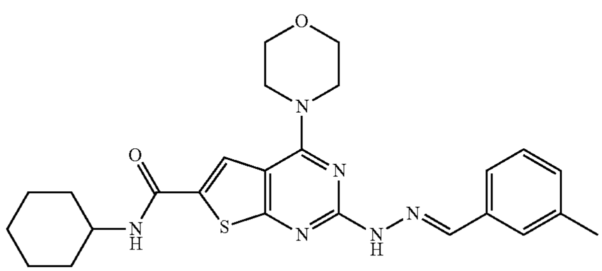 [SMILES: Cc1cccc(/C=N/Nc2nc(N3CCOCC3)c3cc(C(=O)NC4CCCCC4)sc3n2)c1] | N-cyclohexyl-4-morpholino-2-[(2E)-2-(m-tolylmethylene)hydrazino]thieno[2,3-d]pyrimidine-6-carboxamide |
| 171 | 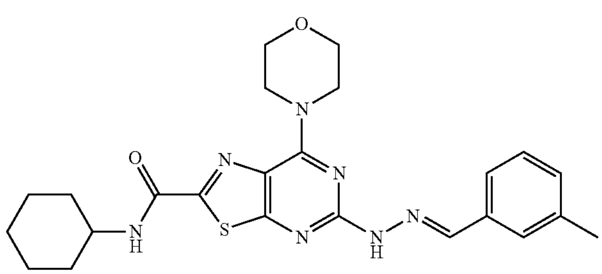 [SMILES: Cc1cccc(/C=N/Nc2nc(N3CCOCC3)c3nc(C(=O)NC4CCCCC4)sc3n2)c1] | N-cyclohexyl-7-morpholino-5-[(2E)-2-(m-tolylmethylene)hydrazino]thiazolo[5,4-d]pyrimidine-2-carboxamide |
| 172 | 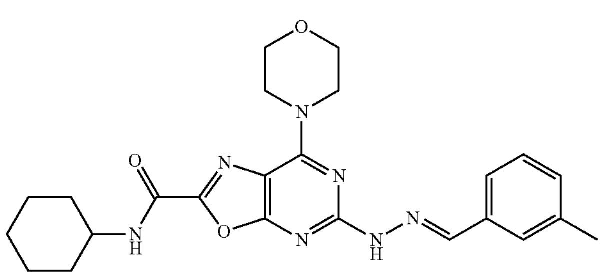 [SMILES: Cc1cccc(/C=N/Nc2nc(N3CCOCC3)c3nc(C(=O)NC4CCCCC4)oc3n2)c1] | N-cyclohexyl-7-morpholino-5-[(2E)-2-(m-tolylmethylene)hydrazino]oxazolo[5,4-d]pyrimidine-2-carboxamide |

TABLE 1-continued

| Ex. No. | Structure | Name |
|---|---|---|
| 173 | 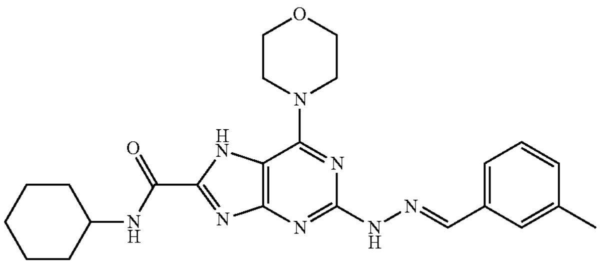 [SMILES: Cc1cccc(/C=N/Nc2nc(N3CCOCC3)c3[nH]c(C(=O)NC4CCCCC4)nc3n2)c1] | N-cyclohexyl-6-morpholino-2-[(2E)-2-(m-tolylmethylene)hydrazino]-7H-purine-8-carboxamide |
| 174 | 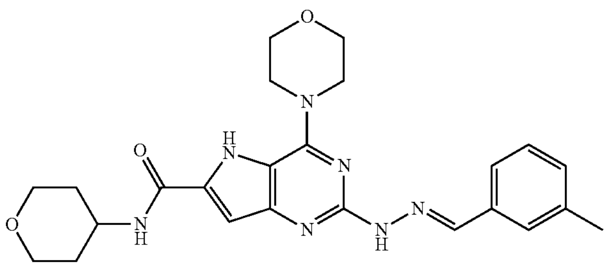 [SMILES: Cc1cccc(/C=N/Nc2nc(N3CCOCC3)c3[nH]c(C(=O)NC4CCOCC4)cc3n2)c1] | 4-morpholino-2-[(2E)-2-(m-tolylmethylene)hydrazino]-N-tetrahydropyran-4-yl-5H-pyrrolo[3,2-d]pyrimidine-6-carboxamide |
| 175 | 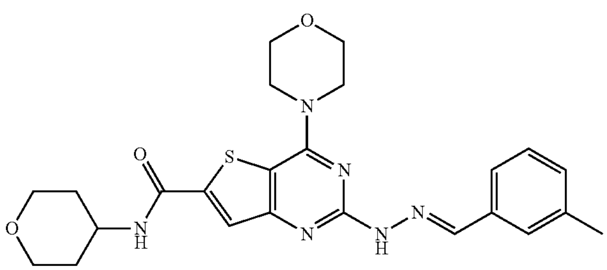 | 4-morpholino-2-[(2E)-2-(m-tolylmethylene)hydrazino]-N-tetrahydropyran-4-yl-thieno[3,2-d]pyrimidine-6-carboxamide |
| 176 | 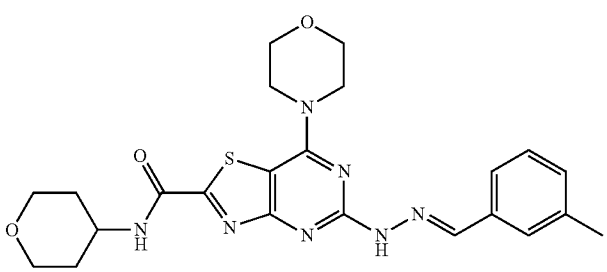 [SMILES: Cc1cccc(/C=N/Nc2nc(N3CCOCC3)c3sc(C(=O)NC4CCOCC4)nc3n2)c1] | 7-morpholino-5-[(2E)-2-(m-tolylmethylene)hydrazino]-N-tetrahydropyran-4-yl-thiazolo[4,5-d]pyrimidine-2-carboxamide |
| 177 | 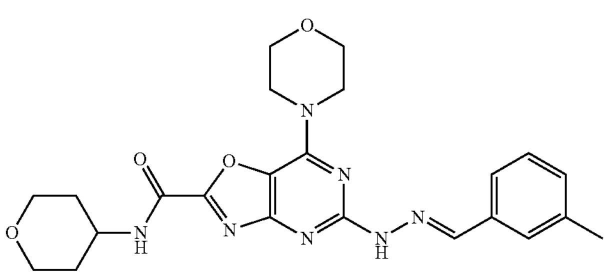 [SMILES: Cc1cccc(/C=N/Nc2nc(N3CCOCC3)c3oc(C(=O)NC4CCOCC4)nc3n2)c1] | 7-morpholino-5-[(2E)-2-(m-tolylmethylene)hydrazino]-N-tetrahydropyran-4-yl-oxazolo[4,5-d]pyrimidine-2-carboxamide |

TABLE 1-continued

| Ex. No. | Structure | Name |
|---|---|---|
| 178 | 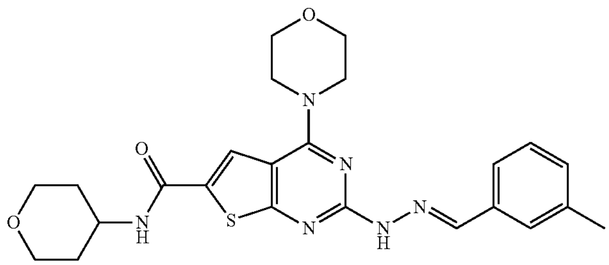 | 4-morpholino-2-[(2E)-2-(m-tolylmethylene)hydrazino]-N-tetrahydropyran-4-yl-thieno[2,3-d]pyrimidine-6-carboxamide |
| 179 | 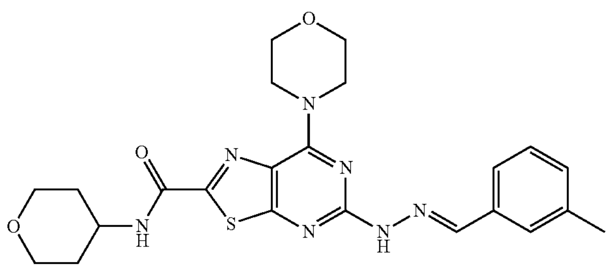 [SMILES: Cc1cccc(/C=N/Nc2nc(N3CCOCC3)c3nc(C(=O)NC4CCOCC4)sc3n2)c1] | 7-morpholino-5-[(2E)-2-(m-tolylmethylene)hydrazino]-N-tetrahydropyran-4-yl-thiazolo[5,4-d]pyrimidine-2-carboxamide |
| 180 | 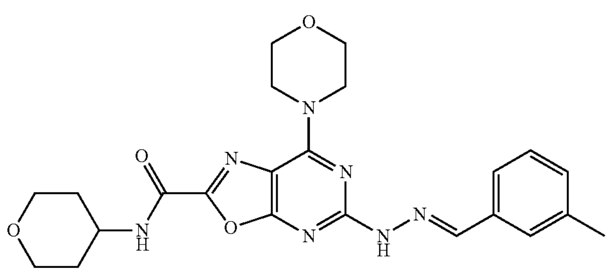 [SMILES: Cc1cccc(/C=N/Nc2nc(N3CCOCC3)c3nc(C(=O)NC4CCOCC4)oc3n2)c1] | 7-morpholino-5-[(2E)-2-(m-tolylmethylene)hydrazino]-N-tetrahydropyran-4-yl-oxazolo[5,4-d]pyrimidine-2-carboxamide |
| 181 | 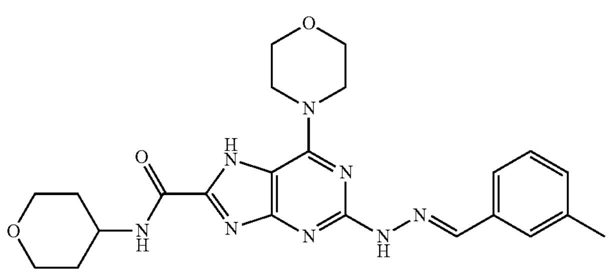 [SMILES: Cc1cccc(/C=N/Nc2nc(N3CCOCC3)c3[nH]c(C(=O)NC4CCOCC4)nc3n2)c1] | 6-morpholino-2-[(2E)-2-(m-tolylmethylene)hydrazino]-N-tetrahydropyran-4-yl-7H-purine-8-carboxamide |
| 182 | 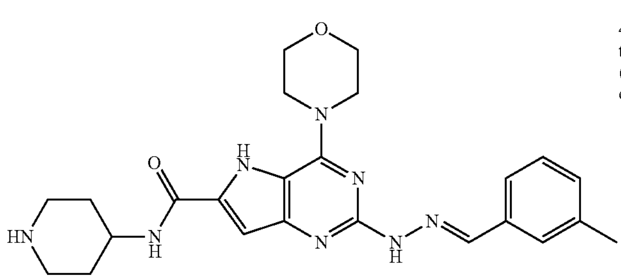 [SMILES: Cc1cccc(/C=N/Nc2nc(N3CCOCC3)c3[nH]c(C(=O)NC4CCNCC4)cc3n2)c1] | 4-morpholino-2-[(2E)-2-(m-tolylmethylene)hydrazino]-N-(4-piperidyl)-5H-pyrrolo[3,2-d]pyrimidine-6-carboxamide |

TABLE 1-continued

| Ex. No. | Structure | Name |
|---|---|---|
| 183 | 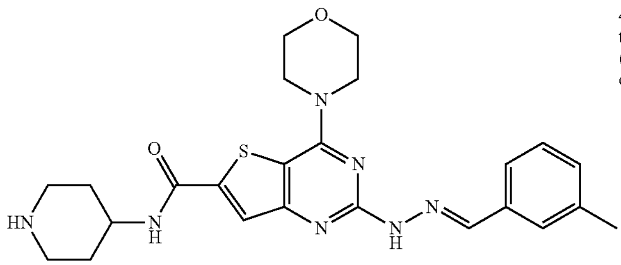 [SMILES: Cc1cccc(/C=N/Nc2nc(N3CCOCC3)c3sc(C(=O)NC4CCNCC4)cc3n2)c1] | 4-morpholino-2-[(2E)-2-(m-tolylmethylene)hydrazino]-N-(4-piperidyl)thieno[3,2-d]pyrimidine-6-carboxamide |
| 184 | 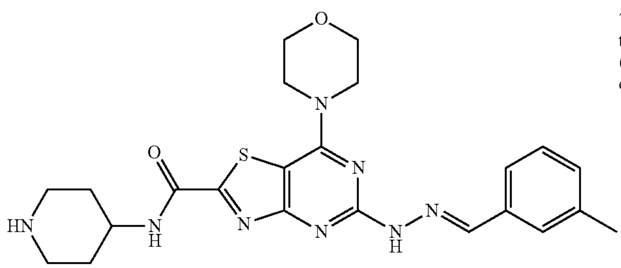 [SMILES: Cc1cccc(/C=N/Nc2nc(N3CCOCC3)c3sc(C(=O)NC4CCNCC4)nc3n2)c1] | 7-morpholino-5-[(2E)-2-(m-tolylmethylene)hydrazino]-N-(4-piperidyl)thiazolo[4,5-d]pyrimidine-2-carboxamide |
| 185 | 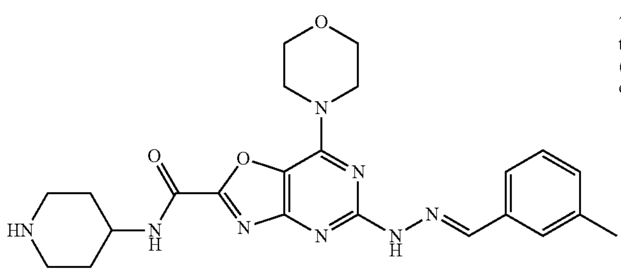 [SMILES: Cc1cccc(/C=N/Nc2nc(N3CCOCC3)c3oc(C(=O)NC4CCNCC4)nc3n2)c1] | 7-morpholino-5-[(2E)-2-(m-tolylmethylene)hydrazino]-N-(4-piperidyl)oxazolo[4,5-d]pyrimidine-2-carboxamide |
| 186 | 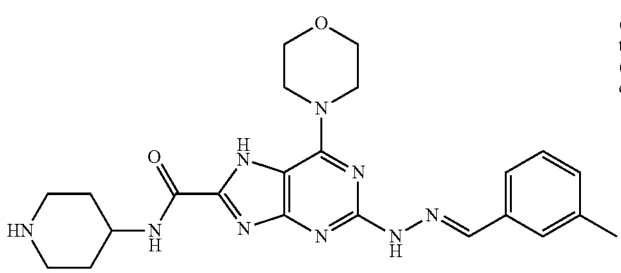 [SMILES: Cc1cccc(/C=N/Nc2nc(N3CCOCC3)c3[nH]c(C(=O)NC4CCNCC4)nc3n2)c1] | 6-morpholino-2-[(2E)-2-(m-tolylmethylene)hydrazino]-N-(4-piperidyl)-7H-purine-8-carboxamide |
| 187 | 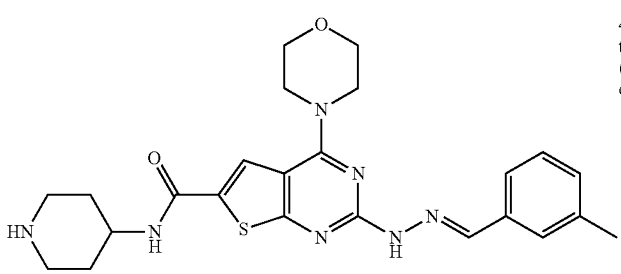 [SMILES: Cc1cccc(/C=N/Nc2nc(N3CCOCC3)c3cc(C(=O)NC4CCNCC4)sc3n2)c1] | 4-morpholino-2-[(2E)-2-(m-tolylmethylene)hydrazino]-N-(4-piperidyl)thieno[2,3-d]pyrimidine-6-carboxamide |

TABLE 1-continued

| Ex. No. | Structure | Name |
|---|---|---|
| 188 | 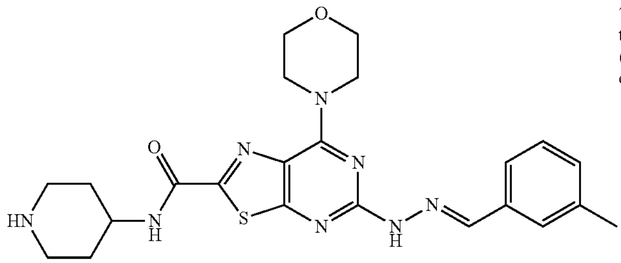 [SMILES: Cc1cccc(/C=N/Nc2nc(N3CCOCC3)c3nc(C(=O)NC4CCNCC4)sc3n2)c1] | 7-morpholino-5-[(2E)-2-(m-tolylmethylene)hydrazino]-N-(4-piperidyl)thiazolo[5,4-d]pyrimidine-2-carboxamide |
| 189 | 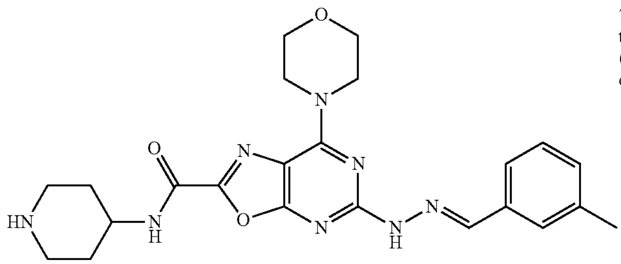 | 7-morpholino-5-[(2E)-2-(m-tolylmethylene)hydrazino]-N-(4-piperidyl)oxazolo[5,4-d]pyrimidine-2-carboxamide |
| 190 | 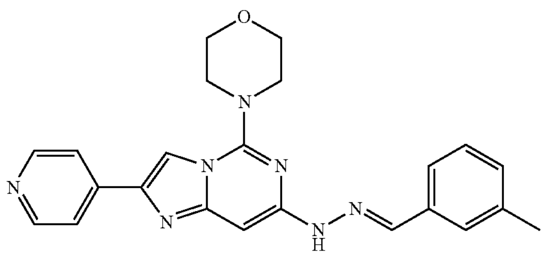 [SMILES: Cc1cccc(/C=N/Nc2cc3nc(-c4ccncc4)cn3c(N3CCOCC3)n2)c1] | 5-morpholino-N-[(E)-m-tolylmethyleneamino]-2-(4-pyridyl)imidazo[1,2-c]pyrimidin-7-amine |
| 191 | 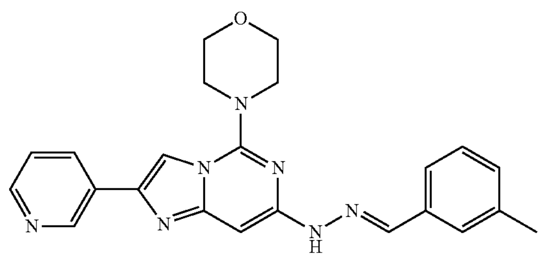 [SMILES: Cc1cccc(/C=N/Nc2cc3nc(-c4cccnc4)cn3c(N3CCOCC3)n2)c1] | 5-morpholino-N-[(E)-m-tolylmethyleneamino]-2-(3-pyridyl)imidazo[1,2-c]pyrimidin-7-amine |
| 192 | 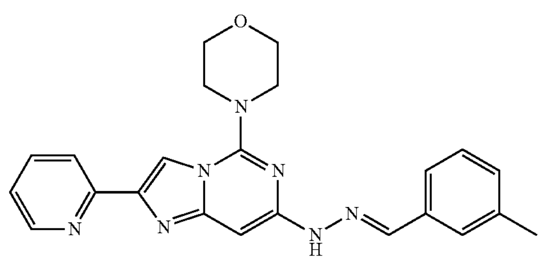 [SMILES: Cc1cccc(/C=N/Nc2cc3nc(-c4ccccn4)cn3c(N3CCOCC3)n2)c1] | 5-morpholino-N-[(E)-m-tolylmethyleneamino]-2-(2-pyridyl)imidazo[1,2-c]pyrimidin-7-amine |
| 193 | 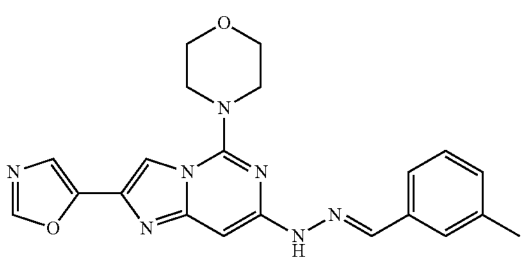 [SMILES: Cc1cccc(/C=N/Nc2cc3nc(-c4cnco4)cn3c(N3CCOCC3)n2)c1] | 5-morpholino-N-[(E)-m-tolylmethyleneamino]-2-oxazol-5-yl-imidazo[1,2-c]pyrimidin-7-amine |

TABLE 1-continued

| Ex. No. | Structure | Name |
|---|---|---|
| 194 | 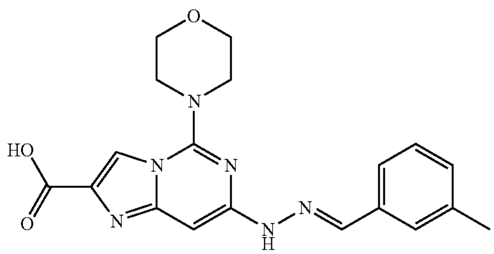 [SMILES: Cc1cccc(/C=N/Nc2cc3nc(C(=O)O)cn3c(N3CCOCC3)n2)c1] | 5-morpholino-7-[(2E)-2-(m-tolylmethylene)hydrazino]imidazo[1,2-c]pyrimidine-2-carboxylic acid |
| 195 | 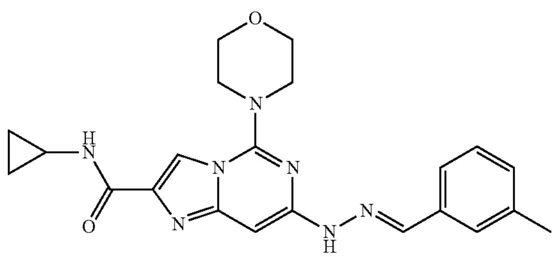 [SMILES: Cc1cccc(/C=N/Nc2cc3nc(C(=O)NC4CC4)cn3c(N3CCOCC3)n2)c1] | N-cyclopropyl-5-morpholino-7-[(2E)-2-(m-tolylmethylene)hydrazino]imidazo[1,2-c]pyrimidine-2-carboxamide |
| 196 | 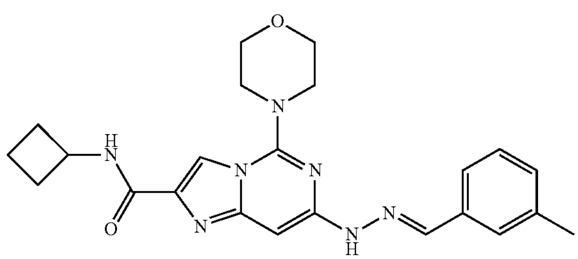 [SMILES: Cc1cccc(/C=N/Nc2cc3nc(C(=O)NC4CCC4)cn3c(N3CCOCC3)n2)c1] | N-cyclobutyl-5-morpholino-7-[(2E)-2-(m-tolylmethylene)hydrazino]imidazo[1,2-c]pyrimidine-2-carboxamide |
| 197 | 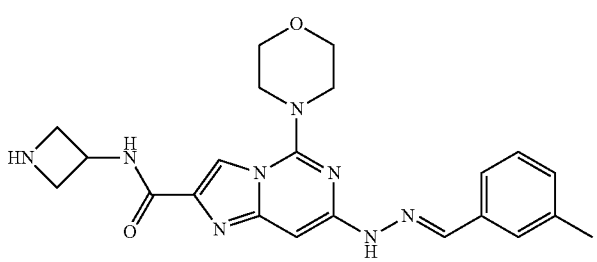 [SMILES: Cc1cccc(/C=N/Nc2cc3nc(C(=O)NC4CNC4)cn3c(N3CCOCC3)n2)c1] | N-(azetidin-3-yl)-5-morpholino-7-[(2E)-2-(m-tolylmethylene)hydrazino]imidazo[1,2-c]pyrimidine-2-carboxamide |
| 198 | 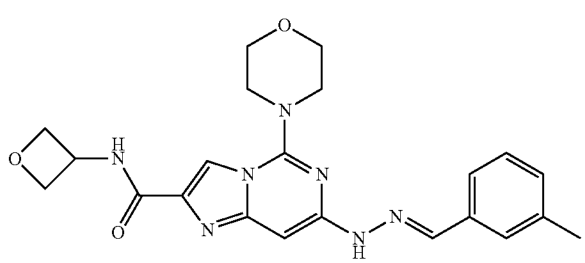 [SMILES: Cc1cccc(/C=N/Nc2cc3nc(C(=O)NC4COC4)cn3c(N3CCOCC3)n2)c1] | 5-morpholino7-[(2E)-2-(m-tolylmethylene)hydrazino]-N-(oxetan-3-yl)imidazo[1,2-c]pyrimidine-2-carboxamide |
| 199 | 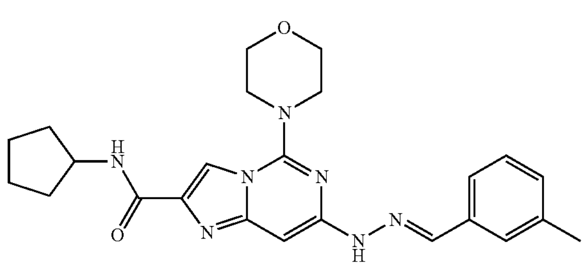 [SMILES: Cc1cccc(/C=N/Nc2cc3nc(C(=O)NC4CCCC4)cn3c(N3CCOCC3)n2)c1] | N-cyclopentyl-5-morpholino-7-[(2E)-2-(m-tolylmethylene)hydrazino]imidazo[1,2-c]pyrimidine-2-carboxamide |

TABLE 1-continued

| Ex. No. | Structure | Name |
|---|---|---|
| 200 | 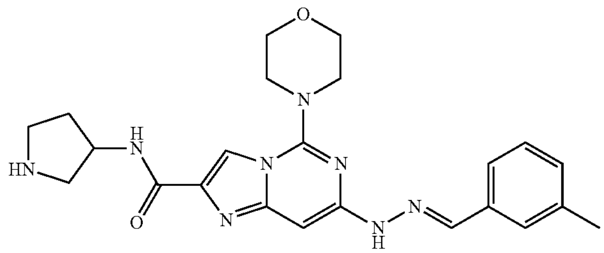 [SMILES: Cc1cccc(/C=N/Nc2cc3nc(C(=O)NC4CCNC4)cn3c(N3CCOCC3)n2)c1] | 5-morpholino-7-[(2E)-2-(m-tolylmethylene)hydrazino]-N-pyrrolidin-3-yl-imidazo[1,2-c]pyrimidine-2-carboxamide |
| 201 | 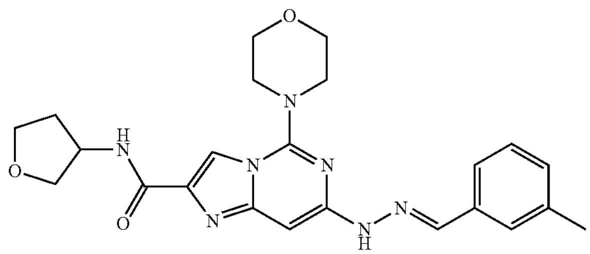 [SMILES: Cc1cccc(/C=N/Nc2cc3nc(C(=O)NC4CCOC4)cn3c(N3CCOCC3)n2)c1] | 5-morpholino-7-[(2E)-2-(m-tolylmethylene)hydrazino]-N-tetrahydrofuran-3-yl-imidazo[1,2-c]pyrimidine-2-carboxamide |
| 202 | 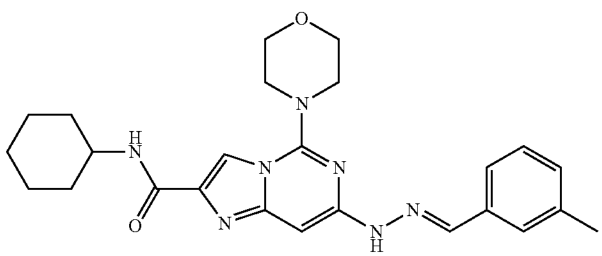 [SMILES: Cc1cccc(/C=N/Nc2cc3nc(C(=O)NC4CCCCC4)cn3c(N3CCOCC3)n2)c1] | N-cyclohexyl-5-morpholino-7-[(2E)-2-(m-tolylmethylene)hydrazino]imidazo[1,2-c]pyrimidine-2-carboxamide |
| 203 | 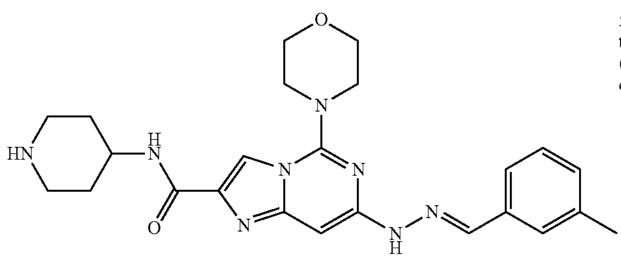 [SMILES: Cc1cccc(/C=N/Nc2cc3nc(C(=O)NC4CCNCC4)cn3c(N3CCOCC3)n2)c1] | 5-morpholino-7-[(2E)-2-(m-tolylmethylene)hydrazino]-N-(4-piperidyl)imidazo[1,2-c]pyrimidine-2-carboxamide |
| 204 | 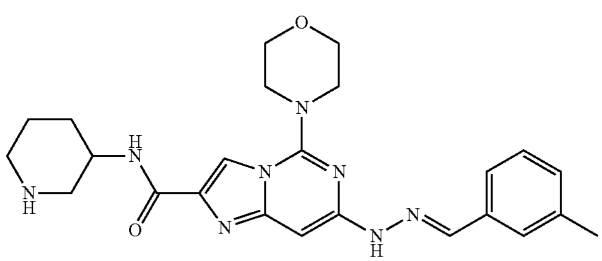 [SMILES: Cc1cccc(/C=N/Nc2cc3nc(C(=O)NC4CCCNC4)cn3c(N3CCOCC3)n2)c1] | 5-morpholino-7-[(2E)-2-(m-tolylmethylene)hydrazino]-N-(3-piperidyl)imidazo[1,2-c]pyrimidine-2-carboxamide |
| 205 | 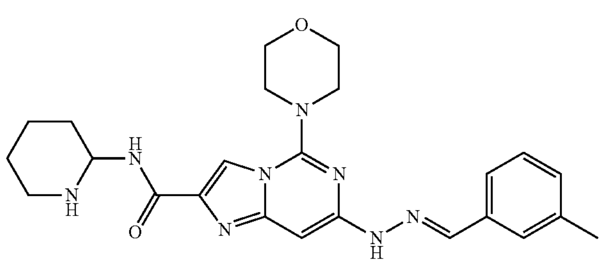 [SMILES: Cc1cccc(/C=N/Nc2cc3nc(C(=O)NC4CCCCN4)cn3c(N3CCOCC3)n2)c1] | 5-morpholino-7-[(2E)-2-(m-tolylmethylene)hydrazino]-N-(2-piperidyl)imidazo[1,2-c]pyrimidine-2-carboxamide |

TABLE 1-continued

| Ex. No. | Structure | Name |
|---|---|---|
| 206 | 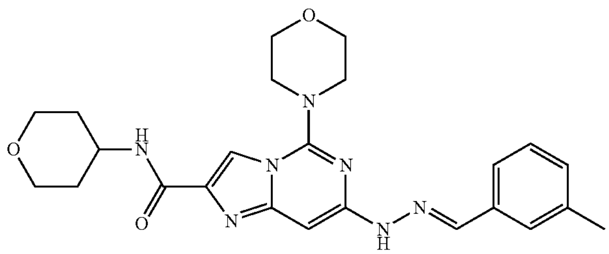 [SMILES: Cc1cccc(/C=N/Nc2cc3nc(C(=O)NC4CCOCC4)cn3c(N3CCOCC3)n2)c1] | 5-morpholino-7-[(2E)-2-(m-tolylmethylene)hydrazino]-N-tetrahydropyran-4-yl-imidazo[1,2-c]pyrimidine-2-carboxamide |
| 207 | 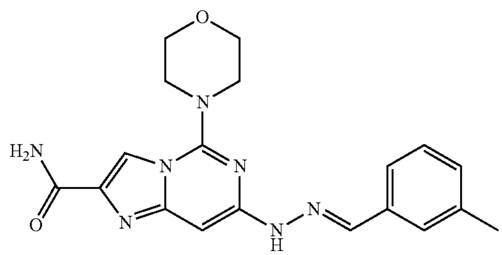 [SMILES: Cc1cccc(/C=N/Nc2cc3nc(C(N)=O)cn3c(N3CCOCC3)n2)c1] | 5-morpholino-7-[(2E)-2-(m-tolylmethylene)hydrazino]imidazo[1,2-c]pyrimidine-2-carboxamide |
| 208 | 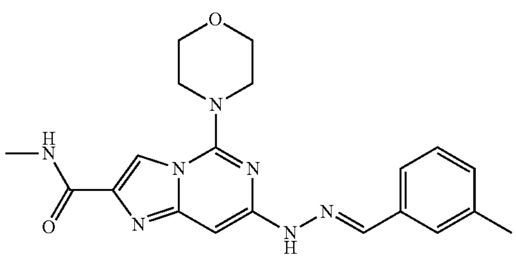 | N-methyl-5-morpholino-7-[(2E)-2-(m-tolylmethylene)hydrazino]imidazo[1,2-c]pyrimidine-2-carboxamide |
| 209 | 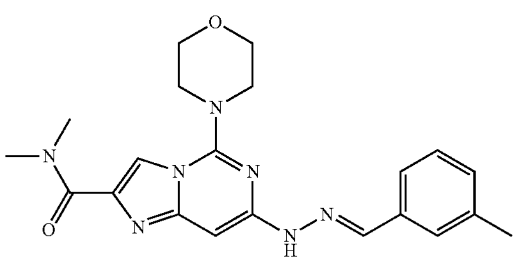 | N,N-dimethyl-5-morpholino-7-[(2E)-2-(m-tolylmethylene)hydrazino]imidazo[1,2-c]pyrimidine-2-carboxamide |
| 210 | 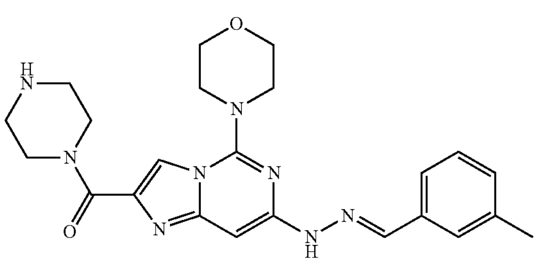 [SMILES: Cc1cccc(/C=N/Nc2cc3nc(C(=O)N4CCNCC4)cn3c(N3CCOCC3)n2)c1] | [5-morpholino-7-[(2E)-2-(m-tolylmethylene)hydrazino]imidazo[1,2-c]pyrimidin-2-yl]-piperazin-1-yl-methanone |
| 211 | 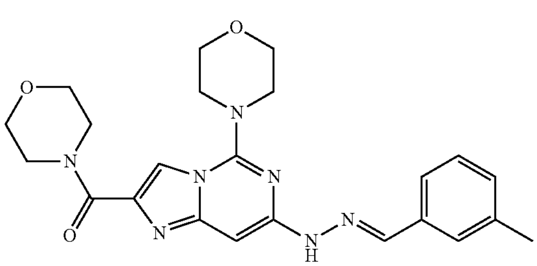 [SMILES: Cc1cccc(/C=N/Nc2cc3nc(C(=O)N4CCOCC4)cn3c(N3CCOCC3)n2)c1] | morpholino-[5-morpholino-7-[(2E)-2-(m-tolylmethylene)hydrazino]imidazo[1,2-c]pyrimidin-2-yl]methanone |

TABLE 1-continued

| Ex. No. | Structure | Name |
|---|---|---|
| 212 | 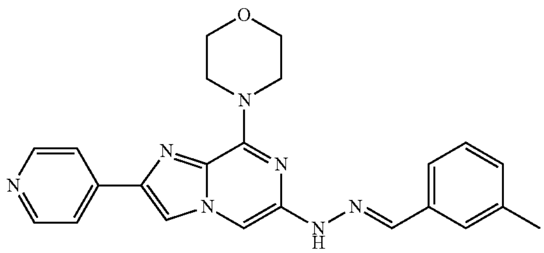 [SMILES: Cc1cccc(/C=N/Nc2cn3cc(-c4ccncc4)nc3c(N3CCOCC3)n2)c1] | 8-morpholino-N-[(E)-m-tolylmethyleneamino]-2-(4-pyridyl)imidazo[1,2-a]pyrazin-6-amine |
| 213 | 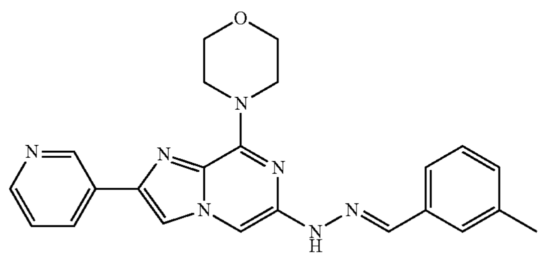 [SMILES: Cc1cccc(/C=N/Nc2cn3cc(-c4cccnc4)nc3c(N3CCOCC3)n2)c1] | 8-morpholino-N-[(E)-m-tolylmethyleneamino]-2-(3-pyridyl)imidazo[1,2-a]pyrazin-6-amine |
| 214 | 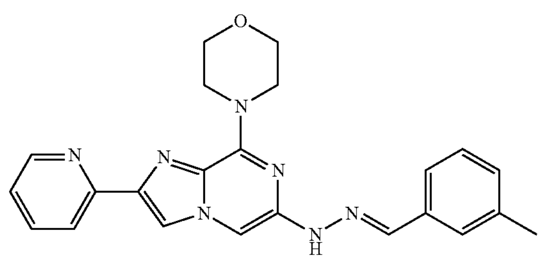 [SMILES: Cc1cccc(/C=N/Nc2cn3cc(-c4ccccn4)nc3c(N3CCOCC3)n2)c1] | 8-morpholino-N-[(E)-m-tolylmethyleneamino]-2-(2-pyridyl)imidazo[1,2-a]pyrazin-6-amine |
| 215 | 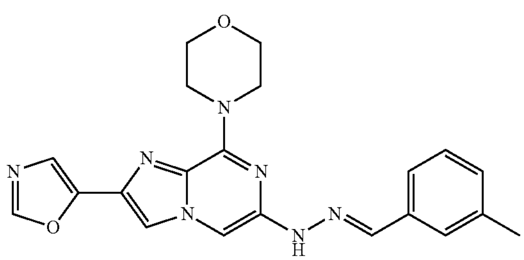 [SMILES: Cc1cccc(/C=N/Nc2cn3cc(-c4cnco4)nc3c(N3CCOCC3)n2)c1] | 8-morpholino-N-[(E)-m-tolylmethyleneamino]-2-oxazol-5-yl-imidazo[1,2-a]pyrazin-6-amine |
| 216 | 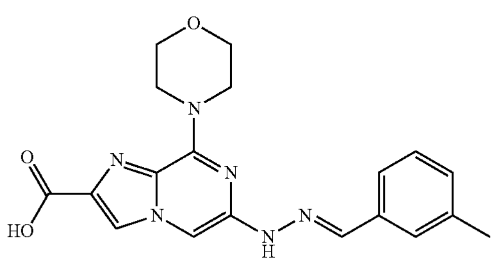 [SMILES: Cc1cccc(/C=N/Nc2cn3cc(C(=O)O)nc3c(N3CCOCC3)n2)c1] | 8-morpholino-6-[(2E)-2-(m-tolylmethylene)hydrazino]imidazo[1,2-a]pyrazine-2-carboxylic acid |
| 217 | 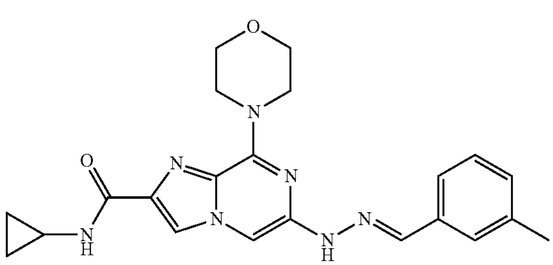 [SMILES: Cc1cccc(/C=N/Nc2cn3cc(C(=O)NC4CC4)nc3c(N3CCOCC3)n2)c1] | N-cyclopropyl-8-morpholino-6-[(2E)-2-(m-tolylmethylene)hydrazino]imidazo[1,2-a]pyrazine-2-carboxamide |

TABLE 1-continued

| Ex. No. | Structure | Name |
| --- | --- | --- |
| 218 | 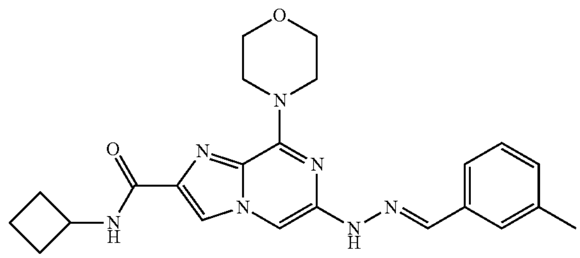 [SMILES: Cc1cccc(/C=N/Nc2cn3cc(C(=O)NC4CCC4)nc3c(N3CCOCC3)n2)c1] | N-cyclobutyl-8-morpholino-6-[(2E)-2-(m-tolylmethylene)hydrazino]imidazo[1,2-a]pyrazine-2-carboxamide |
| 219 | 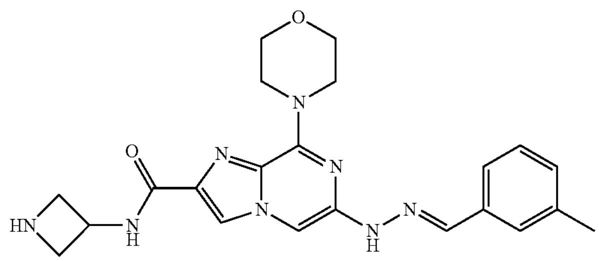 [SMILES: Cc1cccc(/C=N/Nc2cn3cc(C(=O)NC4CNC4)nc3c(N3CCOCC3)n2)c1] | N-(azetidin-3-yl)-8-morpholino-6-[(2E)-2-(m-tolylmethylene)hydrazino]imidazo[1,2-a]pyrazine-2-carboxamide |
| 220 | 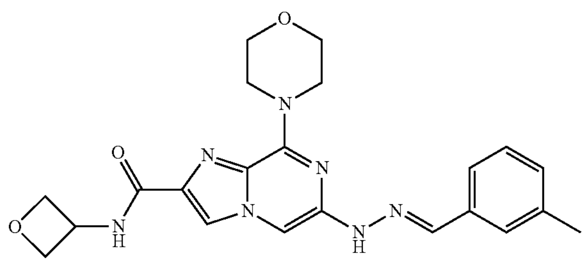 [SMILES: Cc1cccc(/C=N/Nc2cn3cc(C(=O)NC4COC4)nc3c(N3CCOCC3)n2)c1] | 8-morpholino-6-[(2E)-2-(m-tolylmethylene)hydrazino]-N-(oxetan-3-yl)imidazo[1,2-a]pyrazine-2-carboxamide |
| 221 | 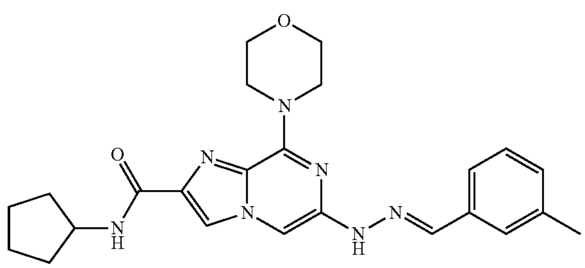 [SMILES: Cc1cccc(/C=N/Nc2cn3cc(C(=O)NC4CCCC4)nc3c(N3CCOCC3)n2)c1] | N-cyclopentyl-8-morpholino-6-[(2E)-2-(m-tolylmethylene)hydrazino]imidazo[1,2-a]pyrazine-2-carboxamide |
| 222 | 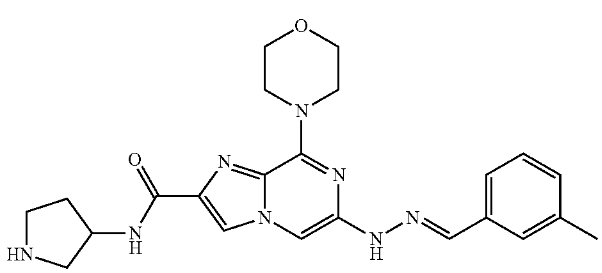 | 8-morpholino-6-[(2E)-2-(m-tolylmethylene)hydrazino]-N-pyrrolidin-3-yl-imidazo[1,2-a]pyrazine-2-carboxamide |
| 223 | 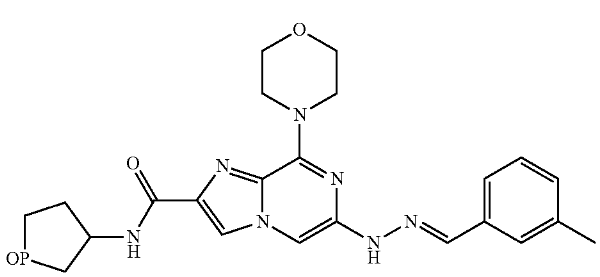 | 8-morpholino-6-[(2E)-2-(m-tolylmethylene)hydrazino]-N-tetrahydrofuran-3-yl-imidazo[1,2-a]pyrazine-2-carboxamide |

TABLE 1-continued

| Ex. No. | Structure | Name |
|---|---|---|
| 224 | 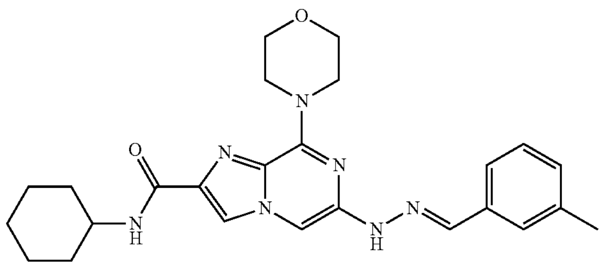 [SMILES: Cc1cccc(/C=N/Nc2cn3cc(C(=O)NC4CCCCC4)nc3c(N3CCOCC3)n2)c1] | N-cyclohexyl-8-morpholino-6-[(2E)-2-(m-tolylmethylene)hydrazino]imidazo[1,2-a]pyrazine-2-carboxamide |
| 225 | 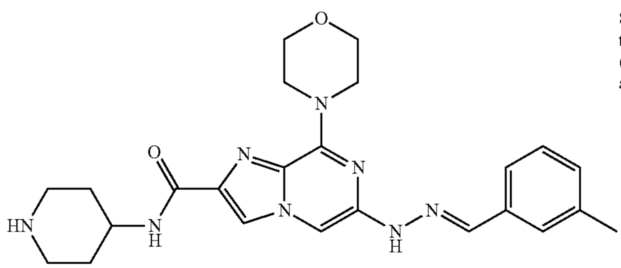 [SMILES: Cc1cccc(/C=N/Nc2cn3cc(C(=O)NC4CCNCC4)nc3c(N3CCOCC3)n2)c1] | 8-morpholino-6-[(2E)-2-(m-tolylmethylene)hydrazino]-N-(4-piperidyl)imidazo[1,2-a]pyrazine-2-carboxamide |
| 226 | 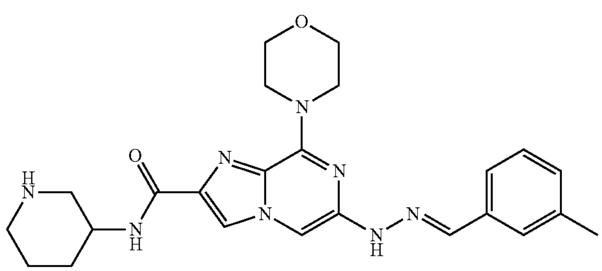 [SMILES: Cc1cccc(/C=N/Nc2cn3cc(C(=O)NC4CCCNC4)nc3c(N3CCOCC3)n2)c1] | 8-morpholino-6-[(2E)-2-(m-tolylmethylene)hydrazino]-N-(3-piperidyl)imidazo[1,2-a]pyrazine-2-carboxamide |
| 227 | 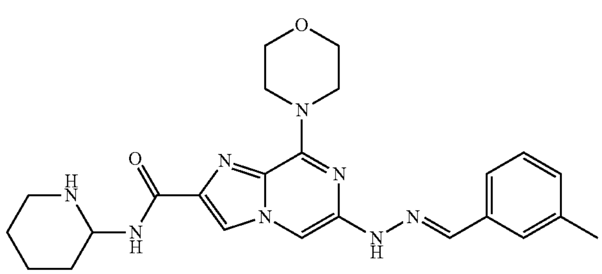 [SMILES: Cc1cccc(/C=N/Nc2cn3cc(C(=O)NC4CCCCN4)nc3c(N3CCOCC3)n2)c1] | 8-morpholino-6-[(2E)-2-(m-tolylmethylene)hydrazino]-N-(2-piperidyl)imidazo[1,2-a]pyrazine-2-carboxamide |
| 228 | 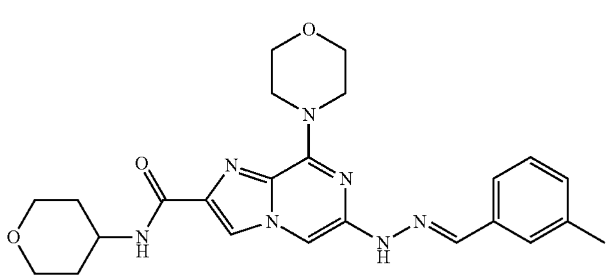 [SMILES: Cc1cccc(/C=N/Nc2cn3cc(C(=O)NC4CCOCC4)nc3c(N3CCOCC3)n2)c1] | 8-morpholino-6-[(2E)-2-(m-tolylmethylene)hydrazino]-N-tetrahydropyran-4-yl-imidazo[1,2-a]pyrazine-2-carboxamide |

TABLE 1-continued

| Ex. No. | Structure | Name |
|---|---|---|
| 229 | 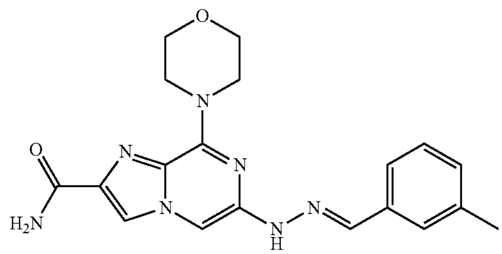 [SMILES: Cc1cccc(/C=N/Nc2cn3cc(C(N)=O)nc3c(N3CCOCC3)n2)c1] | 8-morpholino-6-[(2E)-2-(m-tolylmethylene)hydrazino]imidazo[1,2-a]pyrazine-2-carboxamide |
| 230 | 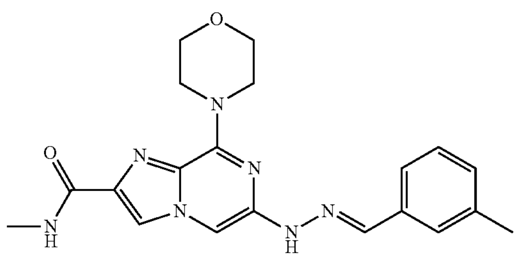 | N-methyl-8-morpholino-6-[(2E)-2-(m-tolylmethylene)hydrazino]imidazo[1,2-a]pyrazine-2-carboxamide |
| 231 | 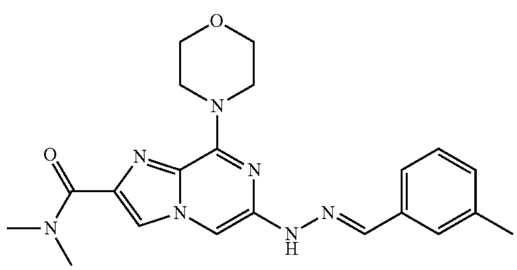 | N,N-dimethyl-8-morpholino-6-[(2E)-2-(m-tolylmethylene)hydrazino]imidazo[1,2-a]pyrazine-2-carboxamide |
| 232 | 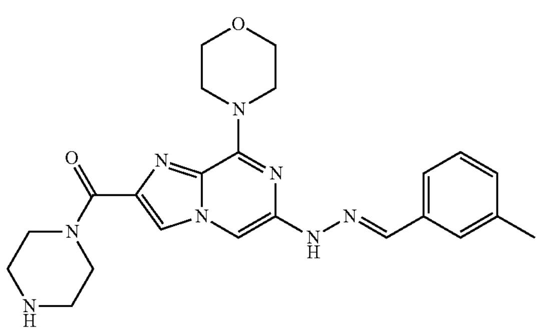 [SMILES: Cc1cccc(/C=N/Nc2cn3cc(C(=O)N4CCNCC4)nc3c(N3CCOCC3)n2)c1] | [8-morpholino-6-[(2E)-2-(m-tolylmethylene)hydrazino]imidazo[1,2-a]pyrazin-2-yl]-piperazin-1-yl-methanone |
| 233 | 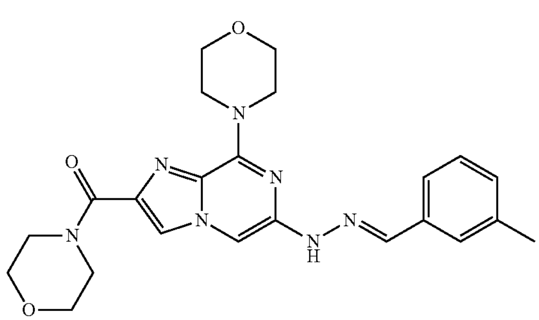 [SMILES: Cc1cccc(/C=N/Nc2cn3cc(C(=O)N4CCOCC4)nc3c(N3CCOCC3)n2)c1] | morpholino-[8-morpholino-6-[(2E)-2-(m-tolylmethylene)hydrazino]imidazo[1,2-a]pyrazin-2-yl]methanone |

TABLE 1-continued

| Ex. No. | Structure | Name |
|---|---|---|
| 234 | 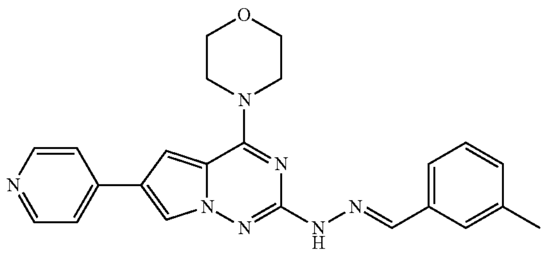 [SMILES: Cc1cccc(/C=N/Nc2nc(N3CCOCC3)c3cc(-c4ccncc4)cn3n2)c1] | 4-morpholino-N-[(E)-m-tolylmethyleneamino]-6-(4-pyridyl)pyrrolo[2,1-f][1,2,4]triazin-2-amine |
| 235 | 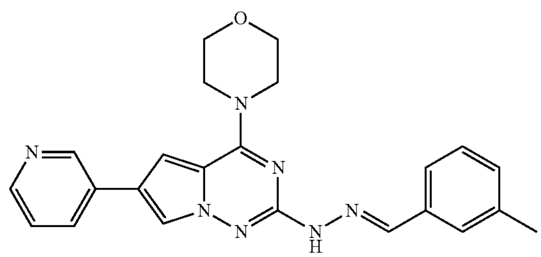 [SMILES: Cc1cccc(/C=N/Nc2nc(N3CCOCC3)c3cc(-c4cccnc4)cn3n2)c1] | 4-morpholino-N-[(E)-m-tolylmethyleneamino]-6-(3-pyridyl)pyrrolo[2,1-f][1,2,4]triazin-2-amine |
| 236 | 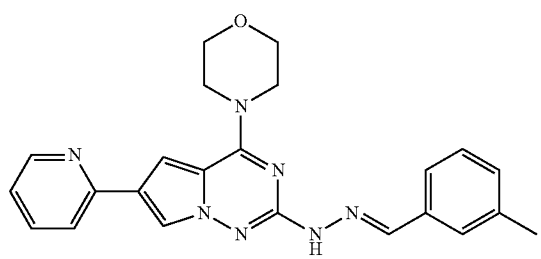 [SMILES: Cc1cccc(/C=N/Nc2nc(N3CCOCC3)c3cc(-c4ccccn4)cn3n2)c1] | 4-morpholino-N-[(E)-m-tolylmethyleneamino]-6-(2-pyridyl)pyrrolo[2,1-f][1,2,4]triazin-2-amine |
| 237 | 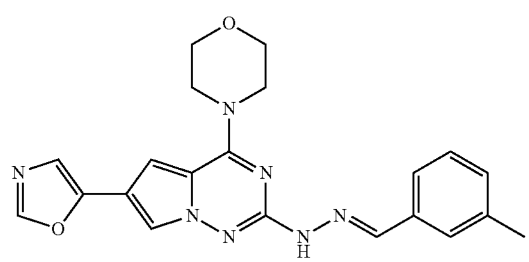 [SMILES: Cc1cccc(/C=N/Nc2nc(N3CCOCC3)c3cc(-c4cnco4)cn3n2)c1] | 4-morpholino-N-[(E)-m-tolylmethyleneamino]-6-oxazol-5-yl-pyrrolo[2,1-f][1,2,4]triazin-2-amine |
| 238 | 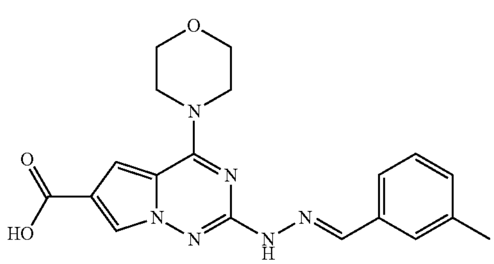 [SMILES: Cc1cccc(/C=N/Nc2nc(N3CCOCC3)c3cc(C(=O)O)cn3n2)c1] | 4-morpholino-2-[(2E)-2-(m-tolylmethylene)hydrazino]pyrrolo[2,1-f][1,2,4]triazine-6-carboxylic acid |
| 239 | 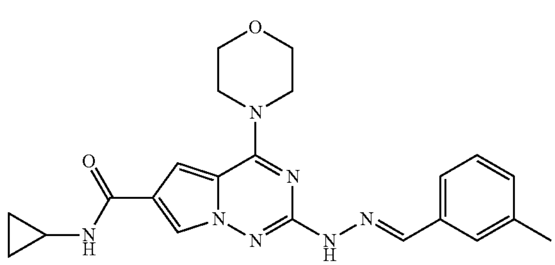 [SMILES: Cc1cccc(/C=N/Nc2nc(N3CCOCC3)c3cc(C(=O)NC4CC4)cn3n2)c1] | N-cyclopropyl-4-morpholino-2-[(2E)-2-(m-tolylmethylene)hydrazino]pyrrolo[2,1-f][1,2,4]triazine-6-carboxamide |

TABLE 1-continued

| Ex. No. | Structure | Name |
|---|---|---|
| 240 | 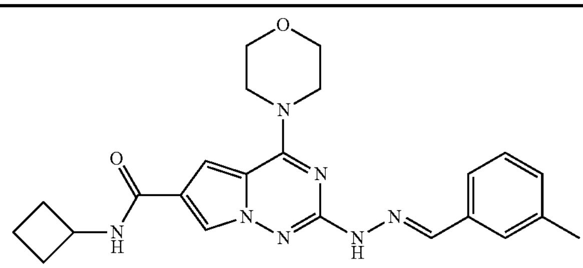 | N-cyclobutyl-4-morpholino-2-[(2E)-2-(m-tolylmethylene)hydrazino]pyrrolo[2,1-f][1,2,4]triazine-6-carboxamide |
| 241 | 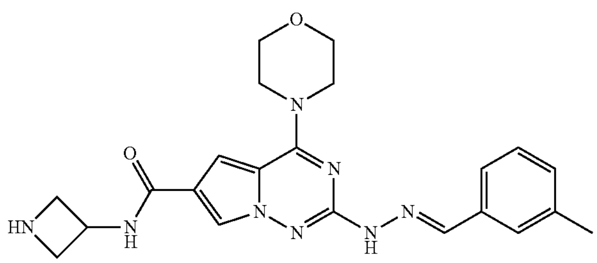 [SMILES: Cc1cccc(/C=N/Nc2nc(N3CCOCC3)c3cc(C(=O)NC4CNC4)cn3n2)c1] | N-(azetidin-3-yl)-4-morpholino-2-[(2E)-2-(m-tolylmethylene)hydrazino]pyrrolo[2,1-f][1,2,4]triazine-6-carboxamide |
| 242 | 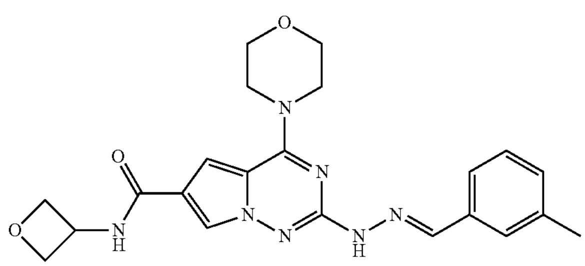 [SMILES: Cc1cccc(/C=N/Nc2nc(N3CCOCC3)c3cc(C(=O)NC4COC4)cn3n2)c1] | 4-morpholino-2-[(2E)-2-(m-tolylmethylene)hydrazino]-N-(oxetan-3-yl)pyrrolo[2,1-f][1,2,4]triazine-6-carboxamide |
| 243 | 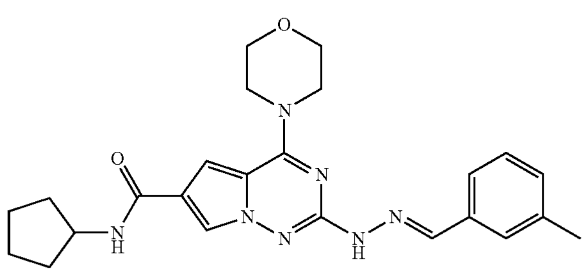 [SMILES: Cc1cccc(/C=N/Nc2nc(N3CCOCC3)c3cc(C(=O)NC4CCCC4)cn3n2)c1] | N-cyclopentyl-4-morpholino-2-[(2E)-2-(m-tolylmethylene)hydrazino]pyrrolo[2,1-f][1,2,4]triazine-6-carboxamide |
| 244 | 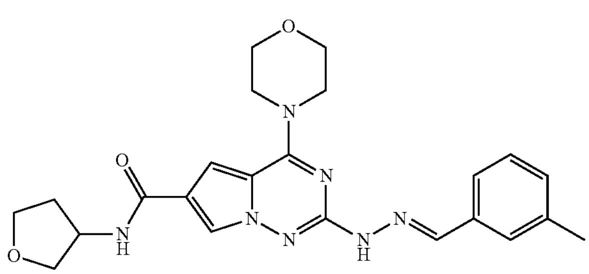 [SMILES: Cc1cccc(/C=N/Nc2nc(N3CCOCC3)c3cc(C(=O)NC4CCOC4)cn3n2)c1] | 4-morpholino-2-[(2E)-2-(m-tolylmethylene)hydrazino]-N-tetrahydrofuran-3-yl-pyrrolo[2,1-f][1,2,4]triazine-6-carboxamide |
| 245 | 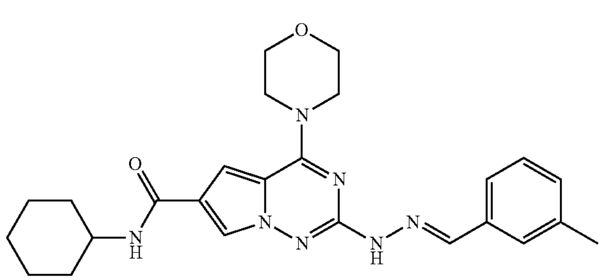 [SMILES: Cc1cccc(/C=N/Nc2nc(N3CCOCC3)c3cc(C(=O)NC4CCCCC4)cn3n2)c1] | N-cyclohexyl-4-morpholino-2-[(2E)-2-(m-tolylmethylene)hydrazino]pyrrolo[2,1-f][1,2,4]triazine-6-carboxamide |

TABLE 1-continued

| Ex. No. | Structure | Name |
|---|---|---|
| 246 | 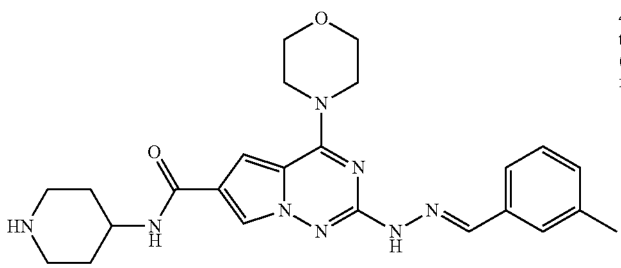 [SMILES: Cc1cccc(/C=N/Nc2nc(N3CCOCC3)c3cc(C(=O)NC4CCNCC4)cn3n2)c1] | 4-morpholino-2-[(2E)-2-(m-tolylmethylene)hydrazino]-N-(4-piperidyl)pyrrolo[2,1-f][1,2,4]triazine-6-carboxamide |
| 247 | 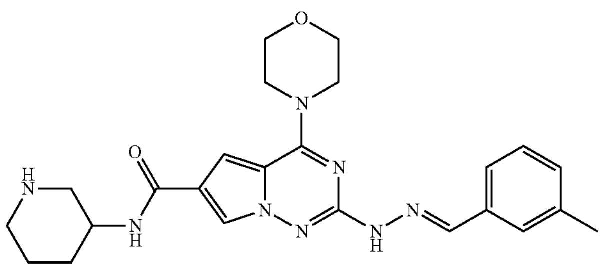 [SMILES: Cc1cccc(/C=N/Nc2nc(N3CCOCC3)c3cc(C(=O)NC4CCCNC4)cn3n2)c1] | 4-morpholino-2-[(2E)-2-(m-tolylmethylene)hydrazino]-N-(3-piperidyl)pyrrolo[2,1-f][1,2,4]triazine-6-carboxamide |
| 248 | 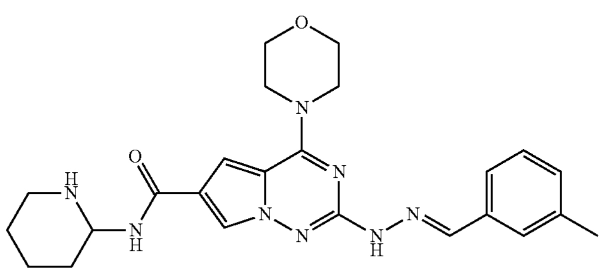 [SMILES: Cc1cccc(/C=N/Nc2nc(N3CCOCC3)c3cc(C(=O)NC4CCCCN4)cn3n2)c1] | 4-morpholino-2-[(2E)-2-(m-tolylmethylene)hydrazino]-N-(2-piperidyl)pyrrolo[2,1-f][1,2,4]triazine-6-carboxamide |
| 249 | 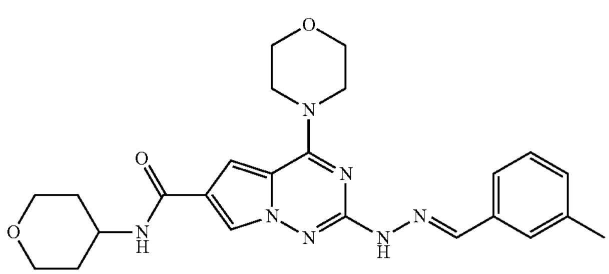 [SMILES: Cc1cccc(/C=N/Nc2nc(N3CCOCC3)c3cc(C(=O)NC4CCOCC4)cn3n2)c1] | 4-morpholino-2-[(2E)-2-(m-tolylmethylene)hydrazino]-N-tetrahydropyran-4-yl-pyrrolo[2,1-f][1,2,4]triazine-6-carboxamide |
| 250 | 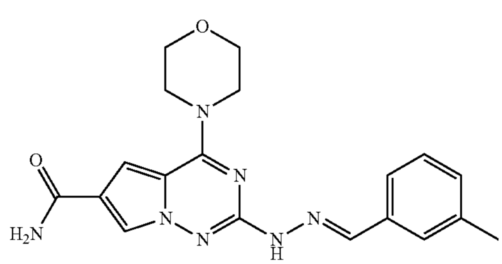 [SMILES: Cc1cccc(/C=N/Nc2nc(N3CCOCC3)c3cc(C(N)=O)cn3n2)c1] | 4-morpholino-2-[(2E)-2-(m-tolylmethylene)hydrazino]pyrrolo[2,1-f][1,2,4]triazine-6-carboxamide |

TABLE 1-continued

| Ex. No. | Structure | Name |
|---|---|---|
| 251 | 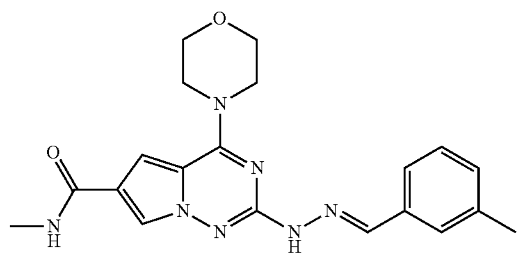 | N-methyl-4-morpholino-2-[(2E)-2-(m-tolylmethylene)hydrazino]pyrrolo[2,1-f][1,2,4]triazine-6-carboxamide |
| 252 | 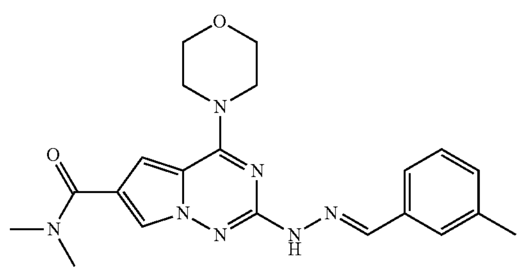 | N,N-dimethyl-4-morpholino-2-[(2E)-2-(m-tolylmethylene)hydrazino]pyrrolo[2,1-f][1,2,4]triazine-6-carboxamide |
| 253 | 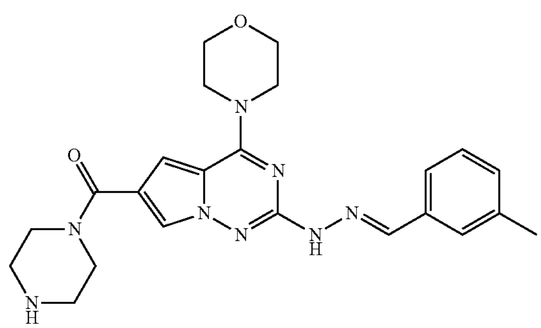 [SMILES: Cc1cccc(/C=N/Nc2nc(N3CCOCC3)c3cc(C(=O)N4CCNCC4)cn3n2)c1] | [4-morpholino-2-[(2E)-2-(m-tolylmethylene)hydrazino]pyrrolo[2,1-f][1,2,4]triazin-6-yl]-piperazin-1-yl-methanone |
| 254 | 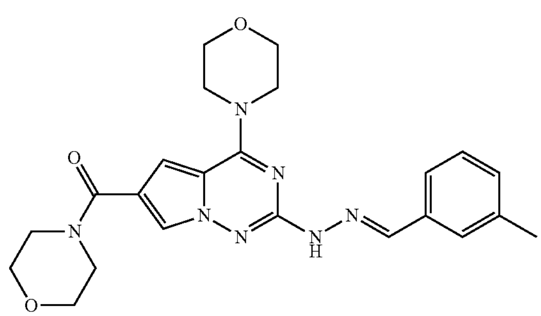 [SMILES: Cc1cccc(/C=N/Nc2nc(N3CCOCC3)c3cc(C(=O)N4CCOCC4)cn3n2)c1] | morpholino-[4-morpholino-2-[(2E)-2-(m-tolylmethylene)hydrazino]pyrrolo[2,1-f][1,2,4]triazin-6-yl]methanone |
| 255 | 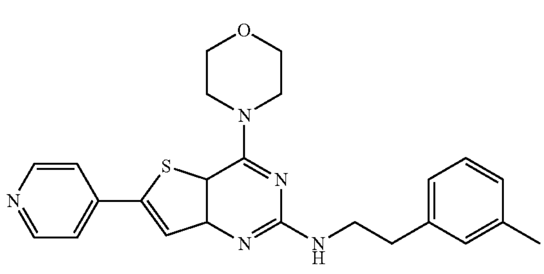 [SMILES: Cc1cccc(CCNC2=NC3C=C(c4ccncc4)SC3C(N3CCOCC3)=N2)c1] | 4-morpholino-N-[2-(m-tolyl)ethyl]-6-(4-pyridyl)thieno[3,2-d]pyrimidin-2-amine. $^1$H NMR (DMSO-$d_6$): δ 2.36 (s, 3H), 2.79 (t, J = 7.3 Hz, 2H), 3.47 (t, J = 7.3 Hz, 2H), 3.73 (bs, 4H), 3.82 (bs, 4H), 6.68 (bs, 1H), 6.97-7.04 (m, 3H), 7.14 (t, J = 7.1 Hz, 1H), 7.77 (d, J = 5.4 Hz, 1H), 7.81 (bs, 1H), 8.63 (d, J = 4.2 Hz, 1H). |

TABLE 1-continued

| Ex. No. | Structure | Name |
|---|---|---|
| 256 | 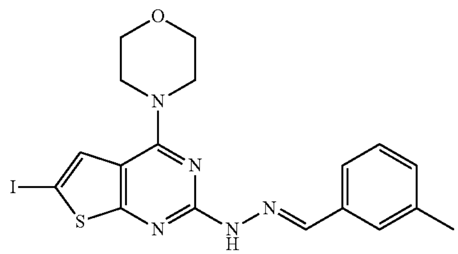 [SMILES: Cc1cccc(/C=N/Nc2nc(N3CCOCC3)c3cc(I)sc3n2)c1] | 6-iodo-4-morpholino-N-[(E)-m-tolylmethyleneamino]thieno[2,3-d]pyrimidin-2-amine. LC-MS: m/z 480 {M + H}+ |
| 257 | 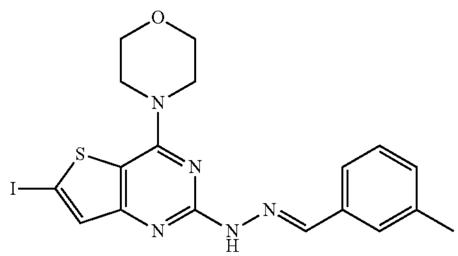 [SMILES: Cc1cccc(/C=N/Nc2nc(N3CCOCC3)c3sc(I)cc3n2)c1] | 6-iodo-4-morpholino-N-[(E)-m-tolylmethyleneamino]thieno[3,2-d]pyrimidin-2-amine<br>$^1$H NMR (DMSO-d$_6$): δ 2.35 (s, 3H), 3.77 (t, J = 4.7 Hz, 4H), 3.95 (t, J = 4.6 Hz, 4H), 7.25 (d, J = 7.8 Hz, 1H), 7.35 (t, J = 7.5 Hz, 1H), 7.73 (d, J = 7.8 Hz, 1H), &.76 (s, 1H), 7.90 (s, 1H), 8.24 (s, 1H), 12.58 (s, 1H). |
| 258 | 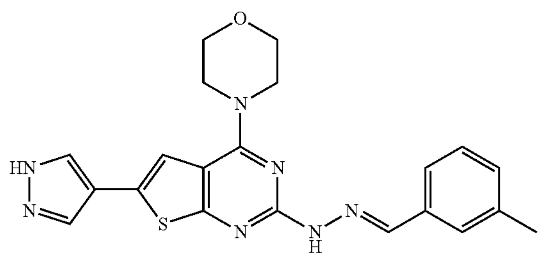 [SMILES: Cc1cccc(/C=N/Nc2nc(N3CCOCC3)c3cc(-c4cn[nH]c4)sc3n2)c1] | 4-morpholino-N-[(E)-m-tolylmethyleneamino]-6-(1H-pyrazol-4-yl)thieno[2,3-d]pyrimidin-2-amine.<br>$^1$H NMR (DMSO-d$_6$): δ 2.32 (s, 3H), 3.74 (t, J = 4.0 Hz, 4H), 3.82 (t, J = 4.0 Hz, 4H), 7.13 (d, J = 7.3 Hz, 1H), 7.25 (t, J = 7.4 Hz, 1H), 7.29-7.51 (m, 3H), 7.88 (s, 1H), 8.04 (s, 1H), 8.14 (s, 1H), 10.88 (s, 1H), 11.04 (s, 1H). |
| 259 | 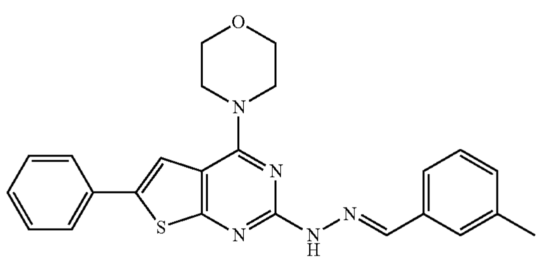 [SMILES: Cc1cccc(/C=N/Nc2nc(N3CCOCC3)c3cc(-c4ccccc4)sc3n2)c1] | 4-morpholino-N-[(E)-m-tolylmethyleneamino]-6-phenyl-thieno[2,3-d]pyrimidin-2-amine.<br>$^1$H NMR (DMSO-d$_6$): δ 2.32 (s, 3H), 3.75 (t, J = 4.0 Hz, 4H), 3.87 (t, J = 4.0H, 4H), 7.14 (d, J = 7.1 Hz, 1H), 7.26-7.46 (m, 6H), 7.73-7.82 (, 3H), 8.06 (s, 1H), 10.95 (s, 1H). |
| 260 | 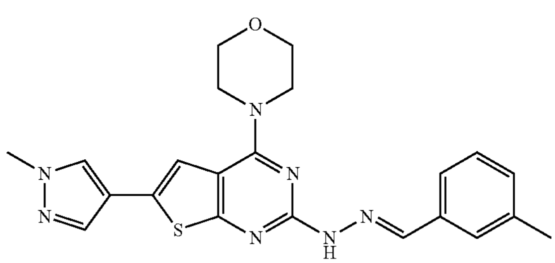 | 6-(1-methylpyrazol-4-yl)-4-morpholino-N-[(E)-m-tolylmethyleneamino]thieno[2,3-d]pyrimidin-2-amine.<br>$^1$H NMR (DMSO-d$_6$): δ 2.33 (s, 1H), 3.75 (t, J-4.2 Hz, 4H), 3.82 (t, J = 4.1 Hz, 4H), 3.84 (s, 3H), 7.13 (d, J = 7.42 Hz, 1H), 7.27 (t, J = 7.5 Hz, 1H), 7.41-7.49 (m, 3H), 7.84 (s, 1H), 8.04 (s, 1H), 8.08 (s, 1H), 10.88 (s, 1H). |
| 261 | 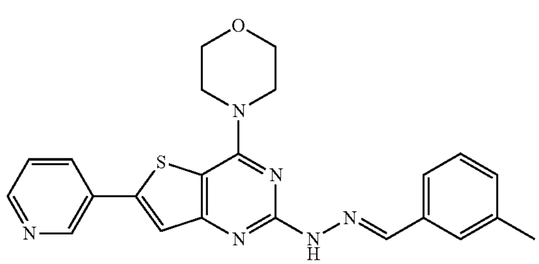 [SMILES: Cc1cccc(/C=N/Nc2nc(N3CCOCC3)c3sc(-c4cccnc4)cc3n2)c1] | 4-morpholino-N-[(E)-m-tolylmethyleneamino]-6-(3-pyridyl)thieno[3,2-d]pyrimidin-2-amine.<br>$^1$H NMR (DMSO-d$_6$): δ 2.33 (s, 3H), 3.76 (t, J-4.0 Hz, 4H), 3.90 (t, J = 4.0 Hz, 4H), 7.14 (d, J = 7.7 Hz, 1H), 7.28 (t, J = 7.84 Hz, 1H), 7.42-7.45 (m, 2H), 7.50-7.53 (m, 1H), 7.85 (s, 1H), 8.05 (s, 1H), 8.20-8.23 (m, 1H), 8.60-8.62 (m, 1H), 8.06 (d, J= 1.7 Hz, 1H), 10.80 (s, 1H). |

TABLE 1-continued

| Ex. No. | Structure | Name |
|---|---|---|
| 262 | 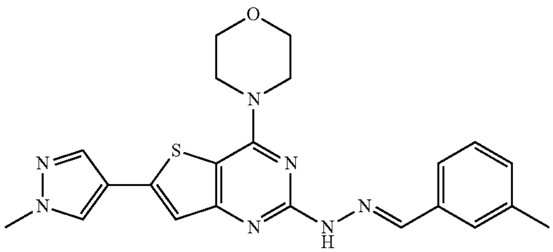 | 6-(1-methylpyrazol-4-yl)-4-morpholino-N-[(E)-m-tolylmethyleneamino]thieno[3,2-d]pyrimidin-2-amine. $^1$H NMR (DMSO-d$_6$): δ 2.32 (s, 3H), 3.74 (t, J = 4.1 Hz, 4H), 3.84 (t, J = 4.0 Hz, 4H), 3.86 (s, 3H), 7.12 (d, J = 7.0 Hz, 1H), 7.27 (t, J = 7.2 Hz, 1H), 7.34 (s, 1H), 7.42-7.44 (m, 2H0, 7.91 (s, 1H), 8.03 (s, 1H), 8.26 (s, 1H), 10.72 (s, 1H). |
| 263 | 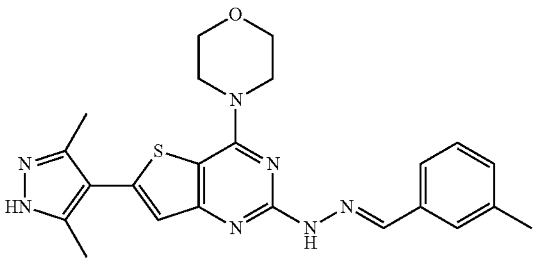 [SMILES: Cc1cccc(/C=N/Nc2nc(N3CCOCC3)c3sc(-c4c(C)n[nH]c4C)cc3n2)c1] | 6-(3,5-dimethyl-1H-pyrazol-4-yl)-4-morpholino-N-[(E)-m-tolylmethyleneamino]thieno[3,2-d]pyrimidin-2-amine. $^1$H NMR (DMSO-d$_6$): δ 2.32 (s, 6H), 2.39 (s, 3H), 3.74 (t, J = 4.0 Hz, 4H), 3.86 (t, J = 4.1 Hz, 4H), 7.11 (s, 1H), 7.13 (d, J = 7.2 Hz, 1H), 7.27 (t, J = 7.6 Hz, 1H), 7.41 (d, J = 6.2 Hz, 1H), 7.45 (s, 1H), 8.04 (s, 1H), 10.69 (s, 1H), 12.64 (s, 1H). LC-MS: m/z 448 [M + H]$^+$ |
| 264 | 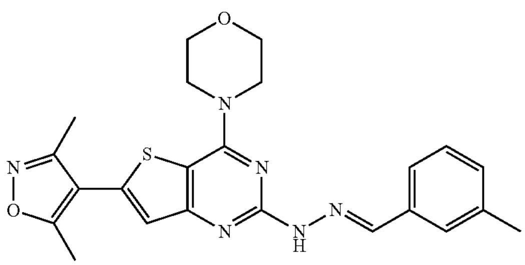 [SMILES: Cc1cccc(/C=N/Nc2nc(N3CCOCC3)c3sc(-c4c(C)noc4C)cc3n2)c1] | 6-(3,5-dimethylisoxazol-4-yl)-4-morpholino-N-[(E)-m-tolylmethyleneamino]thieno[3,2-d]pyrimidin-2-amine. $^1$H NMR (DMSO-d$_6$): δ 2.32 (s, 3H), 2.36 (s, 3H), 2.58 (s, 3H), 3.76 (t, J = 4.8 Hz, 4H), 3.88 (t, J = 4.8 Hz, 4H), 7.13 (d, J = 7.4 Hz, 1H), 7.27 (t, J = 7.5 Hz, 1H), 7.36-7.45 (m, 3H), 8.05 (s, 1H), 10.76 (, 1H). LC-MS: m/z 449 {M + H]$^+$ |
| 265 | 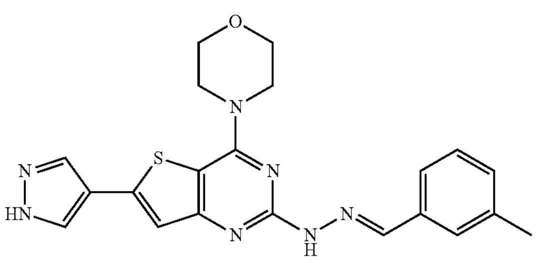 [SMILES: Cc1cccc(/C=N/Nc2nc(N3CCOCC3)c3sc(-c4cn[nH]c4)cc3n2)c1] | 4-morpholino-N-[(E)-m-tolylmethyleneamino]-6-(1H-pyrazol-4-yl)thieno[3,2-d]pyrimidin-2-amine. LC-MS: 420 {M + H]$^+$ |
| 266 | 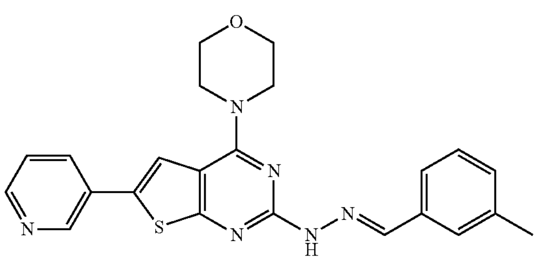 [SMILES: Cc1cccc(/C=N/Nc2nc(N3CCOCC3)c3cc(-c4cccnc4)sc3n2)c1] | 4-morpholino-N-[(E)-m-tolylmethyleneamino]-6-(3-pyridyl)thieno[2,3-d]pyrimidin-2-amine. $^1$H NMR (DMSO-d$_6$): δ 2.33 (s, 3H), 3.75 (t, J = 4.0 Hz, 4H), 3.88 (t, J = 4.2 Hz, 4H), 7.14 (d, J = 7.2 Hz, 1H), 7.28 (t, J = 7.4 Hz, 1H), 7.43-7.46 (m, 3H), 7.97 (s, 1H), 8.07 (s, 1H) ,8.11 (d, J = 6.0 Hz, 1H), 8.49 (d, J = 6.4 Hz, 1H), 8.99 (d, J-1.8 Hz, 1H), 10.99 (s, 1H). |
| 267 | 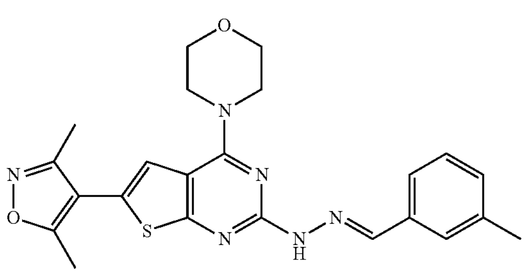 [SMILES: Cc1cccc(/C=N/Nc2nc(N3CCOCC3)c3cc(-c4c(C)noc4C)sc3n2)c1] | 6-(3,5-dimethylisoxazol-4-yl)-4-morpholino-N-[(E)-m-tolylmethyleneamino]thieno[2,3-d]pyrimidin-2-amine. $^1$H NMR (DMSO-d$_6$): δ 2.32 (s, 3H), 2.33 (s, 3H), 2.50 (s, 3H), 3.73 (t, J = 4.1 Hz, 4H), 3.84 (t, J = 4.1 Hz, 4H), 7.14 (d, J = 7.4 Hz, 1H), 7.28 (t, J = 7.6 Hz, 1H), 7.4-7.43 (m, 3H), 8.05 (s, 1H), 10.95 (s, 1H). |

TABLE 1-continued

| Ex. No. | Structure | Name |
|---|---|---|
| 268 | 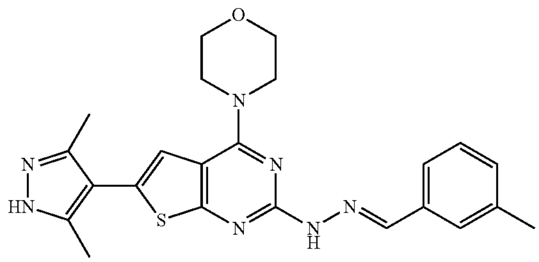 [SMILES: Cc1cccc(/C=N/Nc2nc(N3CCOCC3)c3cc(-c4c(C)n[nH]c4C)sc3n2)c1] | 6-(3,5-dimethyl-1H-pyrazol-4-yl)-4-morpholino-N-[(E)-m-tolylmethyleneamino]thieno[2,3-d]pyrimidin-2-amine. <br> $^1$H NMR (DMSO-$d_6$): δ 2.25 (s, 3H), 2.32 (s, 6H), 3.73 (t, J = 4.8 Hz, 4H), 3.82 (t, J = 4.6 Hz, 4H), 7.12 (d, J = 7.2 Hz, 1H), 1.16 (s, 1H), 7.27 (t, J = 7.6 Hz, 1H), 7.42 (d, J = 7.1 Hz, 1H), 7.45 (s, 1H), 8.04 (s, 1H), 10.87 (s, 1H), 1.45 (s, 1H). |
| 269 | 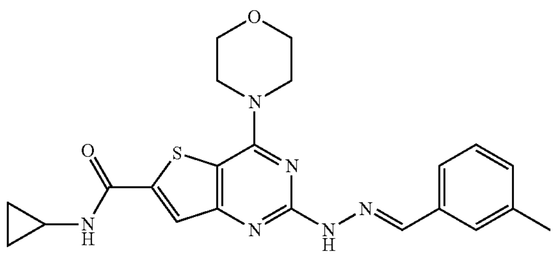 [SMILES: Cc1cccc(/C=N/Nc2nc(N3CCOCC3)c3sc(C(=O)NC4CC4)cc3n2)c1] | N-cyclopropyl-4-morpholino-2-[(2E)-2-(m-tolylmethylene)hydrazino]thieno[3,2-d]pyrimidine-6-carboxamide |
| 270 | 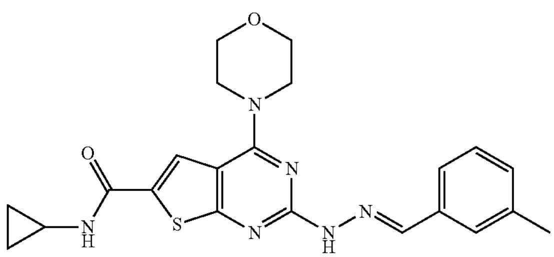 [SMILES: Cc1cccc(/C=N/Nc2nc(N3CCOCC3)c3cc(C(=O)NC4CC4)sc3n2)c1] | N-cyclopropyl-4-morpholino-2-[(2E)-2-(m-tolylmethylene)hydrazino]thieno[2,3-d]pyrimidine-6-carboxamide |
| 271 | 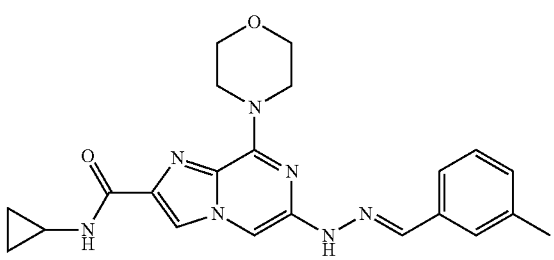 [SMILES: Cc1cccc(/C=N/Nc2cn3cc(C(=O)NC4CC4)nc3c(N3CCOCC3)n2)c1] | N-cyclopropyl-8-morpholino-6-[(2E)-2-(m-tolylmethylene)hydrazino]imidazo[1,2-a]pyrazine-2-carboxamide |
| 272 | 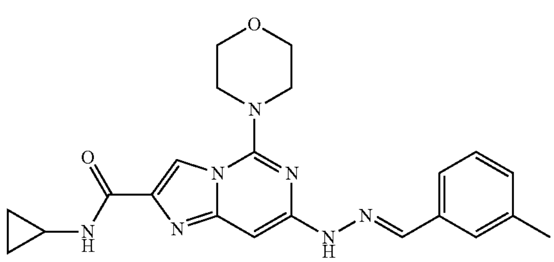 [SMILES: Cc1cccc(/C=N/Nc2cc3nc(C(=O)NC4CC4)cn3c(N3CCOCC3)n2)c1] | N-cyclopropyl-5-morpholino-7-[(2E)-2-(m-tolylmethylene)hydrazino]imidazo[1,2-c]pyrimidine-2-carboxamide |

Biochemical and Biological Examples

Protocol Description

Kinase assays. For most assays, kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 111× stocks in 100% DMSO. Kds were determined using an 11-point 3-fold compound dilution series with three DMSO control points. All compounds for Kd measurements are distributed by acoustic transfer (non-contact dispensing) in 100% DMSO. The compounds were then diluted directly into the assays such that the final concentration of DMSO was 0.9%. All reactions performed in polypropylene 384-well plate. Each was a final volume of 0.02 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 µM non-biotinylated affinity ligand) and incubated at room temperature with shaking for 30 minutes. The kinase concentration in the eluates was measured by qPCR.

Compound Handling

An 11-point 3-fold serial dilution of each test compound was prepared in 100% DMSO at 100× final test concentration and subsequently diluted to 1× in the assay (final DMSO concentration=1%). Most Kds were determined using a compound top concentration=30,000 nM. If the initial Kd determined was <0.5 nM (the lowest concentration tested), the measurement was repeated with a serial dilution starting at a lower top concentration. A Kd value reported as 40,000 nM indicates that the Kd was determined to be >30,000 nM.

The compounds in the Table 2 described below show PIKfyve inhibition, where "A" represents a Kd of less than or equal to 1 nM ("A"≤1 nM), "B" represents a Kd of greater than 1 nM to less than or equal to 10 nM (1 nM<"B"≤10 nM), and "C" represents a Kd of greater than 10 nM to less than or equal to 60 nM (10 nM<"C"≤60 nM).

TABLE 2

| Example # | PIKfyve Kd (nM) |
| --- | --- |
| 1 | B |
| 2 | A |
| 3 | B |
| 4 | A |
| 5 | B |
| 6 | ND |
| 7 | A |
| 8 | ND |
| 9 | B |
| 10 | C |
| 11 | B |
| 12 | A |
| 13 | ND |
| 14 | C |
| 22 | B |
| 255 | C |
| 256 | ND |
| 257 | ND |
| 258 | ND |
| 259 | ND |
| 260 | ND |
| 261 | A |
| 262 | A |
| 263 | A |
| 264 | A |
| 265 | ND |
| 266 | ND |
| 267 | B |
| 268 | B |

ND = not determined

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be understood that certain changes and modifications may be practiced within the scope of the appended claims.

REFERENCES

Côté M, Misasi J, Ren T, Bruchez A, Lee K, Filone C M, et al. Small molecule inhibitors reveal NiemannPick C1 is essential for Ebola virus infection. Nature. 2011; 477: 344-348.

Moller-Tank S, Maury W. Ebola virus entry: a curious and complex series of events. PLoS Pathog. 2015; 11: e1004731.

White J M, Whittaker G R. Fusion of Enveloped Viruses in Endosomes. Traffic. John Wiley & Sons A/S; 2016.

Carette J E, Raaben M, Wong A C, Herbert A S, Obernosterer G, Mulherkar N, et al. Ebola virus entry requires the cholesterol transporter Niemann-Pick C1. Nature. 2011; 477: 340-343.

Miller E H, Obernosterer G, Raaben M, Herbert A S, Deffieu M S, Krishnan A, et al. Ebola virus entry requires the host-programmed recognition of an intracellular receptor. EMBO J. 2012; 31: 1947-1960.

Simmons J A, D'Souza R S, Ruas M, Galione A, Casanova J E, White J M. Ebola virus Glycoprotein Directs Fusion through NPC1+ Endolysosomes. J Virol. American Society for Microbiology; 2015; 90: 605-610.

Mingo R M, Simmons J A, Shoemaker C J, Nelson E A, Schornberg K L, D'Souza R S, et al. Ebola Virus and Severe Acute Respiratory Syndrome Coronavirus Display Late Cell Entry Kinetics: Evidence that Transport to NPC1+ Endolysosomes Is a Rate-Defining Step. J Virol. 2015; 89: 2931-2943.

Chandran K, Sullivan N J, Felbor U, Whelan S P, Cunningham J M. Endosomal proteolysis of the Ebola virus glycoprotein is necessary for infection. Science. 2005; 308: 1643-1645.

Schornberg K, Matsuyama S, Kabsch K, Delos S, Bouton A, White J. Role of Endosomal Cathepsins in Entry Mediated by the Ebola Virus Glycoprotein. J Virol. 2006; 80: 4174-4178.

Elizabeth A. Nelson, Julie Dyall, Thomas Hoenen, Alyson B. Barnes, Huanying Zhou, Janie Y. Liang, Julia Michelotti, William H. Dewey, Lisa Evans DeWald, Richard S. Bennett, Patrick J. Morris, Rajarshi Guha, Carleen KlumppThomas, Crystal McKnight, Yu-Chi Chen, Xin Xu, Amy Wang, Emma Hughes, Scott Martin, Craig Thomas, Peter B. Jahrling, Lisa E. Hensley, Gene G. Olinger, Jr., Judith M. White. PLoSNegl Trop Dis 11(4): e0005540.

Dahlmann F, Biedenkopf N, Babler A, Jahnen-Dechent W, Karsten C B, Gnirss K, et al. Analysis of Ebola Virus Entry Into Macrophages. Journal of Infectious Diseases. 2015.

Martinez O, Johnson J C, Honko A, Yen B, Shabman R S, Hensley L E, et al. Ebola virus exploits a monocyte differentiation program to promote its entry. J Virol. 2013; 87: 3801-3814.

What is claimed is:

1. A compound represented by Formula I

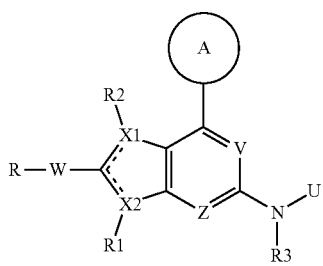

Formula I wherein R is selected from hydrogen, aryl, heteroaryl, alkyl, cycloalkyl, and heterocyclyl, and R is optionally substituted;
wherein each of X1 and X2 is independently selected from O, S, N, and C;
wherein W is C(O)NRa;
wherein n=2-5, and each of Ra and Rb is independently selected from hydrogen, C1-C6 alkyl, aryl, heteroaryl, cycloalkyl, and cycloheteroalkyl, and each of Ra and Rb is optionally substituted;
wherein each of R1 and R2 is optionally present depending on the valence of the atom to which R1 or R2 is attached, and if present, each of R1 and R2 is independently selected from hydrogen, halo, hydroxyl, aryl, heteroaryl, cycloalkyl, and heterocyclyl, and each of R1 and R2 is optionally substituted;
wherein R3 is selected from hydrogen, alkyl, alkylsulfonyl, acyl, alkoxycarbonyl, C-amido, aliphatic ring, aryl, heteroaryl, and aliphatic ring with one or more heteroatoms, and R3 is optionally substituted;
wherein U is selected from hydrogen and a group of one of the following general formulae:

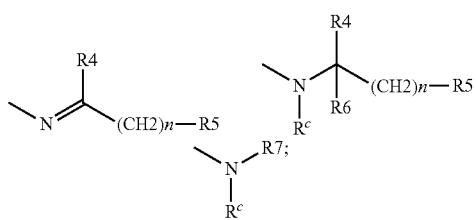

wherein n=0-3;
wherein each of R4, R5, R6, R7, and $R^c$ is independently selected from hydrogen, C1-C6 alkyl, aryl, heteroaryl, cycloalkyl, and heterocyclyl, and each of R4, R5, R6, R7, and $R^c$ is optionally substituted; or
R3 and U together form a 4 to 6 membered heterocyclic or heteroaryl ring, optionally substituted by one or more substituents selected from hydrogen, C1-C6 alkyl, aryl, heteroaryl, cycloalkyl, and heterocyclyl, and wherein the one or more substituents are optionally substituted;
wherein is selected from a single bond, an aromatic bond, and a double bond, such that at least one bond within the five membered ring is a double bond if is not an aromatic bond;
wherein each of V and Z is independently selected from N and CH; and
wherein Ring A is selected from carbocycle, heterocycle, and heteroaryl, and Ring A is optionally substituted, and pharmaceutically acceptable salts or solvates thereof.

2. The compound of claim 1, wherein V is N.
3. The compound of claim 1, wherein Z is N.
4. The compound of claim 1, wherein X1 is S, and wherein X1 is bound to each adjacent C in the five membered ring by an aromatic bond.
5. The compound of claim 1, wherein X2 is S, and wherein X2 is bound to each adjacent C in the five membered ring by an aromatic bond.
6. The compound of claim 1, wherein X1 is O, and wherein X1 is bound to each adjacent C in the five membered ring by an aromatic bond.
7. The compound of claim 1, wherein X2 is O, and wherein X2 is bound to each adjacent C in the five membered ring by an aromatic bond.
8. The compound of claim 1, wherein X1 is NH, and wherein X1 is bound to each adjacent C in the five membered ring by an aromatic bond.
9. The compound of claim 1, wherein X1 is S, wherein X1 is bound to each adjacent C in the five membered ring by an aromatic bond; and
wherein X2 is N, wherein X2 is bound to each adjacent C in the five membered ring by an aromatic bond.
10. The compound of claim 1, wherein X1 is O, wherein X1 is bound to each adjacent C in the five membered ring by an aromatic bond; and
wherein X2 is N, wherein X2 is bound to each adjacent C in the five membered ring by an aromatic bond.
11. The compound of claim 1, wherein X1 is N, wherein X1 is bound to each adjacent C in the five membered ring by an aromatic bond; and
wherein X2 is S, wherein X2 is bound to each adjacent C in the five membered ring by an aromatic bond.
12. The compound of claim 1, wherein X1 is N, wherein X1 is bound to each adjacent C in the five membered ring by an aromatic bond; and
wherein X2 is O, wherein X2 is bound to each adjacent C in the five membered ring by an aromatic bond.
13. The compound of claim 1, wherein X1 is NH, wherein X1 is bound to each adjacent C in the five membered ring by an aromatic bond; and
wherein X2 is N, wherein X2 is bound to each adjacent C in the five membered ring by an aromatic bond.
14. The compound of claim 1, wherein Ring A is the following formula:

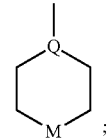

wherein Q is selected from N and CH; and
wherein M is selected from O, S, S(O), S(O2), and NRd, and wherein Rd is selected from hydrogen, hydroxyl, optionally substituted alkyl, and acyl.

15. A compound selected from the group consisting of:
4-morpholino-2-[(2E)-2-(m-tolylmethylene)hydrazino]thieno[3,2-d]pyrimidine-6-carboxamide
N-methyl-4-morpholino-2-[(2E)-2-(m-tolylmethylene)hydrazino]thieno[3,2-d]pyrimidine-6-carboxamide N,N-dimethyl-4-morpholino-2-[(2E)-2-(m-tolylmethylene)hydrazino]thieno[3,2-d]pyrimidine-6-carboxamide morpholino-[4-morpholino-2-[(2E)-2-(m-tolylmethylene)hydrazino]thieno[3,2-d]pyrimidin-6-yl]methanone

[4-morpholino-2-[(2E)-2-(m-tolylmethylene)hydrazino]thieno[3,2-d]pyrimidin-6-yl]-(1-piperidyl)methanone

[4-morpholino-2-[(2E)-2-(m-tolylmethylene)hydrazino]thieno[3,2-d]pyrimidin-6-yl]-piperazin-1-yl-methanone N-cyclobutyl-4-morpholino-2-[(2E)-2-(m-tolylmethylene)hydrazino]thieno[3,2-d]pyrimidine-6-carboxamide N-(azetidin-3-yl)-4-morpholino-2-[(2E)-2-(m-tolylmethylene)hydrazino]thieno[3,2-d]pyrimidine-6-carboxamide N-cyclopentyl-4-morpholino-2-[(2E)-2-(m-tolylmethylene)hydrazino]thieno[3,2-d]pyrimidine-6-carboxamide 4-morpholino-2-[(2E)-2-(m-tolylmethylene)hydrazino]-N-tetrahydrofuran-3-yl-thieno[3,2-d]pyrimidine-6-carboxamide 4-morpholino-2-[(2E)-2-(m-tolylmethylene)hydrazino]-N-pyrrolidin-3-yl-thieno[3,2-d]pyrimidine-6-carboxamide N-cyclohexyl-4-morpholino-2-[(2E)-2-(m-tolylmethylene)hydrazino]thieno[3,2-d]pyrimidine-6-carboxamide 4-morpholino-2-[(2E)-2-(m-tolylmethylene)hydrazino]-N-tetrahydropyran-4-yl-thieno[3,2-d]pyrimidine-6-carboxamide 4-morpholino-2-[(2E)-2-(m-tolylmethylene)hydrazino]-N-(4-piperidyl)thieno[3,2-d]pyrimidine-6-carboxamide N-methyl-4-morpholino-2-[(2E)-2-(m-tolylmethylene)hydrazino]furo[3,2-d]pyrimidine-6-carboxamide N,N-dimethyl-4-morpholino-2-[(2E)-2-(m-tolylmethylene)hydrazino]furo[3,2-d]pyrimidine-6-carboxamide morpholino-[4-morpholino-2-[(2E)-2-(m-tolylmethylene)hydrazino]furo[3,2-d]pyrimidin-6-yl]methanone

[4-morpholino-2-[(2E)-2-(m-tolylmethylene)hydrazino]furo[3,2-d]pyrimidin-6-yl]-(1-piperidyl)methanone

[4-morpholino-2-[(2E)-2-(m-tolylmethylene)hydrazino]furo[3,2-d]pyrimidin-6-yl]-piperazin-1-yl-methanone N-cyclobutyl-4-morpholino-2-[(2E)-2-(m-tolylmethylene)hydrazino]furo[3,2-d]pyrimidine-6-carboxamide 4-morpholino-2-[(2E)-2-(m-tolylmethylene)hydrazino]-N-(oxetan-3-yl)furo[3,2-d]pyrimidine-6-carboxamide N-(azetidin-3-yl)-4-morpholino-2-[(2E)-2-(m-tolylmethylene)hydrazino]furo[3,2-d]pyrimidine-6-carboxamide N-cyclopentyl-4-morpholino-2-[(2E)-2-(m-tolylmethylene)hydrazino]furo[3,2-d]pyrimidine-6-carboxamide 4-morpholino-2-[(2E)-2-(m-tolylmethylene)hydrazino]-N-tetrahydrofuran-3-yl-furo[3,2-d]pyrimidine-6-carboxamide 4-morpholino-2-[(2E)-2-(m-tolylmethylene)hydrazino]-N-pyrrolidin-3-yl-furo[3,2-d]pyrimidine-6-carboxamide N-cyclohexyl-4-morpholino-2-[(2E)-2-(m-tolylmethylene)hydrazino]furo[3,2-d]pyrimidine-6-carboxamide 4-morpholino-2-[(2E)-2-(m-tolylmethylene)hydrazino]-N-tetrahydropyran-4-yl-furo[3,2-d]pyrimidine-6-carboxamide 4-morpholino-2-[(2E)-2-(m-tolylmethylene)hydrazino]-N-(4-piperidyl)furo[3,2-d]pyrimidine-6-carboxamide 4-morpholino-2-[(2E)-2-(m-tolylmethylene)hydrazino]thieno[2,3-d]pyrimidine-6-carboxamide N-methyl-4-morpholino-2-[(2E)-2-(m-tolylmethylene)hydrazino]thieno[2,3-d]pyrimidine-6-carboxamide N,N-dimethyl-4-morpholino-2-[(2E)-2-(m-tolylmethylene)hydrazino]thieno[2,3-d]pyrimidine-6-carboxamide morpholino-[4-morpholino-2-[(2E)-2-(m-tolylmethylene)hydrazino]thieno[2,3-d]pyrimidin-6-yl]methanone

[4-morpholino-2-[(2E)-2-(m-tolylmethylene)hydrazino]thieno[2,3-d]pyrimidin-6-yl]-(1-piperidyl)methanone

[4-morpholino-2-[(2E)-2-(m-tolylmethylene)hydrazino]thieno[2,3-d]pyrimidin-6-yl]-piperazin-1-yl-methanone N-cyclobutyl-4-morpholino-2-[(2E)-2-(m-tolylmethylene)hydrazino]thieno[2,3-d]pyrimidine-6-carboxamide 4-morpholino-2-[(2E)-2-(m-tolylmethylene)hydrazino]-N-(oxetan-3-yl)thieno[3,2-d]pyrimidine-6-carboxamide N-(azetidin-3-yl)-4-morpholino-2-[(2E)-2-(m-tolylmethylene)hydrazino]thieno[2,3-d]pyrimidine-6-carboxamide N-cyclopentyl-4-morpholino-2-[(2E)-2-(m-tolylmethylene)hydrazino]thieno[2,3-d]pyrimidine-6-carboxamide 4-morpholino-2-[(2E)-2-(m-tolylmethylene)hydrazino]-N-tetrahydrofuran-3-yl-thieno[2,3-d]pyrimidine-6-carboxamide 4-morpholino-2-[(2E)-2-(m-tolylmethylene)hydrazino]-N-pyrrolidin-3-yl-thieno[2,3-d]pyrimidine-6-carboxamide N-cyclohexyl-4-morpholino-2-[(2E)-2-(m-tolylmethylene)hydrazino]thieno[2,3-d]pyrimidine-6-carboxamide 4-morpholino-2-[(2E)-2-(m-tolylmethylene)hydrazino]-N-tetrahydropyran-4-yl-thieno[2,3-d]pyrimidine-6-carboxamide 4-morpholino-2-[(2E)-2-(m-tolylmethylene)hydrazino]-N-(4-piperidyl)thieno[2,3-d]pyrimidine-6-carboxamide 4-morpholino-2-[(2E)-2-(m-tolylmethylene)hydrazino]furo[2,3-d]pyrimidine-6-carboxamide N-methyl-4-morpholino-2-[(2E)-2-(m-tolylmethylene)hydrazino]furo[2,3-d]pyrimidine-6-carboxamide N,N-dimethyl-4-morpholino-2-[(2E)-2-(m-tolylmethylene)hydrazino]furo[2,3-d]pyrimidine-6-carboxamide morpholino-[4-morpholino-2-[(2E)-2-(m-tolylmethylene)hydrazino]furo[2,3-d]pyrimidin-6-yl]methanone

[4-morpholino-2-[(2E)-2-(m-tolylmethylene)hydrazino]furo[2,3-d]pyrimidin-6-yl]-(1-piperidyl)methanone

[4-morpholino-2-[(2E)-2-(m-tolylmethylene)hydrazino]furo[2,3-d]pyrimidin-6-yl]-piperazin-1-yl-methanone N-cyclobutyl-4-morpholino-2-[(2E)-2-(m-tolylmethylene)hydrazino]furo[2,3-d]pyrimidine-6-carboxamide 4-morpholino-2-[(2E)-2-(m-tolylmethylene)hydrazino]-N-(oxetan-3-yl)furo[2,3-d]pyrimidine-6-carboxamide N-(azetidin-3-yl)-4-morpholino-2-[(2E)-2-(m-tolylmethylene)hydrazino]furo[2,3-d]pyrimidine-6-carboxamide N-cyclopentyl-4-morpholino-2-[(2E)-2-(m-tolylmethylene)hydrazino]furo[2,3-d]pyrimidine-6-carboxamide 4-morpholino-2-[(2E)-2-(m-tolylmethylene)hydrazino]-N-tetrahydrofuran-3-yl-furo[2,3-d]pyrimidine-6-carboxamide 4-morpholino-2-[(2E)-2-(m-tolylmethylene)hydrazino]-N-pyrrolidin-3-yl-furo[2,3-d]pyrimidine-6-carboxamide N-cyclohexyl-4-morpholino-2-[(2E)-2-(m-tolylmethylene)hydrazino]furo[2,3-d]pyrimidine-6-carboxamide 4-morpholino-2-[(2E)-2-(m-tolylmethylene)hydrazino]-N-tetrahydropyran-4-yl-furo[2,3-d]pyrimidine-6-carboxamide
4-morpholino-2-[(2E)-2-(m-tolylmethylene)hydrazino]-N-(4-piperidyl)furo[2,3-d]pyrimidine-6-carboxamide
4-morpholino-N-[(E)-m-tolylmethyleneamino]-6-(4-pyridyl)-5H-pyrrolo[3,2-d]pyrimidin-2-amine
7-morpholino-N-[(E)-m-tolylmethyleneamino]-2-(4-pyridyl)thiazolo[4,5-d]pyrimidin-5-amine
7-morpholino-N-[(E)-m-tolylmethyleneamino]-2-(4-pyridyl)oxazolo[4,5-d]pyrimidin-5-amine
7-morpholino-N-[(E)-m-tolylmethyleneamino]-2-(4-pyridyl)thiazolo[5,4-d]pyrimidin-5-amine
7-morpholino-N-[(E)-m-tolylmethyleneamino]-2-(4-pyridyl)oxazolo[5,4-d]pyrimidin-5-amine
4-morpholino-N-[(E)-m-tolylmethyleneamino]-6-(3-pyridyl)-5H-pyrrolo[3,2-d]pyrimidin-2-amine
7-morpholino-N-[(E)-m-tolylmethyleneamino]-2-(3-pyridyl)thiazolo[4,5-d]pyrimidin-5-amine
7-morpholino-N-[(E)-m-tolylmethyleneamino]-2-(3-pyridyl)oxazolo[4,5-d]pyrimidin-5-amine
4-morpholino-N-[(E)-m-tolylmethyleneamino]-6-(2-pyridyl)-5H-pyrrolo[3,2-d]pyrimidin-2-amine
7-morpholino-N-[(E)-m-tolylmethyleneamino]-2-(2-pyridyl)thiazolo[4,5-d]pyrimidin-5-amine
7-morpholino-N-[(E)-m-tolylmethyleneamino]-2-(2-pyridyl)oxazolo[4,5-d]pyrimidin-5-amine
6-morpholino-N-[(E)-m-tolylmethyleneamino]-8-(4-pyridyl)-7H-purin-2-amine
6-morpholino-N-[(E)-m-tolylmethyleneamino]-8-(3-pyridyl)-7H-purin-2-amine
6-morpholino-N-[(E)-m-tolylmethyleneamino]-8-(2-pyridyl)-7H-purin-2-amine
N-methyl-4-morpholino-2-[(2E)-2-(m-tolylmethylene)hydrazino]-5H-pyrrolo[3,2-d]pyrimidine-6-carboxamide
N-methyl-7-morpholino-5-[(2E)-2-(m-tolylmethylene)hydrazino]thiazolo[4,5-d]pyrimidine-2-carboxamide
N,N-dimethyl-7-morpholino-5-[(2E)-2-(m-tolylmethylene)hydrazino]thiazolo[4,5-d]pyrimidine-2-carboxamide
N-methyl-7-morpholino-5-[(2E)-2-(m-tolylmethylene)hydrazino]oxazolo[4,5-d]pyrimidine-2-carboxamide
N,N-dimethyl-7-morpholino-5-[(2E)-2-(m-tolylmethylene)hydrazino]oxazolo[4,5-d]pyrimidine-2-carboxamide
N-methyl-7-morpholino-5-[(2E)-2-(m-tolylmethylene)hydrazino]thiazolo[5,4-d]pyrimidine-2-carboxamide
N,N-dimethyl-7-morpholino-5-[(2E)-2-(m-tolylmethylene)hydrazino]thiazolo[5,4-d]pyrimidine-2-carboxamide
N-methyl-7-morpholino-5-[(2E)-2-(m-tolylmethylene)hydrazino]oxazolo[5,4-d]pyrimidine-2-carboxamide
N,N-dimethyl-7-morpholino-5-[(2E)-2-(m-tolylmethylene)hydrazino]oxazolo[5,4-d]pyrimidine-2-carboxamide
N-methyl-6-morpholino-2-[(2E)-2-(m-tolylmethylene)hydrazino]-7H-purine-8-carboxamide
N,N-dimethyl-4-morpholino-2-[(2E)-2-(m-tolylmethylene)hydrazino]-5H-pyrrolo[3,2-d]pyrimidine-6-carboxamide
N,N-dimethyl-6-morpholino-2-[(2E)-2-(m-tolylmethylene)hydrazino]-7H-purine-8-carboxamide
4-morpholino-2-[(2E)-2-(m-tolylmethylene)hydrazino]-N-phenyl-5H-pyrrolo[3,2-d]pyrimidine-6-carboxamide
4-morpholino-2-[(2E)-2-(m-tolylmethylene)hydrazino]-N-phenyl-thieno[3,2-d]pyrimidine-6-carboxamide
7-morpholino-5-[(2E)-2-(m-tolylmethylene)hydrazino]-N-phenyl-thiazolo[4,5-d]pyrimidine-2-carboxamide
7-morpholino-5-[(2E)-2-(m-tolylmethylene)hydrazino]-N-phenyl-oxazolo[4,5-d]pyrimidine-2-carboxamide
7-morpholino-5-[(2E)-2-(m-tolylmethylene)hydrazino]-N-phenyl-thiazolo[5,4-d]pyrimidine-2-carboxamide
7-morpholino-5-[(2E)-2-(m-tolylmethylene)hydrazino]-N-phenyl-oxazolo[5,4-d]pyrimidine-2-carboxamide
6-morpholino-2-[(2E)-2-(m-tolylmethylene)hydrazino]-N-phenyl-7H-purine-8-carboxamide
4-morpholino-2-[(2E)-2-(m-tolylmethylene)hydrazino]-N-(4-pyridyl)-5H-pyrrolo[3,2-d]pyrimidine-6-carboxamide
6-morpholino-2-[(2E)-2-(m-tolylmethylene)hydrazino]-N-(4-pyridyl)-7H-purine-8-carboxamide
7-morpholino-5-[(2E)-2-(m-tolylmethylene)hydrazino]-N-(4-pyridyl)thiazolo[4,5-d]pyrimidine-2-carboxamide
7-morpholino-5-[(2E)-2-(m-tolylmethylene)hydrazino]-N-(4-pyridyl)oxazolo[4,5-d]pyrimidine-2-carboxamide
7-morpholino-5-[(2E)-2-(m-tolylmethylene)hydrazino]-N-(4-pyridyl)thiazolo[5,4-d]pyrimidine-2-carboxamide
7-morpholino-5-[(2E)-2-(m-tolylmethylene)hydrazino]-N-(4-pyridyl)oxazolo[5,4-d]pyrimidine-2-carboxamide
4-morpholino-2-[(2E)-2-(m-tolylmethylene)hydrazino]-N-(3-pyridyl)-5H-pyrrolo[3,2-d]pyrimidine-6-carboxamide
6-morpholino-2-[(2E)-2-(m-tolylmethylene)hydrazino]-N-(3-pyridyl)-7H-purine-8-carboxamide
7-morpholino-5-[(2E)-2-(m-tolylmethylene)hydrazino]-N-(3-pyridyl)thiazolo[4,5-d]pyrimidine-2-carboxamide
7-morpholino-5-[(2E)-2-(m-tolylmethylene)hydrazino]-N-(3-pyridyl)oxazolo[4,5-d]pyrimidine-2-carboxamide
7-morpholino-5-[(2E)-2-(m-tolylmethylene)hydrazino]-N-(3-pyridyl)thiazolo[5,4-d]pyrimidine-2-carboxamide
7-morpholino-5-[(2E)-2-(m-tolylmethylene)hydrazino]-N-(3-pyridyl)oxazolo[5,4-d]pyrimidine-2-carboxamide
4-morpholino-2-[(2E)-2-(m-tolylmethylene)hydrazino]-N-(2-pyridyl)-5H-pyrrolo[3,2-d]pyrimidine-6-carboxamide
6-morpholino-2-[(2E)-2-(m-tolylmethylene)hydrazino]-N-(2-pyridyl)-7H-purine-8-carboxamide
7-morpholino-5-[(2E)-2-(m-tolylmethylene)hydrazino]-N-(2-pyridyl)thiazolo[4,5-d]pyrimidine-2-carboxamide
7-morpholino-5-[(2E)-2-(m-tolylmethylene)hydrazino]-N-(2-pyridyl)oxazolo[4,5-d]pyrimidine-2-carboxamide
7-morpholino-5-[(2E)-2-(m-tolylmethylene)hydrazino]-N-(2-pyridyl)thiazolo[5,4-d]pyrimidine-2-carboxamide
7-morpholino-5-[(2E)-2-(m-tolylmethylene)hydrazino]-N-(2-pyridyl)oxazolo[5,4-d]pyrimidine-2-carboxamide
4-morpholino-2-[(2E)-2-(m-tolylmethylene)hydrazino]-N-(oxetan-3-yl)-5H-pyrrolo[3,2-d]pyrimidine-6-carboxamide 7-morpholino-5-[(2E)-2-(m-tolylmethylene)hydrazino]-N-(oxetan-3-yl)thiazolo[4,5-d]pyrimidine-2-carboxamide 7-morpholino-5-[(2E)-2-(m-tolylmethylene)hydrazino]-N-(oxetan-3-yl)oxazolo[4,5-d]pyrimidine-2-carboxamide 7-morpholino-5-[(2E)-2-(m-tolylmethylene)hydrazino]-N-(oxetan-3-yl)thiazolo[5,4-d]pyrimidine-2-carboxamide 7-morpholino-5-[(2E)-2-(m-tolylmethylene)hydrazino]-N-(oxetan-3-yl)oxazolo[5,4-d]pyrimidine-2-carboxamide 6-morpholino-2-[(2E)-2-(m-tolylmethylene)hydrazino]-N-(oxetan-3-yl)-7H-purine-8-carboxamide N-(azetidin-3-yl)-4-morpholino-2-[(2E)-2-(m-tolylmethylene)hydrazino]-5H-pyrrolo[3,2-d]pyrimidine-6-carboxamide N-(azetidin-3-yl)-7-morpholino-5-[(2E)-2-(m-tolylmethylene)hydrazino]thiazolo[4,5-d]pyrimidine-2-carboxamide N-(azetidin-3-yl)-7-morpholino-5-[(2E)-2-(m-tolylmethylene)hydrazino]oxazolo[4,5-d]pyrimidine-2-carboxamide N-(azetidin-3-yl)-7-morpholino-5-[(2E)-2-(m-tolylmethylene)hydrazino]thiazolo[5,4-d]pyrimidine-2-carboxamide N-(azetidin-3-yl)-7-morpholino-5-[(2E)-2-(m-tolylmethylene)hydrazino]oxazolo[5,4-d]pyrimidine-2-carboxamide N-(azetidin-3-yl)-6-morpholino-2-[(2E)-2-(m-tolylmethylene)hydrazino]-7H-purine-8-carboxamide N-cyclobutyl-4-morpholino-2-[(2E)-2-(m-tolylmethylene)hydrazino]-5H-pyrrolo[3,2-d]pyrimidine-6-carboxamide N-cyclobutyl-7-morpholino-5-[(2E)-2-(m-tolylmethylene)hydrazino]thiazolo[4,5-d]pyrimidine-2-carboxamide N-cyclobutyl-7-morpholino-5-[(2E)-2-(m-tolylmethylene)hydrazino]oxazolo[4,5-d]pyrimidine-2-carboxamide N-cyclobutyl-7-morpholino-5-[(2E)-2-(m-tolylmethylene)hydrazino]thiazolo[5,4-d]pyrimidine-2-carboxamide N-cyclobutyl-7-morpholino-5-[(2E)-2-(m-tolylmethylene)hydrazino]oxazolo[5,4-d]pyrimidine-2-carboxamide N-cyclobutyl-6-morpholino-2-[(2E)-2-(m-tolylmethylene)hydrazino]-7H-purine-8-carboxamide N-cyclopentyl-4-morpholino-2-[(2E)-2-(m-tolylmethylene)hydrazino]-5H-pyrrolo[3,2-d]pyrimidine-6-carboxamide N-cyclopentyl-4-morpholino-2-[(2E)-2-(m-tolylmethylene)hydrazino]thieno[3,2-d]pyrimidine-6-carboxamide N-cyclopentyl-4-morpholino-2-[(2E)-2-(m-tolylmethylene)hydrazino]thieno[2,3-d]pyrimidine-6-carboxamide N-cyclopentyl-7-morpholino-5-[(2E)-2-(m-tolylmethylene)hydrazino]thiazolo[4,5-d]pyrimidine-2-carboxamide N-cyclopentyl-7-morpholino-5-[(2E)-2-(m-tolylmethylene)hydrazino]oxazolo[4,5-d]pyrimidine-2-carboxamide N-cyclopentyl-7-morpholino-5-[(2E)-2-(m-tolylmethylene)hydrazino]thiazolo[5,4-d]pyrimidine-2-carboxamide N-cyclopentyl-7-morpholino-5-[(2E)-2-(m-tolylmethylene)hydrazino]oxazolo[5,4-d]pyrimidine-2-carboxamide N-cyclopentyl-6-morpholino-2-[(2E)-2-(m-tolylmethylene)hydrazino]-7H-purine-8-carboxamide 4-morpholino-2-[(2E)-2-(m-tolylmethylene)hydrazino]-N-tetrahydrofuran-3-yl-5H-pyrrolo[3,2-d]pyrimidine-6-carboxamide 6-morpholino-2-[(2E)-2-(m-tolylmethylene)hydrazino]-N-tetrahydrofuran-3-yl-7H-purine-8-carboxamide 4-morpholino-2-[(2E)-2-(m-tolylmethylene)hydrazino]-N-tetrahydrofuran-3-yl-thieno[3,2-d]pyrimidine-6-carboxamide 7-morpholino-5-[(2E)-2-(m-tolylmethylene)hydrazino]-N-tetrahydrofuran-3-yl-thiazolo[4,5-d]pyrimidine-2-carboxamide 7-morpholino-5-[(2E)-2-(m-tolylmethylene)hydrazino]-N-tetrahydrofuran-3-yl-oxazolo[4,5-d]pyrimidine-2-carboxamide 4-morpholino-2-[(2E)-2-(m-tolylmethylene)hydrazino]-N-tetrahydrofuran-3-yl-thieno[2,3-d]pyrimidine-6-carboxamide 7-morpholino-5-[(2E)-2-(m-tolylmethylene)hydrazino]-N-tetrahydrofuran-3-yl-thiazolo[5,4-d]pyrimidine-2-carboxamide 7-morpholino-5-[(2E)-2-(m-tolylmethylene)hydrazino]-N-tetrahydrofuran-3-yl-oxazolo[5,4-d]pyrimidine-2-carboxamide 4-morpholino-2-[(2E)-2-(m-tolylmethylene)hydrazino]-N-pyrrolidin-3-yl-5H-pyrrolo[3,2-d]pyrimidine-6-carboxamide 4-morpholino-2-[(2E)-2-(m-tolylmethylene)hydrazino]-N-pyrrolidin-3-yl-thieno[3,2-d]pyrimidine-6-carboxamide 7-morpholino-5-[(2E)-2-(m-tolylmethylene)hydrazino]-N-pyrrolidin-3-yl-thiazolo[4,5-d]pyrimidine-2-carboxamide 7-morpholino-5-[(2E)-2-(m-tolylmethylene)hydrazino]-N-pyrrolidin-3-yl-oxazolo[4,5-d]pyrimidine-2-carboxamide 4-morpholino-2-[(2E)-2-(m-tolylmethylene)hydrazino]-N-pyrrolidin-3-yl-thieno[2,3-d]pyrimidine-6-carboxamide 7-morpholino-5-[(2E)-2-(m-tolylmethylene)hydrazino]-N-pyrrolidin-3-yl-thiazolo[5,4-d]pyrimidine-2-carboxamide 7-morpholino-5-[(2E)-2-(m-tolylmethylene)hydrazino]-N-pyrrolidin-3-yl-oxazolo[5,4-d]pyrimidine-2-carboxamide 6-morpholino-2-[(2E)-2-(m-tolylmethylene)hydrazino]-N-pyrrolidin-3-yl7H-purine-8-carboxamide N-cyclohexyl-4-morpholino-2-[(2E)-2-(m-tolylmethylene)hydrazino]-5H-pyrrolo[3,2-d]pyrimidine-6-carboxamide N-cyclohexyl-4-morpholino-2-[(2E)-2-(m-tolylmethylene)hydrazino]thieno[3,2-d]pyrimidine-6-carboxamide N-cyclohexyl-7-morpholino-5-[(2E)-2-(m-tolylmethylene)hydrazino]thiazolo[4,5-d]pyrimidine-2-carboxamide N-cyclohexyl-7-morpholino-5-[(2E)-2-(m-tolylmethylene)hydrazino]oxazolo[4,5-d]pyrimidine-2-carboxamide N-cyclohexyl-4-morpholino-2-[(2E)-2-(m-tolylmethylene)hydrazino]thieno[2,3-d]pyrimidine-6-carboxamide N-cyclohexyl-7-morpholino-5-[(2E)-2-(m-tolylmethylene)hydrazino]thiazolo[5,4-d]pyrimidine-2-carboxamide
N-cyclohexyl-7-morpholino-5-[(2E)-2-(m-tolylmethylene)hydrazino]oxazolo[5,4-d]pyrimidine-2-carboxamide
N-cyclohexyl-6-morpholino-2-[(2E)-2-(m-tolylmethylene)hydrazino]-7H-purine-8-carboxamide
4-morpholino-2-[(2E)-2-(m-tolylmethylene)hydrazino]-N-tetrahydropyran-4-yl-5H-pyrrolo[3,2-d]pyrimidine-6-carboxamide
4-morpholino-2-[(2E)-2-(m-tolylmethylene)hydrazino]-N-tetrahydropyran-4-yl-thieno[3,2-d]pyrimidine-6-carboxamide
7-morpholino-5-[(2E)-2-(m-tolylmethylene)hydrazino]-N-tetrahydropyran-4-yl-thiazolo[4,5-d]pyrimidine-2-carboxamide
7-morpholino-5-[(2E)-2-(m-tolylmethylene)hydrazino]-N-tetrahydropyran-4-yl-oxazolo[4,5-d]pyrimidine-2-carboxamide
4-morpholino-2-[(2E)-2-(m-tolylmethylene)hydrazino]-N-tetrahydropyran-4-yl-thieno[2,3-d]pyrimidine-6-carboxamide
7-morpholino-5-[(2E)-2-(m-tolylmethylene)hydrazino]-N-tetrahydropyran-4-yl-thiazolo[5,4-d]pyrimidine-2-carboxamide
7-morpholino-5-[(2E)-2-(m-tolylmethylene)hydrazino]-N-tetrahydropyran-4-yl-oxazolo[5,4-d]pyrimidine-2-carboxamide
6-morpholino-2-[(2E)-2-(m-tolylmethylene)hydrazino]-N-tetrahydropyran-4-yl-7H-purine-8-carboxamide
4-morpholino-2-[(2E)-2-(m-tolylmethylene)hydrazino]-N-(4-piperidyl)-5H-pyrrolo[3,2-d]pyrimidine-6-carboxamide
4-morpholino-2-[(2E)-2-(m-tolylmethylene)hydrazino]-N-(4-piperidyl)thieno[3,2-d]pyrimidine-6-carboxamide
7-morpholino-5-[(2E)-2-(m-tolylmethylene)hydrazino]-N-(4-piperidyl)thiazolo[4,5-d]pyrimidine-2-carboxamide
7-morpholino-5-[(2E)-2-(m-tolylmethylene)hydrazino]-N-(4-piperidyl)oxazolo[4,5-d]pyrimidine-2-carboxamide
6-morpholino-2-[(2E)-2-(m-tolylmethylene)hydrazino]-N-(4-piperidyl)-7H-purine-8-carboxamide
4-morpholino-2-[(2E)-2-(m-tolylmethylene)hydrazino]-N-(4-piperidyl)thieno[2,3-d]pyrimidine-6-carboxamide
7-morpholino-5-[(2E)-2-(m-tolylmethylene)hydrazino]-N-(4-piperidyl)thiazolo[5,4-d]pyrimidine-2-carboxamide
7-morpholino-5-[(2E)-2-(m-tolylmethylene)hydrazino]-N-(4-piperidyl)oxazolo[5,4-d]pyrimidine-2-carboxamide
5-morpholino-N-[(E)-m-tolylmethyleneamino]-2-(4-pyridyl)imidazo[1,2-c]pyrimidin-7-amine
5-morpholino-N-[(E)-m-tolylmethyleneamino]-2-(3-pyridyl)imidazo[1,2-c]pyrimidin-7-amine
5-morpholino-N-[(E)-m-tolylmethyleneamino]-2-(2-pyridyl)imidazo[1,2-c]pyrimidin-7-amine
5-morpholino-N-[(E)-m-tolylmethyleneamino]-2-oxazol-5-yl-imidazo[1,2-c]pyrimidin-7-amine
5-morpholino-7-[(2E)-2-(m-tolylmethylene)hydrazino]imidazo[1,2-c]pyrimidine-2-carboxylic acid
N-cyclopropyl-5-morpholino-7-[(2E)-2-(m-tolylmethylene)hydrazino]imidazo[1,2-c]pyrimidine-2-carboxamide
N-cyclobutyl-5-morpholino-7-[(2E)-2-(m-tolylmethylene)hydrazino]imidazo[1,2-c]pyrimidine-2-carboxamide
N-(azetidin-3-yl)-5-morpholino-7-[(2E)-2-(m-tolylmethylene)hydrazino]imidazo[1,2-c]pyrimidine-2-carboxamide
5-morpholino-7-[(2E)-2-(m-tolylmethylene)hydrazino]-N-(oxetan-3-yl)imidazo[1,2-c]pyrimidine-2-carboxamide
N-cyclopentyl-5-morpholino-7-[(2E)-2-(m-tolylmethylene)hydrazino]imidazo[1,2-c]pyrimidine-2-carboxamide
5-morpholino-7-[(2E)-2-(m-tolylmethylene)hydrazino]-N-pyrrolidin-3-yl-imidazo[1,2-c]pyrimidine-2-carboxamide
5-morpholino-7-[(2E)-2-(m-tolylmethylene)hydrazino]-N-tetrahydrofuran-3-yl-imidazo[1,2-c]pyrimidine-2-carboxamide
N-cyclohexyl-5-morpholino-7-[(2E)-2-(m-tolylmethylene)hydrazino]imidazo[1,2-c]pyrimidine-2-carboxamide
5-morpholino-7-[(2E)-2-(m-tolylmethylene)hydrazino]-N-(4-piperidyl)imidazo[1,2-c]pyrimidine-2-carboxamide
5-morpholino-7-[(2E)-2-(m-tolylmethylene)hydrazino]-N-(3-piperidyl)imidazo[1,2-c]pyrimidine-2-carboxamide
5-morpholino-7-[(2E)-2-(m-tolylmethylene)hydrazino]-N-(2-piperidyl)imidazo[1,2-c]pyrimidine-2-carboxamide
5-morpholino-7-[(2E)-2-(m-tolylmethylene)hydrazino]-N-tetrahydropyran-4-yl-imidazo[1,2-c]pyrimidine-2-carboxamide
5-morpholino-7-[(2E)-2-(m-tolylmethylene)hydrazino]imidazo[1,2-c]pyrimidine-2-carboxamide
N-methyl-5-morpholino-7-[(2E)-2-(m-tolylmethylene)hydrazino]imidazo[1,2-c]pyrimidine-2-carboxamide
N,N-dimethyl-5-morpholino-7-[(2E)-2-(m-tolylmethylene)hydrazino]imidazo[1,2-c]pyrimidine-2-carboxamide
[5-morpholino-7-[(2E)-2-(m-tolylmethylene)hydrazino]imidazo[1,2-c]pyrimidin-2-yl]-piperazin-1-yl-methanone morpholino-[5-morpholino-7-[(2E)-2-(m-tolylmethylene)hydrazino]imidazo[1,2-c]pyrimidin-2-yl]methanone
8-morpholino-N-[(E)-m-tolylmethyleneamino]-2-(4-pyridyl)imidazo[1,2-a]pyrazin-6-amine
8-morpholino-N-[(E)-m-tolylmethyleneamino]-2-(3-pyridyl)imidazo[1,2-a]pyrazin-6-amine
8-morpholino-N-[(E)-m-tolylmethyleneamino]-2-(2-pyridyl)imidazo[1,2-a]pyrazin-6-amine
8-morpholino-N-[(E)-m-tolylmethyleneamino]-2-oxazol-5-yl-imidazo[1,2-a]pyrazin-6-amine
8-morpholino-6-[(2E)-2-(m-tolylmethylene)hydrazino]imidazo[1,2-a]pyrazine-2-carboxylic acid
N-cyclopropyl-8-morpholino-6-[(2E)-2-(m-tolylmethylene)hydrazino]imidazo[1,2-a]pyrazine-2-carboxamide
N-cyclobutyl-8-morpholino-6-[(2E)-2-(m-tolylmethylene)hydrazino]imidazo[1,2-a]pyrazine-2-carboxamide
N-(azetidin-3-yl)-8-morpholino-6-[(2E)-2-(m-tolylmethylene)hydrazino]imidazo[1,2-a]pyrazine-2-carboxamide
8-morpholino-6-[(2E)-2-(m-tolylmethylene)hydrazino]-N-(oxetan-3-yl)imidazo[1,2-a]pyrazine-2-carboxamide
N-cyclopentyl-8-morpholino-6-[(2E)-2-(m-tolylmethylene)hydrazino]imidazo[1,2-a]pyrazine-2-carboxamide 8-morpholino-6-[(2E)-2-(m-tolylmethylene)hydrazino]-N-pyrrolidin-3-yl-imidazo[1,2-a]pyrazine-2-carboxamide 8-morpholino-6-[(2E)-2-(m-tolylmethylene)hydrazino]-N-tetrahydrofuran-3-yl-imidazo[1,2-a]pyrazine-2-carboxamide N-cyclohexyl-8-morpholino-6-[(2E)-2-(m-tolylmethylene)hydrazino]imidazo[1,2-a]pyrazine-2-carboxamide 8-morpholino-6-[(2E)-2-(m-tolylmethylene)hydrazino]-N-(4-piperidyl)imidazo[1,2-a]pyrazine-2-carboxamide 8-morpholino-6-[(2E)-2-(m-tolylmethylene)hydrazino]-N-(3-piperidyl)imidazo[1,2-a]pyrazine-2-carboxamide 8-morpholino-6-[(2E)-2-(m-tolylmethylene)hydrazino]-N-(2-piperidyl)imidazo[1,2-a]pyrazine-2-carboxamide 8-morpholino-6-[(2E)-2-(m-tolylmethylene)hydrazino]-N-tetrahydropyran-4-yl-imidazo[1,2-a]pyrazine-2-carboxamide 8-morpholino-6-[(2E)-2-(m-tolylmethylene)hydrazino]imidazo[1,2-a]pyrazine-2-carboxamide N-methyl-8-morpholino-6-[(2E)-2-(m-tolylmethylene)hydrazino]imidazo[1,2-a]pyrazine-2-carboxamide N,N-dimethyl-8-morpholino-6-[(2E)-2-(m-tolylmethylene)hydrazino]imidazo[1,2-a]pyrazine-2-carboxamide

[8-morpholino-6-[(2E)-2-(m-tolylmethylene)hydrazino]imidazo[1,2-a]pyrazin-2-yl]-piperazin-1-yl-methanone morpholino-[8-morpholino-6-[(2E)-2-(m-tolylmethylene)hydrazino]imidazo[1,2-a]pyrazin-2-yl]methanone 4-morpholino-N-[(E)-m-tolylmethyleneamino]-6-(4-pyridyl)pyrrolo[2,1-f][1,2,4]triazin-2-amine 4-morpholino-N-[(E)-m-tolylmethyleneamino]-6-(3-pyridyl)pyrrolo[2,1-f][1,2,4]triazin-2-amine 4-morpholino-N-[(E)-m-tolylmethyleneamino]-6-(2-pyridyl)pyrrolo[2,1-f][1,2,4]triazin-2-amine 4-morpholino-N-[(E)-m-tolylmethyleneamino]-6-oxazol-5-yl-pyrrolo[2,1-f][1,2,4]triazin-2-amine 4-morpholino-2-[(2E)-2-(m-tolylmethylene)hydrazino]pyrrolo[2,1-f][1,2,4]triazine-6-carboxylic acid N-cyclopropyl-4-morpholino-2-[(2E)-2-(m-tolylmethylene)hydrazino]pyrrolo[2,1-f][1,2,4]triazine-6-carboxamide N-cyclobutyl-4-morpholino-2-[(2E)-2-(m-tolylmethylene)hydrazino]pyrrolo[2,1-f][1,2,4]triazine-6-carboxamide N-(azetidin-3-yl)-4-morpholino-2-[(2E)-2-(m-tolylmethylene)hydrazino]pyrrolo[2,1-f][1,2,4]triazine-6-carboxamide 4-morpholino-2-[(2E)-2-(m-tolylmethylene)hydrazino]-N-(oxetan-3-yl)pyrrolo[2,1-f][1,2,4]triazine-6-carboxamide N-cyclopentyl-4-morpholino-2-[(2E)-2-(m-tolylmethylene)hydrazino]pyrrolo[2,1-f][1,2,4]triazine-6-carboxamide 4-morpholino-2-[(2E)-2-(m-tolylmethylene)hydrazino]-N-tetrahydrofuran-3-yl-pyrrolo[2,1-f][1,2,4]triazine-6-carboxamide N-cyclohexyl-4-morpholino-2-[(2E)-2-(m-tolylmethylene)hydrazino]pyrrolo[2,1-f][1,2,4]triazine-6-carboxamide 4-morpholino-2-[(2E)-2-(m-tolylmethylene)hydrazino]-N-(4-piperidyl)pyrrolo[2,1-f][1,2,4]triazine-6-carboxamide 4-morpholino-2-[(2E)-2-(m-tolylmethylene)hydrazino]-N-(3-piperidyl)pyrrolo[2,1-f][1,2,4]triazine-6-carboxamide 4-morpholino-2-[(2E)-2-(m-tolylmethylene)hydrazino]-N-(2-piperidyl)pyrrolo[2,1-f][1,2,4]triazine-6-carboxamide 4-morpholino-2-[(2E)-2-(m-tolylmethylene)hydrazino]-N-tetrahydropyran-4-yl-pyrrolo[2,1-f][1,2,4]triazine-6-carboxamide 4-morpholino-2-[(2E)-2-(m-tolylmethylene)hydrazino]pyrrolo[2,1-f][1,2,4]triazine-6-carboxamide N-methyl-4-morpholino-2-[(2E)-2-(m-tolylmethylene)hydrazino]pyrrolo[2,1-f][1,2,4]triazine-6-carboxamide N,N-dimethyl-4-morpholino-2-[(2E)-2-(m-tolylmethylene)hydrazino]pyrrolo[2,1-f][1,2,4]triazine-6-carboxamide

[4-morpholino-2-[(2E)-2-(m-tolylmethylene)hydrazino]pyrrolo[2,1-f][1,2,4]triazin-6-yl]-piperazin-1-yl-methanone morpholino-[4-morpholino-2-[(2E)-2-(m-tolylmethylene)hydrazino]pyrrolo[2,1-f][1,2,4]triazin-6-yl]methanone 4-morpholino-N-[2-(m-tolyl)ethyl]-6-(4-pyridyl)thieno[3,2-d]pyrimidin-2-amine 6-iodo-4-morpholino-N-[(E)-m-tolylmethyleneamino]thieno[2,3-d]pyrimidin-2-amine 6-iodo-4-morpholino-N-[(E)-m-tolylmethyleneamino]thieno[3,2-d]pyrimidin-2-amine 4-morpholino-N-[(E)-m-tolylmethyleneamino]-6-(1H-pyrazol-4-yl)thieno[2,3-d]pyrimidin-2-amine 4-morpholino-N-[(E)-m-tolylmethyleneamino]-6-phenyl-thieno[2,3-d]pyrimidin-2-amine 6-(1-methylpyrazol-4-yl)-4-morpholino-N-[(E)-m-tolylmethyleneamino]thieno[2,3-d]pyrimidin-2-amine 4-morpholino-N-[(E)-m-tolylmethyleneamino]-6-(3-pyridyl)thieno[3,2-d]pyrimidin-2-amine 6-(1-methylpyrazol-4-yl)-4-morpholino-N-[(E)-m-tolylmethyleneamino]thieno[3,2-d]pyrimidin-2-amine 6-(3,5-dimethyl-1H-pyrazol-4-yl)-4-morpholino-N-[(E)-m-tolylmethyleneamino]thieno[3,2-d]pyrimidin-2-amine 6-(3,5-dimethylisoxazol-4-yl)-4-morpholino-N-[(E)-m-tolylmethyleneamino]thieno[3,2-d]pyrimidin-2-amine 4-morpholino-N-[(E)-m-tolylmethyleneamino]-6-(1H-pyrazol-4-yl)thieno[3,2-d]pyrimidin-2-amine 4-morpholino-N-[(E)-m-tolylmethyleneamino]-6-(3-pyridyl)thieno[2,3-d]pyrimidin-2-amine 6-(3,5-dimethylisoxazol-4-yl)-4-morpholino-N-[(E)-m-tolylmethyleneamino]thieno[2,3-d]pyrimidin-2-amine 6-(3,5-dimethyl-1H-pyrazol-4-yl)-4-morpholino-N-[(E)-m-tolylmethyleneamino]thieno[2,3-d]pyrimidin-2-amine N-cyclopropyl-4-morpholino-2-[(2E)-2-(m-tolylmethylene)hydrazino]thieno[3,2-d]pyrimidine-6-carboxamide N-cyclopropyl-4-morpholino-2-[(2E)-2-(m-tolylmethylene)hydrazino]thieno[2,3-d]pyrimidine-6-carboxamide N-cyclopropyl-8-morpholino-6-[(2E)-2-(m-tolylmethylene)hydrazino]imidazo[1,2-a]pyrazine-2-carboxamide and N-cyclopropyl-5-morpholino-7-[(2E)-2-(m-tolylmethylene)hydrazino]imidazo[1,2-c]pyrimidine-2-carboxamide.

16. A pharmaceutical composition comprising the compound of claim 1 and a pharmaceutically acceptable excipient.

17. A method of treating one or more of cancer, systemic or chronic inflammation, rheumatoid arthritis, diabetes, obesity, T-cell mediated autoimmune disease, a disease associated with over production of IL12/IL23, a lysosomal storage disorder, a Filovirus infection, and ischemia in a human patient, comprising identifying a patient in need of such treatment and administering a therapeutically effective amount of a compound of claim 1.

18. A method of inhibiting the activity of PIKfyve in human cells, comprising contacting the human cells with a compound of claim 1.

\* \* \* \* \*